US012686728B2

(12) United States Patent
Hauskins et al.

(10) Patent No.: US 12,686,728 B2
(45) Date of Patent: Jul. 21, 2026

(54) ANTI-IDIOTYPIC ANTIBODIES TO BCMA-TARGETED BINDING DOMAINS AND RELATED COMPOSITIONS AND METHODS

(71) Applicant: Juno Therapeutics, Inc., Seattle, WA (US)

(72) Inventors: Collin Hauskins, Seattle, WA (US); Kimberly Harrington, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 998 days.

(21) Appl. No.: 17/781,693

(22) PCT Filed: Dec. 4, 2020

(86) PCT No.: PCT/US2020/063492
§ 371 (c)(1),
(2) Date: Jun. 1, 2022

(87) PCT Pub. No.: WO2021/113776
PCT Pub. Date: Jun. 10, 2021

(65) Prior Publication Data
US 2023/0028050 A1 Jan. 26, 2023

Related U.S. Application Data

(60) Provisional application No. 63/109,839, filed on Nov. 4, 2020, provisional application No. 63/061,763, filed on Aug. 5, 2020, provisional application No. 62/945,065, filed on Dec. 6, 2019.

(51) Int. Cl.
| | |
|---|---|
| *C07K 16/00* | (2006.01) |
| *C07K 16/28* | (2006.01) |
| *C07K 16/42* | (2006.01) |

(52) U.S. Cl.
CPC ...... *C07K 16/4208* (2013.01); *C07K 16/2878* (2013.01); *C07K 2317/565* (2013.01); *C07K 2317/622* (2013.01)

(58) Field of Classification Search
CPC ............ C07K 16/4208; C07K 16/2878; C07K 2317/565; C07K 2317/622; G01N 33/6854
See application file for complete search history.

(56) References Cited

U.S. PATENT DOCUMENTS

| | | | |
|---|---|---|---|
| 4,452,773 | A | 6/1984 | Molday |
| 4,795,698 | A | 1/1989 | Owen et al. |
| 4,816,567 | A | 3/1989 | Cabilly et al. |
| 5,200,084 | A | 4/1993 | Liberti et al. |
| 5,208,020 | A | 5/1993 | Chari et al. |
| 5,219,740 | A | 6/1993 | Miller et al. |
| 5,225,539 | A | 7/1993 | Winter |
| 5,283,173 | A | 2/1994 | Fields et al. |
| 5,416,064 | A | 5/1995 | Chari et al. |
| 5,468,614 | A | 11/1995 | Fields et al. |
| 5,585,089 | A | 12/1996 | Queen et al. |
| 5,624,821 | A | 4/1997 | Winter et al. |
| 5,635,483 | A | 6/1997 | Pettit et al. |
| 5,712,374 | A | 1/1998 | Kuntsmann et al. |
| 5,714,586 | A | 2/1998 | Kuntsmann et al. |
| 5,739,116 | A | 4/1998 | Hamann et al. |
| 5,767,285 | A | 6/1998 | Hamann et al. |
| 5,770,701 | A | 6/1998 | McGahren et al. |
| 5,770,710 | A | 6/1998 | McGahren et al. |
| 5,773,001 | A | 6/1998 | Hamann et al. |
| 5,780,588 | A | 7/1998 | Pettit et al. |
| 5,877,296 | A | 3/1999 | Hamann et al. |
| 6,040,177 | A | 3/2000 | Riddell et al. |
| 6,123,655 | A | 9/2000 | Fell |
| 6,207,453 | B1 | 3/2001 | Maass et al. |
| 6,407,213 | B1 | 6/2002 | Carter et al. |
| 6,410,319 | B1 | 6/2002 | Raubitschek et al. |
| 6,451,995 | B1 | 9/2002 | Cheung et al. |
| 6,602,684 | B1 | 8/2003 | Umana et al. |
| 6,630,579 | B2 | 10/2003 | Chari et al. |
| 6,733,433 | B1 | 5/2004 | Fell |
| 6,737,056 | B1 | 5/2004 | Presta |
| 6,982,321 | B2 | 1/2006 | Winter |
| 7,070,995 | B2 | 7/2006 | Jensen |
| 7,083,785 | B2 | 8/2006 | Browning et al. |
| 7,087,409 | B2 | 8/2006 | Barbas et al. |

(Continued)

FOREIGN PATENT DOCUMENTS

| | | |
|---|---|---|
| AU | 2012327200 | 5/2013 |
| CN | 105777911 | 7/2016 |

(Continued)

OTHER PUBLICATIONS

US 8,252,592 B2, 08/2012, Sadelain (withdrawn)
U.S. Appl. No. 18/297,562, filed Apr. 7, 2023, by Blythe et al.
Ali et al., "T cells expressing an anti-B-cell maturation antigen chimeric antigen receptor cause remissions of multiple myeloma," Blood (Sep. 2016) 128(13):1688-1700.
Al-Lazikani et al., "Standard conformations for the canonical structures of immunoglobulins," J Mol Biol (1997) 273(4):927-948.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93 (11 pages).

(Continued)

*Primary Examiner* — Lei Yao
(74) *Attorney, Agent, or Firm* — Morrison & Foerster LLP

(57) ABSTRACT

Provided are anti-idiotype antibodies that specifically recognize anti-BCMA antibody moieties, in particular, anti-BC-MA antibody moieties present in recombinant receptors, including chimeric antigen receptors (CARs). The disclosure further relates to uses of antiidiotype antibodies for specifically identifying and/or selecting cells expressing such recombinant receptors, such as anti-BCMA CAR T cells. The disclosure further relates to uses of anti-idiotype antibodies for specifically activating such cells.

20 Claims, 10 Drawing Sheets
Specification includes a Sequence Listing.

(56) References Cited

U.S. PATENT DOCUMENTS

| 7,217,797 | B2 | 5/2007 | Hinton et al. |
| 7,265,209 | B2 | 9/2007 | Jensen |
| 7,354,762 | B2 | 4/2008 | Jensen |
| 7,446,179 | B2 | 11/2008 | Jensen et al. |
| 7,446,190 | B2 | 11/2008 | Sadelain et al. |
| 7,446,191 | B2 | 11/2008 | Jensen |
| 7,498,298 | B2 | 3/2009 | Doronina et al. |
| 7,521,541 | B2 | 4/2009 | Eigenbrot et al. |
| 7,605,236 | B2 | 10/2009 | Ruben et al. |
| 7,732,570 | B2 | 6/2010 | Hinton et al. |
| 7,855,275 | B2 | 12/2010 | Eigenbrot et al. |
| 8,324,353 | B2 | 12/2012 | Jensen |
| 8,339,645 | B2 | 12/2012 | Nakawaki |
| 8,389,282 | B2 | 3/2013 | Sadelain et al. |
| 8,479,118 | B2 | 7/2013 | Lyndersay et al. |
| 8,802,374 | B2 | 8/2014 | Jensen |
| 8,822,647 | B2 | 9/2014 | Jensen |
| 8,911,993 | B2 | 12/2014 | June et al. |
| 9,034,324 | B2 | 5/2015 | Kalled et al. |
| 9,243,058 | B2 | 1/2016 | Armitage et al. |
| 9,650,430 | B2 | 5/2017 | Browning et al. |
| 9,765,342 | B2 | 9/2017 | Kochenderfer |
| 10,174,095 | B2 | 1/2019 | Brogdon et al. |
| 10,562,972 | B2 | 2/2020 | Brentjens et al. |
| 10,821,135 | B2 | 11/2020 | Brentjens et al. |
| 10,918,665 | B2 | 2/2021 | Brentjens et al. |
| 10,947,314 | B2 | 3/2021 | Brentjens et al. |
| 11,000,549 | B2 | 5/2021 | Brentjens et al. |
| 11,066,475 | B2 | 7/2021 | Sather et al. |
| 11,458,167 | B2 | 10/2022 | Jensen |
| 11,623,961 | B2 | 4/2023 | Blythe et al. |
| 11,725,059 | B2 | 8/2023 | Brentjens et al. |
| 12,428,486 | B2 | 9/2025 | Sather et al. |
| 2002/0131960 | A1 | 9/2002 | Sadelain |
| 2002/0164328 | A1 | 11/2002 | Shinkawa et al. |
| 2003/0115614 | A1 | 6/2003 | Kanda et al. |
| 2003/0157108 | A1 | 8/2003 | Presta |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0031613 | A1 | 2/2005 | Nakamura et al. |
| 2005/0123546 | A1 | 6/2005 | Umana et al. |
| 2006/0270045 | A1 | 11/2006 | Cregg et al. |
| 2007/0116690 | A1 | 5/2007 | Yang et al. |
| 2008/0171951 | A1 | 7/2008 | Fell |
| 2009/0169562 | A1 | 7/2009 | Throsby et al. |
| 2009/0203078 | A1 | 8/2009 | Ogawa et al. |
| 2010/0041074 | A1 | 2/2010 | Kimura |
| 2010/0143254 | A1 | 6/2010 | Dall'Acqua et al. |
| 2011/0003380 | A1 | 1/2011 | Miltenyi et al. |
| 2011/0117093 | A1 | 5/2011 | Ruben et al. |
| 2012/0082661 | A1 | 4/2012 | Kalled et al. |
| 2013/0149337 | A1 | 6/2013 | Cooper et al. |
| 2013/0287748 | A1 | 10/2013 | June et al. |
| 2013/0336964 | A1 | 12/2013 | Rovati et al. |
| 2014/0161828 | A1 | 6/2014 | Armitage et al. |
| 2014/0170678 | A1 | 6/2014 | Kasdan et al. |
| 2014/0193433 | A1 | 7/2014 | Borges et al. |
| 2014/0234893 | A1 | 8/2014 | Enenkel |
| 2014/0271635 | A1 | 9/2014 | Brogdon et al. |
| 2015/0051266 | A1 | 2/2015 | Kochenderfer |
| 2015/0330971 | A1 | 11/2015 | Kasdan et al. |
| 2016/0046724 | A1 | 2/2016 | Brogdon et al. |
| 2016/0237139 | A1 | 8/2016 | Pule et al. |
| 2016/0297884 | A1 | 10/2016 | Kuo et al. |
| 2017/0226216 | A1 | 8/2017 | Morgan et al. |
| 2017/0281766 | A1 | 10/2017 | Wiltzius |
| 2017/0283504 | A1 | 10/2017 | Wiltzius |
| 2018/0118842 | A1 | 5/2018 | Brentjens et al. |
| 2018/0334653 | A1 | 11/2018 | O'Neill |
| 2020/0123266 | A1 | 4/2020 | Brentjens et al. |
| 2021/0324100 | A1 | 10/2021 | Sather et al. |
| 2021/0346432 | A1 | 11/2021 | Brentjens et al. |
| 2021/0393689 | A1 | 12/2021 | Sather et al. |
| 2021/0393690 | A1 | 12/2021 | Sather et al. |
| 2022/0096651 | A1 | 3/2022 | Costa et al. |
| 2022/0315660 | A1 | 10/2022 | Brentjens et al. |
| 2023/0087953 | A1 | 3/2023 | Westoby et al. |
| 2023/0149462 | A1 | 5/2023 | Stirner et al. |
| 2023/0346734 | A1 | 11/2023 | Hudecek et al. |
| 2023/0365699 | A1 | 11/2023 | Sather et al. |
| 2024/0335475 | A1 | 10/2024 | Brentjens et al. |

FOREIGN PATENT DOCUMENTS

| CN | 105837693 | 8/2016 |
| EP | 0425235 | 5/1991 |
| EP | 0452342 | 10/1991 |
| EP | 1331266 | 7/2003 |
| EP | 1 468 694 | 10/2004 |
| EP | 1498491 | 1/2005 |
| EP | 1688439 | 8/2006 |
| EP | 1705251 | 9/2006 |
| EP | 2537416 | 12/2012 |
| JP | 2011-178691 | 9/2011 |
| WO | WO 1992/008796 | 5/1992 |
| WO | WO 1994/011026 | 5/1994 |
| WO | WO 1994/028143 | 12/1994 |
| WO | WO 1997/030087 | 8/1997 |
| WO | WO 1998/014052 | 4/1998 |
| WO | WO 1998/058964 | 12/1998 |
| WO | WO 1999/022764 | 5/1999 |
| WO | WO 1999/058572 | 11/1999 |
| WO | WO 2000/014257 | 3/2000 |
| WO | WO 2000/038762 | 7/2000 |
| WO | WO 2000/061739 | 10/2000 |
| WO | WO 2003/011878 | 2/2003 |
| WO | WO 2004/056312 | 7/2004 |
| WO | WO 2005/053742 | 6/2005 |
| WO | WO 2008/116149 | 9/2008 |
| WO | WO 2008/121420 | 10/2008 |
| WO | WO 2009/072003 | 6/2009 |
| WO | WO 2010/033140 | 3/2010 |
| WO | WO 2010/054007 | 5/2010 |
| WO | WO 2010/104949 | 9/2010 |
| WO | WO 2011/041093 | 4/2011 |
| WO | WO 2011/056983 | 5/2011 |
| WO | WO 2011/085103 | 7/2011 |
| WO | WO 2011/128893 | 10/2011 |
| WO | WO 2012/030982 | 3/2012 |
| WO | WO 2012/066058 | 5/2012 |
| WO | WO 2012/079000 | 6/2012 |
| WO | WO 2012/129514 | 9/2012 |
| WO | WO 2012/143498 | 10/2012 |
| WO | WO 2012/163805 | 12/2012 |
| WO | WO 2013/071154 | 5/2013 |
| WO | WO 2013/072406 | 5/2013 |
| WO | WO 2013/072415 | 5/2013 |
| WO | WO 2013/123061 | 8/2013 |
| WO | WO 2013/126726 | 8/2013 |
| WO | WO 2013/154760 | 10/2013 |
| WO | WO 2013/166321 | 11/2013 |
| WO | WO 2014/031687 | 2/2014 |
| WO | WO 2014/055668 | 4/2014 |
| WO | WO 2014/087010 | 6/2014 |
| WO | WO 2014/089335 | 6/2014 |
| WO | WO 2014/097286 | 6/2014 |
| WO | WO 2014/097287 | 6/2014 |
| WO | WO 2014/100385 | 6/2014 |
| WO | WO 2014/134165 | 9/2014 |
| WO | WO 2014/144039 | 9/2014 |
| WO | WO 2014/191128 | 12/2014 |
| WO | WO 2015/142675 | 9/2015 |
| WO | WO 2015/157391 | 10/2015 |
| WO | WO 2015/158671 | 10/2015 |
| WO | WO 2015/158868 | 10/2015 |
| WO | WO 2016/014789 | 1/2016 |
| WO | WO 2016/073602 | 5/2016 |
| WO | WO 2016/090320 | 6/2016 |
| WO | WO 2016/090327 | 6/2016 |
| WO | WO 2016/094304 | 6/2016 |
| WO | WO 2016/130598 | 8/2016 |

(56) References Cited

FOREIGN PATENT DOCUMENTS

| WO | WO 2016/154628 | | 9/2016 |
|---|---|---|---|
| WO | WO 2016/166629 | | 10/2016 |
| WO | WO 2017/027291 | | 2/2017 |
| WO | WO 2017/031104 | | 2/2017 |
| WO | WO 2017/040930 | | 3/2017 |
| WO | WO 2017/041143 | | 3/2017 |
| WO | WO 2017/064084 | | 4/2017 |
| WO | WO 2017/087547 | | 5/2017 |
| WO | WO 2017/096329 | | 6/2017 |
| WO | WO 2017/130223 | | 8/2017 |
| WO | WO 2017/180993 | | 10/2017 |
| WO | WO 2017/181119 | | 10/2017 |
| WO | WO2018/156802 | * | 8/2018 |
| WO | WO 2018/197675 | | 11/2018 |
| WO | WO 2018/204427 | | 11/2018 |
| WO | WO 2019/089798 | | 5/2019 |
| WO | WO 2019/089969 | | 5/2019 |
| WO | WO 2019/090003 | | 5/2019 |
| WO | WO 2019/090364 | | 5/2019 |
| WO | WO 2019/161035 | | 8/2019 |

OTHER PUBLICATIONS

Barber et al., "Chimeric NKG2D receptor-expressing T cells as an immunotherapy for multiple myeloma," Exp. Hematol. (2008) 36; 1318-1328.

Barrett et al., "Chimeric Antigen Receptor Therapy for Cancer," Annual Review of Medicine (2014) 65:333-347.

Bellucci et al., "Graft-versus-tumor response in patients with multiple myeloma is associated with antibody response to BCMA, a plasma-cell membrane receptor," Blood. (2005) 105 (10): 3945-3950.

Benjamin et al., "CD56 targeted chimeric antigen receptors for immunotherapy of multiple myeloma," AACR 103rd Annual Meeting 2012—Mar. 31-Apr. 4, 2012; Abstract 3499.

Boris-Lawrie et al., "Recent advances in retrovirus vector technology," Cur. Opin. Genet. Develop. (1993) 3:102-109.

Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.

Brentjens et al., "CD19-targeted T cells rapidly induce molecular remissions in adults with chemotherapy-refractory acute lymphoblastic leukemia," Sci Transl Med. (2013) 5(177):177ra38 (19 pages).

Brown et al., "Tolerance of single, but not multiple, amino acid replacements in antibody Vh CDR2: a means of minimizing B cells wastage from somatic hypermutation?" J. Immunol. (1996) 156(9):3285-3291.

Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.

Carlens et al., "Ex vivo T lymphocyte expansion for retroviral transduction: influence of serum-free media on variations in cell expansion rates and lymphocyte subset distribution," Exp Hematol (2000) 28(10): 1137-1146.

Carpenter et al., "B-cell Maturation Antigen is a Promising Target for Adoptive T-cell Therapy of Multiple Myeloma," Clin Cancer Res. 19(8):2048-2060 (2013).

Carrillo et al., "The Multiple Sequence Alignment Problem in Biology," SIAM Journal on Applied Mathematics (1988) 48(5):1073-1082.

Carter et al., "Humanization of an anti-p185HER2 antibody for human cancer therapy," PNAS (1992) 89(10):4285-4289.

Casset et al. "A peptide mimetic of an anti-CD4 monoclonal antibody by rational design." BBRC, 307: 198-205 (2003) spelled as Gasset in 892*.

Cavalieri et al., "Human T lymphocytes transduced by lentiviral vectors in the absence of TCR activation maintain an intact immune competence," Blood (2003) 102(2): 497-505.

Chari et al., "Immunoconjugates containing novel maytansinoids: promising anticancer drugs," Cancer Res (1992) 52(1):127-131.

Cheadle et al., "Chimeric antigen receptors for T-cell based therapy," Methods Mol Biol (2012) 907:645-666.

Chen et al., "Selection and Analysis of an Optimized Anti-VEGF Antibody: Crystal Structure of an Affinity-matured Fab in Complex with Antigen," J. Mol. Biol. 293: 865-881 (1999).

Chicaybam et al., "An efficient low cost method for gene transfer to T lymphocytes," PLoS One (2013) 8(3): e60298 (11 pages).

Cho et al., "Human mammalian cell sorting using a highly integrated micro-fabricated fluorescence-activated cell sorter (microFACS)," Lab Chip (2010) 10: 1567-1573.

Chothia et al., "Canonical structures for the hypervariable regions of immunoglobulins," J Mol Biol (1987) 196(4):901-917.

Chothia et al.,. "The outline structure of the T-cell alpha beta receptor," EMBO J. (1988) 7(12): 3745-55.

Clackson et al., "Making antibody fragments using phage display libraries," Nature (1991) 352(6336):624-628.

Clinical Trial Identifier NCT02658929, first posted on Jan. 20, 2016. Last updated on Jan. 23, 2023. "Study of bb2121 in Multiple Myeloma," https://clinicaltrials.gov/ct2/show/NCT02658929.

Clinical Trial Identifier NCT02215967, first posted on Aug. 13, 2014. Last updated on Oct. 8, 2019. "Study of T Cells Targeting B-Cell Maturation Antigen for Previously Treated Multiple Myeloma," https://clinicaltrials.gov/ct2/show/study/NCT02215967?show_desc=Y#desc.

Clinical Trial Identifier NCT02546167, first posted on Sep. 10, 2015. Last updated on Aug. 4, 2020. "CART-BCMA Cells for Multiple Myeloma," https://clinicaltrials.gov/ct2/show/NCT02546167.

Coico (Koyko) et al., "Immunology," translation from English, edited by N.B. Serebryanaya, Mosow, "Akademiya," 2008, p. 37 (in Russian).

Cooper et al., "T-cell clones can be rendered specific for CD19: toward the selective augmentation of the graft-versus-B-lineage leukemia effect," Blood. (2003) 101:1637-1644.

Davila et al., "CD19 CAR-targeted T cells induce long-term remission and B Cell Aplasia in an immunocompetent mouse model of B cell acute lymphoblastic leukemia," PLoS One (2013) 8(4): e61338 (14 pages).

De Felipe et al., "Targeting of proteins derived from self-processing polyproteins containing multiple signal sequences," Traffic (2004) 5(8):616-626.

De Felipe, "Skipping the co-expression problem: the new 2A "Chysel" technology," Genetics Vaccines and Therapy (2004) 2:13 (6 pages).

De Pascalis et al., "Grafting of "Abbreviated" Complementarity-Determining Regions Containing Specificity-Determining Residues Essential for Ligand Contact to Engineer a Less Immunogenic Humanized Monoclonal Antibody," The Journal of Immunology 169:3076-3084 (2002).

Dondelinger et a., "Understanding the Significance and Implications of Antibody Numbering and Antigen-Binding Surface/Residue Definition," Fronts. Immunol. 9 (2018):1-15.

Dubowchik et al., "Doxorubicin immunoconjugates containing bivalent, lysosomally-cleavable dipeptide linkages," Bioorg Med Chem Lett (2002) 12(11):1529-1532.

Dykman et al., "Gold nanoparticles in biology and medicine: recent advances and prospects," Acta Naturae. (2011) 3(2):34-55.

Endo et al., "High-throughput, genome-scale protein production method based on the wheat germ cell-free expression system," Biotechnol Adv (2003) 21(8):695-713.

Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172 (25 pages).

Flatman et al., "Process analytics for purification of monoclonal antibodies," J Chromatogr B Analyt Technol Biomed Life Sci (2007) 848(1):79-87.

Fraietta et al., "Determinants of response and resistance to CD19 chimeric antigen receptor (CAR) T cell therapy of chronic lymphocytic leukemia," Nat Med. (2018) 24(5):563-571.

(56)            References Cited

OTHER PUBLICATIONS

Garfall et al., "Posterior Reversible Encephalopathy Syndrome (PRES) after infusion of anti-Bcma CAR T cells (CART_BCMA) for multiple myeloma: Successful Treatment with Cyclophophamide," Blood (2016) 128(22):5702.

Gerngross, "Advances in the production of human therapeutic proteins in yeasts and filamentous fungi," Nat Biotechnol (2004) 22(11):1409-1414.

Gershoni et al., "Epitope mapping—The first step in developing epitope-based vaccines," Biodrugs, Adis International Ltd, 21 (3 ): 145-156 (2007).

Godin et al., "Microfluidics and photonics for Bio-System-on-a-Chip: a review of advancements in technology towards a microfluidic flow cytometry chip," J Biophoton. (2008) 1(5):355-376.

Harrington et al., "Development of JCARH125: Optimization of a Fully Human Anti-BCMA CAR for Use in the Treatment of Multiple Myeloma," ASH 2017. Abstract. Blood (Dec. 2017) 130:1813.

Harris, "Production of humanized monoclonal antibodies for in vivo imaging and therapy," Biochem Soc Trans (1995) 23(4):1035-1038.

Hinman et al., "Preparation and Characterization of Monoclonal Antibody Conjugates of the Calicheamicins: A Novel and Potent Family of Antitumor Antibiotics," Cancer Research (1993) 53:3336-3342.

Honegger et al., "Yet another numbering scheme for immunoglobulin variable domains: an automatic modeling and analysis tool," J Mol Biol (2001) 309(3):657-670.

Hoogenboom, "H.R. Overview of antibody phage-display technology and its applications," Methods in Moleculare Biology (2002) 178:1-37.

Huang et al., "DNA transposons for modification of human primary T lymphocytes," Methods Mol Biol (2009) 506: 115-126.

Hudecek et al., "Receptor affinity and extracellular domain modifications affect tumor recognition by ROR1-specific chimeric antigen receptor T cells," Clin Cancer Res (2013) 19(12):3153-3164.

Hudecek et al., "The nonsignaling extracellular spacer domain of chimeric antigen receptors is decisive for in vivo antitumor activity," Cancer Immunol Res (2015) 3(2):125-135.

Hurle et al., "Protein engineering techniques for antibody humanization," Curr Opin Biotechnol (1994) 5(4):428-433.

Jeffrey et al., "Dipeptide-based highly potent doxorubicin antibody conjugates," Bioorganic & Medicinal Chemistry Letters (2006) 16(2):358-362.

Jiang et al., "T-cell exhaustion in the tumor microenvironment," Cell Death Dis. (2015) 6(6):e1792 (9 pages).

Johnston, et al., "Biolistic transformation: microbes to mice," Nature (1990) 346: 776-777.

Jones et al., "Replacing the complementarity-determining regions in a human antibody with those from a mouse," Nature (1986) 321(6069):522-525.

Kanda et al., "Comparison of cell lines for stable production of fucose-negative antibodies with enhanced ADCC," Biotechnol Bioeng (2006) 94(4):680-688.

Kapustin et al., "Cryptic splice sites and split genes," Nucleic Acids Res. (2011) 39(14):5837-5844.

Kindt et al., "Antigens and Antibodies," in Chapter 4 of Kuby Immunology, 6th ed., W.H. Freeman and Co., N.Y, (2007) pp. 91, 14 pages.

King et al., "Monoclonal antibody conjugates of doxorubicin prepared with branched peptide linkers: inhibition of aggregation by methoxytriethyleneglycol chains," J Med Chem (2002) 45(19):4336-4343.

Klebanoff et al., "Sorting through subsets: which T-cell populations mediate highly effective adoptive immunotherapy?," J Immunother. (2012) 35(9): 651-660.

Kochenderfer et al., "Adoptive transfer of syngeneic T cells transduced with a chimeric antigen receptor that recognizes murine CD19 can eradicate lymphoma and normal B cells", Blood (2010) 116(19):3875-3886.

Kochenderfer et al., "Treating B-cell cancer with T cells expressing anti-CD19 chimeric antigen receptors," Nature Reviews Clinical Oncology (2013) 10:267-276.

Koste et al., "T-cell receptor transfer into human T cells with ecotropic retroviral vectors," Gene Therapy (2014) 21: 533-538.

Kratz et al., "Prodrugs of Anthracyclines in Cancer Chemotherapy," Current Medicinal Chemistry (2006) 13(5):477-523.

Kuester et al., ed Meibohm (Pharmacokinetics and Pharmacodynamics of Biotech Drugs, Wiley-VHC, chapter 3, p. 45-91 (2006).

Lamminmaki et al. "Crystal Structure of a Recombinant Anti-estradiol Fab Fragment in Complex with 17α-Estradiol" JBC 276:36687-36694 (2001).

Langer, "New methods of drug delivery," Science (1990) 249(4976):1527-1533.

Lefranc et al., "IMGT unique numbering for immunoglobulin and T cell receptor variable domains and Ig superfamily V-like domains," Dev Comp Immunol (2003) 27(1):55-77.

Li et al., "Optimization of humanized IgGs in glycoengineered Pichia pastoris," Nat Biotechnol (2006) 24(2):210-215.

Lode et al., "Targeted Therapy with a Novel Enediyene Antibiotic Calicheamicin $\Theta^I_1$ Effectively Suppresses Growth and Dissemination of Liver metastasis in a Syngeneic Model of Murine Neuroblastoma[1]," Cancer Research (1998) 58:2925-2928.

Lupton et al., "Dominant positive and negative selection using a hygromycin phosphotransferase-thymidine kinase fusion gene," Mol. and Cell Biol. (1991) 11:6: 3374-3378.

Maccallum et al., "Antibody-antigen interactions: contact analysis and binding site topography," J Mol Biol (1996) 262(5):732-745.

Manuri et al., "piggyBac transposon/transposase system to generate CD19-specific T cells for the treatment of B-lineage malignancies," Hum Gene Ther (2010) 21(4): 427-437.

Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.

Miller et al., "Improved retroviral vectors for gene transfer and expression," BioTechniques (1989) 7:980-990.

Miller et al., "Retrovirus packaging cells," Human Gene Therapy (1990) 1:5-14.

Nagy et al., "Stability of cytotoxic luteinizing hormone-releasing hormone conjugate (AN-152) containing doxorubicin 14-O-hemiglutarate in mouse and human serum in vitro: Implications for the desig+A333n of preclinical studies," PNAS (2000) 97(2):829-834.

Nasonov et al., "Belimumab: progress in treatment systemic lupus erythematosus", Scientific and practical rheumatol, 2012, 54(5), pp. 13-19.

Novak et al., "Expression of BCMA, TACI, and BAFF-R in Multiple Myeloma: A Mechanism For Growth And Survival," Blood (2004) 103(2):689-694.

Okazaki et al., "Fucose depletion from human IgG1 oligosaccharide enhances binding enthalpy and association rate between IgG1 and FcgammaRIIIa," J Mol Biol (2004) 336(5):1239-1249.

Ozhegov et al. "Dictionary of a Russian Language: 80,000 words and phraseological expressions," 4th ed. Supplemented, Mosow, "OOO 'A TEMP'" 2006, p. 375.

Padlan et al. "Structure of an antibody-antigen complex: crystal structure of the HyHEL-10 Fab-lysozyme complex" PNAS 86:5938-5942 (1989).

Park et al., "Treating cancer with genetically engineered T cells," Trends Biotechnol. (2011) 29(11): 550-557.

Peinert et al. "Gene-modified T cells as immunotherapy for multiple myeloma and acute myeloid leukemia expressing the Lewis Y antigen" Gene Therapy (2010) 17, 678-686.

Portolano et al., "Lack of promiscuity in autoantigen-specific H and L chain combinations as revealed by human H and L chain "roulette"," J Immunol (1993) 150(3):880-887.

Presta et al., "Antibody engineering," Current Opinion in Structural Biology (1992) 2(4):593-596.

Presta et al., "Humanization of an antibody directed against IgE," J Immunol (1993) 151(5):2623-2632.

(56) References Cited

OTHER PUBLICATIONS

Qian et al., "Progress of Engineering Chimeric Antigen Receptor in Tumor Therapy," Letters in Biotechnology. (2017) 28:2; 188-195 (Article in Chinese) English abstract provided.

Riddell et al., "Phase I study of cellular adoptive immunotherapy using genetically modified CD8+ HIV-specific T cells for HIV seropositive patients undergoing allogeneic bone marrow transplant," Human Gene Therapy (1992) 3:319-338.

Riechmann et al., "Reshaping human antibodies for therapy," Nature (1988) 332(6162):323-327.

Ripka et al., "Two Chinese hamster ovary glycosylation mutants affected in the conversion of GDP-mannose to GDP-fucose," Arch. Biochem. Biophys (1986) 249:533-545.

Rudikoff et al., "Single amino acid substitution altering antigen-binding specificity," Proc Natl Acad Sci U S A. (1982) 79(6): 1979-1983.

Ryan et al., "Antibody targeting of B-cell maturation antigen on malignant plasma cells," Molecular Cancer Therapeutics, American Association for Cancer Research (2007) 69(11):3009-3018.

Sadelain et al., "The basic principles of chimeric antigen receptor design," Cancer Discov. (2013) 3(4): 388-398.

Scarpa et al., "Characterization of recombinant helper retroviruses from Moloney-based vectors in ecotropic and amphotropic packaging cell lines," Virology (1991) 180:849-852.

Scatchard et al., "The Attractions of Proteins for Small Molecules and Ions," Ann. N.Y. Acad. Sci. (1949) 51:660-672.

Sharma et al., "Efficient sleeping beauty DNA transposition from DNA minicircles," Molec Ther Nucl Acids (2013) 2, e74 (10 pages).

Sims et al., "A humanized CD18 antibody can block function without cell destruction," J Immunol (1993) 151(4):2296-2308.

Sitaraman et al., "High-Throughput Protein Expression Using Cell-Free System," Methods Mol Biol (2009) 498:229-244.

Spirin, "High-throughput cell-free systems for synthesis of functionally active proteins," Trends Biotechnol (2004) 22(10):538-545.

Tai et al., "Targeting B-cell maturation antigen in multiple myeloma," Immunotherapy (2015) 7(11):1187-1199.

Terakura et al., "Generation of CD19-chimeric antigen receptor modified CD8+ T cells derived from virus-specific central memory T cells," Blood (2012) 1:72-82.

Torgov et al., "Generation of an Intensely Potent Anthracycline by a Monoclonal Antibody-β-Galactosidase Conjugate," Bioconjugate Chem (2005) 16:717-721.

Turtle et al., "Engineered T cells for anti-cancer therapy," Curr. Opin. Immunol. (2012) 24(5): 633-39.

Vajdos et al. "Comprehensive functional maps of the antigen-binding site of an anti-ErbB2 antibody obtained with shotgun scanning mutagenesis." J. Mol. Biol. 320, 415-428 (2002).

Van Tendeloo et al., "High-level transgene expression in primary human T lymphocytes and adult bone marrow CD34+ cells via electroporation-mediated gene delivery," Gene Therapy (2000) 7(16): 1431-1437.

Vaswani et al., "Humanized antibodies as potential therapeutic drugs," Ann. Allergy, Asthma & Immunol. 1:105-115 (1998).

Verhoeyen et al., "Lentiviral vector gene transfer into human T cells," Methods Mol Biol. (2009) 506: 97-114.

Verhoeyen et al., "Reshaping human antibodies: grafting an antilysozyme activity," Science (1988) 239(4847):1534-1536.

Vietta et al., "Redesigning nature's poisons to create anti-tumor reagents," Science (1987) 238(4830):1098-1104.

Wang et al., "Phenotypic and functional attributes of lentivirus-modified CD19-specific human CD8+ central memory T cells manufactured at clinical scale," J Immunother. (2012) 35(9):689-701.

White et al. "Antibody-Targeted Immunotherapy for Treatment of Malignancy" Ann. Rev. Med. 52:125-145 (2001).

Wilkie et al., "Retargeting of human T cells to tumor-associated MUC1: the evolution of a chimeric antigen receptor," J Immunol. (2008) 180(7):4901-9.

Wilson, "Tech. Sight. Analyzing biomolecular interactions," Science (2002) 295(5562): 2103-2105.

Wolff et al., "Monoclonal Antibody Homodimers: Enhanced Anti-tumor Activity in Nude Mice," Can Res. (1993) 53:2560-2565.

Wu et al., "Adoptive T-cell therapy using autologous tumor-infiltrating lymphocytes for metastatic melanoma: current status and future outlook," Cancer (2012) 18(2): 160-175.

Wu et al. "Humanization of a murine monoclonal antibody by simultaneous optimization of framework and CDR residues." J. Mol. Biol. 294, 151-162 (1999).

Yamane-Ohnuki et al., "Establishment of FUT8 knockout Chinese hamster ovary cells: an ideal host cell line for producing completely defucosylated antibodies with enhanced antibody dependent cellular cytotoxicity," Biotech. Bioeng. (2004) 87: 614-622.

Yanagi, et al., "Transcripts from a single full-length cDNA clone of hepatitis C virus are infectious when directly transfected into the liver of achimpanzee," PNAS, vol. 94(16), Aug. 5, 1997, p. 8738-8743.

U.S. Appl. No. 19/310,817, filed Aug. 26, 2025, by Sather et al.

Akbar et al., "A compact vocabulary of paratope-epitope interactions enables predictability of antibody-antigen binding," Cell Reports (Mar. 16, 2021) 34(11):108856, 21 pages.

Anson et al., "An improved β-galactosidase reporter gene," Journal of Biotechnology (Feb. 19, 2004) 108(1):17-30.

Beckman et al., "Antibody constructs in cancer therapy: protein engineering strategies to improve exposure in solid tumors," Cancer (Jan. 15, 2007, Dec. 11, 2006) 109(2):170-179.

Caron et al., "Engineered Humanized Dimeric Forms of IgG are More Effective Antibodies," J Exp. Med (Oct. 1, 1992) 176(4):1191-1195.

Cespedes et al., "Mouse models in oncogenesis and cancer therapy," Clin Transl Oncol (May 2006) 8(5):318-329.

Creative BioMart, "Anti-Human TNFRSF17 scFv Stable Cell Line-CHO," (Aug. 30, 2013) [according to the properties of the posted document] (Retrieved from the Internet Mar. 23, 2016: <http://www.creativebiomart.net/pdf/CSC-P0544.TNFRSF17.pdf>); p. 1.

Dennis, "Off by a whisker," Nature (Aug. 17, 2006) 442(7104):739-741.

Fujimori et al., "A Modeling Analysis of Monoclonal Antibody Percolation Through Tumors: A Binding-Site Barrier," J Nucl Med (Jul. 1990) 31(7):1191-1198.

Gacerez et al., "How Chimeric Antigen Receptor Design Affects Adoptive T Cell Therapy," J Cell Physiol. (Dec. 2016, e-pub. Jun. 2, 2016) 231(12): 2590-2598.

Guedan et al., "Engineering and Design of Chimeric Antigen Receptors," Mol Ther Methods Clin Dev (Dec. 31, 2018, eCollection Mar. 15, 2019) 12:145-156.

Huang et al., "Genetic Engineering Antibody," South China University of Technology Press (Dec. 1997): p. 63. English translation provided.

Huang et al., "Recombinant immunotherapeutics: current state and perspectives regarding the feasibility and market," Appl. Microbiol. Biotechnol. (Jun. 2010, e-pub. Apr. 27, 2010) 87(2):401-410.

Jena et al. "Redirecting T-cell specificity by introducing a tumor-specific chimeric antigen receptor." Blood, The Journal of the American Society of Hematology (Aug. 19, 2010, e-pub. May 3, 2010) 116(7):1035-1044.

Jonnalagadda et al., "Chimeric antigen receptors with mutated IgG4 Fc spacer avoid fc receptor binding and improve T cell persistence and antitumor efficacy," Mol Ther. (Apr. 2015, e-pub. Nov. 4, 2014) 23(4):757-768.

Lo et al., "Conformational epitope matching and prediction based on protein surface spiral features," BMC Genomics (May 31, 2021) 22(Suppl 2):116, 16 pages.

Marks et al., "How repertoire data are changing antibody science," J. Biol. Chem. (Jul. 17, 2020, e-pub. May 14, 2020) 295(29):9823-9837.

Maus et al., "Zoom Zoom: Racing CARs for Multiple Myeloma," Clin Cancer Res. (Apr. 15, 2013, e-pub. Feb. 26, 2013) 19(8):1917-1919.

Murray R. et al., "Human Biochemistry," Moscow, Mir (1993) vol. 1, p. 34. English translation provided.

NCBI-GENE-TNFRSF17 Tnf receptor superfamily member 17 [Homo sapiens (human)] pp. 1-6 (Sep. 25, 2023, 10:06 AM).

(56)          References Cited

OTHER PUBLICATIONS

Ormhoj et al., "CARs in the lead against Multiple Myeloma," Curr Hematol Malig Rep. (Apr. 2017) 12(2): 119-125.

Parkman R., "Clonal analysis of murine graft-vs-host disease. I. Phenotypic and functional analysis of T lymphocyte clones," J. Immunol. (May 15, 1986) 136(10):3543-3548.

Presnyak et al., "Codon optimality is a major determinant of mRNA stability," Cell (Mar. 12, 2015) 160(6):1111-1124.

Qin et al., "Incorporation of a hinge domain improves the expansion of chimeric antigen receptor T cells," J Hematol Oncol. (Mar. 13, 2017) 10(1):68, 11 pages.

Ramadoss et al., "An Anti-B Cell Maturation Antigen Bispecific Antibody for Multiple Myeloma," J. Am. Chem. Soc. (Apr. 29, 2015, e-pub. Apr. 15, 2015) 137(16):5288-5291.

Rudnick et al., "Affinity and Avidity in Antibody-Based Tumor Targeting." Cancer Biother Radiopharm (Apr. 2009) 24(2):155-161.

Talmadge et al., "Murine Models to Evaluate Novel and Conventional Therapeutic Strategies for Cancer," Am J Pathol (Mar. 2007) 170(3):793-804.

Thurber et al., "Antibody tumor penetration: transport opposed by systemic and antigen-mediated clearance," Adv Drug Deliv Rev (Sep. 2008, e-pub. Apr. 24, 2008) 60(12):1421-1434.

Vajda et al., "Progress toward improved understanding of antibody maturation," Current Opinion in Structural Biology (Apr. 2021, e-pub. Feb. 17, 2021) 67:226-231.

Voskoglou-Nomikos et al., "Clinical Predictive Value of the in Vitro Cell Line, Human Xenograft, and Mouse Allograft Preclinical Cancer Models," Clin Can Res (Sep. 15, 2003) 9(11): 4227-4239.

Worcester, "GSI inhibition may boost BCMA CAR T-cell therapy efficacy in myeloma," Hematology News. Published on Nov. 27, 2017. Retrieved from https://www.mdedge.com/hematology-oncology/article/152733/multiple-myeloma/gsi-inhibition-may-boost-bcma-car-t-cell-therapy, 5 pages.

* cited by examiner

ANTI-IDIOTYPIC ANTIBODIES TO BCMA-TARGETED BINDING DOMAINS AND RELATED COMPOSITIONS AND METHODS

CROSS-REFERENCE TO RELATED APPLICATIONS

This application is a national stage application under 35 U.S.C. § 371 of International Application No. PCT/US2020/063492, filed internationally on Dec. 4, 2020, which claims priority to U.S. provisional application 62/945,065, filed Dec. 6, 2019, entitled "ANTI-IDIOTYPIC ANTIBODIES TO BCMA-TARGETED BINDING DOMAINS AND RELATED COMPOSITIONS AND METHODS," U.S. provisional application 63/061,763, filed Aug. 5, 2020, entitled "ANTI-IDIOTYPIC ANTIBODIES TO BCMA-TARGETED BINDING DOMAINS AND RELATED COMPOSITIONS AND METHODS," and U.S. provisional application 63/109,839, filed Nov. 4, 2020, entitled "ANTI-IDIOTYPIC ANTIBODIES TO BCMA-TARGETED BINDING DOMAINS AND RELATED COMPOSITIONS AND METHODS," the contents of which are incorporated by reference in their entirety for all purposes.

INCORPORATION BY REFERENCE OF SEQUENCE LISTING

The present application is being filed along with a Sequence Listing in electronic format. The Sequence Listing is provided as a file entitled 735042017900SeqList.txt, created May 31, 2022, which is 84,322 bytes in size. The information in the electronic format of the Sequence Listing is incorporated by reference in its entirety.

FIELD

The present disclosure relates in some aspects to anti-idiotype antibodies that bind to or recognize anti-BCMA antibody moieties, in particular, anti-BCMA antibody moieties present in recombinant receptors, including chimeric antigen receptors (CARs). The disclosure further relates to uses of anti-idiotype antibodies for specifically identifying, detecting or selecting cells expressing such recombinant receptors, such as anti-BCMA CAR T cells. The disclosure further relates to uses of anti-idiotype antibodies for specifically activating such cells.

BACKGROUND

Methods are available for adoptive cell therapy using engineered cells expressing recombinant receptors, such as chimeric antigen receptor (CARs) containing extracellular antibody antigen-binding domains. Various strategies are available to assess activity of such cells either in vitro or upon in vivo to a subject. Improved methods are needed to specifically assess activity of CAR-expressing cells. Provided are reagents, compositions, and articles of manufacture that meet such needs.

SUMMARY

Provided herein are agents that bind to or recognize antibodies and antigen-binding fragments thereof, including antibody fragments such as scFvs, and chimeric molecules containing the same, such as chimeric antigen receptors. Also provided are compositions and articles of manufacture containing such agents, including those including a surface to which the agent is bound, such as a solid surface, e.g. a plate or bead. Also among the embodiments provided herein are uses and methods of using such agents, compositions and articles, including for detection, use, manipulation and/or stimulation of cells or therapies containing or suspected of containing the antibody or chimeric molecule, such as in the detection, stimulation or use of CAR-expressing cells.

Provided herein, in some embodiments, is an anti-idiotype antibody or antigen-binding fragment thereof that binds to or recognizes an anti-BCMA target antibody or antigen-binding fragment thereof, wherein the anti-idiotype antibody or antigen-binding fragment comprises: a VH region comprising the amino acid sequence set forth in SEQ ID NO: 84 or 114; and a VL region comprising the amino acid sequence set forth in SEQ ID NO: 85 or 115.

Also provided herein, in some embodiments, is an anti-idiotype antibody or antigen-binding fragment thereof that binds to or recognizes an anti-BCMA target antibody or antigen-binding fragment thereof, wherein the anti-idiotype antibody or antigen-binding fragment comprises: a VH region comprising an amino acid sequence having at least 90% sequence identity to the amino acid sequence set forth in SEQ ID NO: 84 or 114; and a VL region comprising an amino acid sequence having at least 90% sequence identity to the amino acid sequence set forth in SEQ ID NO: 85 or 115.

Also provided herein, in some embodiments, is an anti-idiotype antibody or antigen-binding fragment thereof that binds to or recognizes an anti-BCMA target antibody or antigen-binding fragment thereof, wherein the anti-idiotype antibody or antigen-binding fragment comprises: a VH region comprising a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and a VL region comprising a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

Also provided herein, in some embodiments, is an anti-idiotype antibody or antigen-binding fragment thereof that binds to or recognizes an anti-BCMA target antibody or antigen-binding fragment thereof, wherein the anti-idiotype antibody or antigen-binding fragment comprises: a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 84 or 114; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 85 or 115.

In some of any such embodiments, the VH region comprises a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and the VL region comprises a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

In some of any such embodiments, the VH region comprises a CDR-H1 comprising the amino acid sequence set forth in SEQ ID NO: 74, a CDR-H2 comprising the amino acid sequence set forth in SEQ ID NO: 75, and a CDR-H3 comprising the amino acid sequence set forth in SEQ ID NO: 76; and the VL region comprises a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83.

In some of any such embodiments, the VH region comprises an amino acid sequence set forth in SEQ ID NO: 84, and the VL region comprises an amino acid sequence set forth in SEQ ID NO: 85

In some of any such embodiments, the VH region comprises a CDR-H1 comprising the amino acid sequence set forth in SEQ ID NO: 104, a CDR-H2 comprising the amino acid sequence set forth in SEQ ID NO: 105, and a CDR-H3 comprising the amino acid sequence set forth in SEQ ID NO: 106; and the VL region comprises a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113.

In some of any such embodiments, the VH region comprises an amino acid sequence set forth in SEQ ID NO: 114, and the VL region comprises an amino acid sequence set forth in SEQ ID NO: 115.

In some of any such embodiments, the VH region comprises an amino acid sequence having at least 90% sequence identity to the amino acid sequence set forth in SEQ ID NO: 84, and the VL region comprises an amino acid sequence having at least 90% sequence identity to the amino acid sequence set forth in SEQ ID NO: 85. In some embodiments, the VH region comprises an amino acid sequence having at least 90% sequence identity to the amino acid sequence set forth in SEQ ID NO: 114, and the VL region comprises an amino acid sequence having at least 90% sequence identity to the amino acid sequence set forth in SEQ ID NO: 115.

In some of any such embodiments, the VH region comprises an amino acid sequence set forth in SEQ ID NO: 84, and the VL region comprises an amino acid sequence set forth in SEQ ID NO: 85. In some embodiments, the VH region comprises an amino acid sequence set forth in SEQ ID NO: 114, and the VL region comprises an amino acid sequence set forth in SEQ ID NO: 115.

In some of any such embodiments, the anti-idiotype antibody or antigen-binding fragment thereof comprises: a heavy chain comprising an amino acid sequence having at least 90% sequence identity to the amino acid sequence set forth in SEQ ID NO: 86, and a light chain comprising an amino acid sequence having at least 90% sequence identity to the amino acid sequence set forth in SEQ ID NO: 87. In some of any such embodiments, the anti-idiotype antibody or antigen-binding fragment thereof comprises a heavy chain comprising an amino acid sequence having at least 90% sequence identity to the amino acid sequence set forth in SEQ ID NO: 116, and a light chain comprising an amino acid sequence having at least 90% sequence identity to the amino acid sequence set forth in SEQ ID NO: 117.

In some of any such embodiments, the anti-idiotype antibody or antigen-binding fragment thereof comprises: a heavy chain comprising the amino acid sequence set forth in SEQ ID NO: 86, and a light chain comprising the amino acid sequence set forth in SEQ ID NO: 87. In some of any such embodiments, the anti-idiotype antibody or antigen-binding fragment thereof comprises a heavy chain comprising the amino acid sequence set forth in SEQ ID NO: 116, and a light chain comprising the amino acid sequence set forth in SEQ ID NO: 117.

In some of any such embodiments, the anti-BCMA target antibody or antigen-binding fragment thereof comprises a VH region comprising the amino acid sequence set forth in SEQ ID NO: 25, and a VL region comprising the amino acid sequence set forth in SEQ ID NO: 26. In some of any such embodiments, the anti-BCMA target antibody or antigen-binding fragment thereof is a single chain fragment. In some of any such embodiments, the single chain fragment comprises a flexible linker positioned between the VH region and the VL region. In some of any such embodiments, the flexible linker comprises the amino acid sequence set forth in SEQ ID NO: 14. In some of any such embodiments, the single chain fragment of the ani-BCMA target antibody or antigen-binding fragment thereof is a single chain variable fragment (scFv). In some of any such embodiments, the scFv comprises the amino acid sequence set forth in SEQ ID NO: 27.

In some of any such embodiments, the anti-idiotype antibody or antigen-binding fragment binds to or recognizes an epitope within or including all or a portion of a CDR of the target antibody or antigen-binding fragment.

In some of any such embodiments, the anti-BCMA target antibody or antigen-binding fragment is within or included in an antigen-binding domain of an extracellular portion of a CAR. In some of any such embodiments, the anti-idiotype antibody or antigen-binding fragment binds the anti-BCMA target antibody or antigen-binding fragment comprised within or included in an antigen-binding domain of an extracellular portion of a CAR. In some of any such embodiments, the anti-idiotype antibody or antigen-binding fragment specifically binds the anti-BCMA target antibody or antigen-binding fragment comprised within or included in an antigen-binding domain of an extracellular portion of a CAR.

In some of any such embodiments, the scFv is within or included in an extracellular portion of a CAR. In some of any such embodiments, the anti-idiotype antibody or antigen-binding fragment binds the scFv comprised within or included in an extracellular portion of a CAR. In some of any such embodiments, the anti-idiotype antibody or antigen-binding fragment specifically binds the scFv comprised within or included in an extracellular portion of a CAR. In some of any such embodiments, the CAR further comprises a transmembrane domain linked to the antigen-binding domain via a spacer. In some of any such embodiments, the spacer is an immunoglobulin spacer. In some of any such embodiments, the spacer comprises the amino acid sequence set forth in SEQ ID NO: 50. In some of any such embodiments, the transmembrane domain comprises a transmembrane portion of CD28. In some of any such embodiments, the transmembrane portion of CD28 is human CD28. In some of any such embodiments, the anti-idiotype antibody or antigen-binding fragment thereof does not bind to an epitope in the spacer domain of the CAR.

In some of any such embodiments, the anti-idiotype antibody or antigen-binding fragment thereof does not bind or does not specifically bind to CD28 or a portion thereof. In some of any such embodiments, the CD28 or a portion thereof is human CD28.

In some of any such embodiments, the anti-idiotype antibody or antigen-binding fragment thereof does not bind to an epitope in an Fe domain. In some of any such embodiments, the Fe domain is a human IgG1 Fe domain.

In some of any such embodiments, the anti-BCMA target antibody or antigen-binding fragment thereof binds to or recognizes human BCMA.

In some of any such embodiments, the anti-idiotype antibody or antigen-binding fragment thereof does not cross-react with another anti-BCMA antibody. In some of any such embodiments, the another anti-BCMA antibody is comprised in the extracellular antigen-binding domain of another CAR. In some of any such embodiments, the another anti-BCMA antibody: comprises a VH region comprising an amino acid sequence that has less than 90% sequence identity to the amino acid sequence set forth in SEQ ID NO: 25, and/or a VL region comprising an amino acid sequence that has less than 90% sequence identity to the amino acid sequence set forth in SEQ ID NO: 26. In some of any such embodiments, the another anti-BCMA antibody comprises an scFv that has less than 90% sequence identity to the amino acid sequence set forth in SEQ ID NO: 13. In some of any such embodiments, the another anti-BCMA antibody comprises a CDR-H1 that has 1, 2, 3, or 4 or more amino acid residues that are different from the CDR-H1 amino acid sequence as set forth in SEQ ID NO: 15, and/or a CDR-H2 that has 1, 2, 3, or 4 or more amino acid residues that are different from the CDR-H2 amino acid sequence as set forth in SEQ ID NO: 16, and/or a CDR-H3 that has 1, 2, 3, or 4 or more amino acid residues that are different from the CDR-H3 amino acid sequence as set forth in SEQ ID NO: 17, and/or a CDR-L1 that has 1, 2, 3, or 4 or more amino acid residues that are different from the CDR-L1 amino acid sequence as set forth in SEQ ID NO: 22, and/or a CDR-L2 that has 1, 2, 3, or 4 or more amino acid residues that are different from the CDR-L2 amino acid sequence as set forth in SEQ ID NO: 23, and/or a CDR-L3 that has 1, 2, 3, or 4 or more amino acid residues that are different from the CDR-L3 amino acid sequence as set forth in SEQ ID NO: 24. In some of any such embodiments, the another anti-BCMA antibody binds to or recognizes an epitope of human BCMA that is not the same epitope of human BCMA that the anti-BCMA target antibody or antigen-binding fragment thereof binds to or recognizes.

In some of any such embodiments, the anti-idiotype antibody or antigen-binding fragment thereof is an agonist of a CAR comprising the anti-BCMA target antibody or antigen-binding fragment thereof. In some of any such embodiments, the anti-idiotype antibody or antigen-binding fragment thereof is an agonist of the CAR when in soluble form. In some of any such embodiments, the anti-idiotype antibody or antigen-binding fragment thereof is an agonist of the CAR when immobilized to a support or a stationary phase. In some of any such embodiments, the support or stationary phase is a plate or a bead.

In some of any such embodiments, the anti-idiotype antibody or antigen-binding fragment thereof specifically binds to the anti-BCMA target antibody or antigen-binding fragment thereof.

In some of any such embodiments, the anti-idiotype antibody has a binding affinity (EC50) and/or a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM. In some of any such embodiments, the anti-idiotype antibody has a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17

6 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

In some of any such embodiments, binding of the anti-idiotype antibody or antigen-binding fragment thereof to the anti-BCMA target antibody or antigen-binding fragment thereof is not blocked by human BCMA or human BCMA-Fc.

Also provided herein, in some embodiments, is an anti-idiotype antibody or antigen-binding fragment thereof that binds to or recognizes a anti-BCMA target antibody or antigen-binding fragment thereof, wherein the anti-idiotype antibody or antigen-binding fragment comprises: a VH region comprising the amino acid sequence set forth in SEQ ID NO: 38 or 62; and a VL region comprising the amino acid sequence set forth in SEQ ID NO: 39 or 63. The anti-BCMA target antibody or antigen-binding fragment thereof includes VH and VL sequences of Target Antibody 1 or Target Antibody 2, or includes a VH and VL with CDRs of Target Antibody 1 or Target Antibody 2, as described herein. In some embodiments, the anti-idiotype antibody or antigen-binding fragment thereof that binds to or recognizes an anti-BCMA target antibody or antigen-binding fragment binds both a first anti-BCMA target antibody or antigen-binding fragment thereof and a second anti-BCMA target antibody or antigen-binding fragment thereof, in which the first anti-BCMA target antibodies or antigen-binding fragments include VH and VL sequences of Target Antibody 1, or includes CDRs contained within Target Antibody 1, and the second anti-BCMA target antibodies or antigen-binding fragments include VH and VL sequences of Target Antibody 2, or includes CDRs contained within Target Antibody 2.

Also provided herein, in some embodiments, is an anti-idiotype antibody or antigen-binding fragment thereof that binds to or recognizes a anti-BCMA target antibody or antigen-binding fragment thereof, wherein the anti-idiotype antibody or antigen-binding fragment comprises: a VH region comprising an amino acid sequence having at least 90% sequence identity to the amino acid sequence set forth in SEQ ID NO: 38 or 62; and a VL region comprising an amino acid sequence having at least 90% sequence identity to the amino acid sequence set forth in SEQ ID NO: 39 or 63. The anti-BCMA target antibody or antigen-binding fragment thereof includes VH and VL sequences of Target Antibody 1 or Target Antibody 2, or includes a VH and VL with CDRs of Target Antibody 1 or Target Antibody 2, as described herein. In some embodiments, the anti-idiotype antibody or antigen-binding fragment thereof that binds to or recognizes an anti-BCMA target antibody or antigen-binding fragment binds both a first anti-BCMA target antibody or antigen-binding fragment thereof and a second anti-BCMA target antibody or antigen-binding fragment thereof, in which the first anti-BCMA target antibodies or antigen-binding fragments include VH and VL sequences of Target Antibody 1, or includes CDRs contained within Target Antibody 1, and the second anti-BCMA target antibodies or antigen-binding fragments include VH and VL sequences of Target Antibody 2, or includes CDRs contained within Target Antibody 2.

Also provided herein, in some embodiments, is an anti-idiotype antibody or antigen-binding fragment thereof that binds to or recognizes a anti-BCMA target antibody or antigen-binding fragment thereof, wherein the anti-idiotype antibody or antigen-binding fragment comprises: a VH region comprising a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and a VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61. The anti-BCMA target antibody or antigen-binding fragment thereof includes VH and VL sequences of Target Antibody 1 or Target Antibody 2, or includes a VH and VL with CDRs of Target Antibody 1 or Target Antibody 2, as described herein. In some embodiments, the anti-idiotype antibody or antigen-binding fragment thereof that binds to or recognizes an anti-BCMA target antibody or antigen-binding fragment binds both a first anti-BCMA target antibody or antigen-binding fragment thereof and a second anti-BCMA target antibody or antigen-binding fragment thereof, in which the first anti-BCMA target antibodies or antigen-binding fragments include VH and VL sequences of Target Antibody 1, or includes CDRs contained within Target Antibody 1, and the second anti-BCMA target antibodies or antigen-binding fragments include VH and VL sequences of Target Antibody 2, or includes CDRs contained within Target Antibody 2.

Also provided herein, in some embodiments, is an anti-idiotype antibody or antigen-binding fragment thereof that binds to or recognizes an anti-BCMA target antibody or antigen-binding fragment thereof, wherein the anti-idiotype antibody or antigen-binding fragment comprises: a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 38 or 62; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 39 or 63. The anti-BCMA target antibody or antigen-binding fragment thereof includes VH and VL sequences of Target Antibody 1 or Target Antibody 2, or includes a VH and VL with CDRs of Target Antibody 1 or Target Antibody 2, as described herein. In some embodiments, the anti-idiotype antibody or antigen-binding fragment thereof that binds to or recognizes an anti-BCMA target antibody or antigen-binding fragment binds both a first anti-BCMA target antibody or antigen-binding fragment thereof and a second anti-BCMA target antibody or antigen-binding fragment thereof, in which the first anti-BCMA target antibodies or antigen-binding fragments include VH and VL sequences of Target Antibody 1, or includes CDRs contained within Target Antibody 1, and the second anti-BCMA target antibodies or antigen-binding fragments include VH and VL sequences of Target Antibody 2, or includes CDRs contained within Target Antibody 2.

In some of any such embodiments, the VH region of a provided anti-idiotype antibody or antigen-binding fragment comprises a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and the VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61.

In some of any such embodiments, the VH region of a provided anti-idiotype antibody or antigen-binding fragment comprises a CDR-H1 comprising the amino acid sequence set forth in SEQ ID NO: 28, a CDR-H2 comprising the amino acid sequence set forth in SEQ ID NO: 29, and a CDR-H3 comprising the amino acid sequence set forth in SEQ ID NO: 30; and the VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37.

In some of any such embodiments, the VH region of a provided anti-idiotype antibody or antigen-binding fragment comprises the amino acid sequence set forth in SEQ ID NO: 38, and the VL region comprises the amino acid sequence set forth in SEQ ID NO: 39.

In some of any such embodiments, the VH region of a provided anti-idiotype antibody or antigen-binding fragment comprises a CDR-H1 comprising the amino acid sequence set forth in SEQ ID NO: 52, a CDR-H2 comprising the amino acid sequence set forth in SEQ ID NO: 53, and a CDR-H3 comprising the amino acid sequence set forth in SEQ ID NO: 54; and the VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61.

In some of any such embodiments, the VH region of a provided anti-idiotype antibody or antigen-binding fragment comprises the amino acid sequence set forth in SEQ ID NO: 62, and the VL region comprises the amino acid sequence set forth in SEQ ID NO: 63.

In some of any such embodiments, the VH region of a provided anti-idiotype antibody or antigen-binding fragment comprises an amino acid sequence having at least 90% sequence identity to the amino acid sequence set forth in SEQ ID NO: 38 or 62; and the VL region comprises an amino acid sequence having at least 90% sequence identity to the amino acid sequence set forth in SEQ ID NO: 39 or 63.

In some of any such embodiments, the VH region of a provided anti-idiotype antibody or antigen-binding fragment comprises an amino acid sequence having at least 90% sequence identity to the amino acid sequence set forth in SEQ ID NO: 38, and the VL region comprises an amino acid sequence having at least 90% sequence identity to the amino acid sequence set forth in SEQ ID NO: 39. In some of any such embodiments, the VH region of a provided anti-idiotype antibody or antigen-binding fragment comprises an amino acid sequence having at least 90% sequence identity to the amino acid sequence set forth in SEQ ID NO: 62, and the VL region comprises an amino acid sequence having at least 90% sequence identity to the amino acid sequence set forth in SEQ ID NO: 63.

In some of any such embodiments, the VH region of a provided anti-idiotype antibody or antigen-binding fragment comprises the amino acid sequence set forth in SEQ ID NO: 38 or 62; and the VL region comprises the amino acid sequence set forth in SEQ ID NO: 39 or 63.

In some of any such embodiments, the VH region of a provided anti-idiotype antibody or antigen-binding fragment comprises the amino acid sequence set forth in SEQ ID NO: 38, and the VL region comprises the amino acid sequence set forth in SEQ ID NO: 39. In some of any such embodiments, the VH region of a provided anti-idiotype antibody or antigen-binding fragment comprises the amino acid sequence set forth in SEQ ID NO: 62, and the VL region comprises the amino acid sequence set forth in SEQ ID NO: 63.

In some of any such embodiments, the anti-idiotype antibody or antigen-binding fragment thereof comprises: a heavy chain comprising an amino acid sequence having at least 90% sequence identity to the amino acid sequence set forth in SEQ ID NO: 40 or 64; and a light chain comprising an amino acid sequence having at least 90% sequence identity to the amino acid sequence set forth in SEQ ID NO: 41 or 65.

In some of any such embodiments, the anti-idiotype antibody or antigen-binding fragment thereof comprises: a heavy chain comprising an amino acid sequence having at least 90% sequence identity to the amino acid sequence set forth in SEQ ID NO: 40, and a light chain comprising an amino acid sequence having at least 90% sequence identity to the amino acid sequence set forth in SEQ ID NO: 41. In some of any such embodiments, the anti-idiotype antibody or antigen-binding fragment thereof comprises a heavy chain comprising an amino acid sequence having at least 90% sequence identity to the amino acid sequence set forth in SEQ ID NO: 64, and a light chain comprising an amino acid sequence having at least 90% sequence identity to the amino acid sequence set forth in SEQ ID NO: 65.

In some of any such embodiments, the anti-idiotype antibody or antigen-binding fragment thereof comprises: a heavy chain comprising the amino acid sequence set forth in SEQ ID NO: 40 or 64; and a light chain comprising the amino acid sequence set forth in SEQ ID NO: 41 or 65. In some of any such embodiments, the anti-idiotype antibody or antigen-binding fragment thereof comprises: a heavy chain comprising the amino acid sequence set forth in SEQ ID NO: 40, and a light chain comprising the amino acid sequence set forth in SEQ ID NO: 41. In some of any such embodiments, the anti-idiotype antibody or antigen-binding fragment comprises: or a heavy chain comprising the amino acid sequence set forth in SEQ ID NO: 64, and a light chain comprising the amino acid sequence set forth in SEQ ID NO: 65.

In some of any such embodiments, the anti-BCMA target antibody or antigen-binding fragment thereof, in some cases the first anti-BCMA target antibody or antigen-binding fragment thereof, comprises a VH region comprising the amino acid sequence set forth in SEQ ID NO: 11, and a VL region comprising the amino acid sequence set forth in SEQ ID NO: 12. In some of any such embodiments, the anti-BCMA target antibody or antigen-binding fragment thereof, in some cases the first anti-BCMA target antibody or antigen-binding fragment thereof, is a single chain fragment. In some of any such embodiments, the single chain fragment comprises a flexible linker positioned between the VH region and the VL region. In some of any such embodiments, the flexible linker is or comprises the amino acid sequence set forth in SEQ ID NO: 14. In some of any such embodiments, the anti-BCMA target antibody or antigen-binding fragment thereof (in some cases the first anti-BCMA target antibody or antigen-binding fragment thereof) is a single chain fragment that is an scFv. In some of any such embodiments, the scFv has or comprises the amino acid sequence set forth in SEQ ID NO: 13. In some of any such embodiments, the anti-BCMA target antibody or antigen-binding fragment, in some cases the first anti-BCMA target antibody or antigen-binding fragment, is within or included in an antigen-binding domain of an extracellular portion of a CAR. In some embodiments, the anti-idiotype antibody or antigen-binding fragment binds the anti-BCMA target antibody or antigen-binding fragment (e.g. scFv) comprised within or included in an antigen-binding domain of an extracellular portion of the CAR. In some embodiments, the anti-idiotype antibody or antigen-binding fragment specifically binds the anti-BCMA target antibody or antigen-binding fragment (e.g. scFv) comprised within or included in an antigen-binding domain of an extracellular portion of the CAR. In some of any such embodiments, the antigen-binding domain within or included in the extracellular portion the CAR is an scFv. In some embodiments, the anti-idiotype antibody or antigen-binding fragment binds or recognizes the scFv within or included in an extracellular portion of the CAR. In some of any such embodiments, the anti-BCMA target antibody or antigen-binding fragment, in some cases the first anti-BCMA target antibody or antigen-binding fragment thereof binds to, such as binds to, or recognizes human BCMA. In some of any such embodiments, the anti-BCMA target antibody or antigen-binding fragment, in some cases the first anti-BCMA target antibody or antigen-binding fragment thereof binds to, such as specifically binds to, or recognizes human BCMA.

In some of any such embodiments, the anti-BCMA target antibody or antigen-binding fragment thereof, in some cases the second anti-BCMA target antibody or antigen-binding fragment thereof, comprises a VH region comprising the amino acid sequence set forth in SEQ ID NO: 25, and a VL region comprising the amino acid sequence set forth in SEQ ID NO: 26. In some of any such embodiments, the anti-BCMA target antibody or antigen-binding fragment thereof, in some cases the second anti-BCMA target antibody or antigen-binding fragment thereof, is a single chain fragment. In some of any such embodiments, the single chain fragment comprises a flexible linker positioned between the VH region and the VL region. In some of any such embodiments, the flexible linker is or comprises the amino acid sequence set forth in SEQ ID NO: 14. In some of any such embodiments, the anti-BCMA target antibody or antigen-binding fragment thereof (in some cases the second anti-BCMA target antibody or antigen-binding fragment thereof) is an scFv. In some of any such embodiments, the scFv has or comprises the amino acid sequence set forth in SEQ ID NO: 27. In some of any such embodiments, the anti-BCMA target antibody or antigen-binding fragment, in some cases the second anti-BCMA target antibody or antigen-binding fragment, is within or included in an antigen-binding domain of an extracellular portion of a CAR. In some embodiments, the anti-idiotype antibody or antigen-binding fragment binds the anti-BCMA target antibody or antigen-binding fragment (e.g. scFv) comprised within or included in an antigen-binding domain of an extracellular portion of the CAR. In some embodiments, the anti-idiotype antibody or antigen-binding fragment specifically binds the anti-BCMA target antibody or antigen-binding fragment (e.g. scFv) comprised within or included in an antigen-binding domain of an extracellular portion of the CAR. In some of any such embodiments, the antigen-binding domain within or included in the extracellular portion the CAR is an scFv. In some embodiments, the anti-idiotype antibody or antigen-binding fragment binds or recognizes the scFv within or included in an extracellular portion of the CAR. In some of any such embodiments, the anti-BCMA target antibody or antigen-binding fragment, in some cases the second anti-BCMA target antibody or antigen-binding fragment thereof binds to, such as binds to, or recognizes human BCMA. In some of any such embodiments, the anti-BCMA target antibody or antigen-binding fragment, in some cases the second anti-BCMA target antibody or antigen-binding fragment thereof binds to, such as specifically binds to, or recognizes human BCMA.

In some of any such embodiments, the anti-idiotype antibody or antigen-binding fragment binds to or recognizes: an epitope within or including all or a portion of a CDR of the anti-BCMA target antibody or antigen-binding fragment (in some cases the first anti-BCMA target antibody or antigen-binding fragment and/or the second anti-BCMA target antibody or antigen-binding fragment). In some of any such embodiments, the anti-idiotype antibody or antigen-binding fragment binds to or recognizes: an epitope within or including all or a portion of a CDR of the first anti-BCMA target antibody or antigen-binding fragment. In some of any such embodiments, the anti-idiotype antibody or antigen-binding fragment binds to or recognizes: an epitope within or including all or a portion of a CDR of the second anti-BCMA target antibody or antigen-binding fragment. In some embodiments, the epitope recognized by the anti-idiotype antibody or antigen-binding fragment in the first anti-BCMA target antibody or antigen-binding fragment and the second anti-BCMA target antibody or antigen-binding fragment is the same or overlaps.

In some of any such embodiments, the anti-BCMA target antibody or antigen-binding fragment (e.g. scFv) is comprised within or included in an antigen-binding domain of an extracellular portion of a CAR (also called a target CAR). In some of any such embodiments, both the first and second anti-BCMA target antibody or antigen-binding fragment (e.g. scFv) is comprised within or included in an antigen-binding domain of an extracellular portion of a first CAR and a second CAR, respectively (also called a first target CAR and second target CAR). In some embodiments, the CAR contains an extracellular domain containing an antigen-binding domain that is or includes the anti-BCMA target antibody or antigen-binding fragment thereof, such as an scFv, e.g. set forth in SEQ ID NO:13 or SEQ ID NO:27; a transmembrane domain, and an intracellular domain containing a CD3zeta signaling domain and a costimulatory signaling domain. In some embodiments, the costimulatory signaling domain is an intracellular signaling domain of CD28, such as from a human CD28. In some embodiments, the costimulatory signaling domain is an intracellular signaling domain of 4-1BB, such as from a human 4-1BB. In some of any such embodiments, the CAR, or the first and second CAR individually, further contains a transmembrane domain linked to the antigen-binding domain via a spacer, and an intracellular signaling region containing an ITAM-containing signaling domain and an intracellular signaling domain from a costimulatory receptor. In some embodiments, the intracellular signaling domain is an CD3zeta signaling domain. In some embodiments, the intracellular signaling domain from a costimulatory receptor is a 4-1BB signaling domain. In some of any such embodiments, the spacer of the target CAR, or individually of the first CAR and/or the second CAR, is an immunoglobulin spacer. In some embodiments, the spacer comprises the amino acid sequence set forth in SEQ ID NO: 50. In some of any such embodiments, the anti-idiotype antibody or antigen-binding fragment thereof does not bind to an epitope in the spacer domain of the CAR. In some of any such embodiments, the anti-idiotype antibody or antigen-binding fragment thereof does not bind to an epitope in the spacer domain of the CAR. In some of any such embodiments, the anti-idiotype antibody or antigen-binding fragment thereof does not bind to an epitope in the spacer domain of the first CAR and/or the second CAR. In some of any such embodiments, the anti-idiotype antibody or antigen-binding fragment thereof does not bind to an epitope in the spacer domain of the first CAR and the second CAR.

In some of any such embodiments, the transmembrane domain of the CAR, or individually the first CAR and/or the second CAR, comprises a transmembrane portion of CD28. In some embodiment, the transmembrane domain is a transmembrane domain of human CD28. In some of any such embodiments, the anti-idiotype antibody or antigen-binding fragment thereof does not bind or does not specifically bind to CD28 or a portion thereof, which optionally is human CD28. In some of any such embodiments, the anti-idiotype antibody or antigen-binding fragment thereof does not bind or does not specifically bind to human CD28 or a portion thereof.

In some of any such embodiments, the anti-idiotype antibody or antigen-binding fragment thereof does not bind to an epitope in an Fc domain. In some of any such embodiments, the Fc domain is a human IgG1 Fc domain.

In some of any such embodiments, the anti-idiotype antibody or antigen-binding fragment thereof is an agonist antibody of the target CAR, in some cases the first target CAR or the second CAR CAR. In some embodiments, the anti-idiotype antibody or antigen-binding fragment thereof is an agonist antibody of the first CAR comprising the first anti-BCMA target antibody or antigen-binding fragment thereof, and/or is an agonist of a second CAR comprising the second anti-BCMA target antibody or antigen-binding fragment thereof. In some of any such embodiments, the anti-idiotype antibody or antigen-binding fragment thereof is an agonist when in soluble form. In some embodiments, the anti-idiotype antibody or antigen-binding fragment thereof is an agonist when immobilized to a support or a stationary phase, such as wherein the support or stationary phase is a plate or a bead.

In some of any such embodiments, the anti-idiotype antibody or antigen-binding fragment thereof specifically binds to the first anti-BCMA target antibody or antigen-binding fragment thereof and the second anti-BCMA target antibody or antigen-binding fragment thereof.

In some of any such embodiments, the anti-idiotype antibody has a binding affinity (EC50) and/or a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM. In some of any such embodiments, the anti-idiotype antibody has a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM. In some embodiments, the anti-idiotype antibody has a binding affinity (EC50) and/or a dissociation constant that is the same or substantially the same for binding to the first anti-BCMA target antibody or antigen-binding fragment thereof and the second anti-BCMA target antibody or antigen-binding fragment thereof.

In some of any such embodiments, binding of the anti-idiotype antibody or antigen-binding fragment thereof to the anti-BCMA target antibody or antigen-binding fragment thereof, or the first anti-BCMA target antibody or antigen-binding fragment thereof and/or the second anti-BCMA target antibody or antigen-binding fragment thereof, is not blocked by human BCMA or human BCMA-Fc.

In some of any such embodiments, the anti-idiotype antibody or antigen-binding fragment thereof is humanized. In some of any such embodiments, the anti-idiotype antibody or antigen-binding fragment thereof is recombinant. In some of any such embodiments, the anti-idiotype antibody or antigen-binding fragment thereof is monoclonal. In some of any such embodiments, the anti-idiotype antibody or antigen-binding fragment thereof is an antigen-binding fragment. In some of any such embodiments, the antigen-binding fragment is selected from among Fab fragments, F(ab')₂ fragments, Fab' fragments, Fv fragments, an scFv, and a single domain antibody. In some of any such embodiments, the anti-idiotype antibody or antigen-binding fragment thereof of comprises at least a portion of an immunoglobulin constant region. In some of any such embodiments, the at least a portion of an immunoglobulin constant region comprises an Fc region or a portion of the Fc comprising the CH2 and CH3 domains. In some of any such embodiments, the constant region is derived from human IgG.

In some of any such embodiments, the anti-idiotype antibody or antigen-binding fragment thereof comprises at least a portion of an immunoglobulin constant region of a heavy chain and/or a light chain. In some of any such embodiments, the anti-idiotype antibody or antigen-binding fragment comprises a heavy chain constant region comprising an Fc region or a portion of the Fc comprising the CH2 and CH3 domains and/or a light chain constant region comprising a CL domain. In some of any such embodiments, the constant region is is from IgG, optionally IgG1. In some of any such embodiments, the constant region is is from IgG1. In some of any such embodiments, the light chain constant region is from a kappa light chain.

In some of any such embodiments, the anti-idiotype antibody or antigen-binding fragment thereof is an intact antibody or full-length antibody.

Also provided herein, in some embodiments, is a conjugate, comprising the anti-idiotype antibody or antigen-binding fragment thereof of any of the embodiments provided herein and a heterologous molecule or moiety. In some of any such embodiments, the heterologous molecule or moiety is a label. In some of any such embodiments, the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound and an oligonucleotide. In some of any such embodiments, the heterologous molecule or moiety is a protein, peptide, nucleic acid or small molecule, which optionally is or comprises a toxin or a Strep-Tag. In some of any such embodiments, the heterologous molecule or moiety is a Strep-Tag.

Also provided herein, in some embodiments, is a nucleic acid molecule(s) encoding the heavy chain and/or the light chain of the anti-idiotype antibody or antigen-binding fragment thereof of any of the embodiments provided herein. In some of any such embodiments, the nucleic acid molecule(s) comprise a sequence of nucleotides encoding (i) the heavy chain variable region set forth in SEQ ID NO: 62, (ii) a heavy chain variable region that has at least 90% sequence identity to the amino acid sequence set forth in SEQ ID NO: 62; or (iii) a degenerate sequence of (i) or (ii); and a sequence of nucleotides encoding (iv) the light chain variable region set forth in SEQ ID NO: 63, (v) a light chain variable region that has at least 90% sequence identity to the amino acid sequence set forth in SEQ ID NO: 63; or (vi) a degenerate sequence of (iv) or (v).

In some of any such embodiments, the nucleic acid molecule(s) comprise a sequence of nucleotides encoding (i) the heavy chain variable region set forth in SEQ ID NO: 84, (ii) a heavy chain variable region that has at least 90% sequence identity to the amino acid sequence set forth in SEQ ID NO: 84; or (iii) a degenerate sequence of (i) or (ii); and a sequence of nucleotides encoding (iv) the light chain variable region set forth in SEQ ID NO: 85, (v) a light chain variable region that has at least 90% sequence identity to the amino acid sequence set forth in SEQ ID NO: 85; or (vi) a degenerate sequence of (iv) or (v).

In some of any such embodiments, the nucleic acid molecule(s) comprise a sequence of nucleotides encoding (i) the heavy chain variable region set forth in SEQ ID NO: 114, (ii) a heavy chain variable region that has at least 90% sequence identity to the amino acid sequence of nucleotides set forth in SEQ ID NO: 114; or (iii) a degenerate sequence of (i) or (ii); and a sequence of nucleotides encoding (iv) the light chain variable region set forth in SEQ ID NO: 115, (v) a light chain variable region that has at least 90% sequence identity to the amino acid sequence set forth in SEQ ID NO: 115; or (vi) a degenerate sequence of (iv) or (v).

In some of any such embodiments, the nucleic acid molecule(s) comprise a sequence of nucleotides encoding (i) the heavy chain variable region set forth in SEQ ID NO: 38, (ii) a heavy chain variable region that has at least 90% sequence identity to the sequence of nucleotides set forth in SEQ ID NO: 38; or (iii) a degenerate sequence of (i) or (ii); and a sequence of nucleotides encoding (iv) the light chain variable region set forth in SEQ ID NO: 39, (v) a light chain variable region that has at least 90% sequence identity to the amino acid sequence set forth in SEQ ID NO: 39; or (vi) a degenerate sequence of (iv) or (v).

In some of any such embodiments, the nucleic acid molecule(s) comprise a sequence of nucleotides encoding (i) the heavy chain set forth in SEQ ID NO: 64, (ii) a heavy chain that has at least 90% sequence identity to the amino acid sequence set forth in SEQ ID NO: 64; or (iii) a degenerate sequence of (i) or (ii); and a sequence of nucleotides encoding (iv) the light chain set forth in SEQ ID NO: 65, (v) a light chain that has at least 90% sequence identity to the amino acid sequence set forth in SEQ ID NO: 65; or (vi) a degenerate sequence of (iv) or (v).

In some of any such embodiments, the nucleic acid molecule(s) comprise a sequence of nucleotides encoding (i) the heavy chain set forth in SEQ ID NO: 86, (ii) a heavy chain that has at least 90% sequence identity to the amino acid sequence set forth in SEQ ID NO: 86; or (iii) a degenerate sequence of (i) or (ii); and a sequence of nucleotides encoding (iv) the light chain set forth in SEQ ID NO: 87, (v) a light chain that has at least 90% sequence identity to the amino acid sequence set forth in SEQ ID NO: 87; or (vi) a degenerate sequence of (iv) or (v).

In some of any such embodiments, the nucleic acid molecule(s) comprise a sequence of nucleotides encoding (i) the heavy chain set forth in SEQ ID NO: 116, (ii) a heavy chain that has at least 90% sequence identity to the amino acid sequence set forth in SEQ ID NO: 116; or (iii) a degenerate sequence of (i) or (ii); and a sequence of nucleotides encoding (iv) the light chain set forth in SEQ ID NO: 117, (v) a light chain that has at least 90% sequence identity to the amino acid sequence set forth in SEQ ID NO: 117; or (vi) a degenerate sequence of (iv) or (v).

In some of any such embodiments, the nucleic acid molecule(s) comprise a sequence of nucleotides encoding (i) the heavy chain set forth in SEQ ID NO: 40, (ii) a heavy chain that has at least 90% sequence identity to the sequence of nucleotides set forth in SEQ ID NO: 40; or (iii) a degenerate sequence of (i) or (ii); and a sequence of nucleotides encoding (iv) the light chain set forth in SEQ ID NO: 41, (v) a light chain that has at least 90% sequence identity to the sequence of nucleotides set forth in SEQ ID NO: 41; or (vi) a degenerate sequence of (iv) or (v).

In some of any such embodiments, the nucleotide sequence encoding the heavy chain and/or light chain comprises a signal sequence.

In some of any such embodiments, the nucleic acid molecule(s) comprise one or more nucleotide sequences selected from the group consisting of SEQ ID NOs: 42, 43, 48, 49, 66-69, 88-91, and 118-121.

Also provided herein, in some embodiments, is a vector, comprising the nucleic acid molecule(s) of any of the embodiments provided herein.

Also provided herein, in some embodiments, is cell, comprising the anti-idiotype antibody or antigen-binding fragment thereof of any of the embodiments provided herein, the nucleic acid molecule of any of the embodiments provided herein, or the vector of any of the embodiments provided herein.

Also provided herein, in some embodiments, is a method of producing an anti-idiotype antibody or antigen-binding fragment thereof, comprising expressing the heavy and/or light chain encoded by the nucleic acid molecule(s) of any one of such embodiments or the vector of any one of such embodiments in a suitable host cell and recovering or isolating the antibody.

Also provided herein, in some embodiments, is a method of producing an anti-idiotype antibody or antigen-binding fragment thereof, comprising culturing the cell of any of such embodiments under conditions in which the heavy chain and/or light chain is expressed, and recovering or isolating the antibody.

Also provided herein, in some embodiments, is an anti-idiotype antibody or antigen-binding fragment thereof produced by the method of any of such embodiments.

Also provided herein, in some embodiments, is a composition comprising the anti-idiotype antibody or antigen-binding fragment thereof of any one of such embodiments, the conjugate of any one of such embodiments, or the cell of any one of such embodiments.

In some of any such embodiments, the composition further comprises a pharmaceutically acceptable excipient.

Also provided herein, in some embodiments, is a kit, comprising one or more of the anti-idiotype antibody or antigen-binding fragment thereof of any one of such embodiments, the conjugate of any one of such embodiments, the nucleic acid molecule(s) of any one of such embodiments, and, optionally, instructions for use.

In some of any such embodiments, the kit, further comprises a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

Also provided herein, in some embodiments, is a method of detecting a target antibody or antigen-binding fragment thereof, comprising: (a) contacting a composition comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof; and (b) detecting the anti-idiotype antibody bound to the target antibody or antigen-binding fragment thereof. In some of any such embodiments, the target antibody or antigen-binding fragment thereof is bound to a cell or expressed on the surface of a cell and detecting in (b) comprises detecting cells bound with the anti-idiotype antibody or antigenbinding fragment thereof. In some of any such embodiments, the cell expresses on its surface a CAR comprising the target antibody or antigen-binding fragment thereof.

Also provided herein, in some embodiments, is a method of detecting a CAR comprising a target antibody or antigen-binding fragment thereof, comprising: (a) contacting a cell expressing a CAR comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof; and (b) detecting cells bound with the anti-idiotype antibody or antigen-binding fragment thereof. In some of any such embodiments, the anti-idiotype antibody or antigen-binding fragment thereof is directly or indirectly labeled for detection.

Also provided herein, in some embodiments, is a method of selecting cells from a cell population, comprising: (a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof; and (b) selecting cells bound with the anti-idiotype antibody or antigen-binding fragment thereof. In some of any such embodiments, the cells bound with the anti-idiotype antibody or antigen-binding fragment thereof are selected by affinity-based separation. In some of any such embodiments, the affinity-based separation is immunoaffinity-based separation. In some of any such embodiments, the affinity-based separation is by flow cytometry. In some of any such embodiments, the affinity-based separation is by magnetic activated cell sorting. In some of any such embodiments, the affinity-based separation comprises affinity chromatography. In some of any such embodiments, the anti-idiotype antibody or antigen-binding fragment thereof is reversibly bound or immobilized to a support or a stationary phase.

Also provided herein, in some embodiments, is a method of stimulating cells, comprising incubating an input composition comprising cells expressing a CAR comprising a target antibody or antigen-binding fragment thereof with the anti-idiotype antibody or antigen-binding fragment thereof of any one of such embodiments, or the conjugate of any one of such embodiments, that specifically binds to the target antibody or antigen-binding fragment thereof, thereby generating an output composition comprising stimulated cells.

Also provided herein, in some embodiments, is a method of producing a cell composition, comprising: (a) introducing into cells a nucleic acid molecule(s) encoding a CAR, thereby generating an input composition; and (b) incubating the input composition with the anti-idiotype antibody or antigen-binding fragment thereof of any one of such embodiments, or the conjugate of any one of such embodiments, that specifically binds to an antigen receptor of the CAR, thereby producing the cell composition.

In some of any such embodiments, the introducing in (a) comprises introducing the nucleic acid molecule(s) into the cells by viral transduction, transposition, electroporation, or chemical transfection.

In some of any such embodiments, the introducing in (a) comprises introducing the nucleic acid molecule(s) in the cells by transduction with a viral vector comprising the nucleic acid molecule(s), optionally wherein the viral vector is a retroviral vector or a lentiviral vector. In some embodiments, the viral vector is a retroviral vector or a lentiviral vector.

In some of any such embodiments, the introducing in (a) comprises introducing the nucleic acid molecule(s) in the cells by transposition with a transposon comprising the nucleic acid molecule(s).

In some of any such embodiments, the introducing in (a) comprises introducing the nucleic acid molecule(s) in the cells by electroporation or transfection of a vector comprising the nucleic acid molecule(s).

In some of any such embodiments, the method further comprises a step of activating the cells prior to step (a). In some of any such embodiments, the step of activating the cells comprises contacting the cells with an agonist of CD3 and optionally an agonist of CD28. In some of any such embodiments, the step of activating the cells comprises contacting the cells with an agonist of CD3. In some of any such embodiments, the step of activating the cells further comprises contacting the cells with an agonist of CD28. In some of any such embodiments, the step of activating the cells comprises contacting the cells with a reagent comprising agonistic anti-CD3 and anti-CD28 antibodies.

In some of any such embodiments, the incubation is performed under conditions in which the anti-idiotype antibody or antigen-binding fragment thereof binds to the CAR, thereby inducing or modulating a signal in one or more cells in the input composition.

In some of any such embodiments, the cells comprise T cells. In some of any such embodiments, the T cells comprise CD4+ and/or CD8+ T cells.

In some of any such embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof.

In some of any such embodiments, the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof. In some of any such embodiments, the reagent comprises a streptavidin mutein. In some of any such embodiments, the incubation is for at least or about at least 5 minutes, 10 minutes, 30 minutes, 60 minutes, 2 hours, 6 hours, 12 hours, 24 hours, 36, 48 hours, 72 hours or 96 hours.

In some of any such embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition. In some of any such embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition. In some of any such embodiments, the percentage of CAR-expressing in the output composition compared to the total cells in the composition is increased by greater than 10%, 20%, 40%, 50%, 60%, 70%, 80% or more.

In some of any such embodiments, prior to the introducing and/or the incubating, the cells are not selected or enriched for CAR-expressing cells.

Also provided herein, in some embodiments, is a method of purifying an anti-idiotype antibody or antigen-binding fragment thereof, comprising: (a) contacting a composition comprising a target antibody or antigen-binding fragment thereof with the anti-idiotype antibody or antigen-binding fragment thereof of any one of such embodiments, or the conjugate of any one of such embodiments, that specifically binds to a target antibody or antigen-binding fragment thereof; and (b) isolating complexes comprising the anti-idiotype antibody or antigen-binding fragment thereof.

In some of any such embodiments, the complexes comprising the anti-idiotype antibody or antigen-binding fragment thereof are isolated by affinity-based separation. In some of any such embodiments, the affinity-based separation is immunoaffinity-based separation. In some of any such embodiments, the affinity-based separation is magnetic-based separation. In some of any such embodiments, the affinity-based separation comprises affinity chromatography.

Also provided herein, in some embodiments, is a method of depleting cells, comprising administering, to a subject, a composition comprising the anti-idiotype antibody or antigen-binding fragment thereof of any one of such embodiments, or the conjugate of any one of such embodiments, that specifically binds to a target antibody or antigen-binding fragment thereof, wherein the subject has been administered a cell expressing a CAR comprising the target antibody or antigen-binding fragment thereof.

In some of any such embodiments, the depletion occurs via antibody-dependent cell-mediated cytotoxicity (ADCC).

In some of any such embodiments, the target antibody or antigen-binding fragment thereof is a single chain fragment. In some of any such embodiments, the single chain fragment comprises an scFv. In some of any such embodiments, the single chain fragment is an scFv.

In some of any such embodiments, the target antibody or antigen-binding fragment thereof comprises a VH region comprising the amino acid sequence set forth in SEQ ID NO: 11, and a VL region comprising the amino acid sequence set forth in SEQ ID NO: 12.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 14, and the scFv comprises the amino acid sequence set forth in SEQ ID NO: 13.

In some of any such embodiments, the target antibody or antigen-binding fragment thereof comprises a VH region comprising the amino acid sequence set forth in SEQ ID NO: 25, and a VL region comprising the amino acid sequence set forth in SEQ ID NO: 26.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 14, and the scFv comprises the amino acid sequence set forth in SEQ ID NO: 27.

Also provided herein, in some embodiments, is an article of manufacture comprising the anti-idiotype antibody or antigen-binding fragment thereof of any one of such embodiments, or the conjugate of any one of such embodiments, and instructions for using the anti-idiotype antibody or antigen-binding fragment thereof to: detect a target antibody or antigen-binding fragment thereof or a CAR comprising a target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

Also provided herein, in some embodiments, is an article of manufacture comprising: a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of such embodiments, or the conjugate of any one of such embodiments.

In some of any such embodiments, the binding reagent is a first binding reagent and the article of manufacture further comprises a second binding reagent comprising the extracellular domain or portion thereof of the CAR. In some of any such embodiments, the extracellular domain of the CAR or portion thereof of the first and second binding reagent is the same.

In some of any such embodiments, the article of manufacture further comprises instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising a target antibody that is the or antigen-binding fragment thereof. In some of any such embodiments, the binding reagent, optionally the first and/or second binding reagent, is detectably labeled or capable of producing a detectable signal. In some of any such embodiments, one of the first and second binding reagent is attached to a solid support of is capable of being attached to a solid support and the other of the first and second binding reagent is detectable label or is capable of producing a detectable signal.

In some of any such embodiments, the article of manufacture further comprises a solid support, optionally wherein the one of the first and second binding reagent is linked, directly or indirectly to biotin, and the solid support comprises a streptavidin-coated surface.

In some of any such embodiments, the target antibody or antigen-binding fragment thereof is a single chain fragment. In some of any such embodiments, the single chain fragment comprises an scFv. In some of any such embodiments, the single chain fragment is an scFv.

In some of any such embodiments, the target antibody or antigen-binding fragment thereof comprises a VH region comprising the amino acid sequence set forth in SEQ ID NO: 11, and a VL region comprising the amino acid sequence set forth in SEQ ID NO: 12.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 14, and the scFv comprises the amino acid sequence set forth in SEQ ID NO: 13.

In some of any such embodiments, the target antibody or antigen-binding fragment thereof comprises a VH region comprising the amino acid sequence set forth in SEQ ID NO: 25, and a VL region comprising the amino acid sequence set forth in SEQ ID NO: 26.

In some of any such embodiments, the target antibody or antigen-binding fragment thereof is an scFv and the VH region and the VL region are joined by a flexible linker. In some of any such embodiments, the flexible linker comprises the amino acid sequence set forth in SEQ ID NO: 14, and the scFv comprises the amino acid sequence set forth in SEQ ID NO: 27.

DETAILED DESCRIPTION

Figure 1:
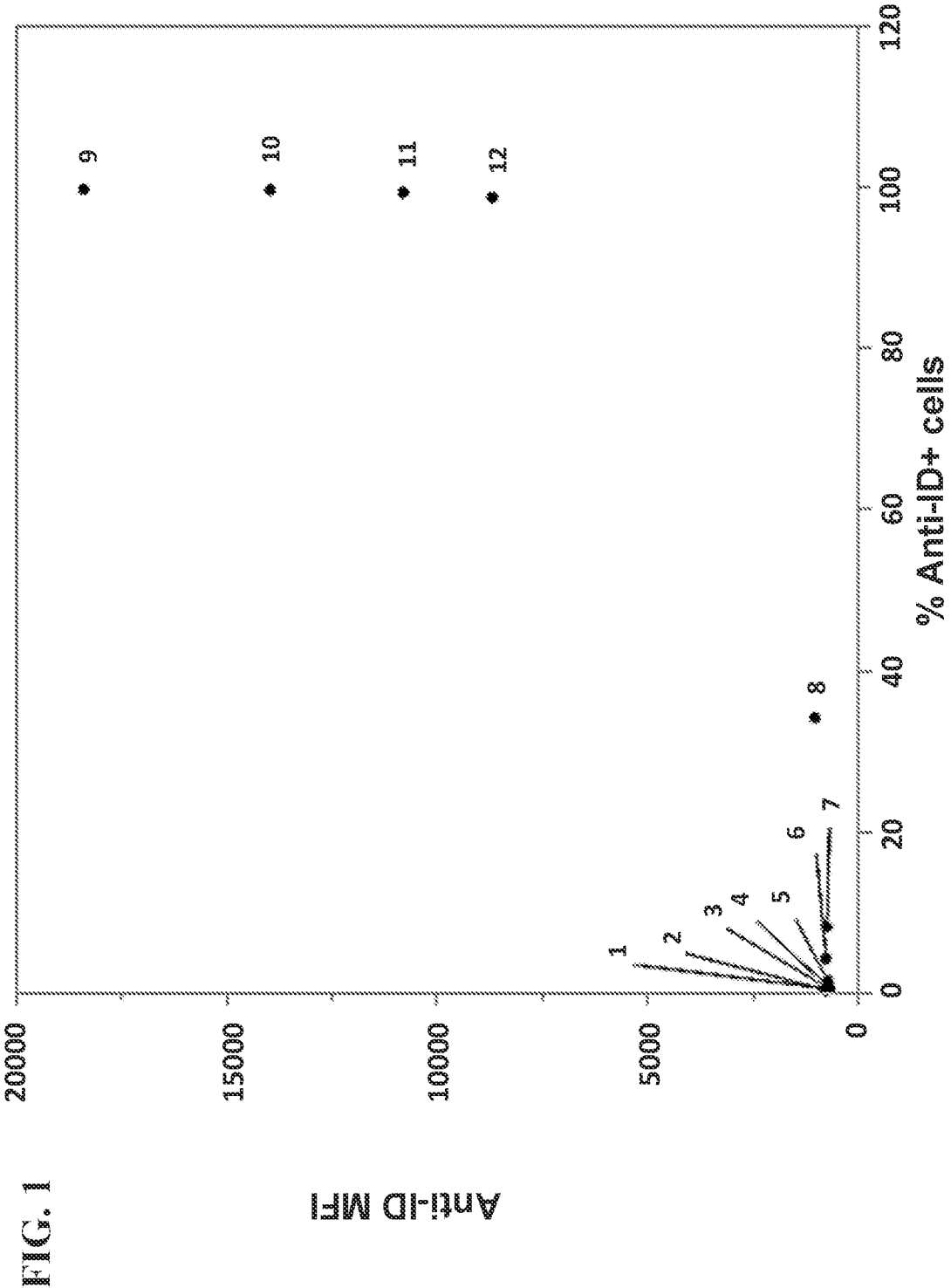
FIG. 1 depicts the results of an assay where anti-ID antibodies were assessed for the ability to specifically bind to T cells engineered with the anti-BCMA CAR 1 by incubating the anti-ID antibodies with T cells engineered with the anti-BCMA CAR 1 and then detecting the level of binding.

Provided herein are agents such as anti-idiotype antibodies and antigen-binding fragments that bind to or recognize anti-BCMA antibody moieties (such as anti-BCMA antibody moieties present in recombinant receptors, including chimeric antigen receptors). Also provided are uses and methods of use thereof, and compositions and articles of manufacture including such agents, including for specifically identifying, selecting, and/or stimulating and/or activating cells expressing or including the target antibodies or fragments such as anti-BCMA CAR T cells. In some embodiments, the provided antibodies can be used for specific identification and/or selection of various anti-BCMA CARs, such as CARs bound to or expressed on a cell surface, and can also be used to specifically activate cells expressing target CARs, such as CAR T cells. In some embodiments, provided are antibodies that are specific to the anti-BCMA antibody designated Target Antibody 1, or an antibody fragment derived therefrom, including antibodies and CARs containing variable regions derived from such antibodies, and/or an antibody containing an idiotope contained therein. In some embodiments, provided are antibodies that are specific to the anti-BCMA antibody designated Target Antibody 2, or an antibody fragment derived therefrom, including antibodies and CARs containing variable regions derived from such antibodies, and/or an antibody containing an idiotope contained therein. In some embodiments, provided are antibodies that are specific to both the anti-BCMA antibody designated Target Antibody 1, or an antibody fragment derived therefrom, and the anti-BCMA antibody designated Target Antibody 2, or an antibody fragment derived therefrom, including antibodies and CARs containing variable regions derived from such antibodies, and/or an antibody containing an idiotope contained therein.

In some embodiments, provided are anti-idiotype antibodies or antigen-binding fragments thereof that are specific to an anti-BCMA antibody or an antibody fragment derived therefrom, including anti-BCMA antibodies and CARs containing variable regions derived from such anti-BCMA antibodies and/or an anti-BCMA antibody containing an idiotope contained therein. In some embodiments, provided are anti-idiotype antibodies that are specific to the anti-BCMA antibody designated Target Antibody 1 or an antibody fragment derived therefrom, including anti-BCMA antibodies and CARs containing variable regions derived from such anti-BCMA antibodies and/or an anti-BCMA antibody containing an idiotope contained therein. In some embodiments, provided are anti-idiotype antibodies that are specific to the anti-BCMA antibody designated Target Antibody 2 or an antibody fragment derived therefrom, including anti-BCMA antibodies and CARs containing variable regions derived from such anti-BCMA antibodies and/or an anti-BCMA antibody containing an idiotope contained therein. In some embodiments, provided are anti-idiotype antibodies that are specific to the anti-BCMA antibody designated Target Antibody 1 or an antibody fragment derived therefrom and the anti-BCMA antibody designated Target Antibody 2 or an antibody fragment derived therefrom, including anti-BCMA antibodies and CARs containing variable regions derived from such anti-BCMA antibodies and/or an anti-BCMA antibody containing an idiotope contained therein.

The provided anti-idiotype antibodies or antigen-binding fragments thereof can be utilized as a reagent for various purposes, including based on ability to detect, identity or select or identify a target antibody present in a recombinant receptor (e.g. CAR); to agonize activity of engineered cells that contains or expresses a recombinant receptor (e.g. CAR) having a extracellular domain containing the target antibody and an intracellular signaling domain; or to antagonize or block binding of a target antibody, e.g. present in a recombinant receptor expressed by an engineered cell, to its target antigen.

In some embodiments, provided are uses and methods of use thereof, and compositions and articles of manufacture including such anti-idiotype antibodies or antigen-binding fragments thereof, including for specifically detecting, identifying, or selecting, engineered cells expressing or including the target antibodies or fragments as part of a recombinant receptor (e.g. CAR) expressed by or on the engineered cells, such as anti-BCMA CAR T cells. In some embodiments, provided anti-idiotype antibodies or antigen-binding fragments thereof can be used for specific identification and/or selection of various anti-BCMA CARs, such as CARs bound to or expressed on a cell surface.

In some embodiments, provided are uses and methods of use thereof, and compositions and articles of manufacture including such anti-idiotype antibodies or antigen-binding fragments thereof, for agnonizing, stimulating or activating engineered cells that contains or expresses a recombinant receptor (e.g. CAR) having a extracellular domain containing an anti-BCMA target antibody and an intracellular signaling domain. In such embodiments, among provided anti-idiotype antibodies and antigen-binding fragments thereof are anti-idiotype antibodies and antigen-binding fragments in which binding to the target antibody or fragment contained as part of the extracellular domain of a recombinant receptor (e.g. a CAR) expressed by or on the engineered cell results in agonist activity to stimulate or activate the engineered cell. In some embodiments, binding to the target antibody composed in the recombinant receptor activates the signaling domain of the recombinant receptor to initiate or mediate downstream signaling events leading to activation of transcription factors or other signaling molecules in the cell, proliferation of the engineered cell, production of cytokines, cytotoxic activity or other effector activities. In some embodiments, provided antibodies can be used to specifically stimulate or activate cells expressing target CARs, such as CAR T cells.

In some aspects, the provided anti-idiotype antibodies offer advantages compared to conventional reagents for detecting, identifying, manipulating and/or affecting and/or engineering cells that express a CAR, and in particular a CAR containing an anti-BCMA antibody scFv extracellular domain or one containing the recognized idiotype. In certain available methods detection of the presence or absence or amount of CAR or CAR-expressing cells (and/or stimulation or manipulation of the CAR), in a sample, is carried out by assessing the presence or absence or amount of a surrogate molecule, such as one included in the construct encoding the CAR and thus serving as an indirect or surrogate marker for its expression. In certain available methods, detection is carried out using a generic antibody reagent and/or a reagent that is not specific for the particular CAR assessed, e.g., as compared to other CARs that may have similar or identical domains other than the antigen-binding region; for example, such antibodies may include anti-species antibodies recognizing spacer or other domains from the species from which a CAR domain was derived, and/or antibodies recognizing particular components used in spacer regions of the target and also other chimeric receptors. In certain available methods designed to detect the presence or absence of CARs, detection is carried out using an agent recognizing a CAR constant region. In some cases, reagents against a surrogate molecule or marker also may not be suitable for specifically stimulating or inducing activation of engineered cells (e.g. CAR-T cells), either because the surrogate marker or molecule does not contain a signaling domain or because the signaling domain mediates signaling via a different signaling pathway from the CAR. In certain available methods, CAR cells are stimulated through the use of general reagents, such as anti-CD3/CD28 recognizing agents. Certain methods use a recombinant ligand of the CAR (e.g., BCMA-Fc). Such methods in certain contexts may not be entirely satisfactory and/or have certain limitations. In some cases, CAR ligands, such as BCMA, may not always be entirely effective, e.g., for use in complex flow cytometry panels or if agonist-mediated stimulation is desired using soluble reagents. In some cases, CAR ligands, such as BCMA or BCMA-Fc, may not always be entirely effective, for example, because the affinity of the ligand for the CAR or its format or structure may not be optimal for certain uses. e.g., for use in complex flow cytometry panels or if agonist-mediated stimulation is desired using soluble reagents. Improved methods and agents are needed, including those providing improved sensitivity and/or selectivity. Provided herein are embodiments meeting such needs.

The provided anti-idiotype antibodies and antigen-binding fragments in some embodiments overcome one or more of these challenges, including challenges related to low binding affinity associated with target antibody ligands and/or non-specific binding associated with antibody reagents directed to target antibody constant regions. The provided anti-idiotype antibodies include antibodies that provide a reagent with both high affinity and specificity for its target antibody or antigen binding fragment thereof. In some embodiments, the provided antibodies exhibit greater specificity and binding affinity for their target antibodies or antigen-binding fragments, such as the anti-BCMA antibody designated Target Antibody 1 and/or the anti-BCMA antibody designated Target Antibody 2, compared to BCMA-Fc and other reagents currently available for detecting or identifying the CAR.

In some embodiments, provided methods and uses include in vitro or ex vivo methods and uses, including those for detecting or quantifying expression on engineered cells of a recombinant receptor (e.g. CAR) containing an anti-BCMA target antibody as part of its extracellular antigen-binding domain, or for assessing or monitoring a functional activity of engineered cells expressing a recombinant receptor (e.g. a CAR). In some embodiments, provided methods and uses include in vivo methods and uses, involving administering the anti-idiotype antibody to a subject that has been or is to be administered engineered cells expressing a recombinant receptor (e.g. CAR) in which an anti-BCMA target antibody is composed in the extracellular domain, including in methods for detecting such engineered cells in the subject; for stimulating or activating such engineered cells in vivo in the subject; or in some cases, for ablating or killing the engineered cells in vivo in the subject. Furthermore, in certain embodiments, among anti-idiotype antibodies and antigen-binding fragments provided herein are those selected as agonists or antagonists of chimeric receptors comprising their target antibodies or antigen-binding fragments, allowing for selective detection, isolation, ablation and/or depletion (for example, killing via antibody-dependent cell-mediated cytotoxicity, ADCC), and/or stimulation or activation of cells with such chimeric receptors bound to or expressed on their surface. Provided herein are anti-idiotype antibody agonists that exhibit activity to stimulate, such as activate, a CAR containing an extracellular binding domain derived from anti-BCMA antibody designated Target Antibody 1 or Target Antibody 2. Provided herein are anti-idiotype antibodies that exhibit antagonistic activity that inactivates a CAR containing an extracellular binding domain derived from anti-BCMA antibody designated Target Antibody 1 or Target Antibody 2. In some aspects, such antibodies can be used in methods of stimulating and expanding specific CAR-expressing cells, including in processes for generating and preparing the CAR-expressing cells.

In certain embodiments, among provided anti-idiotype antibodies and antigen-binding fragments thereof provided herein are those selected as agonists of a recombinant receptor, such as CAR, containing an anti-BCMA target antibody or antigen-binding fragment thereof in its extracellular domain, allowing for selective stimulation or acti-vation of cells with such recombinant receptors (e.g. CARs) bound to or expressed on their surface. In some embodiments, provided herein are anti-idiotype antibodies that are agonists that exhibit activity to stimulate, such as activate, a CAR containing an extracellular binding domain derived from an anti-BCMA antibody or antigen-binding fragment thereof. In some aspects, such antibodies can be used in methods of specifically stimulating or activating CAR-expressing cells. In particular embodiments, the recombinant receptor (e.g. CAR) contains a signaling domain that, when engaged by an agonist anti-idiotype antibody or antigen-binding fragment, is able to induce or activate one or more downstream signaling cascades in the engineered cells resulting in increased activation of transcription factors, alteration of expression of effector genes or activation or inhibition of target protein, phosphorylation or dephosphorylation events in the cells, or one or more effector functions. For example, among provided recombinant receptors containing a target anti-BCMA antibody are anti-BCMA CARs that contain an intracellular domain with a CD3zeta signaling domain and, in some cases, a costimulatory signaling domain (e.g. 4-1BB signaling domain). In some embodiments, binding of a provided agonist anti-idiotype antibody or antigen-binding fragment to the CAR expressed on T cells results in one or more of NF-κB activation, upregulation of Nur77 expression, induction of inflammatory cytokine production (e.g. IFN-gamma, TNF-alpha), T cell proliferation, and/or cytotoxic activity. For example, as shown in examples herein certain anti-idiotype antibodies or antigen binding fragments exhibit agonist activity to stimulate or activate CAR-T cells containing a target anti-BCMA antigen-binding domain, including the ability to induce Nur77 expression (e.g. based on reporter expression in a reporter assay), proliferation and/or production of cytokines. In some embodiments, the methods of stimulation or activation is recombinant receptor (e.g. CAR)-dependent or -specific. In some embodiments, the methods of stimulating or activating the recombinant receptor (e.g. CAR)-engineered cells can be carried out in vitro or ex vivo, such as in methods of specifically stimulating and expanding CAR-expressing cells, including in processes for generating and preparing the CAR-expressing cells. In some embodiments, the methods of stimulation or activation can be carried out in vivo in a subject that has previously received administration of the recombinant receptor (e.g. CAR)-engineered cells, such as to reinvigorate or induce expansion of the engineered cells in vivo in a subject, e.g. at a time at or after the peak number of engineered cells is observed or detected in the subject.

In certain embodiments, among provided anti-idiotype antibodies or antigen-binding fragments thereof provided herein are those that can be used in methods to induce or ablate killing of cells in a subject. In particular aspects of such embodiments, the anti-idiotype antibody is one that contains an Fc region, e.g. is an intact of full-length antibody. In general, the Fc region is responsible for effector functions via binding of Fc to an activating Fc receptor (e.g. FcγRIII), such as expressed on NK cells, which can mediate antibody-dependent cell cytotoxicity (ADCC). In some embodiments, binding to the target antibody of the recombinant receptor (e.g. CAR) expressed on the engineered cells by provided anti-idiotype antibody results in ablation and/or depletion of engineered cells in vivo, for example, by killing via antibody-dependent cell-mediated cytotoxicity, ADCC). In some embodiments, such methods or uses can be carried out in vivo following administration of the anti-idiotype antibody or antigen-binding fragment to a subject, such as at a time after the subject has received administration of the engineered cells. In some embodiments, a provided anti-idiotype antibody may be administered to a subject at a time when activity of the engineered cells (e.g. CAR T-cells) are not longer desired in the subject, for example, if the subject exhibits one or more signs or symptoms of severe toxicity that cannot be otherwise resolved by an anti-inflammatory agent or steroid.

Also provided herein are nucleic acids encoding the provided anti-idiotype antibodies and fragments, and cells, such as recombinant cells, expressing and for production of these anti-idiotype antibodies and fragments. Also provided are methods of making and using the anti-idiotype antibodies and fragments, as well as cells expressing or containing the anti-idiotype antibodies and fragments.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Anti-Idiotype Antibodies

Provided in some aspects are binding molecules, such as anti-idiotype antibodies or antigen-binding fragments thereof ("anti-IDs") that bind to or recognize a target anti-BCMA antibody moiety. In some embodiments, the provided antibodies bind to or recognize more than one target anti-BCMA antibody or antigen-binding fragment thereof, such as a moiety on a first target anti-BCMA antibody or antigen-binding fragment thereof and a moiety on a second target anti-BCMA antibody or antigen-binding fragment thereof.

In some embodiments, the target anti-BCMA antibody or antigen-binding fragment is an antibody or antigen-binding fragment as described in published International PCT Appl. No. WO 2019/090003 or WO 2016/090320, In some embodiments, provided are anti-idiotype antibodies that bind to or recognize a target anti-BCMA antibody that is or is derived from a target antibody referred to herein as "Target Antibody 1," or is an antigen-binding fragment thereof. In some embodiments, the provided antibodies bind to or recognize Target Antibody 1 or an antigen-binding fragment thereof containing the same CDRs as Target Antibody 1. Target Antibody 1 is an anti-BCMA antibody that comprises a heavy chain variable (VH) region comprising the amino acid sequence set forth in SEQ ID NO: 11, and a light chain variable (VL) region comprising the amino acid sequence set forth in SEQ ID NO: 12. Target Antibody 1 comprises a heavy chain complementarity determining region 1 (CDR-H1) having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a light chain complementarity determining region 1 (CDR-L1) having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10. In some embodiments, Target Antibody 1 is a single chain fragment where the VH region and the VL region of the single chain fragment is joined by a flexible linker comprising the amino acid sequence set forth in SEQ ID NO: 14. In some embodiments, Target Antibody 1 is a single chain variable fragment (scFv) comprising the amino acid sequence set forth in SEQ ID NO: 13.

In some embodiments, provided are anti-idiotype antibodies that bind to or recognize a target anti-BCMA antibody that is or is derived from a target antibody referred to herein as "Target Antibody 2" or is an antigen-binding fragment thereof. In some embodiments, the provided antibodies bind to or recognize Target Antibody 2 or an antigen-binding fragment thereof containing the same CDRs as Target Antibody 2. Target Antibody 2 comprises a heavy chain variable (VH) region comprising the amino acid sequence set forth in SEQ ID NO: 25, and a light chain variable (VL) region comprising the amino acid sequence set forth in SEQ ID NO: 26. Target Antibody 2 comprises a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24. In some embodiments, Target Antibody 2 is a single chain fragment where the VH region and the VL region of the single chain fragment is joined by a flexible linker comprising the amino acid sequence set forth in SEQ ID NO: 14. In some embodiments, Target Antibody 2 is an scFv comprising the amino acid sequence set forth in SEQ ID NO: 27.

In some embodiments, the provided antibodies recognize a first target anti-BCMA antibody or antigen-binding fragment thereof that comprises a heavy chain variable (VH) region comprising the amino acid sequence set forth in SEQ ID NO: 11, and a light chain variable (VL) region comprising the amino acid sequence set forth in SEQ ID NO: 12, and recognize a second target anti-BCMA antibody that comprises a heavy chain variable (VH) region comprising the amino acid sequence set forth in SEQ ID NO: 25, and a light chain variable (VL) region comprising the amino acid sequence set forth in SEQ ID NO: 26. In some embodiments, the provided antibodies recognize a first target anti-BCMA antibody or antigen-binding fragment thereof that comprises a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a light chain complementarity determining region 1 (CDR-L1) having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10, and recognize a second target anti-BCMA antibody that comprises a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24. In some embodiments, the provided antibodies recognize a first target anti-BCMA antibody or antigen-binding fragment thereof that is a single chain variable fragment (scFv) comprising the amino acid sequence set forth in SEQ ID NO: 13, and recognize a second target anti-BCMA antibody that is an scFv comprising the amino acid sequence set forth in SEQ ID NO: 27.

In some embodiments, the provided antibodies recognize a second target anti-BCMA antibody or antigen-binding fragment thereof that comprises a heavy chain variable (VH) region comprising the amino acid sequence set forth in SEQ ID NO: 11, and a light chain variable (VL) region comprising the amino acid sequence set forth in SEQ ID NO: 12, and recognize a first target anti-BCMA antibody that comprises a heavy chain variable (VH) region comprising the amino acid sequence set forth in SEQ ID NO: 25, and a light chain variable (VL) region comprising the amino acid sequence set forth in SEQ ID NO: 26. In some embodiments, the provided antibodies recognize a second target anti-BCMA antibody or antigen-binding fragment thereof that comprises a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a light chain complementarity determining region 1 (CDR-L1) having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10, and recognize a first target anti-BCMA antibody that comprises a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24. In some embodiments, the provided antibodies recognize a second target anti-BCMA antibody or antigen-binding fragment thereof that is a single chain variable fragment (scFv) comprising the amino acid sequence set forth in SEQ ID NO: 13, and recognize a first target anti-BCMA antibody that is an scFv comprising the amino acid sequence set forth in SEQ ID NO: 27.

In some embodiments, the provided anti-idiotype antibodies include antibodies or antigen-binding fragments thereof that bind to or recognize a variable domain (Fv), such as a single chain Fv (scFv), derived from Target Antibody 1 or Target Antibody 2. In some embodiments, the anti-idiotype antibodies bind to or recognize a particular epitope or region of an Fv, generally an epitope or region comprising one or more complementarity determining regions. In some embodiments, the anti-idiotype antibodies bind to or recognize an epitope or region overlapping an Fv paratope.

In some embodiments, the provided anti-idiotype antibodies include antibodies or antigen-binding fragments thereof that specifically bind to a variable domain (Fv), such as a single chain Fv (scFv), derived from Target Antibody 1 or Target Antibody 2.

In some embodiments, the provided anti-idiotype antibodies include those that bind to or recognize an anti-BCMA moiety that is contained as part of the extracellular domain of a target chimeric antigen receptor (CAR). In some embodiments, the target CAR contains an antigen-binding portion that contains the target antibody molecule or antigen-binding fragment or portion of the target antibody. In some embodiments, the target CAR includes an antigen-binding domain that is an scFv derived from the VH and VL chains of the target antibody. In some embodiments, there is provided an anti-idiotype antibody that binds to or recognizes an anti-BCMA CAR that contains an scFv derived from the target antibody. Exemplary features of CARs are described further below. In some embodiments, provided herein are anti-idiotype antibodies that bind to or recognize an anti-BCMA CAR that contains an scFv derived from Target Antibody 1. In some embodiments, provided herein are anti-idiotype antibodies that bind to or recognize an anti-BCMA CAR that contains an scFv derived from Target Antibody 2. In some embodiments, provided herein are anti-idiotype antibodies that bind to or recognize both an anti-BCMA CAR that contains an scFv derived from Target Antibody 1 and an anti-BCMA CAR that contains an scFv derived from Target Antibody 2.

The term "antibody" herein is used in the broadest sense and includes polyclonal and monoclonal antibodies, including intact antibodies and functional (antigen-binding) antibody fragments, including fragment antigen binding (Fab) fragments, F(ab')₂ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The term "anti-idiotype antibody" refers to an antibody, including antigen-binding fragments thereof, that recognizes, is targeted to, and/or binds to an idiotope of an antibody, such as an antigen-binding fragment. The idiotopes of an antibody may include, but are not necessarily limited to, residues within one or more of complementarity determining region(s) (CDRs) of the antibody, variable regions of the antibody, and/or partial portions or portions of such variable regions and/or of such CDRs, and/or any combination of the foregoing. The CDR may be one or more selected from the group consisting of CDR-H1, CDR-H2, CDR-H3, CDR-L1, CDR-L2, and CDR-L3. The variable regions of the antibody may be heavy chain variable regions, light chain variable regions, or a combination of the heavy chain variable regions and the light chain variable regions. The partial fragments or portions of the heavy chain variable regions and/or the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the heavy chain variable regions or the light chain variable regions of the antibody; the idiotope may include multiple non-contiguous stretches of amino acids. The partial fragments of the heavy chain variable regions and the light chain variable regions of the antibody may be fragments including 2 or more, 5 or more, or 10 or more contiguous amino acids, for example, from about 2 to about 100, from about 5 to about 100, from about 10 to about 100, from about 2 to about 50, from about 5 to about 50, or from about 10 to about 50 contiguous amino acids within the variable regions, and in some embodiments contain one or more CDRs or CDR fragments. The CDR fragments may be consecutive or non-consecutive 2 or more, or 5 or more amino acids within the CDR. Therefore, the idiotopes of the antibody may be from about 2 to about 100, from about 5 to about 100, from about 10 to about 100, from about 2 to about 50, from about 5 to about 50, or from about 10 to about 50 contiguous amino acids containing one or more CDR or one or more CDR fragments within the heavy chain variable regions or the light chain variable regions of the antibody. In another embodiment, the idiotopes may be a single amino acid which is located at the variable regions of the antibody, for example, CDR sites.

In some embodiments, the idiotope is any single antigenic determinant or epitope within the variable portion of an antibody. In some cases it can overlap the actual antigen-binding site of the antibody, and in some cases it may comprise variable region sequences outside of the antigen-binding site of the antibody. The set of individual idiotopes of an antibody is in some embodiments referred to as the "idiotype" of such antibody.

The terms "complementarity determining region," and "CDR," synonymous with "hypervariable region" or "HVR," are known in the art to refer to non-contiguous sequences of amino acids within antibody variable regions, which confer antigen specificity and/or binding affinity. In general, there are three CDRs in each heavy chain variable region (CDR-H1, CDR-H2, CDR-H3) and three CDRs in each light chain variable region (CDR-L1, CDR-L2, CDR-L3). "Framework regions" and "FR" are known in the art to refer to the non-CDR portions of the variable regions of the heavy and light chains. In general, there are four FRs in each full-length heavy chain variable region (FR-H1, FR-H2, FR-H3, and FR-H4), and four FRs in each full-length light chain variable region (FR-L1, FR-L2, FR-L3, and FR-L4).

The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), MacCallum et al., J. Mol. Biol. 262: 732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1): 55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3): 657-70, ("Aho" numbering scheme).

The boundaries of a given CDR or FR may vary depending on the scheme used for identification. For example, the Kabat scheme is based structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme.

Table 1, below, lists exemplary position boundaries of CDR-L1, CDR-L2, CDR-L3 and CDR-H1, CDR-H2, CDR-H3 as identified by Kabat, Chothia, and Contact schemes, respectively. For CDR-H1, residue numbering is listed using both the Kabat and Chothia numbering schemes. FRs are located between CDRs, for example, with FR-L1 located between CDR-L1 and CDR-L2, and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

| CDR | Kabat | Chothia | Contact |
|---|---|---|---|
| CDR-L1 | L24--L34 | L24--L34 | L30--L36 |
| CDR-L2 | L50--L56 | L50--L56 | L46--L55 |
| CDR-L3 | L89--L97 | L89--L97 | L89--L96 |
| CDR-H1 (Kabat Numbering[1]) | H31--H35B | H26--H32 . . . 34 | H30--H35B |
| CDR-H1 (Chothia Numbering[2]) | H31--H35 | H26--H32 | H30--H35 |
| CDR-H2 | H50--H65 | H52--H56 | H47--H58 |
| CDR-H3 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., "CDR-H1, CDR-H2), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given $V_H$ or $V_L$ amino acid sequence, it is understood that such a CDR has a sequence of the corresponding CDR (e.g., CDR-H3) within the variable region, as defined by any of the aforementioned schemes. In some embodiments, specified CDR sequences are specified.

Likewise, unless otherwise specified, a FR or individual specified FR(s) (e.g., FR-H1, FR-H2), of a given antibody or region thereof, such as a variable region thereof, should be understood to encompass a (or the specific) framework region as defined by any of the known schemes. In some instances, the scheme for identification of a particular CDR, FR, or FRs or CDRs is specified, such as the CDR as defined by the Kabat, Chothia, or Contact method. In other cases, the particular amino acid sequence of a CDR or FR is given.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W. H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352: 624-628 (1991).

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a human single-domain antibody.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some aspects, the antibody fragments are scFvs.

A "humanized" antibody is an antibody in which all or substantially all CDR amino acid residues are derived from non-human CDRs and all or substantially all framework regions (FRs) amino acid residues are derived from human FRs. In some embodiments, the humanized forms of a non-human antibody, e.g., a murine antibody, are chimeric antibodies that contain minimal sequences derived from non-human immunoglobulin. In certain embodiments, the humanized antibodies are antibodies from non-human species having one or more complementarily determining regions (CDRs) from the non-human species and a framework region (FR) from a human immunoglobulin molecule. In some embodiments, a humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity. (See, e.g., Queen, U.S. Pat. No. 5,585,089 and Winter, U.S. Pat. No. 5,225,539.) Such chimeric and humanized monoclonal antibodies can be produced by recombinant DNA techniques known in the art.

In certain embodiments, a humanized antibody is a human immunoglobulin (recipient antibody) in which residues from a heavy chain variable region of the recipient are replaced by residues from a heavy chain variable region of a non-human species (donor antibody) such as mouse, rat, rabbit, or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. In some embodiments, a nucleic acid sequences encoding human variable heavy chains and variable light chains are altered to replace one or more CDR sequences of the human (acceptor) sequence by sequence encoding the respective CDR in the nonhuman antibody sequence (donor sequence). In some embodiments, the human acceptor sequence may comprise FR derived from different genes. In particular embodiments, a humanized antibody will contain substantially all of at least one, and typically two, variable domains, in which all or substantially all of the hypervariable loops correspond to those of a non-human immunoglobulin, and all or substantially all of the FRs are those of a human immunoglobulin sequence. In some embodiments, the humanized antibody optionally will also comprise at least a portion of an immunoglobulin constant region (Fc), typically that of a human immunoglobulin. For further details, see, e.g., Jones et al., Nature 321:522-525 (1986); Riechmann et al., Nature 332:323-329 (1988); and Presta, Curr. Op. Struct. Biol. 2:593-596 (1992). See also, e.g., Vaswani and Hamilton, Ann. Allergy, Asthma & Immunol. 1:105-115 (1998); Harris, Biochem. Soc. Transactions 23:1035-1038 (1995); Hurle and Gross, Curr. Op. Biotech. 5:428-433 (1994); and U.S. Pat. Nos. 6,982, 321 and 7,087,409, incorporated by reference herein. In some embodiments, provided herein are humanized anti-idiotype antibodies.

In particular embodiments, an antibody, e.g., an anti-idiotype antibody, is humanized. In certain embodiments, the antibody is humanized by any suitable known means. For example, in some embodiments, a humanized antibody can have one or more amino acid residues introduced into it from a source which is non-human. These non-human amino acid residues are often referred to as "import" residues, which are typically taken from an "import" variable domain. In particular embodiments, humanization can be essentially performed by following the method of Winter and co-workers (Jones et al. (1986) Nature 321:522-525; Riechmann et al. (1988) Nature 332:323-327; Verhoeyen et al. (1988) Science 239:1534-1536), such as by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In certain embodiments, the humanized antibody is a human antibody in which some hypervariable region residues and possibly some FR residues are substituted by residues from analogous sites in rodent antibodies.

Sequences encoding full length antibodies can be subsequently obtained by joining the rendered variable heavy and variable light chain sequences to human constant heavy chain and constant light chain regions. Suitable human constant light chain sequences include kappa and lambda constant light chain sequences. Suitable human constant heavy chain sequences include IgG1, IgG2 and sequences encoding IgG1 mutants which have rendered immune-stimulating properties. Such mutants may have a reduced ability to activate complement and/or antibody dependent cellular cytotoxicity and are described in U.S. Pat. No. 5,624,821; WO 99/58572, U.S. Pat. No. 6,737,056. A suitable constant heavy chain also includes an IgG1 comprising the substitutions E233P, L234V, L235A, A327G, A330S, P331S and a deletion of residue 236. In another embodiment, the full length antibody comprises an IgA, IgD, IgE, IgM, IgY or IgW sequence.

Suitable human donor sequences can be determined by sequence comparison of the peptide sequences encoded by the mouse donor sequences to a group of human sequences, preferably to sequences encoded by human germ line immunoglobulin genes or mature antibody genes. A human sequence with a high sequence homology, preferably with the highest homology determined may serve as the acceptor sequence to for the humanization process.

In addition to the exchange of human CDRs for mouse CDRs, further manipulations in the human donor sequence may be carried out to obtain a sequence encoding a humanized antibody with optimized properties (such as affinity of the antigen).

Furthermore the altered human acceptor antibody variable domain sequences may also be rendered to encode one or more amino acids (according to the Kabat numbering system) of position 4, 35, 38, 43, 44, 46, 58, 62, 64, 65, 66, 67, 68, 69, 73, 85, 98 of the light variable region and 2, 4, 36, 39, 43, 45, 69, 70, 74, 75, 76, 78, 92 of the heavy variable region corresponding to the non-human donor sequence (Carter and Presta, U.S. Pat. No. 6,407,213).

In particular embodiments, it is generally desirable that antibodies be humanized with retention of high affinity for the antigen and other favorable biological properties. To achieve this goal, in some embodiments, the humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and imported sequences so that the desired antibody characteristic, such as increased affinity for the target antigen(s), is achieved. In general, the hypervariable region residues are directly and most substantially involved in influencing antigen binding.

In particular embodiments, choice of human variable domains, both light and heavy, to be used in making the humanized antibodies can be important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody. See, e.g., Sims et al. (1993) J. Immunol. 151:2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies. See, e.g., Carter et al. (1992) Proc. Natl. Acad. Sci. USA, 89:4285; Presta et al. (1993) J. Immunol., 151:2623.

Among the provided antibodies are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

A. Anti-ID Antibodies Against Target Antibody 2

In some embodiments, provided are anti-idiotype antibodies that bind to or recognize a target anti-BCMA antibody that is or is derived from Target Antibody 2, or is an antigen-binding fragment thereof, as described above. In some embodiments, provided are anti-idiotype antibodies that specifically bind to a target anti-BCMA antibody that is or is derived from Target Antibody 2. Exemplary antibodies or antigen-binding fragments are provided below.

In some embodiments, the provided anti-idiotype antibodies binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes an antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes a target anti-BCMA antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes a target anti-BCMA antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes an scFv having the amino acid sequence set forth in SEQ ID NO: 27.

In some embodiments, the provided anti-idiotype antibodies binds to or recognizes a target anti-BCMA antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes an scFv having the amino acid sequence set forth in SEQ ID NO: 27.

In some embodiments, the provided anti-idiotype antibodies binds to or recognizes an antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes a target anti-BCMA antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes an antibody or antigen-binding fragment thereof that has the same idiotype as Target Antibody 2.

In some embodiments, the provided anti-idiotype antibodies competes for binding to Target Antibody 2 with an antibody or antigen-binding fragment thereof that includes a VH region comprising the amino acid sequence set forth in SEQ ID NO: 84 and a VL region comprising the amino acid sequence set forth in SEQ ID NO: 85. In some embodiments, the provided anti-idiotype antibodies competes for binding to Target Antibody 2 with an antibody or antigen-binding fragment thereof that includes a VH region comprising the amino acid sequence set forth in SEQ ID NO: 114 and a VL region comprising the amino acid sequence set forth in SEQ ID NO: 115.

In some embodiments, the provided anti-idiotype antibodies bind to or recognize an antibody or antigen-binding fragment thereof that competes for binding with Target Antibody 2.

In some embodiments, the provided anti-idiotype antibodies bind to or recognize the antigen-binding domain of Target Antibody 2 that is contained within a CAR. In some embodiments, the provided anti-idiotype antibodies bind to or recognize the antigen-binding domain of Target Antibody 2 as contained within a CAR. In some embodiments, the CAR is any as described in Section II.

In some embodiments, provided are anti-idiotype antibodies or antigen-binding fragments thereof that include a VH region comprising at least 90% sequence identity to the VH region amino acid sequence set forth in SEQ ID NO: 84, such as at least 91%, 92%, 93%, 94%, 95%, 96%, 97%, 98%, or 99% sequence identity thereto; and a VL region comprising at least 90% sequence identity to the VL region amino acid sequence set forth in SEQ ID NO: 85, such as at least 91%, 92%, 93%, 94%, 95%, 96%, 97%, 98%, or 99% sequence identity thereto.

In some embodiments, provided are anti-idiotype antibodies or antigen-binding fragments thereof that include a VH region comprising a CDR-H1 comprising the amino acid sequence set forth in SEQ ID NO: 74, a CDR-H2 comprising the amino acid sequence set forth in SEQ ID NO: 75, and a CDR-H3 comprising the amino acid sequence set forth in SEQ ID NO: 76; and a VL region comprising a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83. In some embodiments, the provided anti-idiotype antibodies or antigen-binding fragments thereof include a VH region comprising a CDR-H1 comprising the amino acid sequence set forth in SEQ ID NO: 77, a CDR-H2 comprising the amino acid sequence set forth in SEQ ID NO: 78, and a CDR-H3 comprising the amino acid sequence set forth in SEQ ID NO: 76; and a VL region comprising a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83. In some embodiments, the provided anti-idiotype antibodies or antigen-binding fragments thereof include a VH region comprising a CDR-H1 comprising the amino acid sequence set forth in SEQ ID NO: 79, a CDR-H2 comprising the amino acid sequence set forth in SEQ ID NO: 80, and a CDR-H3 comprising the amino acid sequence set forth in SEQ ID NO: 76; and a VL region comprising a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83.

In some embodiments, provided are anti-idiotype antibodies or antigen-binding fragments thereof that include a CDR-H1, a CDR-H2, and a CDR-H3, respectively, comprising the amino acid sequences of a CDR-H1, a CDR-H2, and a CDR-H3 contained within the VH region amino acid sequence set forth in SEQ ID NO: 84; and a CDR-L1, a CDR-L2, and a CDR-L3, respectively, comprising the amino acid sequences of a CDR-L1, a CDR-L2, and a CDR-L3 contained within the VL region amino acid sequence set forth in SEQ ID NO: 85.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 84. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 84. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 84.

In some of any such embodiments, the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 85. In some embodiments, the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 85. In some embodiments, the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 85.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 84, and the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 85. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 84, and the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 85. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 84, and the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 85.

In some of any such embodiments, the VH region has the sequence of amino acids set forth in SEQ ID NO: 84. In some of any such embodiments, the VL region has the sequence of amino acids set forth in SEQ ID NO: 85. In some of any such embodiments, the VH region has the sequence of amino acids set forth in SEQ ID NO: 84, and the VL region has the sequence of amino acids set forth in SEQ ID NO: 85.

In some embodiments, the anti-idiotype antibody specific to Target Antibody 2 or an antigen-binding fragment thereof is a single-chain antibody fragment, such as an scFv or diabody. In some embodiments, the single-chain antibody includes one or more linkers joining two antibody domains or regions, such as a variable heavy chain (VH) region and a variable light chain (VL) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some embodiments, the anti-idiotype antibody is an intact antibody or full-length antibody. In some embodiments, the anti-ID may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4.

In some embodiments, provided are anti-idiotype antibodies or antigen-binding fragments thereof that include a heavy chain constant region contained within the amino acid sequence set forth in SEQ ID NO: 86, and a light chain constant region contained within the amino acid sequence set forth in SEQ ID NO: 87. In some embodiments, provided are anti-idiotype antibodies or antigen-binding fragments thereof that include a heavy chain constant region having at least 90% sequence identity to the heavy chain constant region contained within the amino acid sequence set forth in SEQ ID NO: 86, and a light chain constant region having at least 90% sequence identity to the light chain constant region contained within the amino acid sequence set forth in SEQ ID NO: 87.

In some embodiments, provided are anti-idiotype antibodies or antigen-binding fragments thereof that include a heavy chain comprising an amino acid sequence having at least 90% sequence identity to the amino acid sequence set forth in SEQ ID NO: 86, and a light chain comprising an amino acid sequence having at least 90% sequence identity to the amino acid sequence set forth in SEQ ID NO: 87.

In some embodiments, provided are anti-idiotype antibodies or antigen-binding fragments thereof that include a heavy chain comprising the amino acid sequence set forth in SEQ ID NO: 86, and a light chain comprising the amino acid sequence set forth in SEQ ID NO: 87.

In some embodiments, provided are anti-idiotype antibodies or antigen-binding fragments thereof that include a VH region comprising at least 90% sequence identity to the VH region amino acid sequence set forth in SEQ ID NO: 114, such as at least 91%, 92%, 93%, 94%, 95%, 96%, 97%, 98%, or 99% sequence identity thereto; and a VL region comprising at least 90% sequence identity to the VL region amino acid sequence set forth in SEQ ID NO: 115, such as at least 91%, 92%, 93%, 94%, 95%, 96%, 97%, 98%, or 99% sequence identity thereto.

In some embodiments, provided are anti-idiotype antibodies or antigen-binding fragments thereof that include a VH region comprising a CDR-H1 comprising the amino acid sequence set forth in SEQ ID NO: 104, a CDR-H2 comprising the amino acid sequence set forth in SEQ ID NO: 105, and a CDR-H3 comprising the amino acid sequence set forth in SEQ ID NO: 106; and a VL region comprising a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113. In some embodiments, the provided anti-idiotype antibodies or antigen-binding fragments thereof include a VH region comprising a CDR-H1 comprising the amino acid sequence set forth in SEQ ID NO: 107, a CDR-H2 comprising the amino acid sequence set forth in SEQ ID NO: 108, and a CDR-H3 comprising the amino acid sequence set forth in SEQ ID NO: 106; and a VL region comprising a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113. In some embodiments, the provided anti-idiotype antibodies or antigen-binding fragments thereof include a VH region comprising a CDR-H1 comprising the amino acid sequence set forth in SEQ ID NO: 109, a CDR-H2 comprising the amino acid sequence set forth in SEQ ID NO: 110, and a CDR-H3 comprising the amino acid sequence set forth in SEQ ID NO: 106; and a VL region comprising a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113.

In some embodiments, provided are anti-idiotype antibodies or antigen-binding fragments thereof that include a CDR-H1, a CDR-H2, and a CDR-H3, respectively, comprising the amino acid sequences of a CDR-H1, a CDR-H2, and a CDR-H3 contained within the VH region amino acid sequence set forth in SEQ ID NO: 114; and a CDR-L1, a CDR-L2, and a CDR-L3, respectively, comprising the amino acid sequences of a CDR-L1, a CDR-L2, and a CDR-L3 contained within the VL region amino acid sequence set forth in SEQ ID NO: 115.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 114. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 114. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 114.

In some of any such embodiments, the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 115. In some embodiments, the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 115. In some embodiments, the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 115.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 114, and the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 115. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 114, and the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 115. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 114, and the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 115.

In some of any such embodiments, the VH region has the sequence of amino acids set forth in SEQ ID NO: 114. In some of any such embodiments, the VL region has the sequence of amino acids set forth in SEQ ID NO: 115. In some of any such embodiments, the VH region has the sequence of amino acids set forth in SEQ ID NO: 114, and the VL region has the sequence of amino acids set forth in SEQ ID NO: 115.

In some embodiments, the anti-idiotype antibody specific to Target Antibody 2 or an antigen-binding fragment thereof is a single-chain antibody fragment, such as an scFv or diabody. In some embodiments, the single-chain antibody includes one or more linkers joining two antibody domains or regions, such as a variable heavy chain (VH) region and a variable light chain (VL) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some embodiments, the anti-idiotype antibody is an intact antibody or full-length antibody. In some embodiments, the anti-ID may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4.

In some embodiments, provided are anti-idiotype antibodies or antigen-binding fragments thereof that include a heavy chain constant region contained within the amino acid sequence set forth in SEQ ID NO: 116, and a light chain constant region contained within the amino acid sequence set forth in SEQ ID NO: 117. In some embodiments, provided are anti-idiotype antibodies or antigen-binding fragments thereof that include a heavy chain constant region having at least 90% sequence identity to the heavy chain constant region contained within the amino acid sequence set forth in SEQ ID NO: 116, and a light chain constant region having at least 90% sequence identity to the light chain constant region contained within the amino acid sequence set forth in SEQ ID NO: 117.

In some embodiments, provided are anti-idiotype antibodies or antigen-binding fragments thereof that include a heavy chain comprising an amino acid sequence having at least 90% sequence identity to the amino acid sequence set forth in SEQ ID NO: 116, and a light chain comprising an amino acid sequence having at least 90% sequence identity to the amino acid sequence set forth in SEQ ID NO: 117.

In some embodiments, provided are anti-idiotype antibodies or antigen-binding fragments thereof that include a heavy chain comprising the amino acid sequence set forth in SEQ ID NO: 116, and a light chain comprising the amino acid sequence set forth in SEQ ID NO: 117.

In some embodiments, the anti-idiotype antibody is an antigen-binding fragment. In some embodiments, the antigen-binding fragment is selected from the group consisting of fragment antigen binding (Fab) fragments, F(ab')₂ fragments, Fab' fragments, Fv fragments, a single chain variable fragment (scFv) or a single domain antibody.

Accordingly, provided are single-chain antibody fragments, such as scFvs and diabodies, particularly human single-chain fragments, typically comprising linker(s) joining two anti-idiotype antibody domains or regions, such $V_H$ and $V_L$ domains. The linker typically is a peptide linker, e.g., a flexible and/or soluble peptide linker, such as one rich in glycine and serine.

In some aspects, the linkers rich in glycine and serine (and/or threonine) include at least 80, 85, 90, 91, 92, 93, 94, 95, 96, 97, 98, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length.

In some embodiments, the anti-idiotype antibodies include isolated antibodies. In some embodiments, the anti-ID is humanized, recombinant, and/or monoclonal. In some embodiments, the anti-ID is human.

In some embodiments, the anti-idiotype antibody specific for Target Antibody 2 is humanized. In particular embodiments, all or substantially all CDR amino acid residues of the humanized anti-idiotype antibody specific for Target Antibody 2 are derived from anti-Target Antibody 2 nonhuman CDRs. In some embodiments, the humanized anti-idiotype antibody specific for Target Antibody 2 includes at least a portion of an antibody constant region derived from a human antibody.

In certain embodiments, the humanized anti-idiotype antibody specific for Target Antibody 2 includes a human immunoglobulin (recipient antibody) in which residues from the heavy chain variable region of the recipient are replaced by residues from a heavy chain variable region of the nonhuman anti-idiotype antibody specific for Target Antibody 2. In some instances, FR residues of the human immunoglobulin are replaced by corresponding non-human residues. In some embodiments, the humanized antibody contains FR derived from different genes. In some embodiments, the humanized anti-idiotype antibody specific for Target Antibody 2 contains at least a portion of an immunoglobulin constant region (Fc), typically that of a human immunoglobulin.

In some embodiments, the humanized anti-idiotype antibody specific for Target Antibody 2 contains an altered human acceptor antibody variable domain sequences that have been rendered to encode one or more amino acid residues of position 4, 35, 38, 43, 44, 46, 58, 62, 64, 65, 66, 67, 68, 69, 73, 85, 98 (Kabat) of the light variable region and 2, 4, 36, 39, 43, 45, 69, 70, 74, 75, 76, 78, 92 (Kabat) of the heavy variable region corresponding to the non-human donor sequence.

In certain embodiments, the anti-idiotype antibody specific for Target Antibody 2 is humanized. In particular embodiments, the humanized anti-idiotype antibody specific for Target Antibody 2 contains one or more of a CDR-L1, CDR-L2, CDR-L3 and CDR-H1, CDR-H2, CDR-H3 region of a non-human anti-idiotype antibody that is specific for Target Antibody 2. In some embodiments, some or all of the CDR-L1, CDR-L2, CDR-L3 and CDR-H1, CDR-H2, CDR-H3 region of contain one or more amino acid modifications. In some embodiments, the modifications replacing a non-human amino acid residue with a human residue. In particular embodiments, the one or more of the CDR-L1, CDR-L2, CDR-L3 and CDR-H1, CDR-H2, CDR-H3 are inserted into the FR regions of a human antibody. In particular embodiments, the CDR-L1, CDR-L2, CDR-L3 and CDR-H1, CDR-H2, CDR-H3 of the nonhuman anti-idiotype antibody are the CDRs of the VH and VL regions having amino acid sequences set forth in SEQ ID NOs: 84 and 85, respectively. In particular embodiments, the CDR-L1, CDR-L2, CDR-L3 and CDR-H1, CDR-H2, CDR-H3 of the nonhuman anti-idiotype antibody are the CDRs of the VH and VL regions having amino acid sequences set forth in SEQ ID NOs: 114 and 115, respectively. In some embodiments, all of the CDR-L1, CDR-L2, CDR-L3 and CDR-H1, CDR-H2, CDR-H3 of the anti-idiotype antibody specific for Target Antibody 2 are inserted into the FRs of the human antibody. In particular embodiments, the CDR and FR regions are the regions as identified by Kabat, Chothia, AbM, and/or and Contact schemes.

In particular embodiments, one or more or all of the CDR-L1, CDR-L2, CDR-L3 and CDR-H1, CDR-H2, CDR-H3 of the nonhuman anti-idiotype antibody specific for Target Antibody 2 are inserted into framework regions of a human antibody. In certain embodiments, the human antibody is an IgA, IgD, IgE, IgG, and IgM antibody. In particular embodiments, the human antibody is one of a subclass of human IgA, IgD, IgE, IgG, and IgM, e.g., human $IgG_1$, $IgG_2$, $IgG_3$, $IgG_4$, $IgA_1$, or $IgA_2$. In some embodiments, one or more or all of the CDR-L1, CDR-L2, CDR-L3 and CDR-H1, CDR-H2, CDR-H3 of the nonhuman anti-idiotype antibody specific for Target Antibody 2 are inserted into framework regions of an antigen binding region that is from and/or is derived from a human antibody. In certain embodiments, the antigen binding fragment is from and/or is derived from a human IgA, IgD, IgE, IgG, and IgM antibody. The subunit structures and three-dimensional configurations of different classes of human immunoglobulins are well known and described generally in, for example, Abbas et al. Cellular and Mol. Immunology, 4th ed. (W.B. Saunders, Co., 2000). In some embodiments, the human antibody or antigen binding fragment thereof may be part of a larger fusion molecule, formed by covalent or non-covalent association of the human antibody with one or more other proteins or peptides.

In some embodiments, one or more or all of the CDR-L1, CDR-L2, CDR-L3 and CDR-H1, CDR-H2, CDR-H3 of the nonhuman anti-idiotype antibody specific for Target Antibody 2 are inserted into framework regions of a human antibody or antigen-binding fragment thereof having all or a portion of an Fc region. In certain embodiments, the humanized anti-idiotype antibody specific for Target Antibody 2 contains all or a portion of an Fc region. In some embodiments, the Fc region has one or more modifications, such as an amino acid modification (e.g. a substitution, insertion, or deletion) at one or more amino acid positions. Such modifications can be made, for example, to improve half-life, alter binding to one or more types of Fc receptors, and/or alter effector functions. In some embodiments, modified Fc regions have altered (e.g., decreased) binding to FcαRs, relative to that of an unmodified Fc region. In certain embodiments, the humanized anti-idiotype antibody contains all or a portion of a modified Fc region having an altered (e.g., decreased) binding to Fc receptor relative to that of an unmodified Fc region. Non-limiting examples of Fc modifications that alter its binding to the Fc receptors are described, for example, in U.S. Pat. Nos. 7,217,797 and 7,732,570; and U.S. Application Nos. US 2010/0143254 and 2010/0143254.

In some embodiments, the dissociation constant ($K_D$) and/or the off rate ($k_{off}$) of any of the provided anti-idiotype antibodies or antigen-binding fragments thereof that bind to or recognize Target Antibody 2 or an antigen-binding fragment thereof is lower than that of other reagents that bind to or recognize Target Antibody 2 or an antigen-binding fragment thereof. In some embodiments, the dissociation constant and/or the off rate is lower than that of BCMA-Fc. In some embodiments, the dissociation constant and the off rate is lower than that of BCMA-Fc. In some aspects, a lower dissociation constant allows for stronger binding between Target Antibody 2, antigen-binding fragments thereof, or CARs containing same and the provided anti-idiotype antibodies or antigen-binding fragments thereof. In some aspects, a lower off rate allows for longer binding between Target Antibody 2, antigen-binding fragments thereof, or CARs containing same and the provided anti-idiotype antibodies or antigen-binding fragments thereof. Thus, in some aspects, detection, isolation, and stimulation of Target Antibody 2, antigen-binding fragments thereof, or CARs containing same is improved by use of the provided anti-idiotype antibodies or antigen-binding fragments thereof, relative to use of other reagents (e.g., BCMA-Fc). For instance, use of the provided anti-idiotype antibodies or antigen-binding fragments thereof can allow for stable binding to Target Antibody 2, antigen-binding fragments thereof, or CARs containing same, thereby improving the detection and isolation of these targets. Similarly, such use can allow for more persistent stimulation of said CARs and cells, e.g., T cells, engineered to express same.

In certain embodiments, the binding affinity (EC50) and/or the dissociation constant of any of the provided anti-idiotype antibodies or antigen-binding fragments thereof that bind to or recognize Target Antibody 2 or an antigen-binding fragment thereof, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the EC50 of any of the provided anti-idiotype antibodies or antigen-binding fragments thereof that bind to or recognize Target Antibody 2 or an antigen-binding fragment thereof, is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In certain embodiments, the dissociation constant of any of the provided anti-idiotype antibodies or antigen-binding fragments thereof that bind to or recognize Target Antibody 2 or an antigen-binding fragment thereof, is at or about or less than at or about 100 nM, 50 nM, 40 nM, 30 nM, 25 nM, 20 nM, 19, 18, 17, 16, 15, 14, 13, 12, 11, 10, 9, 8, 7, 6, 5, 4, 3, 2, or 1 nM, such as between at or about 1 nM and at or about 15 nM, e.g., between at or about 5 and at or about 10 nM. In certain embodiments, the extent of binding of any of the provided anti-idiotype antibodies or antigen-binding fragments thereof that bind to or recognize Target Antibody 2 or an antigen-binding fragment thereof to a moiety unrelated to the target anti-BCMA moiety is less than, at, or about 10% of the binding of the antibody to the target anti-BCMA moiety as measured, e.g., by a radioimmuno-assay (RIA). In some embodiments, any of the provided anti-idiotype antibodies or antigen-binding fragments thereof that bind to or recognize Target Antibody 2 or an antigen-binding fragment thereof is an agonist of a CAR containing the antigen-binding domain of Target Antibody 2 when immobilized on a support, such as a bead or a plate.

In some embodiments, the anti-idiotype antibody or anti-gen-binding fragment thereof thereof that binds to or recognizes Target Antibody 2 or an antigen-binding fragment thereof is an agonist of a CAR containing the antigen-binding domain of Target Antibody 2 when in soluble form. In some embodiments, the anti-idiotype antibodies or anti-gen-binding fragments thereof that bind to or recognize Target Antibody 2 or an antigen-binding fragment thereof and comprises a VH region comprising the amino acid sequence set forth in SEQ ID NO: 114 and a VL region comprising the amino acid sequence set forth in SEQ ID NO: 115 is an agonist of a CAR containing the antigen-binding domain of Target Antibody 2 when in soluble form.

In some embodiments, the anti-idiotype antibody or anti-gen-binding fragment thereof that binds to or recognizes Target Antibody 2 or an antigen-binding fragment thereof is not blocked by exposure to soluble BCMA or by BCMA-Fc. In some embodiments, the anti-idiotype antibody or antigen-binding fragment thereof that binds to or recognizes Target Antibody 2 or an antigen-binding fragment thereof and comprises a VH region comprising the amino acid sequence of SEQ ID NO: 84 and a VL region comprising the amino acid sequence of SEQ ID NO: 85 is not blocked by exposure to soluble BCMA or by BCMA-Fc.

Also provided are nucleic acids encoding the provided anti-idiotype antibodies or antigen-binding fragments thereof that bind to or recognize Target Antibody 2 or an antigen-binding fragment thereof. Among the provided nucleic acids are those encoding the anti-idiotype antibodies described herein. The nucleic acids may include those encompassing natural and/or non-naturally occurring nucleotides and bases, e.g., including those with backbone modifications.

In some embodiments, the nucleic acid molecule(s) encoding anti-idiotype antibodies and/or portions, e.g., chains, thereof comprise a sequence of nucleotides that encode the VH region and comprises the sequence of nucleotides set forth in SEQ ID NO: 90, and a sequence of nucleotides that encode the VL region and comprises the sequence of nucleotides set forth in SEQ ID NO: 91. In some embodiments, the nucleic acid molecule(s) encoding anti-idiotype antibodies and/or portions, e.g., chains, thereof comprise a sequence of nucleotides that encode the heavy chain and comprises the sequence of nucleotides set forth in SEQ ID NO: 88, and a sequence of nucleotides that encode the light chain and comprises the sequence of nucleotides set forth in SEQ ID NO: 89.

In some embodiments, the nucleic acid molecule(s) encoding anti-idiotype antibodies and/or portions, e.g., chains, thereof comprise a sequence of nucleotides that encode the VH region and comprises the sequence of nucleotides set forth in SEQ ID NO: 120, and a sequence of nucleotides that encode the VL region and comprises the sequence of nucleotides set forth in SEQ ID NO: 121. In some embodiments, the nucleic acid molecule(s) encoding anti-idiotype antibodies and/or portions, e.g., chains, thereof comprise a sequence of nucleotides that encode the heavy chain and comprises the sequence of nucleotides set forth in SEQ ID NO: 118, and a sequence of nucleotides that encode the light chain and comprises the sequence of nucleotides set forth in SEQ ID NO: 119.

Also provided are vectors containing the nucleic acids, host cells containing the vectors, e.g., for producing the antibodies. Also provided are methods for producing the antibodies. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, a method of making the anti-idiotype antibody is provided, wherein the method comprises culturing a host cell comprising a nucleic acid encoding the antibody, as provided above, under conditions suitable for expression of the antibody, and optionally recovering the antibody from the host cell (or host cell culture medium).

Exemplary nucleic acids and vectors include those having the sequences set forth in one or more of SEQ ID NOs: 88-91, and 118-121, and CDR-encoding portions thereof, as well as sequences containing at least at or about 90, 91, 92, 93, 94, 95, 96, 97, 98, or 99% identity thereto. The nucleic acid may encode an amino acid sequence comprising the $V_L$ and/or an amino acid sequence comprising the $V_H$ of the anti-idiotype antibody (e.g., the light and/or heavy chains of the antibody).

B. Anti-ID Antibodies Against Target Antibody 1 and/or Target Antibody 2

In some embodiments, provided are anti-idiotype antibodies that binds to or recognizes (1) a target anti-BCMA antibody that is or is derived from Target Antibody 1, or is an antigen-binding fragment thereof, as described above, and/or (2) a target anti-BCMA antibody that is or is derived from Target Antibody 2, or is an antigen-binding fragment thereof, as described above. In some embodiments, provided are anti-idiotype antibodies that binds to or recognizes (1) a target anti-BCMA antibody that is or is derived from Target Antibody 1, or is an antigen-binding fragment thereof, as described above, and (2) a target anti-BCMA antibody that is or is derived from Target Antibody 2, or is an antigen-binding fragment thereof, as described above. In some embodiments, provided are anti-idiotype antibodies that binds to or recognizes (1) a target anti-BCMA antibody that is or is derived from Target Antibody 1, or is an antigen-binding fragment thereof, as described above, or (2) a target anti-BCMA antibody that is or is derived from Target Antibody 2, or is an antigen-binding fragment thereof, as described above. In some embodiments, provided are anti-idiotype antibodies that bind to or recognize a target anti-BCMA antibody or an antigen-binding fragment thereof that is or is derived from Target Antibody 1 to a greater extent than it to a target anti-BCMA antibody or an antigen-binding fragment thereof that is or is derived from Target Antibody 2. In some embodiments, provided are anti-idiotype antibodies that bind to or recognize a target anti-BCMA antibody or an antigen-binding fragment thereof that is or is derived from Target Antibody 2 to a greater extent than it to a target anti-BCMA antibody or an antigen-binding fragment thereof that is or is derived from Target Antibody 1. Accordingly, in some embodiments, provided are anti-idiotype antibodies that bind to or recognize more than one target anti-BCMA antibody, e.g., two different anti-BCMA antibodies, such as Target Antibody 1 and Target Antibody 2. In some embodiments, provided are anti-idiotype antibodies that specifically bind to a target anti-BCMA antibody that is or is derived from Target Antibody 1, and specifically bind to a target anti-BCMA antibody that is or is derived from Target Antibody 2. In some embodiments, provided are anti-idiotype antibodies that specifically bind to a target anti-BCMA antibody that is or is derived from Target Antibody 1, or specifically bind to a target anti-BCMA antibody that is or is derived from Target Antibody 2. Exemplary antibodies or antigen-binding fragments thereof are provided below.

In some embodiments, Target Antibody 1 is referred to as a first target antibody or antigen-binding fragment thereof. In some embodiments, Target Antibody 2 is referred to as a first target antibody or antigen-binding fragment thereof. In some embodiments, Target Antibody 1 is referred to as a second target antibody or antigen-binding fragment thereof. In some embodiments, Target Antibody 2 is referred to as a second target antibody or antigen-binding fragment thereof. In some embodiments, Target Antibody 1 is referred to as a first target antibody or antigen-binding fragment thereof, and Target Antibody 2 is referred to as a second target antibody or antigen-binding fragment thereof.

In some embodiments, the provided anti-idiotype antibodies binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 11, and a VL region having at least 90%, 91%, 92%, 93%, 94%, 95%, 96%, 97%, 98%, or 99% sequence identity to the amino acid sequence set forth in SEQ ID NO: 12; and binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes an antibody or antigen-binding fragment thereof that includes a VH region having the amino acid sequence set forth in SEQ ID NO: 11, and a VL region having the amino acid sequence set forth in SEQ ID NO: 12; and binds to or recognizes an antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes a target anti-BCMA antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 11, and a VL region having at least 90%, 91%, 92%, 93%, 94%, 95%, 96%, 97%, 98%, or 99% sequence identity to the amino acid sequence set forth in SEQ ID NO: 12; and binds to or recognizes a target anti-BCMA antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes a target anti-BCMA antibody or antigen-binding fragment thereof that includes a VH region having the amino acid sequence set forth in SEQ ID NO: 11, and a VL region having the amino acid sequence set forth in SEQ ID NO: 12; and binds to or recognizes a target anti-BCMA antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 11, and a VL region having at least 90%, 91%, 92%, 93%, 94%, 95%, 96%, 97%, 98%, or 99% sequence identity to the amino acid sequence set forth in SEQ ID NO: 12; or binds to or recognizes an antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes an antibody or antigen-binding fragment thereof that includes a VH region having the amino acid sequence set forth in SEQ ID NO: 11, and a VL region having the amino acid sequence set forth in SEQ ID NO: 12; or binds to or recognizes an antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes a target anti-BCMA antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 11, and a VL region having at least 90%, 91%, 92%, 93%, 94%, 95%, 96%, 97%, 98%, or 99% sequence identity to the amino acid sequence set forth in SEQ ID NO: 12; or binds to or recognizes a target anti-BCMA antibody or antigen-binding fragment thereof that includes a VH region having at least 90%, 91%, 92%, 93%, 94%, 95%, 96%, 97%, 98%, or 99% sequence identity to the amino acid sequence set forth in SEQ ID NO: 25, and a VL region having at least 90%, 91%, 92%, 93%, 94%, 95%, 96%, 97%, 98%, or 99% sequence identity to the amino acid sequence set forth in SEQ ID NO: 26. In some embodiments, the provided anti-idiotype antibodies binds to or recognizes a target anti-BCMA antibody or antigen-binding fragment thereof that includes a VH region having the amino acid sequence set forth in SEQ ID NO: 11, and a VL region having the amino acid sequence set forth in SEQ ID NO: 12; or binds to or recognizes a target anti-BCMA antibody or antigen-binding fragment thereof that includes a VH region having the amino acid sequence set forth in SEQ ID NO: 25, and a VL region having the amino acid sequence set forth in SEQ ID NO: 26.

In some embodiments, the provided anti-idiotype antibodies binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 13; and binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes an scFv having the amino acid sequence set forth in SEQ ID NO: 13; and binds to or recognizes an scFv having the amino acid sequence set forth in SEQ ID NO: 27.

In some embodiments, the provided anti-idiotype antibodies binds to or recognizes a target anti-BCMA antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 13; and binds to or recognizes a target anti-BCMA antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes a target anti-BCMA antibody that is an scFv having the amino acid sequence set forth in SEQ ID NO: 13; and binds to or recognizes a target anti-BCMA antibody that is an scFv having the amino acid sequence set forth in SEQ ID NO: 27.

In some embodiments, the provided anti-idiotype antibodies binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 13; or binds to or recognizes an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes an scFv having the amino acid sequence set forth in SEQ ID NO: 13; and binds to or recognizes an scFv having the amino acid sequence set forth in SEQ ID NO: 27.

In some embodiments, the provided anti-idiotype antibodies binds to or recognizes a target anti-BCMA antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 13; or binds to or recognizes a target anti-BCMA antibody that is an scFv that includes an amino acid sequence having at least 90%, 91%, 92%, 93%, 94%, 95%, 96%, 97%, 98%, or 99% sequence identity to the amino acid sequence set forth in SEQ ID NO: 27. In some embodiments, the provided anti-idiotype antibodies binds to or recognizes a target anti-BCMA antibody that is an scFv having the amino acid sequence set forth in SEQ ID NO: 13; and binds to or recognizes a target anti-BCMA antibody that is an scFv having the amino acid sequence set forth in SEQ ID NO: 27.

In some embodiments, the provided anti-idiotype antibodies binds to or recognizes an antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10; and binds to or recognizes an antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes a target anti-BCMA antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10; and binds to or recognizes a target anti-BCMA antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes an antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10; or binds to or recognizes an antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes a target anti-BCMA antibody or antigen-binding fragment thereof that includes a CDR-H1 having the amino acid sequence set forth in SEQ ID NO: 1, a CDR-H2 having the amino acid sequence set forth in SEQ ID NO: 2, and a CDR-H3 having the amino acid sequence set forth in SEQ ID NO: 3; and a CDR-L1 having the amino acid sequence set forth in SEQ ID NO: 8, a CDR-L2 having the amino acid sequence set forth in SEQ ID NO: 9, and a CDR-L3 having the amino acid sequence set forth in SEQ ID NO: 10; or binds to or recognizes a target anti-BCMA antibody or antigen-binding fragment thereof that includes a CDR-H1 having the amino acid sequence set forth in SEQ ID NO: 15, a CDR-H2 having the amino acid sequence set forth in SEQ ID NO: 16, and a CDR-H3 having the amino acid sequence set forth in SEQ ID NO: 17; and a CDR-L1 having the amino acid sequence set forth in SEQ ID NO: 22, a CDR-L2 having the amino acid sequence set forth in SEQ ID NO: 23, and a CDR-L3 having the amino acid sequence set forth in SEQ ID NO: 24.

In some embodiments, the provided anti-idiotype antibodies binds to or recognizes an antibody or antigen-binding fragment thereof that has the same idiotype as Target Antibody 1; and binds to or recognizes an antibody or antigen-binding fragment thereof that has the same idiotype as Target Antibody 2. In some embodiments, the provided anti-idiotype antibodies binds to or recognizes an antibody or antigen-binding fragment thereof that has the same idiotype as Target Antibody 1; or binds to or recognizes an antibody or antigen-binding fragment thereof that has the same idiotype as Target Antibody 2.

In some embodiments, the provided anti-idiotype antibodies binds to or recognizes a target anti-BCMA antibody or antigen-binding fragment thereof that has the same idiotype as Target Antibody 1; and binds to or recognizes a target anti-BCMA antibody or antigen-binding fragment thereof that has the same idiotype as Target Antibody 2. In some embodiments, the provided anti-idiotype antibodies binds to or recognizes a target anti-BCMA antibody or antigen-binding fragment thereof that has the same idiotype as Target Antibody 1; or binds to or recognizes a target anti-BCMA antibody or antigen-binding fragment thereof that has the same idiotype as Target Antibody 2.

In some embodiments, the provided anti-idiotype antibodies competes for binding to Target Antibody 1 with an antibody or antigen-binding fragment thereof that includes a VH region comprising the amino acid sequence set forth in SEQ ID NO: 62 and a VL region comprising the amino acid sequence set forth in SEQ ID NO: 63; and/or competes for binding to Target Antibody 2 with an antibody or antigen-binding fragment thereof that includes a VH region comprising the amino acid sequence set forth in SEQ ID NO: 84 and a VL region comprising the amino acid sequence set forth in SEQ ID NO: 85.

In some embodiments, the provided anti-idiotype antibodies competes for binding to Target Antibody 1 with an antibody or antigen-binding fragment thereof that includes a VH region comprising the amino acid sequence set forth in SEQ ID NO: 62 and a VL region comprising the amino acid sequence set forth in SEQ ID NO: 63; or competes for binding to Target Antibody 2 with an antibody or antigen-binding fragment thereof that includes a VH region comprising the amino acid sequence set forth in SEQ ID NO: 84 and a VL region comprising the amino acid sequence set forth in SEQ ID NO: 85.

In some embodiments, the provided anti-idiotype antibodies competes for binding to Target Antibody 1 with an antibody or antigen-binding fragment thereof that includes a VH region comprising the amino acid sequence set forth in SEQ ID NO: 62 and a VL region comprising the amino acid sequence set forth in SEQ ID NO: 63; and/or competes for binding to Target Antibody 2 with an antibody or antigen-binding fragment thereof that includes a VH region comprising the amino acid sequence set forth in SEQ ID NO: 114 and a VL region comprising the amino acid sequence set forth in SEQ ID NO: 115.

In some embodiments, the provided anti-idiotype antibodies competes for binding to Target Antibody 1 with an antibody or antigen-binding fragment thereof that includes a VH region comprising the amino acid sequence set forth in SEQ ID NO: 62 and a VL region comprising the amino acid sequence set forth in SEQ ID NO: 63; or competes for binding to Target Antibody 2 with an antibody or antigen-binding fragment thereof that includes a VH region comprising the amino acid sequence set forth in SEQ ID NO: 114 and a VL region comprising the amino acid sequence set forth in SEQ ID NO: 115.

In some embodiments, the provided anti-idiotype antibodies bind to or recognize an antibody or antigen-binding fragment thereof that competes for binding with Target Antibody 1; and bind to or recognize an antibody or antigen-binding fragment thereof that competes for binding with Target Antibody 2. In some embodiments, the provided anti-idiotype antibodies bind to or recognize an antibody or antigen-binding fragment thereof that competes for binding with Target Antibody 1; or bind to or recognize an antibody or antigen-binding fragment thereof that competes for binding with Target Antibody 2.

In some embodiments, the provided anti-idiotype antibodies bind to or recognize a target anti-BCMA antibody or antigen-binding fragment thereof that competes for binding with Target Antibody 1; and bind to or recognize a target anti-BCMA antibody or antigen-binding fragment thereof that competes for binding with Target Antibody 2. In some embodiments, the provided anti-idiotype antibodies bind to or recognize a target anti-BCMA antibody or antigen-binding fragment thereof that competes for binding with Target Antibody 1; or bind to or recognize a target anti-BCMA antibody or antigen-binding fragment thereof that competes for binding with Target Antibody 2.

In some embodiments, the provided anti-idiotype antibodies bind to or recognize the antigen-binding domain of Target Antibody 1 that is contained within a CAR; and bind to or recognize the antigen-binding domain of Target Antibody 2 that is contained within a CAR. In some embodiments, the provided anti-idiotype antibodies bind to or recognize the antigen-binding domain of Target Antibody 1 that is contained within a CAR; or bind to or recognize the antigen-binding domain of Target Antibody 2 that is contained within a CAR.

In some embodiments, the provided anti-idiotype antibodies bind to or recognize the antigen-binding domain of Target Antibody 1 as contained within a CAR; and bind to or recognize the antigen-binding domain of Target Antibody 2 as contained within a CAR. In some embodiments, the provided anti-idiotype antibodies bind to or recognize the antigen-binding domain of Target Antibody 1 as contained within a CAR; or bind to or recognize the antigen-binding domain of Target Antibody 2 as contained within a CAR. In some embodiments, the CAR is any as described in Section II.

In some embodiments, provided are anti-idiotype antibodies or antigen-binding fragments thereof that include a VH region comprising at least 90% sequence identity to the VH region amino acid sequence set forth in SEQ ID NO: 38, such as at least 91%, 92%, 93%, 94%, 95%, 96%, 97%, 98%, or 99% sequence identity thereto; and a VL region comprising at least 90% sequence identity to the VL region amino acid sequence set forth in SEQ ID NO: 39, such as at least 91%, 92%, 93%, 94%, 95%, 96%, 97%, 98%, or 99% sequence identity thereto. In some of any such embodiments, the VH region comprises the amino acid sequence of SEQ ID NO: 38. In some of any such embodiments, the VL region comprises the amino acid sequence of SEQ ID NO: 39. In some of any such embodiments, the VH region comprises the amino acid sequence of SEQ ID NO: 38, and the VL region comprises the amino acid sequence of SEQ ID NO: 39.

In some embodiments, provided are anti-idiotype antibodies or antigen-binding fragments thereof that include a VH region comprising a CDR-H1 comprising the amino acid sequence set forth in SEQ ID NO: 28, a CDR-H2 comprising the amino acid sequence set forth in SEQ ID NO: 29, and a CDR-H3 comprising the amino acid sequence set forth in SEQ ID NO: 30; and a VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37. In some embodiments, provided are anti-idiotype antibodies or antigen-binding fragments thereof that include a VH region comprising a CDR-H1 comprising the amino acid sequence set forth in SEQ ID NO: 31, a CDR-H2 comprising the amino acid sequence set forth in SEQ ID NO: 32, and a CDR-H3 comprising the amino acid sequence set forth in SEQ ID NO: 30; and a VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37. In some embodiments, provided are anti-idiotype antibodies or antigen-binding fragments thereof that include a VH region comprising a CDR-H1 comprising the amino acid sequence set forth in SEQ ID NO: 33, a CDR-H2 comprising the amino acid sequence set forth in SEQ ID NO: 34, and a CDR-H3 comprising the amino acid sequence set forth in SEQ ID NO: 30; and a VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37.

In some embodiments, provided are anti-idiotype antibodies or antigen-binding fragments thereof that include a CDR-H1, a CDR-H2, and a CDR-H3, respectively, comprising the amino acid sequences of a CDR-H1, a CDR-H2, and a CDR-H3 contained within the VH region amino acid sequence set forth in SEQ ID NO: 38; and a CDR-L1, a CDR-L2, and a CDR-L3, respectively, comprising the amino acid sequences of a CDR-L1, a CDR-L2, and a CDR-L3 contained within the VL region amino acid sequence set forth in SEQ ID NO: 39.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 38. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 38. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 38.

In some of any such embodiments, the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 39. In some embodiments, the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 39. In some embodiments, the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 39.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 38, and the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 39. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 38, and the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 39. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 38, and the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 39.

In some of any such embodiments, the VH region has the sequence of amino acids set forth in SEQ ID NO: 38. In some of any such embodiments, the VL region has the sequence of amino acids set forth in SEQ ID NO: 39. In some of any such embodiments, the VH region has the sequence of amino acids set forth in SEQ ID NO: 38, and the VL region has the sequence of amino acids set forth in SEQ ID NO: 39.

In some of any such embodiments, provided are anti-idiotype antibodies or antigen-binding fragments thereof that include a VH region comprising a CDR-H1 comprising the amino acid sequence set forth in SEQ ID NO: 28, a CDR-H2 comprising the amino acid sequence set forth in SEQ ID NO: 29, and a CDR-H3 comprising the amino acid sequence set forth in SEQ ID NO: 30; and a VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37; a VH region comprising the amino acid set forth in SEQ ID NO: 38; a VL region comprising the amino acid set forth in SEQ ID NO: 39; a heavy chain comprising the amino acid sequence set forth in SEQ ID NO: 40, and a light chain comprising the amino acid sequence set forth in SEQ ID NO: 41.

In some embodiments, the anti-idiotype antibody that binds to or recognizes Target Antibody 1 or an antigen-binding fragment thereof, and Target Antibody 2 or an antigen-binding fragment thereof, is a single-chain antibody fragment, such as an scFv or diabody. In some embodiments, the single-chain antibody includes one or more linkers joining two antibody domains or regions, such as a variable heavy chain (VH) region and a variable light chain (VL) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some embodiments, the anti-idiotype antibody is an intact antibody or full-length antibody. In some embodiments, the anti-ID may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4.

In some embodiments, provided are anti-idiotype antibodies or antigen-binding fragments thereof that include a heavy chain constant region contained within the amino acid sequence set forth in SEQ ID NO: 40, and a light chain constant region contained within the amino acid sequence set forth in SEQ ID NO: 41. In some embodiments, provided are anti-idiotype antibodies or antigen-binding fragments thereof that include a heavy chain constant region having at least 90% sequence identity to the heavy chain constant region contained within the amino acid sequence set forth in SEQ ID NO: 40, and a light chain constant region having at least 90% sequence identity to the light chain constant region contained within the amino acid sequence set forth in SEQ ID NO: 41.

In some embodiments, provided are anti-idiotype antibodies or antigen-binding fragments thereof that include a heavy chain comprising an amino acid sequence having at least 90% sequence identity to the amino acid sequence set forth in SEQ ID NO: 40, and a light chain comprising an amino acid sequence having at least 90% sequence identity to the amino acid sequence set forth in SEQ ID NO: 41.

In some embodiments, provided are anti-idiotype antibodies or antigen-binding fragments thereof that include a heavy chain comprising the amino acid sequence set forth in SEQ ID NO: 40, and a light chain comprising the amino acid sequence set forth in SEQ ID NO: 41.

Also provided are nucleic acids encoding the provided anti-idiotype antibodies or antigen-binding fragments thereof that bind to or recognize Target Antibody and Target Antibody 2, or antigen-binding fragments thereof. Among the provided nucleic acids are those encoding the anti-idiotype antibodies described herein. The nucleic acids may include those encompassing natural and/or non-naturally occurring nucleotides and bases, e.g., including those with backbone modifications. In some embodiments, the nucleic acid molecule(s) encoding anti-idiotype antibodies and/or portions, e.g., chains, thereof comprise a sequence of nucleotides that encode the VH region and comprises the sequence of nucleotides set forth in SEQ ID NO: 48, and a sequence of nucleotides that encode the VL region and comprises the sequence of nucleotides set forth in SEQ ID NO: 49. In some embodiments, the nucleic acid molecule(s) encoding anti-idiotype antibodies and/or portions, e.g., chains, thereof comprise a sequence of nucleotides that encode the heavy chain and comprises the sequence of nucleotides set forth in SEQ ID NO: 42, and a sequence of nucleotides that encode the light chain and comprises the sequence of nucleotides set forth in SEQ ID NO: 43.

Also provided are vectors containing the nucleic acids, host cells containing the vectors, e.g., for producing the antibodies. Also provided are methods for producing the antibodies. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, a method of making the anti-idiotype antibody is provided, wherein the method comprises culturing a host cell comprising a nucleic acid encoding the antibody, as provided above, under conditions suitable for expression of the antibody, and optionally recovering the antibody from the host cell (or host cell culture medium).

Exemplary nucleic acids and vectors include those having the sequences set forth in one or more of SEQ ID NOs: 42, 43, 48, and 49, and CDR-encoding portions thereof, as well as sequences containing at least at or about 90, 91, 92, 93, 94, 95, 96, 97, 98, or 99% identity thereto. The nucleic acid may encode an amino acid sequence comprising the $V_L$ and/or an amino acid sequence comprising the $V_H$ of the anti-idiotype antibody (e.g., the light and/or heavy chains of the antibody).

In some embodiments, the provided anti-idiotype antibodies or antigen-binding fragments thereof include a VH region comprising at least 90% sequence identity to the VH region amino acid sequence set forth in SEQ ID NO: 62, such as at least 91%, 92%, 93%, 94%, 95%, 96%, 97%, 98%, or 99% sequence identity thereto; and a VL region comprising at least 90% sequence identity to the VL region amino acid sequence set forth in SEQ ID NO: 63, such as at least 91%, 92%, 93%, 94%, 95%, 96%, 97%, 98%, or 99% sequence identity thereto.

In some embodiments, the provided anti-idiotype antibodies or antigen-binding fragments thereof includes VH region comprising a CDR-H1 comprising the amino acid sequence set forth in SEQ ID NO: 52, a CDR-H2 comprising the amino acid sequence set forth in SEQ ID NO: 53, and a CDR-H3 comprising the amino acid sequence set forth in SEQ ID NO: 54; and a VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61. In some embodiments, the provided anti-idiotype antibodies or antigen-binding fragments thereof include a VH region comprising a CDR-H1 comprising the amino acid sequence set forth in SEQ ID NO: 55, a CDR-H2 comprising the amino acid sequence set forth in SEQ ID NO: 56, and a CDR-H3 comprising the amino acid sequence set forth in SEQ ID NO: 54; and a VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61. In some embodiments, the provided anti-idiotype antibodies or antigen-binding fragments thereof include a VH region comprising a CDR-H1 comprising the amino acid sequence set forth in SEQ ID NO: 57, a CDR-H2 comprising the amino acid sequence set forth in SEQ ID NO: 58, and a CDR-H3 comprising the amino acid sequence set forth in SEQ ID NO: 54; and a VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61.

In some embodiments, provided are anti-idiotype antibodies or antigen-binding fragments thereof that include a CDR-H1, a CDR-H2, and a CDR-H3, respectively, comprising the amino acid sequences of a CDR-H1, a CDR-H2, and a CDR-H3 contained within the VH region amino acid sequence set forth in SEQ ID NO: 62; and a CDR-L1, a CDR-L2, and a CDR-L3, respectively, comprising the amino acid sequences of a CDR-L1, a CDR-L2, and a CDR-L3 contained within the VL region amino acid sequence set forth in SEQ ID NO: 63.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 62. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 62. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 62.

In some of any such embodiments, the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 63. In some embodiments, the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 63. In some embodiments, the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 63.

In some of any such embodiments, the VH region contains a framework region 1 (FR1), a FR2, a FR3, and/or a FR4 sequence having at least 90% sequence identity, respectively, to a FR1, FR2, FR3, and/or FR4 of the amino acid sequence set forth in SEQ ID NO: 62, and the VL region comprises a framework region 1 (FR1), a FR2, a FR3, and/or a FR4 having at least 90% sequence identity, respectively, to the FR1, FR2, FR3, and/or FR4 of the amino acid sequence set forth in SEQ ID NO: 63. In some embodiments, the VH region contains a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 62, and the VL region comprises a framework region 1 (FR1), a FR2, a FR3, and/or a FR4 sequence having at least 91%, 92%, 93%, 94%, 95%, 96%, 97%, 98%, 98%, 99% sequence identity, respectively, to a FR1, FR2, FR3, and/or FR4 of the amino acid sequence set forth in SEQ ID NO: 63. In some embodiments, the VH region contains a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 62, and the VL region comprises a framework region 1 (FR1), a FR2, a FR3, and a FR4 sequence having at least 90%, 91%, 92%, 93%, 94%, 95%, 96%, 97%, 98%, 98%, 99% sequence identity, respectively, to a FR1, FR2, FR3, and FR4 of the amino acid sequence set forth in SEQ ID NO: 63.

In some of any such embodiments, the VH region has the sequence of amino acids set forth in SEQ ID NO: 62. In some of any such embodiments, the VL region has the sequence of amino acids set forth in SEQ ID NO: 63. In some of any such embodiments, the VH region has the sequence of amino acids set forth in SEQ ID NO: 62, and the VL region has the sequence of amino acids set forth in SEQ ID NO: 63.

In some embodiments, the anti-idiotype antibody specific to Target Antibody 1 or an antigen-binding fragment thereof is a single-chain antibody fragment, such as an scFv or diabody. In some embodiments, the single-chain antibody includes one or more linkers joining two antibody domains or regions, such as a variable heavy chain (VH) region and a variable light chain (VL) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline.

In some embodiments, the anti-idiotype antibody is an intact antibody or full-length antibody. In some embodiments, the anti-ID may contain at least a portion of an immunoglobulin constant region, such as one or more constant region domains. In some embodiments, the constant regions include a light chain constant region (CL) and/or a heavy chain constant region 1 (CH1). In some embodiments, the anti-ID includes a CH2 and/or CH3 domain, such as an Fc region. In some embodiments, the Fc region is an Fc region of a human IgG, such as IgG1 or IgG4.

In some embodiments, provided are anti-idiotype antibodies or antigen-binding fragments thereof that include a heavy chain constant region contained within the amino acid sequence set forth in SEQ ID NO: 64, and a light chain constant region contained within the amino acid sequence set forth in SEQ ID NO: 65. In some embodiments, provided are anti-idiotype antibodies or antigen-binding fragments thereof that include a heavy chain constant region having at least 90% sequence identity to the heavy chain constant region contained within the amino acid sequence set forth in SEQ ID NO: 64, and a light chain constant region having at least 90% sequence identity to the light chain constant region contained within the amino acid sequence set forth in SEQ ID NO: 65.

In some embodiments, provided are anti-idiotype antibodies or antigen-binding fragments thereof that include a heavy chain comprising an amino acid sequence having at least 90% sequence identity to the amino acid sequence set forth in SEQ ID NO: 64, and a light chain comprising an amino acid sequence having at least 90% sequence identity to the amino acid sequence set forth in SEQ ID NO: 65.

In some embodiments, provided are anti-idiotype antibodies or antigen-binding fragments thereof that include a heavy chain comprising the amino acid sequence set forth in SEQ ID NO: 64, and a light chain comprising the amino acid sequence set forth in SEQ ID NO: 65.

Also provided are nucleic acids encoding the provided anti-idiotype antibodies or antigen-binding fragments thereof that bind to or recognize Target Antibody 1 or an antigen-binding fragment thereof. Among the provided nucleic acids are those encoding the anti-idiotype antibodies described herein. The nucleic acids may include those encompassing natural and/or non-naturally occurring nucleotides and bases, e.g., including those with backbone modifications. In some embodiments, the nucleic acid molecule(s) encoding anti-idiotype antibodies and/or portions, e.g., chains, thereof comprise a sequence of nucleotides that encode the VH region and comprises the sequence of nucleotides set forth in SEQ ID NO: 67, and a sequence of nucleotides that encode the VL region and comprises the sequence of nucleotides set forth in SEQ ID NO: 68. In some embodiments, the nucleic acid molecule(s) encoding anti-idiotype antibodies and/or portions, e.g., chains, thereof comprise a sequence of nucleotides that encode the heavy chain and comprises the sequence of nucleotides set forth in SEQ ID NO: 66, and a sequence of nucleotides that encode the light chain and comprises the sequence of nucleotides set forth in SEQ ID NO: 69.

Also provided are vectors containing the nucleic acids, host cells containing the vectors, e.g., for producing the antibodies. Also provided are methods for producing the antibodies. In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the $V_L$ of the antibody and an amino acid sequence comprising the $V_H$ of the antibody, or (2) a first vector comprising a nucleic acid that encodes an amino acid sequence comprising the $V_L$ of the antibody and a second vector comprising a nucleic acid that encodes an amino acid sequence comprising the $V_H$ of the antibody. In some embodiments, a method of making the anti-idiotype antibody is provided, wherein the method comprises culturing a host cell comprising a nucleic acid encoding the antibody, as provided above, under conditions suitable for expression of the antibody, and optionally recovering the antibody from the host cell (or host cell culture medium).

Exemplary nucleic acids and vectors include those having the sequences set forth in one or more of SEQ ID NOs: 66-69, and CDR-encoding portions thereof, as well as sequences containing at least at or about 90, 91, 92, 93, 94, 95, 96, 97, 98, or 99% identity thereto. The nucleic acid may encode an amino acid sequence comprising the $V_L$ and/or an amino acid sequence comprising the $V_H$ of the anti-idiotype antibody (e.g., the light and/or heavy chains of the antibody).

In some embodiments, the anti-idiotype antibody is an antigen-binding fragment. In some embodiments, the antigen-binding fragment is selected from the group consisting of fragment antigen binding (Fab) fragments, F(ab')$_2$ fragments, Fab' fragments, Fv fragments, a single chain variable fragment (scFv) or a single domain antibody.

Accordingly, provided are single-chain antibody fragments, such as scFvs and diabodies, particularly human single-chain fragments, typically comprising linker(s) joining two anti-idiotype antibody domains or regions, such $V_H$ and $V_L$ domains. The linker typically is a peptide linker, e.g., a flexible and/or soluble peptide linker, such as one rich in glycine and serine.

In some aspects, the linkers rich in glycine and serine (and/or threonine) include at least 80, 85, 90, 91, 92, 93, 94, 95, 96, 97, 98, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length.

In some embodiments, the anti-idiotype antibodies include isolated antibodies. In some embodiments, the anti-ID is humanized, recombinant, and/or monoclonal. In some embodiments, the anti-ID is human.

In some embodiments, the anti-idiotype antibody that binds to or recognizes Target Antibody 1 and/or Target Antibody 2 is humanized. In particular embodiments, all or substantially all CDR amino acid residues of the humanized anti-idiotype antibody that binds to or recognizes Target Antibody 1 and/or Target Antibody 2 are derived from anti-Target Antibody 1/2 non-human CDRs. In some embodiments, the humanized anti-idiotype antibody that binds to or recognizes Target Antibody 1 and/or Target Antibody 2 includes at least a portion of an antibody constant region derived from a human antibody.

In certain embodiments, the humanized anti-idiotype antibody that binds to or recognizes Target Antibody 1 and/or Target Antibody 2 includes a human immunoglobulin (recipient antibody) in which residues from the heavy chain variable region of the recipient are replaced by residues from a heavy chain variable region of the nonhuman anti-idiotype antibody that binds to or recognizes Target Antibody 1 and/or Target Antibody 2. In some instances, FR residues of the human immunoglobulin are replaced by corresponding non-human residues. In some embodiments, the humanized antibody contains FR derived from different genes. In some embodiments, the humanized anti-idiotype antibody that binds to or recognizes Target Antibody 1 and/or Target Antibody 2 contains at least a portion of an immunoglobulin constant region (Fc), typically that of a human immuno-globulin.

In some embodiments, the humanized anti-idiotype antibody that binds to or recognizes Target Antibody 1 and/or Target Antibody 2 contains an altered human acceptor antibody variable domain sequences that have been rendered to encode one or more amino acid residues of position 4, 35, 38, 43, 44, 46, 58, 62, 64, 65, 66, 67, 68, 69, 73, 85, 98 (Kabat) of the light variable region and 2, 4, 36, 39, 43, 45, 69, 70, 74, 75, 76, 78, 92 (Kabat) of the heavy variable region corresponding to the non-human donor sequence.

In certain embodiments, the anti-idiotype antibody that binds to or recognizes Target Antibody 1 and/or Target Antibody 2 is humanized. In particular embodiments, the humanized anti-idiotype antibody that binds to or recognizes Target Antibody 1 and/or Target Antibody 2 contains one or more of a CDR-L1, CDR-L2, CDR-L3 and CDR-H1, CDR-H2, CDR-H3 region of a non-human anti-idiotype antibody that binds to or recognizes Target Antibody 1 and/or Target Antibody 2. In some embodiments, some or all of the CDR-L1, CDR-L2, CDR-L3 and CDR-H1, CDR-H2, CDR-H3 region of contain one or more amino acid modifications. In some embodiments, the modifications replacing a non-human amino acid residue with a human residue. In particular embodiments, the one or more of the CDR-L1, CDR-L2, CDR-L3 and CDR-H1, CDR-H2, CDR-H3 are inserted into the FR regions of a human antibody. In particular embodiments, the CDR-L1, CDR-L2, CDR-L3 and CDR-H1, CDR-H2, CDR-H3 of the nonhuman anti-idiotype antibody are the CDRs of the VH and VL regions having amino acid sequences set forth in SEQ ID NOs: 38 and 39, respectively. In some embodiments, all of the CDR-L1, CDR-L2, CDR-L3 and CDR-H1, CDR-H2, CDR-H3 of the anti-idiotype antibody that binds to or recognizes Target Antibody 1 are inserted into the FRs of the human antibody. In particular embodiments, the CDR and FR regions are the regions as identified by Kabat, Chothia, AbM, and/or and Contact schemes.

In particular embodiments, one or more or all of the CDR-L1, CDR-L2, CDR-L3 and CDR-H1, CDR-H2, CDR-H3 of the nonhuman anti-idiotype antibody that binds to or recognizes Target Antibody 1 and/or Target Antibody 2 are inserted into framework regions of a human antibody. In certain embodiments, the human antibody is an IgA, IgD, IgE, IgG, and IgM antibody. In particular embodiments, the human antibody is one of a subclass of human IgA, IgD, IgE, IgG, and IgM, e.g., human $IgG_1$, $IgG_2$, $IgG_3$, $IgG_4$, $IgA_1$, or $IgA_2$. In some embodiments, one or more or all of the CDR-L1, CDR-L2, CDR-L3 and CDR-H1, CDR-H2, CDR-H3 of the nonhuman anti-idiotype antibody that binds to or recognizes Target Antibody 1 and/or Target Antibody 2 are inserted into framework regions of an antigen binding region that is from and/or is derived from a human antibody. In certain embodiments, the antigen binding fragment is from and/or is derived from a human IgA, IgD, IgE, IgG, and IgM antibody. The subunit structures and three-dimensional con-figurations of different classes of human immunoglobulins are well known and described generally in, for example, Abbas et al. Cellular and Mol. Immunology, 4th ed. (W.B. Saunders, Co., 2000). In some embodiments, the human antibody or antigen binding fragment thereof may be part of a larger fusion molecule, formed by covalent or non-cova-lent association of the human antibody with one or more other proteins or peptides.

In some embodiments, one or more or all of the CDR-L1, CDR-L2, CDR-L3 and CDR-H1, CDR-H2, CDR-H3 of the nonhuman anti-idiotype antibody that binds to or recognizes Target Antibody 1 and/or Target Antibody 2 are inserted into framework regions of a human antibody or antigen-binding fragment thereof having all or a portion of an Fc region. In certain embodiments, the humanized anti-idiotype antibody that binds to or recognizes Target Antibody 1 and/or Target Antibody 2 contains all or a portion of an Fc region. In some embodiments, the Fc region has one or more modifications, such as an amino acid modification (e.g. a substitution, insertion, or deletion) at one or more amino acid positions. Such modifications can be made, for example, to improve half-life, alter binding to one or more types of Fc receptors, and/or alter effector functions. In some embodiments, modi-fied Fc regions have altered (e.g., decreased) binding to FcαRs, relative to that of an unmodified Fc region. In certain embodiments, the humanized anti-idiotype antibody con-tains all or a portion of a modified Fc region having an altered (e.g., decreased) binding to Fc receptor relative to that of an unmodified Fc region. Non-limiting examples of Fc modifications that alter its binding to the Fc receptors are described, for example, in U.S. Pat. Nos. 7,217,797 and 7,732,570; and U.S. Application Nos. US 2010/0143254 and 2010/0143254.

In some embodiments, the dissociation constant ($K_D$) and/or the off rate ($k_{off}$) of any of the provided anti-idiotype antibodies or antigen-binding fragments thereof that bind to or recognize Target Antibody 1 and/or Target Antibody 2 or an antigen-binding fragment thereof is lower than that of other reagents that bind to or recognize Target Antibody 1 and/or Target Antibody 2 or an antigen-binding fragment thereof. In some embodiments, the dissociation constant and/or the off rate is lower than that of BCMA-Fc. In some embodiments, the dissociation constant and the off rate is lower than that of BCMA-Fc. In some aspects, a lower dissociation constant allows for stronger binding between Target Antibody 1 and/or Target Antibody 2, antigen-bind-ing fragments thereof, or CARs containing same and the provided anti-idiotype antibodies or antigen-binding frag-ments thereof. In some aspects, a lower off rate allows for longer binding between Target Antibody 1 and/or Target Antibody 2, antigen-binding fragments thereof, or CARs containing same and the provided anti-idiotype antibodies or antigen-binding fragments thereof. Thus, in some aspects, detection, isolation, and stimulation of Target Antibody 1 and/or Target Antibody 2, antigen-binding fragments thereof, or CARs containing same is improved by use of the provided anti-idiotype antibodies or antigen-binding fragments thereof, relative to use of other reagents (e.g., BCMA-Fc). For instance, use of the provided anti-idiotype antibodies or antigen-binding fragments thereof can allow for stable binding to Target Antibody 1 and/or Target Antibody 2, antigen-binding fragments thereof, or CARs containing same, thereby improving the detection and isolation of these targets. Similarly, such use can allow for more persistent stimulation of said CARs and cells, e.g., T cells, engineered to express same.

In certain embodiments, the binding affinity (EC50) and/or the dissociation constant of any of the provided anti-idiotype antibodies or antigen-binding fragments thereof that bind to or recognize Target Antibody 1 and/or Target Antibody 2, or antigen-binding fragments thereof, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the EC50 of any of the provided anti-idiotype antibodies or antigen-binding fragments thereof that bind to or recognize Target Antibody 1 and/or Target Antibody 2, or antigen-binding fragments thereof, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the dissociation constant of any of the provided anti-idiotype antibodies or antigen-binding fragments thereof that bind to or recognize Target Antibody 1 and/or Target Antibody 2, or antigen-binding fragments thereof, is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the extent of binding of any of the provided anti-idiotype antibodies or antigen-binding fragments thereof that bind to or recognize Target Antibody 1 and/or Target Antibody 2, or antigen-binding fragments thereof, to a moiety unrelated to the target anti-BCMA moiety (e.g., Target Antibody 1 or Target Antibody 2) is less than, at, or about 10% of the binding of the antibody to the target anti-BCMA moiety as measured, e.g., by a radioimmunoassay (RIA). In some embodiments, any of the provided anti-idiotype antibodies or antigen-binding fragments thereof that bind to or recognize Target Antibody 1 and/or Target Antibody 2, or antigen-binding fragments thereof is an agonist of a CAR containing the antigen-binding domain of Target Antibody 1 or Target Antibody 2 when immobilized on a support, such as a bead or a plate. In some embodiments, the anti-idiotype antibodies or antigen-binding fragments thereof that bind to or recognize Target Antibody 1 and/or Target Antibody 2, or antigen-binding fragments thereof is an agonist of a CAR containing the antigen-binding domain of Target Antibody 1 or Target Antibody 2 when in soluble form. In some embodiments, any of the provided anti-idiotype antibodies or antigen-binding fragments thereof that bind to or recognize Target Antibody 1 and/or Target Antibody 2, or antigen-binding fragments thereof is not blocked by exposure to soluble BCMA or by BCMA-Fc. In some embodiments, the anti-idiotype antibodies or antigen-binding fragments thereof that bind to or recognize Target Antibody 1 and/or Target Antibody 2, or antigen-binding fragments thereof, and comprises a VH region comprising the amino acid sequence set forth in SEQ ID NO: 38, and a VL region comprising the amino acid sequence set forth in SEQ ID NO: 39, is an agonist of a CAR containing the antigen-binding domain of Target Antibody 1 or Target Antibody 2 when in soluble form. In some embodiments, the anti-idiotype antibodies or antigen-binding fragments thereof that bind to or recognize Target Antibody 1 and/or Target Antibody 2, or antigen-binding fragments thereof, and comprises a VH region comprising the amino acid sequence set forth in SEQ ID NO: 38, and a VL region comprising the amino acid sequence set forth in SEQ ID NO: 39, is not blocked by exposure to soluble BCMA or by BCMA-Fc.

C. Exemplary Features

Anti-idiotype antibodies provided herein may be identified, screened for, or characterized for their physical/chemical properties and/or biological activities by various known assays. In one aspect, the anti-idiotype antibody is tested for its antigen binding activity, e.g., by known methods such as ELISA, Western blotting, and/or flow cytometric assays, including cell-based binding assays, for example, assessing binding of the anti-idiotype antibody (e.g., conjugated to a fluorescent marker or tagged) to a cell presenting the target anti-BCMA antibody moiety, in some cases compared to results using cells that do not express the target anti-BCMA antibody moiety. Binding affinity may be measured as Kd or EC50.

In some embodiments of any of the provided anti-idiotype antibodies, e.g. any of the provided antibodies in Section A above, the target anti-BCMA antibody moiety is Target Antibody 2 or is an antibody derived from Target Antibody 2.

In some embodiments of any of the provided anti-idiotype antibodies, e.g. any of the provided antibodies in Section B above, the target anti-BCMA antibody moiety is (i) Target Antibody 1 or is an antibody derived from Target Antibody 1, and/or (ii) Target Antibody 2 or is an antibody derived from Target Antibody 2.

In some embodiments, an anti-idiotype antibody or antigen binding fragment that binds or recognizes the target anti-BCMA moiety is one that specifically binds or preferentially binds (used interchangeably) the target anti-BCMA moiety. In some embodiments, an anti-idiotype antibody or antigen binding fragment that binds or recognizes a target anti-BCMA antibody is one that specifically binds or preferentially binds (used interchangeably) a target anti-BCMA antibody. In some embodiments, the anti-idiotype antibodies and antigen-binding fragments thereof that specifically bind to the target anti-BCMA antibody include antibodies having specific epitopic specificity. In some embodiments, an antibody that is said to specifically bind an antigen is when it preferentially recognizes its target antigen in a complex mixture of proteins and/or macromolecules. In some embodiments, an antibody is said to specifically bind or preferentially bind an antigen when the equilibrium dissociation constant is $<10^{-7}$ or $10^{-8}$ M. In some embodiments, the equilibrium dissociation constant may be $<10^{-9}$ M or $<10^{-10}$ M. In further embodiments, the equilibrium dissociation constant may be $<10^{-11}$ M or less. In some embodiments, an antibody specifically binds or preferentially binds to a target if it binds with greater affinity, avidity, more readily, and/or with greater duration than it binds to other substances. For instance, an anti-idiotype antibody or antigen-binding fragment specifically or preferentially binds a target anti-BCMA antibody if it reacts or associates more frequently, more rapidly, with greater duration and/or with greater affinity with the target anti-BCMA antibody, e.g. contained in a CAR, than it does with a non-target antibody, e.g. contained in a CAR. It is understood that specific binding or preferential binding does not necessarily require (although it can include) exclusive binding. Methods to determine such specific or preferential binding include immunoassays and other binding assays.

A variety of assays are known for assessing binding affinity and/or determining whether an antibody specifically binds to a particular binding partner. It is within the level of a skilled artisan to determine the binding affinity of an antibody, such as by using any of a number of binding assays that are well known in the art. Various binding assays are known and include, but are not limited to, for example, ELISA $K_D$, KinExA, flow cytometry, and/or surface plasmon resonance devices), including those described herein. Such methods include, but are not limited to, methods involving BIAcore®, Octet®, or flow cytometry. For example, in some embodiments, a BIAcore® instrument can be used to determine the binding kinetics and constants of a complex between two proteins using surface plasmon resonance (SPR) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent). SPR measures changes in the concentration of molecules at a sensor surface as molecules bind to or dissociate from the surface. The change in the SPR signal is directly proportional to the change in mass concentration close to the surface, thereby allowing measurement of binding kinetics between two molecules. The dissociation constant for the complex can be determined by monitoring changes in the refractive index with respect to time as buffer is passed over the chip. Other suitable assays for measuring the binding of one protein to another include, for example, immunoassays such as enzyme linked immunosorbent assays (ELISA) and radioimmunoassays (RIA), or determination of binding by monitoring the change in the spectroscopic or optical properties of the proteins through fluorescence, UV absorption, circular dichroism, or nuclear magnetic resonance (NMR). Other exemplary assays include, but are not limited to, Western blot, ELISA, analytical ultracentrifugation, spectroscopy, flow cytometry, sequencing and other methods for detection of binding of proteins.

In particular embodiments, the antibodies and antigen-binding fragments thereof disclosed herein preferentially bind to the target anti-BCMA antibody compared to a non-target antibody, such that the binding affinity of the antibodies for the target anti-BCMA antibody is at least 5 fold, at least 10 fold, at least 100 fold, or at least 1000 fold greater than the binding affinity of the antibodies for non-target antibodies. The non-target antibody includes antibodies against different antigens (e.g., other than BCMA), or can include antibodies against BCMA that contain one or more different CDRs than the target anti-BCMA antibody or bind to a different epitope or binding site of BCMA.

In some embodiments, the anti-idiotype antibody specifically binds with minimal cross-reactivity to other antibodies. In some embodiments, the anti-idiotype antibody does not cross-react with an antibody moiety against a different antigen from the target anti-BCMA antibody moiety.

In some embodiments, the anti-idiotype antibody does not cross-react with an anti-BCMA antibody moiety different from the target anti-BCMA antibody moiety. In some embodiments, the target anti-BCMA antibody moiety is derived from Target Antibody 1. In some embodiments, the target anti-BCMA antibody moiety is derived from Target Antibody 1, and the anti-idiotype antibody does not cross-react with an anti-BCMA antibody moiety derived from Target Antibody 2. In some embodiments, the target anti-BCMA antibody moiety is derived from Target Antibody 2. In some embodiments, the target anti-BCMA antibody moiety is derived from Target Antibody 2, and the anti-idiotype antibody does not cross-react with an anti-BCMA antibody moiety derived from Target Antibody 1.

In some embodiments, the anti-idiotype antibody does cross-react with an anti-BCMA antibody moiety different from the target anti-BCMA antibody moiety. In some embodiments, the target anti-BCMA antibody moiety is derived from Target Antibody 1, and the anti-idiotype antibody does cross-react with an anti-BCMA antibody moiety derived from Target Antibody 2. In some embodiments, the target anti-BCMA antibody moiety is derived from Target Antibody 2, and the anti-idiotype antibody does cross-react with an anti-BCMA antibody moiety derived from Target Antibody 1.

In some embodiments, the anti-idiotype antibody binds to or recognizes a target anti-BCMA antibody moiety that is part of a fusion protein, such as a recombinant receptor. In some embodiments, the anti-idiotype antibody does not bind to any epitope in the fusion protein outside of the target anti-BCMA antibody moiety. For example, in some embodiments, the target anti-BCMA antibody moiety is, or is part of, the antigen-binding domain of a chimeric antigen receptor (CAR), and the anti-idiotype antibody does not bind any epitope outside of the antigen-binding domain. In some embodiments, the CAR antigen-binding domain comprises or consists of an scFv.

In some embodiments, the anti-idiotype antibody binds to or recognizes a target anti-BCMA antibody moiety that is an scFv contained in a CAR. In some embodiments, the anti-idiotype antibody binds to or recognizes an epitope overlapping one or more complementarity determining regions (CDRs) of the target anti-BCMA scFv. In some embodiments, the anti-idiotype antibody does not bind any epitopes in the CAR outside of the scFv; in some embodiments, it does not bind to a reference antibody. In some embodiments, the reference antibody binds to or recognizes the same antigen as the target antibody, e.g., to the BCMA and/or comprises one or more variable heavy and/or variable light framework region(s) having at least 90, 95, 96, 97, 98, or 99% identity to the corresponding framework region(s) of the target antibody (in some aspects, the one or more framework regions comprise an FR1, FR2, FR3, and/or FR4 of the heavy and/or the light chain); and/or contains the same heavy and/or light chain v-gene (or v-gene usage) as the target antibody and/or is derived from the same v-gene sequence as the target antibody. In some aspects, the reference antibody is Target Antibody 1. In some aspects, the reference antibody is Target Antibody 2.

In some embodiments, the CAR comprising an anti-idiotype antibody or antigen-binding fragment thereof comprises a spacer linking the scFv to its transmembrane domain, and the anti-idiotype antibody does not bind any epitope in the spacer. In some embodiments, the spacer is a sequence derived from CD28, such as an extracellular portion from CD28. In some embodiments, the spacer comprises the amino acid sequence of SEQ ID NO: 50. In some embodiments, the anti-idiotype antibody does not bind any epitope in an Fc domain, such as the Fc domain of IgG1. In some embodiments, the Fc domain is an IgG1 Fc domain lacking the hinge region.

In some embodiments, the anti-idiotype antibody does not cross-react with a different CAR. In some embodiments, the anti-idiotype antibody does not cross-react with a different anti-BCMA CAR. In some embodiments, the anti-idiotype antibody does not cross-react with an anti-BCMA antibody moiety, e.g., of a reference antibody, having one or more different idiotopes compared to the target anti-BCMA scFv. In some embodiments, the anti-idiotype antibody binds to or recognizes a target anti-BCMA scFv of a CAR derived from the Target Antibody 1. In some embodiments, the target anti-BCMA antibody moiety is derived from the Target Antibody 1, and the anti-idiotype antibody does not cross-react with a CAR containing an anti-BCMA antibody moiety derived from the Target Antibody 2. In some embodiments, the anti-idiotype antibody binds to or recognizes a target anti-BCMA scFv of a CAR derived from the Target Antibody 2. In some embodiments, the target anti-BCMA antibody moiety is derived from the Target Antibody 2, and the anti-idiotype antibody does not cross-react with a CAR containing anti-BCMA antibody moiety derived from the Target Antibody 1.

In some embodiments, the anti-idiotype antibody is an agonist of the CAR. An anti-idiotype antibody or antigen-binding fragment thereof is said to be "an agonist" of a CAR containing in its extracellular antigen-binding domain a target anti-BCMA antibody or antigen-binding fragment thereof when binding of the anti-idiotype antibody or antigen-binding fragment thereof to the anti-BCMA target antibody increases an activity of cells (e.g. T cells) expressing the CAR, e.g., increased Nur77 expression, increased proliferation, increased cytokine production (e.g. IFN-gamma or TNFalpha), and/or increased cytotoxic acitivty, or other effector activity of the cells. For instance, in some embodiments, binding of the anti-idiotype antibody or antigen-binding fragment thereof to an anti-BCMA target antibody contained in the extracellular antigen-binding domain of the CAR is able to stimulate or activate the CAR to thereby induce or mediate one or more activities of cells expressing the CAR.

In some embodiments, the anti-idiotype antibody is an agonist of the CAR when in solution, such as when the anti-idiotype antibody is soluble or is not immobilized on a support, such as a bead or a plate. In some embodiments, any of the provided anti-idiotype antibodies or antigen-binding fragments thereof is an agonist of a CAR containing in its extracellular antigen-binding domain the target anti-BCMA antibody when the anti-idiotype antibody is in solution, such as when the anti-idiotype antibody is soluble or is not immobilized on a support, such as a bead or a plate. In some embodiments, any of the provided anti-idiotype antibodies or antigen-binding fragments thereof that bind to or recognize the target anti-BCMA antibody, or an antigen-binding fragment thereof, is an agonist of a CAR containing in its extracellular antigen-binding domain the target anti-BCMA antibody when the anti-idiotype antibody is in solution, such as when the anti-idiotype antibody is soluble or is not immobilized on a support, such as a bead or a plate.

In some embodiments, the anti-idiotype antibody is an agonist of the CAR. In some embodiments, the anti-idiotype antibody is an agonist of the CAR when in soluble form. In some embodiments, the anti-idiotype antibody is an agonist of the CAR when immobilized on a support, such as a bead. In some embodiments, any of the provided anti-idiotype antibodies or antigen-binding fragments thereof is an agonist of a CAR containing the antigen-binding domain of the target antibody when immobilized on a support, such as a bead or a plate. In some embodiments, any of the provided anti-idiotype antibodies or antigen-binding fragments thereof that bind to or recognize Target Antibody 1, or an antigen-binding fragment thereof, is an agonist of a CAR containing the antigen-binding domain of Target Antibody 1 when immobilized on a support, such as a bead or a plate. In some embodiments, any of the provided anti-idiotype antibodies or antigen-binding fragments thereof that bind to or recognize Target Antibody 2, or an antigen-binding fragment thereof, is an agonist of a CAR containing the antigen-binding domain of Target Antibody 2 when immobilized on a support, such as a bead or a plate. In some embodiments, any of the provided anti-idiotype antibodies or antigen-binding fragments thereof that bind to or recognize Target Antibody 1 and Target Antibody 2, or an antigen-binding fragment thereof, is an agonist of a CAR containing the antigen-binding domain of Target Antibody 1 or Target Antibody 2 when immobilized on a support, such as a bead or a plate. In some embodiments, any of the provided anti-idiotype antibodies or antigen-binding fragments thereof that bind to or recognize Target Antibody 1 and/or Target Antibody 2, or an antigen-binding fragment thereof, is an agonist of a CAR containing the antigen-binding domain of Target Antibody 1 or Target Antibody 2 when immobilized on a support, such as a bead or a plate. In some embodiments, any of the provided anti-idiotype antibodies or antigen-binding fragments thereof is an agonist of a CAR containing the antigen-binding domain of the target antibody when in soluble form. In some embodiments, any of the provided anti-idiotype antibodies or antigen-binding fragments thereof that bind to or recognize Target Antibody 2, or an antigen-binding fragment thereof is an agonist of a CAR containing the antigen-binding domain of Target Antibody 1 when in soluble form. An anti-indiotype antibody or antigen-binding fragment thereof is said to be "an agonist" of a CAR containing a target antibody or antigen-binding fragment thereof when the anti-indiotype antibody or antigen-binding fragment thereof is capable of increasing an activity of the CAR, e.g., T-cell stimulation of cells engineered to express the CAR, by binding to, or otherwise associating with, the CAR.

In some embodiments, an activity of cells includes one or more functions or phenotypes of cells, e.g. T cells, engineered with the recombinant receptor (e.g. CAR). In particular embodiments, the cells are target anti-BCMA CAR-expressing T cells and the activity includes one or more functions or phenotypes of the T cells. In some embodiments, assays for functional activity of T cells include, but are not limited to, cytokine production (e.g. by ELISPOT or ELISA), intracellular cytokine staining, cellular proliferation, or cytotoxic lymphocyte (CTL) assay. In some embodiments, proliferative responses of the T cells can be measured, e.g. by incorporation of $^3$H-thymidine, BrdU (5-Bromo-2'-Deoxyuridine) or 2'-deoxy-5-ethynyluridine (EdU) into their DNA or dye dilution assays, using dyes such as carboxyfluorescein diacetate succinimmunomodulatory compoundyl ester (CFSE), CellTrace Violet, or membrane dye PKH26.

In some embodiments, assessing the functional activity of cells e.g., T cells, includes measuring cytokine production from T cells after contacting target anti-BCMA CAR-expressing T cells with the anti-idiotype antibody or antigenbinding fragment thereof. In some cases, such measured cytokines can include, without limitation, interlekukin-2 (IL-2), interferon-gamma (IFNγ), interleukin-4 (IL-4), TNF-alpha (TNFα), interleukin-6 (IL-6), interleukin-10 (IL-10), interleukin-12 (IL-12), granulocyte-macrophage colony-stimulating factor (GM-CSF), CD107a, and/or TGF-beta (TGFβ). Assays to measure cytokines are well known in the art, and include but are not limited to, ELISA, intracellular cytokine staining, cytometric bead array, RT-PCR, ELIS-POT, flow cytometry and bio-assays in which cells responsive to the relevant cytokine are tested for responsiveness (e.g. proliferation) in the presence of a test sample.

In some embodiments, assessing a functional activity of cells, e.g. T cells, includes assessing cell phenotypes, e.g., expression of particular cell surface markers, after contacting target anti-BCMA CAR-expressing T cells with the anti-idiotype antibody or antigen-binding fragment thereof. In some embodiments, the T cells, e.g., T cells administered for T cell therapy, are assessed for expression of T cell activation markers, T cell exhaustion markers, and/or T cell differentiation markers. T cell activation markers, T cell exhaustion markers, and/or T cell differentiation markers for assessment include any markers known in the art for particular subsets of T cells, e.g., CD25, CD38, human leukocyte antigen-DR (HLA-DR), CD69, CD44, CD137, KLRG1, $CD62L^{low}$, $CCR7^{low}$, CD71, CD2, CD54, CD58, CD244, CD160, programmed cell death protein 1 (PD-1), lymphocyte activation gene 3 protein (LAG-3), T-cell immunoglobulin domain and mucin domain protein 3 (TIM-3), cytotoxic T lymphocyte antigen-4 (CTLA-4), band T lymphocyte attenuator (BTLA) and/or T-cell immunoglobulin and immunoreceptor tyrosine-based inhibitory motif domain (TIGIT) (see, e.g., Liu et al., Cell Death and Disease (2015) 6, e1792). In some embodiments, the assessed cell surface marker is CD25, PD-1 and/or TIM-3. In some embodiments, the assessed cell surface marker is CD25.

In some embodiments, any of the provided anti-idiotype antibodies or antigen-binding fragments thereof that bind to or recognize Target Antibody 2, or an antigen-binding fragment thereof is not blocked by exposure to soluble BCMA or by BCMA-Fc. In some embodiments, any of the provided anti-idiotype antibodies or antigen-binding fragments thereof that bind to or recognize Target Antibody 1 and Target Antibody 2, or an antigen-binding fragment thereof is an agonist of a CAR containing the antigen-binding domain of Target Antibody 1 or Target Antibody 2 when in soluble form. In some embodiments, any of the provided anti-idiotype antibodies or antigen-binding fragments thereof that bind to or recognize Target Antibody 1 and Target Antibody 2, or an antigen-binding fragment thereof is not blocked by exposure to soluble BCMA or by BCMA-Fc.

In some embodiments, binding of any of the provided anti-idiotype antibodies or antigen-binding fragments thereof to the target anti-BCMA antibody is not blocked by exposure to soluble BCMA or by BCMA-Fc. In some embodiments, the degree of binding (e.g. percent cells positive, mean fluorescent intensity or other parameter as a measure of binding) is substantially the same when the anti-idiotype antibody or antigen-binding fragment thereof is contacted with a target anti-BCMA antibody, or a cell engineered with a recombinant receptor (e.g. CAR) containing in its extracellular binding domain a target anti-BCMA antibody, in the presence of soluble BCMA or BCMA-Fc as compared to the absence of the soluble BCMA or BCMA-Fc. In some embodiment, binding that is substantially the same means that the degree of binding in the presence of soluble BCMA or BCMA-Fc (e.g. percent cells positive, mean fluorescent intensity or other parameter as a measure of binding) is retained, such as is no less than 85%, 90%, 92%, 95%, 97% or 100%, of the binding in the absence of the soluble BCMA or BCMA-Fc.

In some embodiments, the anti-idiotype antibody is an antagonist of the CAR. In some embodiments, binding any of the provided anti-idiotype antibodies or antigen-binding fragments thereof to the target anti-BCMA antibody is blocked by exposure to soluble BCMA or by BCMA-Fc. In some embodiments, the degree of binding (e.g. percent cells positive, mean fluorescent intensity or other parameter as a measure of binding) is decreased or reduced when the anti-idiotype antibody or antigen-binding fragment thereof is contacted with the target anti-BCMA antibody, or a cell engineered with a recombinant receptor (e.g. CAR) containing in its extracellular binding domain the target anti-BCMA antibody, in the presence of soluble BCMA or BCMA-Fc as compared to the absence of the soluble BCMA or BCMA-Fc. In some embodiments, binding that is decreased or reduced means that the degree of binding in the presence of the soluble BCMA or BCMA-Fc (e.g. percent cells positive, mean fluorescent intensity or other parameter as a measure of binding) is reduced, such as is less than 60%, 50%, 40%, 30%, 20%, 10% or less of the binding in the absence of the soluble BCMA or BCMA-Fc.

In some embodiments, the provided anti-idiotype antibodies are capable of binding a target anti-BCMA moiety, such as Target Antibody 1 or Target Antibody 2, with at least a certain affinity, as measured by any of a number of known methods. In some embodiments, the affinity is represented by an equilibrium dissociation constant ($K_D$); in some embodiments, the affinity is represented by $EC_{50}$. In certain embodiments, the binding affinity (EC50) and/or the dissociation constant of the anti-idiotype antibody to the anti-BCMA moiety is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the EC50 of the anti-idiotype antibody to the anti-BCMA moiety is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In certain embodiments, the dissociation constant of the anti-idiotype antibody to the anti-BCMA moiety is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM, such as between at or about 1 nM and at or about 15 nM, e.g., between at or about 5 and at or about 10 nM. In one embodiment, the extent of binding of an anti-idiotype antibody to a moiety unrelated to the target anti-BCMA moiety is less than, at, or about 10% of the binding of the antibody to the target anti-BCMA moiety as measured, e.g., by a radioimmuno-assay (RIA).

In some embodiments, the provided anti-idiotype antibodies are capable of binding a target anti-BCMA moiety, such as Target Antibody 1 or Target Antibody 2, with better affinity and/or better kinetics than other reagents, such as BCMA-Fc. In some embodiments, the provided anti-idiotype antibodies have a lower equilibrium dissociation constant than does BCMA-Fc. In some embodiments, the provided anti-idiotype antibodies have a lower off rate than does BCMA-Fc. In some embodiments, the equilibrium dissociation constant and the off rate are lower for the provided anti-idiotype antibodies than for BCMA-Fc.

In some embodiments, any of the provided anti-idiotype antibodies or antigen-binding fragments thereof this not blocked by exposure to soluble BCMA or by BCMA-Fc. In some embodiments, any of the provided anti-idiotype antibodies or antigen-binding fragments thereof that bind to or recognize Target Antibody 2, or an antigen-binding fragment thereof, is not blocked by exposure to soluble BCMA or by BCMA-Fc. In some embodiments, any of the provided anti-idiotype antibodies or antigen-binding fragments thereof that bind to or recognize Target Antibody 1 and Target Antibody 2, or an antigen-binding fragment thereof, is not blocked by exposure to soluble BCMA or by BCMA-Fc.

D. Methods of Producing the Antibodies

Also provided are methods of making an anti-idiotype antibody, such as of any of the provided embodiments. In some embodiments, for recombinant production of the anti-idiotype antibody, nucleic acid encoding an antibody, e.g., as described above, may be isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Accordingly, provided herein are methods of producing an anti-idiotype antibody or antigen-binding fragment thereof, such as any of the embodiments provided herein, comprising expressing the heavy chain and/or light chain encoded by a nucleic acid molecule(s) or vector as provided herein in a suitable host cell, and recovering or isolating the antibody.

In addition to prokaryotes, eukaryotic microbes such as filamentous fungi or yeast are suitable cloning or expression hosts for antibody-encoding vectors, including fungi and yeast strains whose glycosylation pathways have been modified to mimic or approximate those in human cells, resulting in the production of an antibody with a partially or fully human glycosylation pattern. See Gerngross, Nat. Biotech. 22: 1409-1414 (2004), and Li et al., Nat. Biotech. 24: 210-215 (2006).

Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells; and NSO cells. In some embodiments, the antibody heavy chains and/or light chains may be expressed in yeast. See, e.g., U.S. Publication No. US 2006/0270045 A1. In some embodiments, a particular eukaryotic host cell is selected based on its ability to make desired post-translational modifications to the heavy chains and/or light chains. For example, in some embodiments, CHO cells produce polypeptides that have a higher level of sialylation than the same polypeptide produced in 293 cells.

In some embodiments, the anti-idiotype antibody is produced in a cell-free system. Exemplary cell-free systems are described, e.g., in Sitaraman et al., *Methods Mol. Biol.* 498: 229-44 (2009); Spirin, *Trends Biotechnol.* 22: 538-45 (2004); Endo et al., *Biotechnol. Adv.* 21: 695-713 (2003).

The provided embodiments further include vectors and host cells and other expression systems for expressing and producing the antibodies and other binding proteins, including eukaryotic and prokaryotic host cells, including bacteria, filamentous fungi, and yeast, as well as mammalian cells such as human cells, as well as cell-free expression systems.

Host cells comprising any of the nucleic acids or vectors described herein are also provided. In some embodiments, a host cell that expresses an anti-idiotype antibody or antigen binding fragment described herein is provided. The provided anti-idiotype antibody or antigen binding fragment expressed in host cells can be purified by any suitable method. Such methods include, but are not limited to, the use of affinity matrices or hydrophobic interaction chromatography. Suitable affinity ligands include the target anti-BCMA antibody, or agents that bind Fc regions. For example, a Protein A, Protein G, Protein A/G, or an antibody affinity column may be used to bind the Fc region and to purify an anti-idiotype antibody that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies.

The anti-idiotype antibodies or antibody moieties can be humanized antibodies or human antibodies. A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Among the provided anti-idiotype antibodies or antibody moieties are human antibodies. A "human antibody" is an antibody with an amino acid sequence corresponding to that of an antibody produced by a human or a human cell, or non-human source that utilizes human antibody repertoires or other human antibody-encoding sequences, including human antibody libraries. The term excludes humanized forms of non-human antibodies comprising non-human antigen-binding regions, such as those in which all or substantially all CDRs are non-human.

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic animals, the endogenous immunoglobulin loci have generally been inactivated. Human antibodies also may be derived from human antibody libraries, including phage display and cell-free libraries, containing antibody-encoding sequences derived from a human repertoire.

E. Immunoconjugates

In some embodiments, the anti-idiotype antibody is or is part of an immunoconjugate (anti-idiotype antibody immunoconjugate), in which the anti-idiotype antibody is conjugated to one or more heterologous molecule(s), such as, but not limited to, a cytotoxic or an imaging agent. Cytotoxic agents include, but are not limited to, radioactive isotopes (e.g., At211, I131, I125, Y90, Re186, Re188, Sm153, Bi212, P32, Pb212 and radioactive isotopes of Lu); chemotherapeutic agents (e.g., maytansinoids, taxanes, methotrexate, adriamicin, *vinca* alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins. In some embodiments, the antibody is conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

Among the anti-idiotype antibody immunoconjugates are antibody-drug conjugates (ADCs), in which an anti-idiotype antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498,298); a dolastatin; a calicheamicin or derivative thereof (see U.S. Pat. Nos. 5,712,374, 5,714, 586, 5,739,116, 5,767,285, 5,770,701, 5,770,710, 5,773,001, and 5,877,296; Hinman et al., *Cancer Res.* 53: 3336-3342 (1993); and Lode et al., *Cancer Res.* 58: 2925-2928 (1998)); an anthracycline such as daunomycin or doxorubicin (see Kratz et al., *Current Med. Chem.* 13: 477-523 (2006); Jeffrey et al., *Bioorganic & Med. Chem. Letters* 16: 358-362 (2006); Torgov et al., *Bioconj. Chem.* 16: 717-721 (2005); Nagy et al., *Proc. Natl. Acad. Sci. USA* 97: 829-834 (2000); Dubowchik et al., *Bioorg. & Med. Chem. Letters* 12: 1529-1532 (2002); King et al., *J. Med. Chem.* 45: 4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

Also among the anti-idiotype antibody immunoconjugates are those in which the antibody is conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes.

Also among the anti-idiotype antibody immunoconjugates are those in which the anti-idiotype antibody is conjugated to a radioactive atom to form a radioconjugate. Exemplary radioactive isotopes include At$^{211}$, I$^{131}$, I$^{125}$, Y$^{90}$, Re$^{186}$, Re$^{188}$, Sm$^{153}$, Bi$^{212}$, P$^{32}$, Pb$^{212}$ and radioactive isotopes of Lu.

Conjugates of an anti-idiotype antibody and cytotoxic agent may be made using any of a number of known protein coupling agents, e.g., linkers, (see Vitetta et al., *Science* 238: 1098 (1987)), WO94/11026. The linker may be a "cleavable linker" facilitating release of a cytotoxic drug in the cell, such as acid-labile linkers, peptidase-sensitive linkers, photolabile linkers, dimethyl linkers, and disulfide-containing linkers (Chari et al., *Cancer Res.* 52: 127-131 (1992); U.S. Pat. No. 5,208,020).

Also provided are anti-idiotype antibody immunoconjugates comprising an anti-idiotype antibody attached to a label, e.g., a detectable label, which can generate a detectable signal, indirectly or directly. These anti-idiotype antibody immunoconjugates can be used for research or diagnostic applications. The label is preferably capable of producing, either directly or indirectly, a detectable signal. For example, the label may be radio-opaque or a radioisotope, such as $^3$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

Examples of detectable labels include but are not limited to radionucleotides, enzymes, coenzymes, fluorescers, chemiluminescers, chromogens, enzyme substrates or cofactors, enzyme inhibitors, prosthetic group complexes, free radicals, particles, dyes, and the like. Examples of suitable enzymes include horseradish peroxidase, alkaline phosphatase, 0-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin, coumarin, Alexa488, Oregon green 488, rhodamine green, Alexa 532, Cy3, Bodipy 588/586, Alexa586, TAMRA, Rox, Alexa 594, Texas red, Bodipy 630/650, Cy5, Alexa647, IR Dye 680, IR Dye 680, IR Dye 700 DX, Cy5.5, Alexa 750, IR Dye 800CW, IR Dye 800, Atto 532, and Atto 465.

In some embodiments, the anti-idiotype antibody immunoconjugate is detectable indirectly. For example, a secondary antibody that is specific for the anti-idiotype antibody immunoconjugate and contains a detectable label can be used to detect the anti-idiotype antibody immunoconjugate.

F. Variants

In certain embodiments, the anti-idiotype antibodies include one or more amino acid variations, e.g., substitutions, deletions, insertions, and/or mutations, compared to the sequence of an anti-idiotype antibody described herein. Exemplary variants include those designed to improve the binding affinity and/or other biological properties of the anti-idiotype antibody. Amino acid sequence variants of an anti-idiotype antibody may be prepared by introducing appropriate modifications into the nucleotide sequence encoding the anti-idiotype antibody, or by peptide synthesis. Such modifications include, for example, deletions from, and/or insertions into and/or substitutions of residues within the amino acid sequences of the anti-idiotype antibody. Any combination of deletion, insertion, and substitution can be made to arrive at the final construct, provided that the final construct possesses the desired characteristics, e.g., antigen-binding.

In certain embodiments, the anti-idiotype antibodies include one or more amino acid substitutions, e.g., as compared to an anti-idiotype antibody sequence described herein. Sites of interest for substitutional mutagenesis include the CDRs and FRs. Amino acid substitutions may be introduced into an anti-idiotype antibody of interest and the products screened for a desired activity, e.g., retained/ improved antigen binding, decreased immunogenicity, improved half-life, and/or improved effector function, such as the ability to promote antibody-dependent cellular cytotoxicity (ADCC) or complement-dependent cytotoxicity (CDC). In some embodiments, the variant anti-idiotype antibody exhibits retained or improved binding to a target anti-BCMA antibody or fragment thereof. For example, in some embodiments, the variant anti-idiotype antibody exhibits an increase in binding affinity to the target anti-BCMA antibody of at least about 10% (such as at least about any of 20, 30, 40, 50, 60, 70, 80, 90, 100, 200, 300, 400, 500, 1000% or more) as compared to the unmodified anti-idiotype antibody.

In some embodiments, one or more residues within a CDR of a parent antibody (e.g. a humanized or human antibody) is/are substituted. In some embodiments, the substitution is made to revert a sequence or position in the sequence to a germline sequence, such as an antibody sequence found in the germline (e.g., human germline), for example, to reduce the likelihood of immunogenicity, e.g., upon administration to a human individual.

In some embodiments, alterations are made in CDR "hotspots," residues encoded by codons that undergo mutation at high frequency during the somatic maturation process (see, e.g., Chowdhury, Methods Mol. Biol. 207: 179-196 (2008)), and/or residues that contact antigen, with the resulting variant $V_H$ or $V_L$ being tested for binding affinity. Affinity maturation by constructing and reselecting from secondary libraries has been described, e.g., in Hoogenboom et al. in Methods in Molecular Biology 178: 1-37 (O'Brien et al., ed., Human Press, Totowa, NJ, (2001)). In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves CDR-directed approaches, in which several CDR residues (e.g., 4-6 residues at a time) are randomized. CDR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. Such alterations may, for example, be outside of antigen contacting residues in the CDRs. In certain embodiments of the variant $V_H$ and $V_L$ sequences provided above, each CDR either is unaltered, or contains no more than one, two or three amino acid substitutions.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

Modifications

In certain embodiments, the antibody is altered to increase or decrease the extent to which the antibody is glycosylated, for example, by removing or inserting one or more glycosylation sites by altering the amino acid sequence and/or by modifying the oligosaccharide(s) attached to the glycosylation sites, e.g., using certain cell lines.

Exemplary modifications, variants, and cell lines are described, e.g., in Patent Publication Nos. US 2003/0157108, US 2004/0093621, US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336: 1239-1249 (2004); Yamane-Ohnuki et al. Biotech. Bioeng. 87: 614 (2004). Ripka et al. Arch. Biochem. Biophys. 249: 533-545 (1986); US Pat Appl No US 2003/0157108 A1, Presta, L; and WO 2004/056312 A1, Yamane-Ohnuki et al. Biotech. Bioeng. 87: 614 (2004); Kanda, Y. et al., Biotechnol. Bioeng., 94(4): 680-688 (2006); and WO2003/085107); WO 2003/011878 (Jean-Mairet et al.); U.S. Pat. No. 6,602,684 (Umana et al.); and US 2005/0123546 (Umana et al.); WO 1997/30087 (Patel et al.); WO 1998/58964 (Raju, S.); and WO 1999/22764 (Raju, S.).

Among the modified antibodies are those having one or more amino acid modifications in the Fc region, such as those having a human Fc region sequence or other portion of a constant region (e.g., a human IgG1, IgG2, IgG3 or IgG4 Fc region) comprising an amino acid modification (e.g. a substitution) at one or more amino acid positions.

Such modifications can be made, e.g., to improve half-life, alter binding to one or more types of Fc receptors, and/or alter effector functions.

Also among the variants are cysteine engineered antibodies such as "thioMAbs" and other cysteine engineered variants, in which one or more residues of an antibody are substituted with cysteine residues, in order to generate reactive thiol groups at accessible sites, e.g., for use in conjugation of agents and linker-agents, to produce immunoconjugates. Cysteine engineered antibodies are described, e.g., in U.S. Pat. Nos. 7,855,275 and 7,521,541.

In some embodiments, the antibodies are modified to contain additional nonproteinaceous moieties, including water soluble polymers. Exemplary polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

II. Chimeric Antigen Receptors (Cars) and Genetically Engineered Cells

In some embodiments, the provided anti-idiotypic antibodies bind to or recognize an antigen-binding portion of a chimeric antigen receptor (CAR), such as an anti-BCMA CAR containing an antigen-binding portion derived from Target Antibody 1 or Target Antibody 2. In some embodiments, the provided anti-idiotype antibodies bind to such CARs expressed on a cell, such as cells used in connection with adoptive cell therapy. In some embodiments, the cells include one or more nucleic acids introduced via genetic engineering, and thereby express the recombinant or genetically engineered CAR products of such nucleic acids. In some embodiments, chimeric receptors when genetically engineered into immune cells can modulate T cell activity, and, in some cases, can modulate T cell differentiation or homeostasis, thereby resulting in genetically engineered cells with improved longevity, survival and/or persistence in vivo, such as for use in adoptive cell therapy methods. In some embodiments, the provided anti-idiotypic antibodies can be used in methods to modulate one or more of these activities, including to activate, stimulate and/or expand engineered cells expressing the target CAR.

In some embodiments, the cells include one or more nucleic acids introduced via genetic engineering in accord with the provided methods, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types. In particular embodiments, the nucleic acids contain a gene that encodes a CAR.

In some embodiments, the provided methods may be carried out simultaneously, sequentially or concurrently with one or more processing steps for manufacturing or preparing genetically engineered cells. The processing steps of the methods may include any one or more of a number of cell processing steps, alone or in combination. In particular embodiments, the processing steps include transduction or transfection of the cells with one or more nucleic acids, e.g., a heterologous polynucleotide comprising a gene encoding a recombinant receptor. In certain embodiments, cells are transduced with viral vector particles containing a retroviral vector, such as one encoding a recombinant product for expression in the cells. In certain embodiments, the cells are transfected with one or more non-viral nucleic acids, e.g., an episomal plasmid or a transposon. The methods may further and/or alternatively include other processing steps, such as steps for the isolation, separation, selection, washing, suspension, dilution, concentration, and/or formulation of the cells. In some cases, the methods also can include an ex vivo step for cultivation, stimulation or expansion of cells (e.g., stimulation of the cells, for example, to induce their proliferation and/or activation), which, in some cases, can be carried out in accord with the provided methods. In some embodiments, the methods include isolating cells from the subject, preparing, processing, culturing, and/or engineering them, and re-introducing them into the same subject, before or after cryopreservation.

In some embodiments, the method includes processing steps carried out in an order in which: cells, e.g., primary cells, are first isolated, such as selected or separated, from a biological sample; selected cells are incubated with viral vector particles for transduction; and transduced cells are formulated in a composition. In some cases, transduced cells are activated, expanded or propagated ex vivo, such as by stimulation in the presence of a stimulation reagent, such as in accord with the provided methods. In some embodiments, the method can include one or more processing steps from among washing, suspending, diluting and/or concentrating cells, which can occur prior to, during, or simultaneous with or subsequent to one or more of the isolation, such as separation or selection, transduction, stimulation, and/or formulation steps.

In particular embodiments, the cells to be transfected or transduced are not isolated, selected, or enriched prior to contact with the one or more nucleic acids. In some embodiments, the cells are not selected prior to contacting the cells with the one or more nucleic acids. In some embodiments, the cells to be transfected or transduced are not enriched prior to contacting the cells with the one or more nucleic acids.

In some embodiments, one or more of the cell processing steps in connection with preparing, processing and/or incubating cells in connection with the provided method, including in connection with preparing a composition containing genetically engineered cells, can be carried out in the internal cavity of a centrifugal chamber, such as a substantially rigid chamber that is generally cylindrical in shape and rotatable around an axis of rotation, which can provide certain advantages compared to other available methods. In some embodiments, all processing steps are carried out in the same centrifugal chamber. In some embodiments, one or more processing steps are carried out in different centrifugal chambers, such as multiple centrifugal chambers of the same type. Such methods include any of those as described in International Publication Number WO2016/073602.

Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Depending on the particular process (e.g., dilution, wash, transduction, formulation), it is within the level of a skilled artisan to choose a particular kit that is appropriate for the process. Exemplary kits for use with such systems include, but are not limited to, single-use kits sold by BioSafe SA under product names CS-430.1, CS-490.1, CS-600.1 or CS-900.2.

In some embodiments, the system is included with and/or placed into association with other instrumentation, including instrumentation to operate, automate, control and/or monitor aspects of the various processing steps performed in the system. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced or transfected and the vector particles, e.g., viral vector particles or non-viral plasmids, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or compositions during the methods. The containers can be connected at one or more positions in the system, such as at a position corresponding to an input line, diluent line, wash line, waste line and/or output line.

In some embodiments, the system, such as a closed system, is sterile. In some embodiments, all connections of components of the system, such as between tubing line and a container via a connector, are made under sterile conditions. In some embodiments, connections are made under laminar flow. In some embodiments, connections are made using a sterile connection device that produces sterile connections, such as sterile welds, between a tubing and a container. In some embodiments, a sterile connection device effects connection under thermal condition high enough to maintain sterility, such as temperatures of at least 200° C., such as at least 260° C. or 300° C.

In some embodiments, the system may be disposable, such as a single-use kit. In some embodiments, a single-use kit can be utilized in a plurality of cycles of a process or processes, such as at least 2, 3, 4, 5 or more times, for example, in processes that occur in a continuous or a semi-continuous manner. In some embodiments, the system, such as a single-use kit, is employed for processing of cells from a single patient. In aspects of the methods, the processes need not be performed in the same closed system, such as in the same centrifugal chamber, but can be performed under a different closed system, such as in a different centrifugal chamber; in some embodiments, such different centrifugal chambers are at the respective points in the methods placed in association with the same system, such as placed in association with the same centrifuge. In some embodiments, all processing steps are performed in a closed system, in which all or a subset of each one or more processing step is performed in the same or a different centrifugal chamber.

A. Target Chimeric Antigen Receptors (CARs)

In some embodiments, the provided anti-idiotypic antibodies bind or recognize the extracellular domain of a target CAR that contains an antigen binding domain of an antibody or antibody fragment that provides specificity for a desired antigen (e.g., tumor antigen) and which is operably linked or connected to an intracellular signaling domain. In some embodiments, the CAR contains an antigen binding domain that is the antigen binding domain of a target antibody or antigen-binding fragment thereof as provided herein. In some embodiments, the provided anti-idiotype antibodies bind or recognize the extracellular domain of a target CAR that contains an antigen binding domain of an a target anti-BCMA antibody or antibody fragment that provides specificity for a BCMA antigen (e.g., expressed on a tumor) that is operably linked or connected to an intracellular signaling domain. In some embodiments, the CAR contains an antigen binding domain that is the antigen binding domain of an anti-BCMA target antibody or antigen-binding fragment thereof as provided herein, such as described in Section I. In some embodiments, the antigen binding domain includes the Target Antibody 1 or an antibody fragment of portion derived from Target Antibody 1. In some embodiments, the antigen binding domain includes the Target Antibody 2 or an antibody fragment of portion derived from Target Antibody 2. Accordingly, in some embodiments, provided herein are anti-idiotypic antibodies or antigen-binding fragments thereof that bind or recognize the extracellular domain of a target CAR that contains a target antibody or antigen-binding fragment thereof, such as Target Antibody 1 or Antibody 2, or an antigen-binding fragment thereof. In some embodiments, the intracellular signaling domain is an activating intracellular domain portion, such as a T cell activating domain, providing a primary activation signal. In some embodiments, the intracellular signaling domain contains or additionally contains a costimulatory signaling domain to facilitate effector functions. In some embodiments, provided herein are anti-idiotypic antibodies or antigen-binding fragments thereof that bind or recognize the extracellular domain of a CAR as described in, e.g., WO 2019/090003 (PCT/US2018/058811) or WO 2016/090320 (PCT/US2015/064112), the contents of which are hereby incorporated by reference. In some embodiments, the anti-idiotypic antibodies or antigen-binding fragments thereof bind to or recognize a CAR as described in, e.g., WO 2019/090003 (PCT/US2018/058811) or WO 2016/090320 (PCT/US2015/064112). In some embodiments, the CAR provided herein that contains a target antibody or antigen-binding fragment thereof is an anti-BCMA CAR as described in, e.g., WO 2019/090003 (PCT/US2018/058811) or WO 2016/090320 (PCT/US2015/064112).

In some embodiments, engineered cells, such as T cells, are provided that express a CAR with specificity for a particular antigen (or marker or ligand), such as an antigen expressed on the surface of a particular cell type. In some embodiments, the antigen is a polypeptide. In some embodiments, it is a carbohydrate or other molecule. In some embodiments, the antigen is selectively expressed or over-expressed on cells of the disease or condition, e.g., the tumor or pathogenic cells, as compared to normal or non-targeted cells or tissues. In other embodiments, the antigen is expressed on normal cells and/or is expressed on the engineered cells.

In particular embodiments, the recombinant receptor, such as a chimeric receptor, contains an intracellular signaling region, which includes a cytoplasmic signaling domain (also interchangeably called an intracellular signaling domain), such as a cytoplasmic (intracellular) region capable of inducing a primary activation signal in a T cell, for example, a cytoplasmic signaling domain of a T cell receptor (TCR) component (e.g. a cytoplasmic signaling domain of a zeta chain of a CD3-zeta (CD3ζ) chain or a functional variant or signaling portion thereof) that comprises an immunoreceptor tyrosine-based activation motif (ITAM).

In some embodiments, the chimeric receptor further contains an extracellular ligand-binding domain that binds to or recognizes a ligand (e.g. antigen). In some embodiments, the chimeric receptor is a CAR that contains an extracellular antigen-recognition domain that binds to or recognizes an antigen. In some embodiments, the ligand, such as an antigen, is a protein expressed on the surface of cells. In some embodiments, the CAR is a TCR-like CAR and the antigen is a processed peptide antigen, such as a peptide antigen of an intracellular protein, which, like a TCR, is recognized on the cell surface in the context of a major histocompatibility complex (MHC) molecule.

Exemplary antigen receptors, including CARs, and methods for engineering and introducing such receptors into cells, include those described, for example, in international patent application publication numbers WO200014257, WO2013126726, WO2012/129514, WO2014031687, WO2013/166321, WO2013/071154, WO2013/123061 U.S. patent application publication numbers US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European patent application number EP2537416, and/or those described by Sadelain et al., Cancer Discov. 2013 April; 3(4): 388-398; Davila et al. (2013) PLoS ONE 8(4): e61338; Turtle et al., Curr. Opin. Immunol., 2012 October; 24(5): 633-39; Wu et al., Cancer, 2012 Mar. 18(2): 160-75. In some aspects, the antigen receptors include a CAR as described in U.S. Pat. No. 7,446,190, and those described in International Patent Application Publication No.: WO/2014055668 A1. Examples of the CARs include CARs as disclosed in any of the aforementioned publications, such as WO2014031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35(9): 689-701; and Brentjens et al., Sci Transl Med. 2013 5(177). See also WO2014031687, U.S. Pat. Nos. 8,339,645, 7,446,179, US 2013/0149337, U.S. Pat. Nos. 7,446,190, and 8,389,282.

In some embodiments, the CAR is constructed with a specificity for a particular antigen (or marker or ligand), such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more antigen binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy (VH) and variable light (VL) chains of a monoclonal antibody (mAb).

In some embodiments, the antibody or antigen-binding portion thereof is expressed on cells as part of a CAR. In some embodiments, the extracellular antigen binding domain is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

In some embodiments, the CAR contains an antibody or an antigen-binding fragment (e.g. scFv) that binds to or recognizes BCMA, such as an intact antigen, expressed on the surface of a cell. In some embodiments, the antibody or antigen-binding fragment (scFv) includes CDRs contained in Target Antibody 1, In some embodiments, the antigen is BCMA and is bound by an anti-BCMA antibody, such as Target Antibody 1 or an antigen-binding fragment derived from Target Antibody 1, or Target Antibody 2 or an antigen-binding fragment derived from Target Antibody 2.

In some embodiments, the antigen-binding proteins, antibodies and antigen binding fragments thereof recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; variable heavy chain (VH) regions, single-chain antibody molecules such as scFvs and single-domain VH single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150: 880-887 (1993); Clarkson et al., Nature 352:624-628 (1991).

Single-domain antibodies are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known in the art.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

The chimeric receptors, such as CARs, generally include an extracellular antigen binding domain, such as a portion of an antibody molecule (e.g. Target Antibody 1 or Target Antibody 2), generally a variable heavy (VH) chain region and/or variable light (VL) chain region of the antibody, e.g., an scFv antibody fragment.

In some embodiments, the chimeric antigen receptor includes an extracellular portion containing an antibody or antibody fragment. In some aspects, the chimeric antigen receptor includes an extracellular portion containing the antibody or fragment and an intracellular signaling domain. In some embodiments, the antibody or fragment includes an scFv. In some embodiments, the scFv is derived from Target Antibody 1 and comprises the sequence of amino acids set forth in SEQ ID NO: 13. In some embodiments, the scFv is derived from Target Antibody 2 and comprises the sequence of amino acids set forth in SEQ ID NO: 27.

In some embodiments, the recombinant receptor such as the CAR, such as the antibody portion thereof, further includes a spacer, which may be or include at least a portion of an immunoglobulin constant region or variant or modified version thereof, such as a hinge region, e.g., an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include IgG4 hinge alone, IgG4 hinge linked to CH2 and CH3 domains, or IgG4 hinge linked to the CH3 domain. In some embodiments, the spacer has the sequence set forth in SEQ ID NO: 50. In some embodiments, the spacer includes a sequence of a hinge region, a $C_H2$ and a $C_H3$ region. In some embodiments, one of more of the hinge, $C_H2$ and $C_H3$ is derived all or in part from IgG4 or IgG2. In some cases, the hinge, $C_H2$ and $C_H3$ is derived from IgG4. In some aspects, one or more of the hinge, $C_H2$ and $C_H3$ is chimeric and contains sequence derived from IgG4 and IgG2. In some examples, the spacer contains an IgG4/2 chimeric hinge, an IgG2/4 $C_H2$, and an IgG4 $C_H3$ region. In some embodiments, the encoded spacer is or contains (i) the sequence set forth in SEQ ID NO: 50; (ii) a functional variant of SEQ ID NO: 50 that has at least 95%, 96%, 97%, 98% or 99% sequence identity to SEQ ID NO: 50; or (iii) a contiguous portion of (i) or (ii) that is at least 125 amino acids in length. In some embodiments, the encoded spacer is or includes the sequence set forth in SEQ ID NO: 50. Exemplary spacers include, but are not limited to, those described in Hudecek et al. (2013) *Clin. Cancer Res.*, 19: 3153, international patent application publication number WO2014031687, U.S. Pat. No. 8,822,647, published app. No. US2014/0271635, WO 2019/090003 (PCT/US2018/058811), or WO 2016/090320 (PCT/US2015/064112), the contents of which are hereby incorporated by reference.

In some embodiments, the antigen receptor comprises an intracellular domain linked directly or indirectly to the extracellular domain. In some embodiments, the chimeric antigen receptor includes a transmembrane domain linking the extracellular domain and the intracellular signaling domain. In some embodiments, the transmembrane domain is fused to the extracellular domain. In some embodiments, the intracellular signaling domain comprises an ITAM. For example, in some aspects, the antigen recognition domain (e.g. extracellular domain) generally is linked to one or more intracellular signaling components, such as signaling components that mimic activation through an antigen receptor complex, such as a TCR complex, in the case of a CAR, and/or signal via another cell surface receptor. In some embodiments, the chimeric receptor comprises a transmembrane domain linked or fused between the extracellular domain (e.g. scFv) and intracellular signaling domain. Thus, in some embodiments, the antigen-binding component (e.g., antibody) is linked to one or more transmembrane and intracellular signaling domains.

In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28.

In some embodiments, the extracellular domain and transmembrane domain can be linked directly or indirectly. In some embodiments, the extracellular domain and transmembrane are linked by a spacer, such as any described herein. In some embodiments, the receptor contains extracellular portion of the molecule from which the transmembrane domain is derived, such as a CD28 extracellular portion.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

The receptor, e.g., the CAR, generally includes at least one intracellular signaling component or components. In some aspects, the CAR includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from CD3 zeta chain, FcR gamma, CD3 gamma, CD3 delta and CD3 epsilon. In some embodiments, cytoplasmic signaling molecule(s) in the CAR contain(s) a cytoplasmic signaling domain, portion thereof, or sequence derived from CD3 zeta.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding portion is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor γ, CD8, CD4, CD25, or CD16. For example, in some aspects, the CAR or other chimeric receptor includes a chimeric molecule between CD3-zeta (CD3-ζ) or Fc receptor γ and CD8, CD4, CD25 or CD16.

In some embodiments, upon ligation of the CAR or other chimeric receptor, the cytoplasmic domain or intracellular signaling domain of the receptor activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptors to initiate signal transduction following antigen receptor engagement, and/or any derivative or variant of such molecules, and/or any synthetic sequence that has the same functional capability.

In the context of a natural TCR, full activation generally requires not only signaling through the TCR, but also a costimulatory signal. Thus, in some embodiments, to promote full activation, a component for generating secondary or co-stimulatory signal is also included in the CAR. In other embodiments, the CAR does not include a component for generating a costimulatory signal. In some aspects, an additional CAR is expressed in the same cell and provides the component for generating the secondary or costimulatory signal.

T cell activation is in some aspects described as being mediated by two classes of cytoplasmic signaling sequences: those that initiate antigen-dependent primary activation through the TCR (primary cytoplasmic signaling sequences), and those that act in an antigen-independent manner to provide a secondary or co-stimulatory signal (secondary cytoplasmic signaling sequences). In some aspects, the CAR includes one or both of such signaling components.

In some embodiments, the chimeric antigen receptor contains an intracellular domain of a T cell costimulatory molecule. In some embodiments, the CAR includes a signaling domain and/or transmembrane portion of a costimulatory receptor, such as CD28, 4-1BB, OX40, DAP10, and ICOS. In some aspects, the same CAR includes both the activating and costimulatory components. In some embodiments, the chimeric antigen receptor contains an intracellular domain derived from a T cell costimulatory molecule or a functional variant thereof, such as between the transmembrane domain and intracellular signaling domain. In some aspects, the T cell costimulatory molecule is CD28 or 41BB.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR. In some embodiments, the cells further include inhibitory CARs (iCARs, see Fedorov et al., Sci. Transl. Medicine, 5(215) (December, 2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In certain embodiments, the intracellular signaling domain comprises a CD28 transmembrane and signaling domain linked to a CD3 (e.g., CD3-zeta) intracellular domain. In some embodiments, the intracellular signaling domain comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and an activation domain, e.g., primary activation domain, in the cytoplasmic portion. Exemplary CARs include intracellular components of CD3-zeta, CD28, and 4-1BB.

In some embodiments, the antigen receptor further includes a marker and/or cells expressing the CAR or other antigen receptor further includes a surrogate marker, such as a cell surface marker, which may be used to confirm transduction or engineering of the cell to express the receptor. In some aspects, the marker includes all or part (e.g., truncated form) of CD34, a NGFR, or epidermal growth factor receptor, such as truncated version of such a cell surface receptor (e.g., tEGFR). In some embodiments, the nucleic acid encoding the marker is operably linked to a polynucleotide encoding for a linker sequence, such as a cleavable linker sequence, e.g., T2A. For example, a marker, and optionally a linker sequence, can be any as disclosed in published patent application No. WO2014031687. For example, the marker can be a truncated EGFR (tEGFR) that is, optionally, linked to a linker sequence, such as a T2A cleavable linker sequence. In embodiments, the tEGFR contains the amino acid sequence set forth in SEQ ID NO: 51. In some embodiments, the tEGFR contains an amino acid sequence with or with about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or greater than 99% sequence identify to the sequences set forth in SEQ ID NO: 51.

In some embodiments, the marker is a molecule, e.g., cell surface protein, not naturally found on T cells or not naturally found on the surface of T cells, or a portion thereof. In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

In some cases, CARs are referred to as first, second, and/or third generation CARs. In some aspects, a first generation CAR is one that solely provides a CD3-chain induced signal upon antigen binding; in some aspects, a second-generation CARs is one that provides such a signal and costimulatory signal, such as one including an intracellular signaling domain from a costimulatory receptor such as CD28 or CD137; in some aspects, a third generation CAR is one that includes multiple costimulatory domains of different costimulatory receptors.

In some embodiments, the chimeric antigen receptor includes an extracellular portion containing the antibody or fragment described herein, e.g., a target antibody or antigen-binding fragment thereof, such as Target Antibody 1 or Target Antibody 2, or an antigen-binding fragment thereof, or an anti-BCMA antibody or antigen-binding fragment thereof as described in, e.g., WO 2019/090003 (PCT/US2018/058811) or WO 2016/090320 (PCT/US2015/064112), the contents of which are hereby incorporated by reference. In some aspects, the chimeric antigen receptor includes an extracellular portion containing the antibody or fragment described herein and an intracellular signaling domain. In some embodiments, the antibody or fragment includes an scFv or a single-domain $V_H$ antibody and the intracellular domain contains an ITAM. In some aspects, the intracellular signaling domain includes a signaling domain of a zeta chain of a CD3-zeta (CD3ζ) chain. In some embodiments, the chimeric antigen receptor includes a transmembrane domain disposed between the extracellular domain and the intracellular signaling region.

In some aspects, the transmembrane domain contains a transmembrane portion of CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 4-1BB.

For example, in some embodiments, the CAR contains an antibody, e.g., an antibody fragment, a transmembrane domain that is or contains a transmembrane portion of CD28 or a functional variant thereof, and an intracellular signaling domain containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 96 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 96.

In some embodiments, the chimeric antigen receptor contains an intracellular domain of a T cell costimulatory molecule. In some aspects, the T cell costimulatory molecule is CD28 or 4-1BB.

In some embodiments, the intracellular signaling region comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 97 or 98 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 97 or 98. In some embodiments, the intracellular region comprises an intracellular costimulatory signaling domain of 4-1BB or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 99 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 99.

In some embodiments, the intracellular signaling region comprises a human CD3 chain, optionally a CD3 zeta stimulatory signaling domain or functional variant thereof, such as an 112 AA cytoplasmic domain of isoform 3 of human CD3 (Accession No.: P20963.2) or a CD3 zeta signaling domain as described in U.S. Pat. Nos. 7,446,190 or 8,911,993. In some embodiments, the intracellular signaling region comprises the sequence of amino acids set forth in SEQ ID NO: 100 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 100.

In some aspects, the spacer contains only a hinge region of an IgG, such as only a hinge of IgG4 or IgG1, such as the hinge only spacer set forth in SEQ ID NO: 101. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to CH2 and CH3 domains, such as set forth in SEQ ID NO: 103. In some embodiments, the spacer is an Ig hinge, e.g., an IgG4 hinge, linked to a CH3 domain only, such as set forth in SEQ ID NO: 102. In some embodiments, the spacer is or comprises a glycine-serine rich sequence or other flexible linker such as known flexible linkers.

For example, in some embodiments, the CAR includes an antibody such as an antibody fragment, including scFvs, a spacer, such as a spacer containing a portion of an immunoglobulin molecule, such as a hinge region and/or one or more constant regions of a heavy chain molecule, such as an Ig-hinge containing spacer, a transmembrane domain containing all or a portion of a CD28-derived transmembrane domain, a CD28-derived intracellular signaling domain, and a CD3 zeta signaling domain. In some embodiments, the CAR includes an antibody or fragment, such as scFv, a spacer such as any of the Ig-hinge containing spacers, a CD28-derived transmembrane domain, a 4-1BB-derived intracellular signaling domain, and a CD3 zeta-derived signaling domain.

In some embodiments, nucleic acid molecules encoding such CAR constructs further includes a sequence encoding a T2A ribosomal skip element and/or a tEGFR sequence, e.g., downstream of the sequence encoding the CAR. In some embodiments, T cells expressing an antigen receptor (e.g. CAR) can also be generated to express a truncated EGFR (EGFRt) as a non-immunogenic selection epitope (e.g. by introduction of a construct encoding the CAR and EGFRt separated by a T2A ribosome switch to express two proteins from the same construct), which then can be used as a marker to detect such cells (see e.g. U.S. Pat. No. 8,802,374). In some embodiments, a single promoter may direct expression of an RNA that contains, in a single open reading frame (ORF), two or three genes (e.g. encoding the molecule involved in modulating a metabolic pathway and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as T2A, can cause the ribosome to skip (ribosome skipping) synthesis of a peptide bond at the C-terminus of a 2A element, leading to separation between the end of the 2A sequence and the next peptide downstream (see, for example, de Felipe. *Genetic Vaccines and Ther.* 2:13 (2004) and deFelipe et al. *Traffic* 5:616-626 (2004)). Many 2A elements are known in the art. Examples of 2A sequences that can be used in the methods and nucleic acids disclosed herein, without limitation, 2A sequences from the foot-and-mouth disease virus (F2A, e.g., SEQ ID NO: 132), equine rhinitis A virus (E2A, e.g., SEQ ID NO: 130), Thosea asigna virus (T2A, e.g., SEQ ID NO: 127 or 134), and porcine teschovirus-1 (P2A, e.g., SEQ ID NO: 128 or 129) as described in U.S. Patent Publication No. 20070116690.

The recombinant receptors, such as CARs, expressed by the cells administered to the subject generally recognize or bind to a molecule that is expressed in, associated with, and/or specific for the disease or condition or cells thereof being treated. Upon binding, e.g., specific binding, to the molecule, e.g., antigen, the receptor generally delivers an immunostimulatory signal, such as an ITAM-transduced signal, into the cell, thereby promoting an immune response targeted to the disease or condition. For example, in some embodiments, the cells express a CAR that binds to an antigen expressed by a cell or tissue of the disease or condition or associated with the disease or condition. The receptor may be another receptor such as an immunoinhibitory or costimulatory signal-promoting receptor, such as a CCR or iCAR or non-signaling receptor, e.g., for use in depletion or elimination of cells using the antibodies.

B. Genetically Engineered Cells and Methods of Producing Cells

Among the cells expressing the chimeric antigen receptors are engineered cells. The genetic engineering generally involves introduction of a nucleic acid encoding the recombinant or engineered component into a composition containing the cells, such as by retroviral transduction, transfection, or transformation. Various methods for the introduction of genetically engineered components, e.g., recombinant receptors, e.g., CARs, are well known and may be used. Exemplary methods include those for transfer of nucleic acids encoding the receptors, including via viral, e.g., retroviral or lentiviral, transduction, transposons, and electroporation.

1. Vectors and Methods for Genetic Engineering

Also provided are one or more polynucleotides (e.g., nucleic acid molecules) encoding chimeric antigen receptors (CARs), vectors for genetically engineering cells to express such CARs and methods for producing the engineered cells. In some embodiments, the vector contains the nucleic acid encoding the CAR. In some cases, the vector is a viral vector, such as a retroviral vector, e.g., a lentiviral vector or a gammaretroviral vector.

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28(10): 1137-46; Alonso-Camino et al. (2013) Mol Ther Nucl Acids 2, e93; Park et al., Trends Biotechnol. 2011 Nov. 29(11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207, 453; 5,219,740; Miller and Rosman (1989) BioTechniques 7: 980-990; Miller, A. D. (1990) Human Gene Therapy 1: 5-14; Scarpa et al. (1991) Virology 180: 849-852; Burns et al. (1993) Proc. Natl. Acad. Sci. USA 90: 8033-8037; and Boris-Lawrie and Temin (1993) Cur. Opin. Genet. Develop. 3: 102-109.

Methods of lentiviral transduction are known. Exemplary methods are described in, e.g., Wang et al. (2012) J. Immunother. 35(9): 689-701; Cooper et al. (2003) Blood. 101:

1637-1644; Verhoeyen et al. (2009) Methods Mol Biol. 506: 97-114; and Cavalieri et al. (2003) Blood. 102(2): 497-505.

In some embodiments, recombinant nucleic acids are transferred into T cells via electroporation (see, e.g., Chicaybam et al, (2013) PLoS ONE 8(3): e60298 and Van Tedeloo et al. (2000) Gene Therapy 7(16): 1431-1437). In some embodiments, recombinant nucleic acids are transferred into T cells via transposition (see, e.g., Manuri et al. (2010) Hum Gene Ther 21(4): 427-437; Sharma et al. (2013) Molec Ther Nucl Acids 2, e74; and Huang et al. (2009) Methods Mol Biol 506: 115-126). Other methods of introducing and expressing genetic material in immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346: 776-777 (1990)); and strontium phosphate DNA co-precipitation (Brash et al., Mol. Cell Biol., 7: 2031-2034 (1987)).

Other approaches and vectors for transfer of the nucleic acids encoding the recombinant products are those described, e.g., in international patent application, Publication No.: WO2014055668, and U.S. Pat. No. 7,446,190.

In some embodiments, the cells, e.g., T cells, may be transfected either during or after expansion, e.g. with a T cell receptor (TCR) or a chimeric antigen receptor (CAR). This transfection for the introduction of the gene of the desired receptor can be carried out with any suitable retroviral vector, for example. The genetically modified cell population can then be liberated from the initial stimulus (the anti-CD3/anti-CD28 stimulus, for example) and subsequently be stimulated with a second type of stimulus e.g. via a de novo introduced receptor). This second type of stimulus may include an antigenic stimulus in form of a peptide/MHC molecule, the cognate (cross-linking) ligand of the genetically introduced receptor (e.g. natural ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907: 645-66 or Barrett et al., Chimeric Antigen Receptor Therapy for Cancer Annual Review of Medicine Vol. 65: 333-347 (2014). In some embodiments, the cells are stimulated with a provided anti-idiotype antibody in accord with the provided methods.

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

Among additional nucleic acids, e.g., genes for introduction are those to improve the efficacy of therapy, such as by promoting viability and/or function of transferred cells; genes to provide a genetic marker for selection and/or evaluation of the cells, such as to assess in vivo survival or localization; genes to improve safety, for example, by making the cell susceptible to negative selection in vivo as described by Lupton S. D. et al., Mol. and Cell Biol., 11: 6 (1991); and Riddell et al., Human Gene Therapy 3: 319-338 (1992); see also the publications of PCT/US91/08442 and PCT/US94/05601 by Lupton et al. describing the use of bifunctional selectable fusion genes derived from fusing a dominant positive selectable marker with a negative selectable marker. See, e.g., Riddell et al., U.S. Pat. No. 6,040,177, at columns 14-17.

2. Cells and Preparation of Cells for Genetic Engineering

Provided herein are cells, including engineered cells that contain a chimeric antigen receptor (CAR). Also provided are population of such cells and compositions containing such cells. Among the compositions are input compositions containing cells in which one or more cells is known or likely or will express a recombinant receptor capable of being recognized or bound by a binding molecule present on one or more particles to which the cells are incubated or contacted. Also among the compositions are compositions produced by the provided methods, including output compositions in which is contained stimulated or expanded cells, including compositions enriched for cells containing a recombinant receptor bound or recognized by the binding molecule of the particle, such as in which cells expressing the recombinant receptor, e.g. chimeric receptor, make up at least 50, 60, 70, 80, 90, 91, 92, 93, 94, 95, 96, 97, 98, 99, or more percent of the total cells in the composition or cells of a certain type such as T cells or CD8+ or CD4+ cells. Thus, provided are genetically engineered cells expressing the recombinant receptors e.g., CARs.

Among the compositions are pharmaceutical compositions and formulations for administration, such as for adoptive cell therapy. Also provided are methods for engineering, producing or generating such cells, therapeutic methods for administering the cells and compositions to subjects, e.g., patients, and methods for detecting, selecting, isolating or separating such cells.

In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

The cells generally are eukaryotic cells, such as mammalian cells, and typically are human cells. In some embodiments, the cells are derived from the blood, bone marrow, lymph, or lymphoid organs, are cells of the immune system, such as cells of the innate or adaptive immunity, e.g., myeloid or lymphoid cells, including lymphocytes, typically T cells and/or NK cells. Other exemplary cells include stem cells, such as multipotent and pluripotent stem cells, including induced pluripotent stem cells (iPSCs).

The cells typically are primary cells, such as those isolated directly from a subject and/or isolated from a subject and frozen. In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation. With reference to the subject to be treated, the cells may be allogeneic and/or autologous. Among the methods include off-the-shelf methods. In some aspects, such as for off-the-shelf technologies, the cells are pluripotent and/or multipotent, such as stem cells, such as induced pluripotent stem cells (iPSCs). In some embodiments, the methods include isolating cells from the subject, preparing, processing, culturing, and/or engineering them, and re-introducing them into the same subject, before or after cryopreservation.

Among the sub-types and subpopulations of T cells and/or of CD4+ and/or of CD8+ T cells are naïve T ($T_N$) cells, effector T cells ($T_{EFF}$), memory T cells and sub-types thereof, such as stem cell memory T ($T_{SCM}$), central memory T ($T_{CM}$), effector memory T ($T_{EM}$), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, alpha/beta T cells, and delta/gamma T cells.

In some embodiments, the cells are natural killer (NK) cells. In some embodiments, the cells are monocytes or granulocytes, e.g., myeloid cells, macrophages, neutrophils, dendritic cells, mast cells, eosinophils, and/or basophils.

In some embodiments, the cells include one or more nucleic acids introduced via genetic engineering, and thereby express recombinant or genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature, including one comprising chimeric combinations of nucleic acids encoding various domains from multiple different cell types.

In some embodiments, preparation of the engineered cells includes one or more culture and/or preparation steps. The cells for introduction of the nucleic acid encoding the transgenic receptor such as the CAR, may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered.

Accordingly, the cells in some embodiments are primary cells, e.g., primary human cells. The samples include tissue, fluid, and other samples taken directly from the subject, as well as samples resulting from one or more processing steps, such as separation, centrifugation, genetic engineering (e.g. transduction with viral vector), washing, and/or incubation. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample from which the cells are derived or isolated is blood or a blood-derived sample, or is or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some embodiments, the cells are derived from cell lines, e.g., T cell lines. The cells in some embodiments are obtained from a xenogeneic source, for example, from mouse, rat, non-human primate, and pig.

In some embodiments, isolation of the cells includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets. In some embodiments, prior to the selection and/or enrichment of cells, the sample or the cells in the sample can be rested or held prior to further processing steps. In some embodiments, the sample is maintained at or held at a temperature of from or from about 2° C. to 8° C. for up to 48 hours, such as for up to 12 hours, 24 hours or 36 hours. In certain embodiments, the cells are not selected and/or enriched prior to contacting the cells with the one or more nucleic acids. In some embodiments, the sample or the cells can be rested or held prior to contacting or incubating the cells with one or more nucleic acids. In certain embodiments, the sample is maintained at or held at a temperature of from or from about 2° C. to 8° C. for up to 48 hours, such as for up to 12 hours, 24 hours or 36 hours prior to contacting or incubating the cells with one or more nucleic acids.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the methods include density-based cell separation methods, such as the preparation of white blood cells from peripheral blood by lysing the red blood cells and centrifugation through a Percoll or Ficoll gradient.

In some embodiments, the isolation methods include the separation of different cell types based on the expression or presence in the cell of one or more specific molecules, such as surface markers, e.g., surface proteins, intracellular markers, or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that binds to such markers, followed generally by washing steps and separation of cells having bound the antibody or binding partner, from those cells having not bound to the antibody or binding partner.

Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that identifies a cell type in a heterogeneous population, such that separation is best carried out based on markers expressed by cells other than the desired population.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28$^+$, CD62L$^+$, CCR7$^+$, CD27$^+$, CD127$^+$, CD4$^+$, CD8$^+$, CD45RA$^+$, and/or CD45RO$^+$ T cells, are isolated by positive or negative selection techniques.

For example, CD3$^+$, CD28$^+$ T cells can be positively selected using CD3/CD28 conjugated magnetic beads (e.g., DYNABEADS® M-450 CD3/CD28 T Cell Expander). In particular embodiments, cells are contacted with anti-CD3/anti-CD28 conjugated magnetic beads (e.g., DYNABEADS® M-450 CD3/CD28 T Cell Expander) to expand CD3$^+$, CD28+ T cells prior to contacting the cells with the one or more nucleic acids. In certain embodiments, the cells are not contacted with anti-CD3/anti-CD28 conjugated magnetic beads prior to contacting the cells with the one or more nucleic acids.

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that bind to one or more surface markers expressed or expressed (marker$^+$) at a relatively higher level (marker$^{high}$) on the positively or negatively selected cells, respectively.

In some embodiments, T cells are separated from a PBMC sample by negative selection of markers expressed on non-T cells, such as B cells, monocytes, or other white blood cells, such as CD14. In some aspects, a CD4$^+$ or CD8$^+$ selection step is used to separate CD4$^+$ helper and CD8$^+$ cytotoxic T cells. Such CD4$^+$ and CD8$^+$ populations can be further sorted into sub-populations by positive or negative selection for markers expressed or expressed to a relatively higher degree on one or more naive, memory, and/or effector T cell subpopulations.

In some embodiments, CD8$^+$ cells are further enriched for or depleted of naive, central memory, effector memory, and/or central memory stem cells, such as by positive or negative selection based on surface antigens associated with the respective subpopulation. In some embodiments, enrichment for central memory T (T$_{CM}$) cells is carried out to increase efficacy, such as to improve long-term survival, expansion, and/or engraftment following administration, which in some aspects is particularly robust in such subpopulations. See Terakura et al. (2012) Blood. 1: 72-82; Wang et al. (2012) *J Immunother.* 35(9): 689-701. In some embodiments, combining T$_{CM}$-enriched CD8$^+$ T cells and CD4$^+$ T cells further enhances efficacy.

In embodiments, memory T cells are present in both CD62L+ and CD62L$^-$ subsets of CD8$^+$ peripheral blood lymphocytes. PBMC can be enriched for or depleted of CD62L-CD8$^+$ and/or CD62L$^+$ CD8$^+$ fractions, such as using anti-CD8 and anti-CD62L antibodies.

In some embodiments, the enrichment for central memory T (T$_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8$^+$ population enriched for T$_{CM}$ cells is carried out by depletion of cells expressing CD4, CD14, CD45RA, and positive selection or enrichment for cells expressing CD62L. In one aspect, enrichment for central memory T (T$_{CM}$) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8$^+$ cell population or subpopulation, also is used to generate the CD4$^+$ cell population or subpopulation, such that both the positive and negative fractions from the CD4-based separation are retained and used in subsequent steps of the methods, optionally following one or more further positive or negative selection steps.

In a particular example, a sample of PBMCs or other white blood cell sample is subjected to selection of CD4$^+$ cells, where both the negative and positive fractions are retained. The negative fraction then is subjected to negative selection based on expression of CD14 and CD45RA, and positive selection based on a marker characteristic of central memory T cells, such as CD62L or CCR7, where the positive and negative selections are carried out in either order.

CD4$^+$ T helper cells are sorted into naïve, central memory, and effector cells by identifying cell populations that have cell surface antigens. CD4$^+$ lymphocytes can be obtained by standard methods. In some embodiments, naive CD4$^+$ T lymphocytes are CD45RO$^-$, CD45RA$^+$, CD62L$^+$, CD4$^+$ T cells. In some embodiments, central memory CD4$^+$ cells are CD62L+ and CD45RO'. In some embodiments, effector CD4$^+$ cells are CD62L$^-$ and CD45RO$^-$.

In one example, to enrich for CD4$^+$ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ).

In some aspects, the sample or composition of cells to be separated is incubated with small, magnetizable or magnetically responsive material, such as magnetically responsive particles or microparticles, such as paramagnetic beads (e.g., such as Dynabeads or MACS beads). The magnetically responsive material, e.g., particle, generally is directly or indirectly attached to a binding partner, e.g., an antibody, that binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners, or molecules, such as secondary antibodies or other reagents, which bind to such antibodies or binding partners, which are attached to the magnetic particle or bead, bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, and magnetizable particles or antibodies conjugated to cleavable linkers. In some embodiments, the magnetizable particles are biodegradable.

In some embodiments, the affinity-based selection is via magnetic-activated cell sorting (MACS) (Miltenyi Biotec, Auburn, CA). Magnetic Activated Cell Sorting (MACS) systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380 A1. In one example, the system is a system as described in International Publication Number WO2016/073602.

In some embodiments, the system or apparatus carries out one or more, e.g., all, of the isolation, processing, engineering, and formulation steps in an integrated or self-contained system, and/or in an automated or programmable fashion. In some aspects, the system or apparatus includes a computer and/or computer program in communication with the system or apparatus, which allows a user to program, control, assess the outcome of, and/or adjust various aspects of the processing, isolation, engineering, and formulation steps.

In some aspects, the separation and/or other steps is carried out using CliniMACS system (Miltenyi Biotec), for example, for automated separation of cells on a clinical-scale level in a closed and sterile system. Components can include an integrated microcomputer, magnetic separation unit, peristaltic pump, and various pinch valves. The integrated computer in some aspects controls all components of the instrument and directs the system to perform repeated procedures in a standardized sequence. The magnetic separation unit in some aspects includes a movable permanent magnet and a holder for the selection column. The peristaltic pump controls the flow rate throughout the tubing set and, together with the pinch valves, ensures the controlled flow of buffer through the system and continual suspension of cells.

The CliniMACS system in some aspects uses antibody-coupled magnetizable particles that are supplied in a sterile, non-pyrogenic solution. In some embodiments, after labelling of cells with magnetic particles the cells are washed to remove excess particles. A cell preparation bag is then connected to the tubing set, which in turn is connected to a bag containing buffer and a cell collection bag. The tubing set consists of pre-assembled sterile tubing, including a pre-column and a separation column, and are for single use only. After initiation of the separation program, the system automatically applies the cell sample onto the separation column. Labelled cells are retained within the column, while unlabeled cells are removed by a series of washing steps. In some embodiments, the cell populations for use with the methods described herein are unlabeled and are not retained in the column. In some embodiments, the cell populations for use with the methods described herein are labeled and are retained in the column. In some embodiments, the cell populations for use with the methods described herein are eluted from the column after removal of the magnetic field, and are collected within the cell collection bag.

In certain embodiments, separation and/or other steps are carried out using the CliniMACS Prodigy system (Miltenyi Biotec). The CliniMACS Prodigy system in some aspects is equipped with a cell processing unity that permits automated washing and fractionation of cells by centrifugation. The CliniMACS Prodigy system can also include an onboard camera and image recognition software that determines the optimal cell fractionation endpoint by discerning the macroscopic layers of the source cell product. For example, peripheral blood is automatically separated into erythrocytes, white blood cells and plasma layers. The CliniMACS Prodigy system can also include an integrated cell cultivation chamber which accomplishes cell culture protocols such as, e.g., cell differentiation and expansion, antigen loading, and long-term cell culture. Input ports can allow for the sterile removal and replenishment of media and cells can be monitored using an integrated microscope. See, e.g., Klebanoff et al. (2012) *J Immunother.* 35(9): 651-660, Terakura et al. (2012) Blood. 1: 72-82, and Wang et al. (2012) *J Immunother.* 35(9): 689-701.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) *Lab Chip* 10, 1567-1573; and Godin et al. (2008) J Biophoton. 1(5): 355-376. In both cases, cells can be labeled with multiple markers, allowing for the isolation of well-defined T cell subsets at high purity.

In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are generally then frozen to −80° C. at a rate of 1° per minute and stored in the vapor phase of a liquid nitrogen storage tank.

In some embodiments, the cells are incubated and/or cultured prior to or in connection with genetic engineering. The incubation steps can include culture, cultivation, stimulation, activation, and/or propagation. The incubation and/or engineering may be carried out in a culture vessel, such as a unit, chamber, well, column, tube, tubing set, valve, vial, culture dish, bag, or other container for culture or cultivating cells. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the stimulating conditions or agents include one or more agent, e.g., ligand, which is capable of activating an intracellular signaling domain of a TCR complex. In some aspects, the agent turns on or initiates TCR/CD3 intracellular signaling cascade in a T cell. Such agents can include antibodies, such as those specific for a TCR, e.g. anti-CD3. In some embodiments, the stimulating conditions include one or more agent, e.g. ligand, which is capable of stimulating a costimulatory receptor, e.g., anti-CD28. In some embodiments, such agents and/or ligands may be, bound to solid support such as a bead, and/or one or more cytokines. Optionally, the expansion method may further comprise the step of adding anti-CD3 and/or anti CD28 antibody to the culture medium (e.g., at a concentration of at least about 0.5 ng/ml). In some embodiments, the stimulating agents include IL-2, IL-15 and/or IL-7. In some aspects, the IL-2 concentration is at least about 10 units/mL.

In some aspects, incubation is carried out in accordance with techniques such as those described in U.S. Pat. No. 6,040,177 to Riddell et al., Klebanoff et al. (2012) J Immunother. 35(9): 651-660, Terakura et al. (2012) Blood. 1: 72-82, and/or Wang et al. (2012) J Immunother. 35(9): 689-701.

In some embodiments, the T cells are expanded by adding to a culture-initiating composition feeder cells, such as non-dividing peripheral blood mononuclear cells (PBMC), (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division. In some aspects, the feeder cells are added to culture medium prior to the addition of the populations of T cells.

In some embodiments, the stimulating conditions include temperature suitable for the growth of human T lymphocytes, for example, at least about 25 degrees Celsius, generally at least about 30 degrees, and generally at or about 37 degrees Celsius. Optionally, the incubation may further comprise adding non-dividing EBV-transformed lymphoblastoid cells (LCL) as feeder cells. LCL can be irradiated with gamma rays in the range of about 6000 to 10,000 rads. The LCL feeder cells in some aspects is provided in any suitable amount, such as a ratio of LCL feeder cells to initial T lymphocytes of at least about 10:1.

III. Compositions

Also provided are compositions including the binding molecules, such as anti-idiotype antibodies or antigen-binding fragments thereof, as provided herein, including pharmaceutical compositions and formulations. Also provided are compositions including the anti-idiotype antibodies or antigen-binding fragments thereof, as provided herein, including pharmaceutical compositions and formulations. The compositions and formulations generally include one or more optional acceptable carriers or excipients.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell, binding molecule, and/or antibody, and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

In some aspects, the composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Acceptable carriers include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Formulations of the antibodies can include lyophilized formulations and aqueous solutions.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the binding molecule in a solvent, such as in admixture with a suitable carrier, diluent, or excipient such as sterile water, physiological saline, glucose, dextrose, or the like. The compositions can also be lyophilized. The compositions can contain auxiliary substances such as wetting, dispersing, or emulsifying agents (e.g., methylcellulose), pH buffering agents, gelling or viscosity enhancing additives, preservatives, flavoring agents, colors, and the like, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. Prolonged absorption of the injectable pharmaceutical form can be brought about by the use of agents delaying absorption, for example, aluminum monostearate and gelatin.

The compositions can also be lyophilized. The compositions can contain auxiliary substances such as wetting, dispersing, or emulsifying agents (e.g., methylcellulose), pH buffering agents, gelling or viscosity enhancing additives, preservatives, colors, and the like. Standard texts may in some aspects be consulted to prepare suitable preparations.

The formulations to be used for in vivo administration are generally sterile. Sterility may be readily accomplished, e.g., by filtration through sterile filtration membranes.

IV. Methods and Uses

In some embodiments, provided herein are methods involving the use of one or more anti-idiotype antibodies. In some aspects, provided herein are methods for measuring or detecting a target antibody, such as a CAR or a cell expressing a CAR, and methods for modifying the activity of the target antibody, such as the activity of a CAR or the activity of a cell expressing a CAR. In some aspects, provided herein are methods for measuring or detecting a target antibody, such as a CAR or a cell expressing a CAR. In certain embodiments, the one or more anti-idiotype antibodies bind, detect, identify, purify, select, and/or quantify the CAR and/or cells expressing the CAR. In some aspects, also provided herein are methods for modifying the activity of the target antibody, such as the activity of a CAR or the activity of a cell expressing a CAR. In some embodiments, the methods provided herein provide one or more steps of contacting and/or incubating the one or more anti-idiotype antibodies with a cell or a sample containing or thought to be containing cells that express a chimeric antigen receptor (CAR). In some embodiments, the anti-idiotype antibody is treated, incubated, and/or contacted with the composition or sample under conditions that allow for the formation of a complex between the anti-idiotype antibody and the target antibody, e.g., the CAR. In some aspects, the complex may be utilized for the purposes of detecting, isolating, and/or measuring the CAR. In some embodiments, the formation of the complex modifies the activity of the target antibody, e.g., the CAR, such as by stimulating receptor signaling activity, or in some embodiments, antagonizing the activity of the target antibody, e.g., the CAR, by preventing the association of the CAR with an antigen. In some embodiments, the CAR is a CAR expressing Target Antibody 1 or Target Antibody 2, or an antigen-binding fragment thereof, or is a CAR as described in, e.g., WO 2019/090003 or WO 2016/090320, the contents of which are hereby incorporated by reference.

A. Detection/Isolation Methods

In some embodiments, there are provided methods involving use of one or more of the anti-idiotype antibodies, and/or molecules (such as conjugates and complexes) containing one or more of such anti-idiotype antibodies, for detecting, binding, selecting, and/or isolating an antibody, e.g., a target antibody. In certain embodiments, the methods provide one or more steps of contacting, incubating, and/or exposing the one or more anti-idiotype antibodies to a sample and/or composition.

In some embodiments, the methods include (a) contacting a composition comprising a target antibody or antigen-binding fragment thereof (e.g., Target Antibody 1 or Target Antibody 2, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) detecting the anti-idiotype antibody or antigen-binding fragment thereof bound to the target antibody or antigen-binding fragment thereof.

In some embodiments, the methods include (a) contacting a cell expressing a CAR comprising a target antibody or antigen-binding fragment thereof (e.g., Target Antibody 1 or Target Antibody 2, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) detecting the anti-idiotype antibody or antigen-binding fragment thereof bound to the target antibody or antigen-binding fragment thereof.

In some embodiments, the methods include (a) contacting a cell population expressing a CAR comprising a target antibody or antigen-binding fragment thereof (e.g., Target Antibody 1 or Target Antibody 2, or an antigen-binding fragment thereof) or a cell bound to a target antibody or antigen-binding fragment thereof (e.g., Target Antibody 1 or Target Antibody 2, or an antigen-binding fragment thereof) with an anti-idiotype antibody or antigen-binding fragment thereof provided herein, or an anti-idiotype antibody immunoconjugate provided herein, that binds to or recognizes the target antibody or antigen-binding fragment thereof, and (b) selecting cells bound with the anti-idiotype antibody or antigen-binding fragment thereof.

In some embodiments, the sample and/or composition has, is likely to have, and/or is suspected of having a target antibody and/or antigen binding fragment thereof that is bound by and/or recognized by the one or more anti-idiotype antibodies. In certain embodiments, the antibody or antigen binding fragment thereof that is bound by or recognized by the one or more anti-idiotype antibodies contains one or more fusion domains and/or is a fusion protein. In certain embodiments, the target antibody and/or antigen binding fragment thereof is a CAR. In certain embodiments, the anti-idiotype antibody, binds to and/or recognizes an anti-BCMA antibody (e.g., Target Antibody 1, Target Antibody 2), or an antigen-binding fragment thereof, including a chimeric molecule or conjugate including a CAR, containing such anti-BCMA antibody (e.g., antibody fragment). In certain embodiments, the anti-idiotype antibody, binds to and/or recognizes more than one anti-BCMA antibody (e.g., Target Antibody 1 and Target Antibody 2), or an antigen-binding fragment thereof, including a chimeric molecule or conjugate including a CAR, containing such anti-BCMA antibody (e.g., antibody fragment).

In some embodiments, an anti-BCMA target antibody or antigen-binding fragment is bound to a cell or expressed on the surface of a cell. In some embodiments, an anti-BCMA target antibody or antigen-binding fragment is contained in a chimeric antigen receptor (CAR), such as a CAR expressed on the surface of a cell. In some embodiments, the cell is a stem cell, e.g., an iPSC, or an immune cell. In some embodiments, the immune cell is a T cell. The T cell can include a CD4+ T cell or a CD8+ T cell, or any subset thereof. For instance, the T cell can be a naïve T ($T_N$) cell, effector T cell ($T_{EFF}$), memory T cell, tumor-infiltrating lymphocyte (TIL), immature T cell, mature T cell, helper T cells, cytotoxic T cell, mucosa-associated invariant T (MAIT) cell, naturally occurring and adaptive regulatory T (Treg) cell, helper T cell, such as a TH1 cell, TH2 cell, TH3 cell, TH17 cell, TH9 cell, TH22 cell, follicular helper T cell, alpha/beta T cell, and/or a delta/gamma T cells. In some embodiments, the cell is from a tissue, e.g., heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons.

In some embodiments, the cell is a T cell isolated or selected from a sample from a subject (e.g. human subject) and engineered to express the target CAR containing in its extracellular antigen-binding domain an anti-BCMA target antibody. For instance, in some embodiments, a composition of CAR-expressing T cells can be produced by a process that includes isolating or selecting T cells (e.g. CD3+, or CD4+ and/or CD8+ T cells) from an apheresis or leukapheresis sample from a subject (e.g. human subject), activating the isolated to selected T cells (e.g. with anti-CD3/anti-CD28 reagent, such as anti-CD3/anti-CD28 beads (e.g. Dynabeads), and then transducing the activated cells with a vector encoding the target anti-BCMA CAR containing in its extracellular antigen-binding domain an anti-BCMA target antibody. In some cases, the transduced T cells may be further incubated or cultured in the presence of one or more stimulatory reagents (e.g. recombinant IL-2, IL-7 and/or IL-15) under conditions for proliferation or expansion of the CAR-expressing T cells. In some embodiments, provided methods can include contacting a composition of T cells containing target anti-BCMA CAR-expressing T cells with a provided anti-idiotype antibody or antigen-binding fragment and detecting or selecting T cells bound with the anti-idiotype antibody or antigen-binding fragment. In some embodiments, the provided methods can be used to quantify or determine the number of target anti-BCMA CAR-expressing T cells in the composition of T cells as a percentage or number compared to the total cells or total T cells in the composition.

In particular embodiments, target antibody, e.g., the CAR is not bound or contained within a cell, for example, in some embodiments, the target antibody is secreted. In certain embodiments, the antibody has been detached, removed, and/or lysed from the surface of a cell.

The methods in some embodiments include incubating, treating, and/or contacting a sample and/or a composition containing or suspected of containing the target antibody with the anti-idiotype antibody. In certain embodiments, the incubating is under conditions permissive for binding of the anti-idiotype antibody to the target antibody present in the composition, for example to form a complex containing the anti-idiotype antibody and the target antibody.

The methods in some embodiments include incubating, treating, and/or contacting a sample and/or a composition containing or suspected of containing the target anti-BCMA antibody, or a target anti-BCMA CAR containing the target antibody, with the anti-idiotype antibody. For instance, the sample or composition can include a composition of cells, such as T cells, known or suspected of containing cells expressing the target anti-BCMA CAR. In certain embodiments, the incubating is under conditions permissive for binding of the anti-idiotype antibody to the target anti-BCMA antibody present in the composition, for example to form a complex containing the anti-idiotype antibody and the target anti-BCMA antibody.

In some embodiments, the sample and/or composition contains or is suspected of containing the target antibody, e.g., a CAR. In certain embodiments, the sample and/or composition contains or is suspected of containing cells that express the target antibody, e.g., a CAR. In particular embodiments, the cells are T cells that express a CAR having an extracellular antigen-binding domain containing the target anti-BCMA antibody. In some embodiments the T cells are CD3+ T cells. In some embodiments, the T cells are CD8+ T cells. In some embodiments, the T cells are CD4+ T cells. In some embodiments, the composition contains T cells expressing a targeting anti-BCMA CAR that includes CD4+ and CD8+ T cells. In some embodiments, the sample or composition is a sample of T cells produced or engineered with the target anti-BCMA CAR ex vivo, for example, from T cells isolated from a biological sample from the subject (e.g. apheresis or leukapheresis sample). In some embodiments, the sample or composition is a sample known or suspected of containing target anti-BCMA CAR-expressing T cells obtained directly from a sample from a subject, for example, a subject that had been previously administered a dose of a therapeutic composition containing target anti-BCMA CAR-expressing Tcells. In certain embodiments, the sample is a biological sample. In particular embodiments, the sample is a serum sample or a blood sample. In some embodiments, the biological sample contains one or more immune cells. In some embodiments, the biological sample is or is derived from a tissue, such as connective tissue, muscle tissue, nervous tissue, or epithelial tissue. In particular embodiments, the biological sample is or is derived from heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons. In particular embodiments, the biological sample is taken, collected, and/or obtained from a human subject. In certain embodiments, the sample contains cells that are live and/or intact. In some embodiments, the sample is or contains a homogenate and/or cells that have been disrupted and/or lysed. In some embodiments, the biological sample contains proteins and/or antibodies that have been isolated from blood, serum, and/or a tissue.

In particular embodiments, the anti-idiotype antibody forms or is capable of forming a complex with a target antibody, e.g., a CAR. In particular embodiments, the anti-idiotype antibody forms or is capable of forming a complex with a target antibody, e.g., contained in a CAR. In particular embodiments, the complex is detected, measured, quantified, and/or assessed, for example, to allow for the detection, identification, measurement, and/or quantification of the target antibody, for example in a composition or a sample. In certain embodiments, the methods include detecting whether a complex is formed between the anti-idiotype antibody and the target antibody in the sample, and/or detecting the presence or absence or level of such binding. In some embodiments, the complex contains a detectable label. In particular embodiments, the anti-idiotype antibody is an immunoconjugate that contains a detectable label. In certain embodiments, the anti-idiotype antibody contains, is conjugated with, bound to, and/or attached to the detectable label. In some embodiments, the complex contains an anti-body that binds to and/or recognizes the anti-idiotype anti-body, e.g., a secondary antibody, that in conjugated with, bound to, and/or attached to a detectable label.

In some embodiments, methods for detecting, quantify-ing, detecting, and/or assessing a target antibody, for example in a sample or composition, includes detecting a complex of the target antibody and the anti-idiotype anti-body. In some embodiments, the complex contains a detect-able label. In some embodiments, the antibodies provided herein can be conjugated directly or indirectly to a moiety that is capable of detection. In some examples, one or more of the antibodies are modified to permit detection of binding. For example, antibodies can be conjugated to a detectable molecule that permits either direct detection or detection via secondary agents. In some embodiments, the label is a detectable label (e.g., a fluorescent dye label). In some embodiments, the label is an affinity label (e.g., a biotin label). Methods for directly or indirectly attaching label to an antibody are well known in the art. Labels and labeling kits are commercially available such as from Invitrogen Corp, Carlsbad, Calif. In some embodiments, the label is compatible for use in a detection assay. In some embodi-ments, the label is compatible for use in a diagnostic assay. Labels contemplated herein include, but are not limited to, fluorescent dyes, fluorescent proteins, radioisotopes, chro-mophores, metal ions, gold particles (e.g., colloidal gold particles), silver particles, particles with strong light scat-tering properties, magnetic particles (e.g., magnetic bead particles such as Dynabeads® magnetic beads), polypep-tides (e.g., FLAG™ tag, human influenza hemagglutinin (HA) tag, etc.), enzymes such as peroxidase (e.g., horserad-ish peroxidase) or a phosphatase (e.g., alkaline phos-phatase), streptavidin, biotin, luminescent compounds (e.g., chemiluminescent substrates), oligonucleotides, members of a specific binding pair (e.g., a ligands and its receptor) and other labels well known in the art that are used for visual-izing or detecting an antibody when directly or indirectly attached to said antibody. In some embodiments, the label is a horseradish peroxidase, which can be detecting by adding an appropriate substrate that produces a color change in the presence of horseradish peroxidase. In some embodiments, the label is a colloidal gold particles, which can be detecting by detecting a color change in the solution due to aggrega-tion of the gold particles. Other methods for detecting gold particle labeled antibodies are well known in the art (see Dykman et al. (2011) Acta Naturae. 3(2):34-55). In some examples, the antibodies can be detected using a secondary reagent, such as by a secondary antibody reagent that binds to the primary antibodies as provided herein and that is coupled to a detectable protein, such as a fluorescent probe or detectable enzyme, such as horseradish peroxidase.

In certain embodiments, the complex is probed and/or contacted with a detectable label. In some embodiments, the complex is detected by any suitable method or means, such as but not limited to flow cytometry, immunocytochemistry, immunohistochemistry, western blot analysis, and ELISA. In some embodiments, the cells bound with the anti-idiotype antibody or antigen-binding fragment thereof are selected by affinity-based separation, e.g., immunoaffinity-based sepa-ration. In some embodiments, the affinity-based separation is by flow cytometry. In some embodiments, the affinity-based separation is by magnetic activated cell sorting. In some embodiments, the affinity-based separation is by affinity chromatography. In some embodiments, the affinity-based separation is by affinity chromatography and the anti-idiotype antibody or antigen-binding fragment thereof is revers-ibly bound or immobilized to a support or a stationary phase.

In some embodiments, the sample or composition is mixed with the anti-idiotype antibody or antigen-binding fragment in the presence of or on or in a solid support or a device comprising a solid support. In some embodiments, the sample or composition is mixed with the one or more anti-idiotype antibody or antigen-binding fragment to pro-duce a mixture and the mixture is subsequently applied to a solid support or a device comprising a solid support. In some of the embodiments herein, the anti-idiotype antibody or antigen-binding fragment is directly or indirectly attached to the solid support. In some embodiments, the contacting includes incubation of the sample or composition and the anti-idiotype antibody or antigen-binding fragment. The one or more incubations can be for a time that is suitable to allow the sample to contact the one or more antibody such as for at least or at least about 30 seconds, 1 minute, 5 minutes, 10 minutes, 15 minutes, 20 minutes, 30 minutes, 45 minutes, 1 hour, 2 hours, 3 hours, 6 hours, or 12 hours or more but no more than about 24 hours after contacting a sample with the one or more antibody as described herein. In some embodi-ments, the contacting occurs at a temperature of from or from about 0° C. to about 50° C., such as typically 2° C. to 8° C. or 23° C. to 28° C. or 37° C. to 42° C. In some embodiments, methods can include one or more washing steps after the contacting or incubating under conditions to retain bound anti-idiotype antibody or antigen-binding frag-ment on the solid support and/or to separate the complex away from portions of the sample not part of the complex.

In some embodiments, the contacted is carried out under conditions to form a complex comprising the antibody or antigen-binding fragment bound to an anti-BCMA target antibody, e.g. contained in a CAR expressed by a cell in the composition. In some embodiments, detection of binding can be achieved by detection techniques commonly known in the art for detecting the binding between a protein target and binding agent (e.g. an antibody) such as, but not limited to, spectrophotometry, high performance liquid chromatog-raphy (HPLC), immunoassays such as enzyme-linked immunosorbent assay (ELISA), western blot, automated imaging, immunohistochemistry, flow cytometry, high-throughput screening of an array such as a microarray or nanoarray and surface plasmon resonance. In some embodi-ments, the antibodies provided herein can detect an anti-BCMA target antibody, e.g. contained in a CAR expressed by a cell in the composition, using any binding assay or immunoassay known to one of skill in the art including, but not limited to, enzyme linked immunosorbent assay (ELISA) or other similar immunoassay, including a sand-wich ELISA or competitive ELISA; immunohistochemistry (IHC); flow cytometry, or western blot.

In some embodiments, the provided methods for detect-ing, quantifying, and/or assessing a target antibody, for example in a sample or composition, are performed using a cartridge-based flow method (see, e.g., WO 2011/128893, WO 2014/097286, WO 2014/097287, US 2014/0170678, US 2015/0330971, the contents of which are incorporated by reference in their entireties). In some embodiments, the cartridge-based flow method is performed using a microflu-idic device, for instance a device including a microfluidics cartridge and a cartridge handling unit. In certain aspects, use of a cartridge-based flow method obviates the need for special cleaning, maintenance, or use of sheath fluid in the cartridge handling unit. In some embodiments, such meth-ods can be used as part of manufacturing, analytic, and/or quality control methods, e.g., in association with the generation of cell therapies expressing recombinant polypeptides, e.g., CARs, containing an antibody or fragment thereof recognized by the anti-idiotype antibody provided herein. In some embodiments, such methods can be used for testing purposes, including to detect, assay, and/or confirm expression of the engineered receptor, e.g., in cells engineered for use in therapy in an individual. In some embodiments, such methods are used to determine the dose of CAR-T cells to be administered to an individual. In certain embodiments, the cell compositions can be tested at any stage in the process of generating CAR expressing T cells. In particular embodiments, a sample of cells may be collected from a cell composition at any stage of the process and stored, e.g., by cryofreezing and/or cyropreservation, for later testing and/or analysis. The compositions tested may be pharmaceutical compositions e.g., including those containing the cells and a pharmaceutically acceptable recipient and/or cryopreservative agent.

In some embodiments, the cartridge-based flow method is an automated method (e.g., one requiring minimal operator input). In certain aspects, the automated method reduces costs associated with operators and/or expensive equipment. In certain aspects, the automated method is easier to perform and faster than those using traditional assays, e.g., flow cytometry assays. In certain aspects, the automated method reduces the processing time of a sample, for instance down to about 30 to 40 minutes per sample. In some embodiments, the automated method is more consistent and robust than those performed using traditional assays.

In some embodiments, the microfluidic device is a benchtop instrument. In certain aspects, the smaller footprint of the microfluidic device allows for deployment of the device directly in cell processing or testing rooms. In certain aspects, the amount of samples that would need to be moved between rooms and/or labs is reduced, thereby reducing chain of identity and/or chain of custody concerns associated with transferring samples.

In some embodiments, the microfluidic cartridge contains a sample composition chamber. In some embodiments, the microfluidic cartridge contains a blister compartment. In some embodiments, the microfluidic cartridge contains a treatment compartment adapted for fluid mixing, said treatment compartment in fluid communication with the sample composition chamber and the blister. In some embodiments, the microfluidic cartridge contains an evaluation chamber including a reading zone, wherein the evaluation chamber is in fluid communication with the treatment chamber. In some embodiments, the reading zone allows for analysis of the sample as it passes through the reading zone.

In some embodiments, the sample is placed inside the sample composition chamber. In some embodiments, the blister contains an anti-idiotype antibody or antigen-binding fragment thereof provided herein. In some embodiments, the anti-idiotype antibody or antigen-binding fragment thereof is conjugated to a detectable label, e.g., a fluorescent tag. In some embodiments, the microfluidic cartridge is inserted into the cartridge handling unit. In some embodiments, the cartridge handling unit contacts and/or mixes the sample with the anti-idiotype antibody or antigen-binding fragment thereof in the treatment compartment. In some embodiments, the contacting and/or mixing leads to formation of a complex of the target antibody, e.g., CAR, and the anti-idiotype antibody or antigen-binding fragment thereof.

In other embodiments, the sample is added to a tube containing a dried-down anti-idiotype antibody or antigen-binding fragment thereof. In some embodiments, the anti-idiotype antibody or antigen-binding fragment thereof is conjugated to a detectable label, e.g., a fluorescent tag. In some embodiments, the tube further contains other dried-down reagents, e.g., other labelled antibodies, dyes, or lysing agents. In some embodiments, the tube is vortexed for mixing and/or rehydration of the dried-down reagents. In some embodiments, the sample after mixing is placed inside the sample composition chamber. In some embodiments, the microfluidic cartridge is inserted into the cartridge handling unit.

In some embodiments, the cartridge handling unit flows individual cells of the sample through the reading zone. In some embodiments, the cartridge handling unit measures fluorescent signals from the anti-idiotype antibody or antigen-binding fragment thereof bound to the target antibody, e.g. CAR. In some embodiments, the fluorescent signals are measured using an optoelectronic unit. In some embodiments, the fluorescent signals are analyzed using spectral analysis.

In some embodiments, the target antibody or antigen-binding fragment is bound to a cell or expressed on the surface of a cell. In particular embodiments, target antibody, e.g., the CAR is not bound or contained within a cell, for example, in some embodiments, the target antibody is secreted. In certain embodiments, the antibody has been detached, removed, and/or lysed from the surface of a cell.

In some embodiments, the target antibody or antigen-binding fragment is contained in a chimeric antigen receptor (CAR), such as a CAR expressed on the surface of a cell. In some embodiments, the cell is a stem cell, e.g., an iPSC, or an immune cell. In some embodiments, the immune cell is a T cell, e.g., a CD4+ T cell, a CD8+ T cell, naïve T ($T_N$) cell, effector T cell ($T_{EFF}$), memory T cell, tumor-infiltrating lymphocyte (TIL), immature T cell, mature T cell, helper T cells, cytotoxic T cell, mucosa-associated invariant T (MAIT) cell, naturally occurring and adaptive regulatory T (Treg) cell, helper T cell, such as a TH1 cell, TH2 cell, TH3 cell, TH17 cell, TH9 cell, TH22 cell, follicular helper T cell, alpha/beta T cell, and/or a delta/gamma T cells. In some embodiments, the cell is from a tissue, e.g., heart, vasculature, salivary glands, esophagus, stomach, liver, gallbladder, pancreas, intestines, colon, rectum, hypothalamus, pituitary gland, pineal gland, thyroid, parathyroid, adrenal gland, kidney, ureter, bladder, urethra, lymphatic system, skin, muscle, brain, spinal cord, nerves, ovaries, uterus, testes, prostate, pharynx, larynx, trachea, bronchi, lungs, diaphragm, bone, cartilage, ligaments, or tendons.

In some of any such embodiments, the target antibody is an anti-BCMA antibody. In some of any such embodiments, the anti-BCMA antibody is Target Antibody 1, e.g., as described in section I. In some of any such embodiments, the anti-BCMA antibody is Target Antibody 2, e.g., as described in section I.A.

In some of any such embodiments, the anti-idiotype antibody or antigen-binding fragment thereof is an anti-idiotype antibody or antigen-binding fragment thereof that binds to or recognizes Target Antibody 1. In some of any such embodiments, the anti-idiotype antibody or antigen-binding fragment thereof is an anti-idiotype antibody or antigen-binding fragment thereof that binds to or recognizes Target Antibody 2, such as any such anti-idiotype antibody or antigen-binding fragment thereof as described herein, e.g., in section I.A. In some of any such embodiments, the anti-idiotype antibody or antigen-binding fragment thereof is an anti-idiotype antibody or antigen-binding fragment thereof that binds to or recognizes Target Antibody 1 and/or Target Antibody 2, such as any such anti-idiotype antibody or antigen-binding fragment thereof as described herein, e.g., in section I.B.

B. Use in Cell Stimulation

In some embodiments, the provided anti-idiotype antibodies or antigen-binding fragments thereof are agonists and/or exhibit specific activity to stimulate cells expressing a target antibody including conjugates or chimeric receptors containing the same, such as an anti-BCMA antibody (e.g., Target Antibody 1 or Target Antibody 2), or an antigen-binding fragment thereof. In some embodiments, provided are methods involving use of the provided anti-idiotype antibodies, and molecules (such as conjugates and complexes) containing one or more of such anti-idiotype antibodies, for stimulation or activation of CAR-expressing or other chimeric receptor-expressing cells, such as T cells. In some aspects, the CAR or other receptor comprises the target antibody, such as an anti-BCMA antibody (e.g., Target Antibody 1 or Target Antibody 2), or an antigen-binding fragment thereof.

In some embodiments, the methods can be used in connection with methods of preparing genetically engineered T cells, such as in methods of expanding genetically engineered T cells or other cells into which a nucleic acid molecule encoding the chimeric receptor such as the CAR comprising the target antibody has been introduced, e.g., by transfection, transduction, or a non-viral means of nucleic acid transfer, such as transposon-based approaches. In some aspects, the target antibody is an anti-BCMA antibody (e.g., Target Antibody 1 or Target Antibody 2), or an antigen-binding fragment thereof. In particular embodiments, the target antibody is or contains a CAR, e.g., an anti-BCMA CAR. In particular embodiments, the anti-BCMA CAR contains an scFv that is from and/or is derived from an anti-BCMA antibody, such as Target Antibody 1 or Target Antibody 2.

The methods in some embodiments include incubating a sample comprising T cells transduced with a CAR with the anti-idiotype antibody. In certain embodiments, the methods further include detecting whether the CAR T cells are activated or stimulated, such as by assessing the viability, proliferation, and/or expression of activation markers in the CAR T cells. In some embodiments, the target antibody is an anti-BCMA antibody. In some embodiments, the target antibody is or is derived from Target Antibody 1, or an antigen-binding fragment thereof, or Target Antibody 2, or an antigen-binding fragment thereof.

In some embodiments, there is provided a method of simulating cells, comprising incubating an input composition comprising cells expressing a CAR comprising a target antibody, such as Target Antibody 1 or Target Antibody 2, or an antigen-binding fragment thereof, with an anti-idiotype antibody or antigen-binding fragment thereof described herein that binds to or recognizes the target antibody, thereby generating an output composition comprising stimulated cells. In some embodiments, the incubation is performed under conditions in which the anti-idiotype antibody or antigen-binding fragment thereof binds to the CAR, thereby inducing or modulating a signal in one or more cells in the input composition. In some embodiments, the cells comprise T cells. In some embodiments, the T cells comprise CD4+ and/or CD8+ T cells.

In some embodiments, provided herein is a method of stimulating or expanding cells that express a CAR, by incubating an input composition containing cells expressing a CAR with an anti-ID antibody that binds to and/or recognizes the CAR. In some embodiments, binding between the anti-ID antibody and the CAR induces expansion of the cells expressing the CAR, thereby producing an output composition comprising expanded cells.

In some embodiments, provided herein is a method of purifying an anti-idiotype antibody or antigen-binding fragment thereof, comprising: (a) contacting a composition comprising a target antibody or antigen-binding fragment thereof with an anti-idiotype antibody or antigen-binding fragment thereof provided herein, or an immunoconjugate as provided herein, that binds to or recognizes the target antibody or antigen-binding fragment thereof, and (b) isolating complexes comprising the anti-idiotype antibody or antigen-binding fragment thereof. In some embodiments, the complexes comprising the anti-idiotype antibody or antigen-binding fragment thereof are isolated by affinity-based separation. In some embodiments, the affinity-based separation is immunoaffinity-based separation. In some of any such embodiments, the affinity-based separation is magnetic-based separation. In some of any such embodiments, the affinity-based separation is affinity chromatography.

In some embodiments, anti-idiotype antibody is contacted to or incubated with an input composition of one or more cells to generate an output composition. In certain embodiments, the input cells and/or the input composition is a composition and/or a plurality of cells that are, or are desired to be, treated, incubated, or contacted under conditions that will produce one or more changes to at least a portion of the cells of the input composition, thereby converting the input composition into an output composition. In some embodiments, the input cells are a composition of immune cells, for example, a composition of T cells that contain cells expressing a CAR. In particular embodiments, at least a portion of the cells in the input composition are activated, expanded, and/or enriched in the generated output composition by practice of the provided methods.

In certain embodiments, the anti-idiotype antibody expands or enriches the CAR expressing cells of an input composition. In some embodiments, the input composition comprises eukaryotic cells, such as mammalian cells. In certain embodiments, the input composition contains human cells. In some embodiments, the input composition contains cells that are derived from the blood, bone marrow, lymph, or lymphoid organs. In particular embodiments, the input composition contains cells of the immune system, i.e., cells of innate or adaptive immunity, e.g., myeloid or lymphoid cells, including lymphocytes, typically T cells and/or NK cells. In some embodiments, the input composition contains stem cells, such as multipotent and pluripotent stem cells, including induced pluripotent stem cells (iPSCs). In particular embodiments, the input composition contains $CD3^+$ cells. In certain embodiments, the input composition contains $CD4^+$ cells. In some embodiments, the input composition contains $CD8^+$ cells. In some embodiments, the input composition is a composition of CD4+ cells. In particular embodiments, the input composition is a composition of CD8+ cells.

In some embodiments, the methods and agents are capable of stimulating T cells deficient in or that have downregulated one or more natural signaling molecules such as one or more costimulatory receptors or antigen receptors or cytokine receptors but that express the chimeric receptor, e.g., the CAR, recognized by the anti-Id antibody. In some embodiments, cells of the input composition are low or negative for surface expression of CD28 or other costimulatory molecule or other signaling molecule. Thus in some embodiments, the provided agents and methods have certain advantages compared to certain other activation or stimulatory agents or methods that which may require or depend upon surface expression of CD28 or other endogenous signaling molecule, to provide the desired signal and/or the full extent of such signal, e.g., to provide costimulatory signal and/or to achieve full activation/In some embodiments, the provided agents and methods are advantageous in such regards compared to anti-CD3/anti-CD28 reagents (e.g. beads); in some aspects, the provided anti-ID antibodies are advantageous in being able to stimulate or achieve a desired effect such as activation or proliferation of cells that are low or negative for CD28 or other natural signaling molecule. In some aspects, signaling through the CAR by stimulation with an anti-ID antibody results in both a primary and secondary (costimulatory) signal via the CAR using only the single reagent. In some embodiments, the input composition comprises CD3+ cells that express low levels of CD28 or other endogenous signaling molecule. In some embodiments, the input composition comprises CD3+ cells that are CD28 negative or are negative for other endogenous signaling molecule. In some embodiments, the anti-ID antibody stimulates activation and/or expansion of cells expressing low levels of CD28 or cells that are CD28 negative. In some embodiments, the cells are contacted with anti-idiotype antibody or antigen-binding fragment that is immobilized or bound to a solid support. In some embodiments, the solid support is a bead. In some embodiments, the solid support is the surface of a well or plate, e.g., a cell culture plate. In some examples, the anti-ID antibody is soluble. In certain embodiments, the cells are not contacted with anti-CD3/anti-CD28 conjugated reagents prior to contacting the cells with the anti-idiotype antibody or antigen-binding fragment.

In certain embodiments, the anti-idiotype antibody is applied to, contacted to, or incubated with an input composition of cells that have been transduced or transfected with a nucleotide encoding a CAR. In particular embodiments, incubating, treating, and/or contacting input cells with the anti-idiotype antibody results in an expansion and/or enrichment of cells expressing the CAR. In particular embodiments, incubating, treating, and/or contacting input cells with the anti-idiotype antibody does not result in an expansion and/or enrichment of cells that do not express the CAR. In particular embodiments, incubating, treating, and/or contacting input cells with the anti-idiotype antibody results in an expansion and/or enrichment of cells that do not express the CAR that is at least 50%, at least 75%, at least 85%, at least 90%, at least 95%, at least 99%, at least 99.9% or at least 99.99% less than the expansion and/or enrichment of cells that express the CAR. In some embodiments, the anti-idiotype antibodies provided herein are used to expand CAR expressing cells of an input composition that experienced a low transduction and/or transfection efficiency, and/or that contains a low amount CAR expressing cells. In certain embodiments, the anti-idiotype antibody selectively expands and/or enriches cells that express a CAR.

Some embodiments contemplate that the anti-idiotype antibody is more effective for expanding and/or enriching cells of an input composition with a low transduction or transfection efficiency and/or have a low amount of cells that express the CAR than by expanding and/or enriching the cells by polyclonal stimulation, e.g., anti-CD3 and/or anti-CD28 antibody stimulation. In particular embodiments, polyclonal stimulation results in expansion of cells that express the CAR and cells that do not express the CAR in the input composition, and therefore, in some embodiments, may fail to enrich CAR expressing cells, particular when the input composition has a low number of CAR expressing cells. In contrast, in some embodiments, incubation with an anti-idiotype antibody results in a selective expansion of CAR expressing cells and will therefore, in certain embodiments, result in selective expansion and/or enrichment of the CAR expressing cells. In some embodiments, incubating, contacting, and/or treating input cells with the anti-idiotype antibody results in a greater enrichment and/or expansion of CAR expressing cells than by polyclonal stimulation.

In particular embodiments, the anti-idiotype antibody is incubated with, applied to, and/or contacted with input cells that were transfected and/or transduced with a lower amount of viral particles, ratio of copies of the viral vector particles to cells, and/or infectious units (IU), than input cells that are expanded and/or enriched by polyclonal stimulation. For example, in some embodiments, the input composition that is incubated with the anti-idiotype antibody is generated from cells that were transduced with or with at least 0.5, 1, 2, 3, 4, 5, 10, 15, 20, 30, 40, 50, or 60 fewer IU per cell than the input composition that is expanded and/or enriched by polyclonal stimulation. In some embodiments, the input composition that is incubated with the anti-idiotype antibody is generated from cells that were transduced with a titer of viral vector particles with or with at least $1 \times 10^5$ IU/mL, $5 \times 10^5$ IU/mL, $1 \times 10^6$ IU/mL, $5 \times 10^6$ IU/mL, $6 \times 10^6$ IU/mL, $7 \times 10^6$ IU/mL, $8 \times 10^6$ IU/mL, $9 \times 10^6$ IU/mL, or $1 \times 10^7$ IU/mL less than the input composition that is expanded and/or enriched by polyclonal stimulation.

In particular embodiments, transducing cells with a high IU/cell will lead to high transduction efficiency but, in some embodiments, may also lead to transfected cells with a high vector copy number (VCN), which can present safety risks and may not meet regulatory standards. In particular embodiments, lowering the IU/cell that cells are transduced with will reduce transduction efficiency but will lower VCN. In particular embodiments, increasing the IU/cell that cells are transduced with will increase transduction efficiency but will also increase VCN.

In some embodiments, an input composition contains a population of cells that have been transduced or transfected, or cells that are derived from cells that have been transduced or transfected, with one or more nucleic acids encoding a CAR, that is bound by or recognized by the anti-idiotype antibody. In some embodiments, the input composition contains less than 80%, less than 75%, less than 70%, less than 65%, less than 60%, less than 55%, less than 50%, less than 45%, less than 40%, less than 35%, less than 30%, less than 25%, less than 20%, less than 15%, less than 10%, less than 5%, or less than 1% of the cells are CAR expressing cells. In particular embodiments, the cells from the input composition have been transfected or transduced as described in Section II. In certain embodiments, the input cells contains a population of cells that have been transduced or transfected, or cells that are derived from cells that have been transduced or transfected, with one or more nucleic acids encoding an anti-BCMA CAR, such as an anti-BCMA CAR that contains an scFv that is from and/or is derived from an anti-BCMA antibody such as Target Antibody 1 or Target Antibody 2.

In particular embodiments, the incubation, contacting, or treatment of cells from the input composition with the anti-idiotype antibody is performed under conditions for stimulation, expansion, and/or activation of cells which conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the cells of the input composition have been transfected or transduced with one nucleic acid comprising a gene encoding a CAR and the cells are contacted, incubated, or treated with the anti-idiotype antibody that binds to or recognizes the recombinant receptor. In some embodiments, the cells of the input composition are treated, incubated, or contacted with the anti-idiotype antibody after the cells transduced or transfected nucleic acid encoding a CAR. In particular embodiments, the cells of the input composition are treated, incubated, or contacted with the anti-idiotype antibody immediately, within about 1 minute, within about 5 minutes, within about 30 minutes, within about 1 hour, within about 2 hours, within about 4 hours, within about 6 hours, within about 8 hours, within about 12 hours, within about 24 hours, within about 2 days, within about 3 days, within about 4 days, within about 5 days, within about 6 days, within about 1 week, within about 2 weeks, within about 3 weeks, within about 4 weeks, within about 5 weeks, or within about 6 weeks after the cells of the input composition have been transduced or transfected.

In some embodiments, cells of the input composition are treated, incubated, and/or contacted with soluble anti-idiotype antibody, contacted with an antibody that is not cross-linked and/or contacted with an antibody that is not bound or attached to a solid support.

In some embodiments, the methods result in proliferation, activation, stimulation, cytokine release, or other functional outcome such as upregulation of an activation marker or cytokine release or production, of cells expressing the chimeric receptor such as the CAR recognized by the anti-Id antibody. In some aspects, such proliferation or other functional response or readout is induced in such cells to a degree that is similar to or greater than that induced by incubation of the cells with an agent and/or conditions that stimulates proliferation of T cells, such as anti-CD3/CD28 beads and/or crosslinked anti-CD3. In some aspects, the methods do not involve crosslinking of the anti-idiotype antibody. In some aspects of any of the embodiments, the anti-idiotype agents are capable of inducing the specified proliferation or functional outcome or degree thereof, without crosslinking of the anti-idiotype antibody. In some aspects, anti-idiotype agents herein are advantageous in their ability to stimulate or cause a particular functional outcome of T cells or other immune cells expressing the target receptor, without the need to crosslink the anti-Id antibody or use a secondary agent. In some aspects, the result is achieved with soluble or plate-bound form of the anti-idiotype antibody. In some aspects, the result is achieved with the anti-idiotype antibody coupled to a bead.

In particular embodiments, the cells of the input composition are treated, incubated, and/or contacted with between 10 pg/ml and 100 µg/ml, between 1 pg/ml and 1 ng/ml, between 1 ng/ml and 1 µg/l between 100 ng/ml and 1.0 pg/ml, between 1 ng/ml and 100 ng/ml, between 10 ng/ml and 1.0 µg/ml, between 100 ng/ml and 10 pg/ml, between 250 ng/ml and 10 µg/ml, between 250 pg/ml and 1 ng/ml, between 1 µg/ml and 10 µg/ml, between 250 ng and about 2.5 µg/ml, or between 1 µg/ml and 10 µg/ml.

In some embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof. In some embodiments, the solid support is a surface of a plate or a well. In some embodiments, the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof. In some embodiments, the reagent comprises a streptavidin mutein. In one exemplary embodiment, the anti-idiotypic antibody comprises a streptavidin-binding peptide or other streptavidin binding moiety capable of binding to a streptavidin or streptavidin mutein molecule present on or immobilized on the soluble reagent, which, in some cases, can be dissociated in the presence of a competition substance, such as biotin. Exemplary of such systems include those described in PCT published patent application No. WO2015/158868.

In particular embodiments, the cells of the input composition are treated, incubated, and/or contacted with anti-idiotype antibody that is attached, bound, coated, and/or conjugated to a solid surface or support, e.g., a plate or a well. In certain embodiments, the anti-idiotype antibody has been attached, bound, coated, and/or conjugated to the solid surface or support by incubating the solid surface or support with a concentration of the anti-idiotype antibody. In particular embodiments, the solid surface or support is incubated with between 10 ng/ml and 100 µg/ml, between 100 ng/ml and 1.0 µg/ml, between 250 ng/ml and 10 µg/ml, between 250 ng/ml and 1 µg/ml, between 1 µg/ml and 10 µg/ml, between 250 ng and 2.5 µg/ml, or between 1 µg/ml and 10 µg/ml the anti-idiotype antibody. In some embodiments, the solid surface or support is incubated with between 250 ng/ml and 10 µg/ml. In certain embodiments, the solid surface or support is incubated with or with about 0.25 µg/ml, 0.5 µg/ml, 1.0 µg/ml, 1.25 µg/ml, 2 µg/ml, 2.5 µg/ml, 5 µg/ml or 10 µg/ml the anti-idiotype antibody.

In some embodiments, the incubation is for at least or about at least 5 minutes, 10 minutes, 30 minutes, 60 minutes, 2 hours, 6 hours, 12 hours, 24 hours, 36, 48 hours, 72 hours or 96 hours. In some embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition. In some embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more. In some embodiments, prior to incubating, the cells are not selected or enriched for CAR-expressing cells.

In certain embodiments, the anti-idiotype antibody are contacted or incubated with cells from the input composition, e.g. comprising cells that express a CAR, for an amount of time to expand one or more cells of the input composition, such as to expand cells of the input composition that express the recombinant receptor. In particular embodiments, the cells from the input composition are contacted, incubated, or treated with the anti-idiotype antibody for at least about 12 hours, at least about 24 hours, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, or at least about 4 weeks. In particular embodiments, the cells from the input composition are contacted, incubated, or treated with the anti-idiotype antibody for less than about 1 day, less than about 2 days, less than about 3 days, less than about 4 days, less than about 5 days, less than about 6 days, or less than or about 12 days. In some embodiments, the cells from the input composition are contacted, incubated, or treated with the anti-idiotype antibody for between about 1 day and about 14 days, between about 3 days, and 7 days, or for between 4 days and 6 days.

In particular embodiments, cells from an input composition, e.g. comprising cells that express a CAR, are incubated, contacted, or treated with anti-idiotype antibody at temperatures greater than room temperature to expand the cells of the input composition that express the recombinant receptor. In some embodiments, the treatment, incubation, or contacting is performed at a temperature greater than about 25° C., such as generally greater than or greater than about 32° C., 35° C. or 37° C. In some embodiments, the treatment, contacting, or incubation is performed at a temperature of at or about 37° C.±2° C., such as at a temperature of at or about 37° C.

In some embodiments, at least 50%, at least 55%, at least 60%, at least 65%, at least 70%, at least 75%, at least 80%, at least 85%, at least 90%, at least 95%, at least 97%, at least 99%, at least 99.9%, about 100%, or 100% of the cells of the output composition express the CAR.

In particular embodiments, the number of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells that express the CAR in the input composition.

In particular embodiments, the percentage of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells that express the CAR in the input composition.

In some embodiments, the number of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells of an output composition that received polyclonal stimulation, incubation with anti-CD3 and anti-CD28 antibodies.

In certain embodiments, the percentage of cells that express the CAR in the output composition that was incubated, treated, and/or contacted with the anti-idiotype antibody is at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 95%, at least 100%, at least 2-fold, at least 3-fold, at least 4-fold, at least 5-fold, at least 6-fold, at least 7-fold, at least 8-fold, at least 9-fold, at least 10-fold, at least 15-fold, at least 20-fold, at least 25-fold, at least 50-fold, or at least 100-fold greater than the number of cells of an output composition that received polyclonal stimulation, incubation with anti-CD3 and anti-CD28 antibodies.

In some embodiments, the cells that express the CAR in the output composition that was incubated, treated, and/or contacted with the anti-idiotype antibody contain at least a 1%, at least a 5%, at least a 10%, at least a 15%, at least a 20%, at least a 25%, at least a 30%, at least a 35%, at least a 40%, at least a 45%, at least a 50%, at least a 55%, at least a 60%, at least a 65%, at least 70%, at least 75%, at least 80%, at least 85%, at least 95%, or at least a 99% lower VCN than cells of an output composition that received polyclonal stimulation, e.g., incubation with anti-CD3 and anti-CD28 antibodies. In some embodiments, the average VCN of CAR expressing cells of the output no more than at or about 10, 5, 4, 2.5, 1.5, or 1.

In some embodiments, such methods can be used as part of the manufacturing, analytic, and/or quality control methods, e.g., in association with the generation of cell therapies expressing recombinant polypeptides containing an antibody or fragment thereof recognized by the anti-idiotype antibody, such as the CAR T cells, for testing purpose, including to test expression and/or potency of the engineered receptor, e.g., in cells engineered for use in therapy in an individual. In certain embodiments, the cell compositions may be tested at any stage in the process of generating CAR expressing T cells. In particular embodiments, a sample of cells may be collected from a cell composition at any stage of the process and stored, e.g., by cryofreezing and/or cyropreservation, for later testing and/or analysis. The compositions tested may be pharmaceutical compositions e.g., including those containing the cells and a pharmaceutically acceptable recipient and/or cryopreservative agent.

In some embodiments, the anti-idiotype antibody stimulates cells expressing a target antibody, e.g., a CAR, in vivo. Particular embodiments contemplate that CAR-T cell therapies are effective in the treatment of cancer and other diseases and disorders. However, in certain contexts, available approaches to CAR-T cell therapy may not always be entirely satisfactory. For example, in some embodiments, the exposure and persistence of CAR expressing cells in the subject is reduced or declines over time. Yet, observations indicate that, in some cases, increased exposure of the CAR expressing cells may improve efficacy and therapeutic outcomes in CAR-T cell therapy. Thus, in some embodiments, the anti-idiotype antibody is administered to boost, augment and/or increase persistence and/or expansion of CAR expressing cells.

In certain embodiments, the anti-idiotype antibody is administered to a subject, such as a subject who has previously been administered a therapeutic cell composition containing CAR expressing cells. In some embodiments, administering the anti-idiotype antibody to a subject promotes re-expansion of the CAR expressing cells in the subject, which, in some cases, may reach or exceed the initial peak level of expansion prior to the administration of the anti-idiotype antibody. In some embodiments, the anti-idiotype antibody is administered to modulate expansion and/or persistence of the CAR expressing cells at times when the levels of the CAR expressing cells have declined or are not detectable. In some embodiments, CAR expressing cells that re re-expanded by the anti-idiotype antibody exhibit increased potency in a subject to which it is administered, for example, as compared to the potency prior to administration of the anti-idiotype antibody.

In certain embodiments, administration of the anti-idiotype antibody increases or enhances persistence of the CAR expressing cells in the subject. In some embodiments, the CAR expressing cells are detectable in the subject at or at least 7 days, 14 days, 21 days, 28 days, 35 days, 42 days, 49 days, 56 days, 63 days, 2 months, 3 months, 4 months, 5 months, 6 months, or more than 6 months following the administration of the anti-idiotype antibody. In some aspects, increased exposure of the subject to the cells includes expansion and/or increased expansion of the cells.

In some embodiments, the CAR-expressing cells expand in the subject following administration of the anti-idiotype antibody. In particular embodiments, administering the anti-idiotype antibody results in a maximum concentration in the blood or serum or other bodily fluid or organ or tissue of the subject, of at least 100, 500, 1000, 1500, 2000, 5000, 10,000 or 15,000 copies of a nucleic acid encoding the CAR per microgram of DNA, or at least 0.1, 0.2, 0.3, 0.4, 0.5, 0.6, 0.7, 0.8, or 0.9 CAR-expressing cells per microliter. In some embodiments, the cells expressing the CAR are detected as at least 10, 20, 30, 40, 50, or 60% of total PBMCs in the blood of the subject, and/or at such a level for at least 1, 2, 3, 4, 5, 6, 7, 8, 9, 10, 11, 12, 24, 36, 48, or 52 weeks following the administration of the anti-idiotype antibody or for 1, 2, 3, 4, or 5, or more years following administration of the anti-idiotype antibody. In some aspects, administering the anti-idiotype antibody results in at least a 2-fold, at least a 4-fold, at least a 10-fold, or at least a 20-fold increase in copies of nucleic acid encoding the recombinant receptor, e.g., CAR, per microgram of DNA, e.g., in the serum, plasma, blood or tissue, e.g., tumor sample, of the subject. In particular embodiments, administering the anti-idiotype antibody results in at least a 2-fold, at least a 4-fold, at least a 10-fold, or at least a 20-fold increase in the number of circulating CAR expressing cells in the subject.

In some aspects, at least about $1\times10^2$, at least about $1\times10^3$, at least about $1\times10^4$, at least about $1\times10^5$, or at least about $1\times10^6$ or at least about $5\times10^6$ or at least about $1\times10^7$ or at least about $5\times10^7$ or at least about $1\times10^8$ CAR-expressing cells and/or at least 10, 25, 50, 100, 200, 300, 400, or 500, or 1000 CAR expressing cells per microliter, e.g., at least 10 per microliter, are detectable or are present in the subject or fluid, plasma, serum, tissue, or compartment thereof, such as in the blood, e.g., peripheral blood, or disease site following administration of the anti-idiotype antibody. In some embodiments, such a number or concentration of cells is detectable in the subject for at least about 20 days, at least about 40 days, or at least about 60 days, or at least about 3, 4, 5, 6, 7, 8, 9, 10, 11, or 12 months, or at least 2 or 3 years, following administration of the anti-idiotype antibody.

Various delivery systems are known and can be used to administer the anti-idiotype antibody. In certain embodiments, the anti-idiotype antibody is administered by encapsulation in and/or attachment to liposomes, microparticles, and microcapsules. Methods of administering the anti-idiotype antibody include but are not limited to intradermal, intramuscular, intraperitoneal, intravenous, subcutaneous, intranasal, epidural, and oral routes. The anti-idiotype antibody may be administered by any convenient route, for example by infusion, by bolus injection, by absorption through epithelial or mucocutaneous linings (e.g., oral, rectal and intestinal mucosa, etc.), and may be administered together with other biologically active agents. Administration can be systemic or local. Pulmonary administration can also be employed, e.g., by use of an inhaler or nebulizer, and formulation with an aerosolizing agent. In certain embodiments, the anti-idiotype antibody is delivered in a vesicle, in particular a liposome (Langer, 1990, Science 249:1527-1533), for example a cationic liposome (WO 98140052).

In some embodiments, there is provided a method of producing a cell composition, comprising introducing into cells a nucleic acid molecule encoding a CAR, thereby generating an input composition, and incubating the input composition with an anti-idiotype antibody or antigen-binding fragment thereof that binds to or recognizes the antigen-binding domain of the CAR, thereby producing the cell composition. In some embodiments, the anti-idiotype antibody or antigen-binding fragment thereof is an immunoconjugate as provided herein that includes the anti-idiotype antibody or antigen-binding fragment thereof. In some embodiments, the CAR comprises a target antibody or antigen-binding fragment thereof that binds to or recognizes BCMA. In some embodiments, the target antibody is Target Antibody 1 or Target Antibody 2, or an antigen-binding fragment thereof. In some embodiments, the anti-idiotype antibody or antigen-binding fragment thereof is an anti-idiotype antibody or antigen-binding fragment thereof described herein. In some embodiments, the anti-idiotype antibody or antigen-binding fragment thereof is an agonist of the CAR. In some embodiments, the anti-idiotype antibody or antigen-binding fragment thereof is an antagonist of the CAR. In some embodiments, the introducing comprises introducing the nucleic acid molecule into the cells by viral transduction, transposition, electroporation, or chemical transfection. In some embodiments, the introducing comprises introducing the nucleic acid molecule in the cells by transduction with a retroviral vector comprising the nucleic acid molecule, by transduction with a lentiviral vector comprising the nucleic acid molecule, by transposition with a transposon comprising the nucleic acid molecule, or by electroporation or transfection of a vector comprising the nucleic acid molecule.

In some embodiments, the method further comprises a step of stimulating or activating the cells prior to introducing the nucleic acid molecule encoding the CAR. In some embodiments, activating the cells comprises contacting the cells with an agonist of CD3 and optionally an agonist of CD28. In some embodiments, activating the cells comprising contacting the cells with a reagent comprising agonistic anti-CD3 and anti-CD28 antibodies. In some such embodiments, during at least a portion of the contacting with an anti-CD3/anti-CD28 and/or during at least a portion of introducing the nucleic acid encoding the CAR, the method includes incubating or contacting the cells with the anti-idiotypic antibody or antigen-binding In some embodiments, the incubation is performed under conditions in which the anti-idiotype antibody or antigen-binding fragment thereof binds to the CAR, thereby inducing or modulating a signal in one or more cells in the input composition. In some embodiments, the cells comprise T cells.

In some such embodiments, the T cells comprise CD4+ and/or CD8+ T cells. In some embodiments, the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof. In some embodiments, the anti-idiotype antibody or antigenbinding fragment thereof is immobilized to a soluble reagent, which optionally is or comprises a plurality of binding sites capable of reversibly binding to the anti-idiotype antibody or antigen-binding fragment thereof. In some embodiments, the reagent comprises a streptavidin mutein. In one exemplary embodiment, the anti-idiotypic antibody comprises a streptavidin-binding peptide or other streptavidin binding moiety capable of binding to a streptavidin or streptavidin mutein molecule present on or immobilized on the soluble reagent, which, in some cases, can be dissociated in the presence of a competition substance, such as biotin. Exemplary of such systems include those described in PCT published patent application No. WO2015/158868. In some embodiments, the incubation is for at least or about at least 5 minutes, 10 minutes, 30 minutes, 60 minutes, 2 hours, 6 hours, 12 hours, 24 hours, 36, 48 hours, 72 hours or 96 hours. In some embodiments, the input composition comprises less than or less than about 60%, less than or less than about 50%, less than or less than about 40%, less than or less than about 30%, less than or less than about 20% or less than or less than about 10% CAR-expressing cells as a percentage of the total cells in the composition. In some embodiments, the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more. In some embodiments, prior to incubating, the cells are not selected or enriched for CAR-expressing cells.

In some embodiments, there is provided a method of monitoring activity of a CAR comprising a target antibody, such as Target Antibody 1 or Target Antibody 2, or an antigen-binding fragment thereof, including the steps of incubating a sample comprising T cells transduced with the CAR with an agonistic anti-idiotype antibody or antigen-binding fragment thereof that targets or binds the CAR; and/or determining the presence, absence or amount of activation, stimulation and/or expansion of the CAR T cells, thereby monitoring the activity of the CAR-T cells. In some embodiments, such methods can be used for validating the CAR, in which case the method can include c) validating the CAR based on the level of activation, stimulation and/or expansion of CAR-T cells.

In some embodiments, activation, stimulation and/or expansion of CAR T cells is assessed by determining the viability, proliferation, and/or expression of T cell activation markers in the CAR T cells following a period of incubation with the anti-idiotype antibody. In some embodiments, viability of CAR T cells is assessed by calculating the percent of living versus total T cells transduced with the CAR following incubation with the anti-idiotype antibody. In some embodiments, proliferation of CAR T cells is assessed by dye dilution of a dye used to stain the CAR T cells prior to incubation with the anti-idiotype antibody. In some embodiments, expression of T cell activation markers is assessed by flow cytometry with staining for antibodies recognizing the T cell activation markers. In some embodiments, the T cell activation markers are selected from the group consisting of CD25, CD26, CD27, CD28, CD30, CD69, CD71, CD134, CD137, and CD154. In some embodiments, the period of incubation is from about 1 to about 10 days (such as about any of 1, 2, 3, 4, 5, 6, 7, 8, 9, or 10 days, including any ranges between these values).

In some embodiments, there is provided a method of monitoring a preparation of CAR T cells, wherein the CAR comprises a target antibody, such as Target Antibody 1 or Target Antibody 2, or an antigen-binding fragment thereof, comprising a) incubating a portion of the preparation with an agonistic anti-idiotype antibody or antigen-binding fragment thereof that targets or binds the CAR; and b) determining the presence, absence or amount of activation, stimulation and/or expansion of the CAR T cells. In some embodiments, the preparation of CAR-T cells can be cells produced or manufactured under particular conditions desirable to be tested. In some embodiments, the monitoring is carried out in connection with a release assay, such as for validating the cells prior to administration to a subject. In some aspects, the method further includes c) validating the preparation based on the level of activation of the CAR T cells. In some embodiments, activation of CAR T cells in the preparation is assessed by determining the viability, proliferation, and/or expression of T cell activation markers in the CAR T cells following a period of incubation with the anti-idiotype antibody. In some embodiments, viability of CAR T cells is assessed by calculating the percent of living versus total T cells transduced with the CAR following incubation with the anti-idiotype antibody. In some embodiments, proliferation of CAR T cells is assessed by dye dilution of a dye used to stain the CAR T cells prior to incubation with the anti-idiotype antibody. In some embodiments, expression of T cell activation markers is assessed by flow cytometry with staining for antibodies recognizing the T cell activation markers. In some embodiments, the T cell activation markers are selected from the group consisting of CD25, CD26, CD27, CD28, CD30, CD69, CD71, CD134, CD137, and CD154. In some embodiments, the period of incubation is from about 1 to about 10 days (such as about any of 1, 2, 3, 4, 5, 6, 7, 8, 9, or 10 days, including any ranges between these values).

In some embodiments, the target antibody is an anti-BCMA antibody. In some of any such embodiments, the anti-BCMA antibody is Target Antibody 1. In some of any such embodiments, the anti-BCMA antibody is Target Antibody 2, e.g., as described in section I.A.

In some of any such embodiments, the anti-idiotype antibody or antigen-binding fragment thereof is an anti-idiotype antibody or antigen-binding fragment thereof that binds to or recognizes Target Antibody 1. In some of any such embodiments, the anti-idiotype antibody or antigen-binding fragment thereof is an anti-idiotype antibody or antigen-binding fragment thereof that binds to or recognizes Target Antibody 2, such as any such anti-idiotype antibody or antigen-binding fragment thereof as described herein, e.g., in section I.A. In some of any such embodiments, the anti-idiotype antibody or antigen-binding fragment thereof is an anti-idiotype antibody or antigen-binding fragment thereof that binds to or recognizes Target Antibody 1 and/or Target Antibody 2, such as any such anti-idiotype antibody or antigen-binding fragment thereof as described herein, e.g., in section I.B.

C. Use in Cell Inactivation/Depletion

In some embodiments, the provided anti-idiotype antibodies or antigen-binding fragments thereof are antagonists and/or exhibit specific activity to inhibit, ablate, and/or deplete (for example, kill via antibody-dependent cell-mediated cytotoxicity, ADCC) cells expressing a target antibody, such as an anti-BCMA antibody (e.g., Target Antibody 1 or Target Antibody 2), or an antigen-binding fragment thereof. Also provided are methods involving use of the provided anti-idiotype antibodies, and molecules (such as conjugates and complexes) containing one or more of such anti-idiotype antibodies, for inactivation, ablation, and/or depletion of CAR T cells, wherein the CAR comprises a target antibody, such as an anti-BCMA antibody (e.g., Target Antibody 1 or Target Antibody 2), or an antigen-binding fragment thereof.

The methods in some embodiments include treating, contacting, and/or incubating a composition and/or a sample comprising T cells transduced with a CAR with the anti-idiotype antibody. In certain embodiments, the methods further include detecting whether the CAR T cells are inactivated, such as by assessing the viability, proliferation, and/or expression of activation markers in the CAR T cells. In some embodiments, the methods are in association with a therapy comprising administration of CAR T cells. The methods in some embodiments include administering the anti-idiotype antibody to an individual. In one embodiment, an anti-idiotype antibody or conjugate is used to ablate and/or deplete (such as kill) CAR T cells in an individual. In some embodiments, the target antibody is an anti-BCMA antibody. In some embodiments, the target antibody is or is derived from Target Antibody 1 or Target Antibody 2, or an antigen-binding fragment thereof.

In some embodiments, the anti-idiotype antibody is administered to deplete, reduce, and/or decrease the number of CAR expressing cells in a subject. In particular embodiments, administration of the anti-idiotype antibody depletes, reduces, and/or decreases the amount of CAR expressing cells, e.g., circulating CAR-T cells, by at least 25%, at least 50%, at least 60%, at least 70%, at least 80%, at least 90%, at least 95%, at least 99%, at least 99.9%, 100% or about 100%. In certain embodiments, the depletion, reduction, and/or decrease is in relation to an amount of CAR expressing cells in the subject prior to the administration of the anti-idiotype antibody. In particular embodiments, the depletion, reduction, and/or decrease is in relation to an amount of CAR expressing cells in a subject that is not administered the anti-idiotype antibody. In some embodiments, CAR expressing cells are not detectable in the subject following administration of the anti-idiotype antibody. In particular embodiments, the anti-idiotype antibody is a human or humanized antibody.

In some embodiments, there is provided a method of inactivating CAR T cells, wherein the CAR comprises a target antibody, such as Target Antibody 1 or Target Antibody 2, or an antigen-binding fragment thereof, comprising incubating a sample comprising the CAR T cells with an antagonistic anti-idiotype antibody or antigen-binding fragment thereof targeting the CAR, thereby inactivating the CAR T cells in the sample. In some embodiments, the anti-idiotype antibody is used in an amount sufficient to attenuate the activation of the CAR T cells in the sample. In some embodiments, the anti-idiotype antibody is used in an amount sufficient to substantially inactivate the CAR T cells in the sample. In some embodiments, incubation with the anti-idiotype antibody results in ablation and/or depletion of CAR T cells in the sample. In some embodiments, the anti-idiotype antibody is used in an amount sufficient to result in clearance of the CAR T cells in the sample.

In some embodiments, the anti-idiotype antibody is administered to deplete, reduce, and/or decrease the activity of the CAR and/or the CAR expressing cells in a subject. In particular embodiments, administration of the anti-idiotype antibody reduces and/or decreases stimulation and/or activation of the CAR and/or the CAR expressing cell by at least 25%, at least 50%, at least 60%, at least 70%, at least 80%, at least 90%, at least 95%, at least 99%, at least 99.9%, 100% or about 100%. In certain embodiments, the reduction and/or decrease is in relation to the stimulation and/or activity of the CAR and/or CAR expressing cells in the subject prior to the administration of the anti-idiotype antibody. In particular embodiments, the reduction and/or decrease is in relation to stimulation and/or activity of the CAR and/or CAR expressing cells in a subject that is not administered the anti-idiotype antibody. In some embodiments, the activity and/or stimulation refers to one or more aspects of CAR receptor or CAR T cell activity and may be assessed by any suitable known means, including by any means provided herein. In some embodiments, activity and/or stimulation of the CAR and/or CAR expressing cells are not detectable in the subject following administration of the anti-idiotype antibody. In particular embodiments, the anti-idiotype antibody is a human or humanized antibody.

In some embodiments, the anti-idiotype antibody is administered to prevent, reduce, and/or decrease the binding and/or the ability of the CAR and/or the CAR expressing cells to bind to the antigen. In particular embodiments, administration of the anti-idiotype antibody reduces and/or decreases antigen binding of the CAR and/or the CAR expressing cell by at least 25%, at least 50%, at least 60%, at least 70%, at least 80%, at least 90%, at least 95%, at least 99%, at least 99.9%, 100% or about 100%. In certain embodiments, the reduction and/or decrease is in relation to the antigen binding and/or the ability of the CAR and/or CAR expressing cells to bind to the antigen in the subject prior to the administration of the anti-idiotype antibody. In particular embodiments, the reduction, and/or decrease is in relation to antigen binding and/or the ability to bind the antigen of the CAR and/or CAR expressing cells in a subject that is not administered the anti-idiotype antibody. In particular embodiments, the anti-idiotype antibody is a human or humanized antibody.

In some embodiments, there is provided a method of ablating and/or depleting (such as killing) CAR T cells, wherein the CAR comprises a target antibody, such as Target Antibody 1 or Target Antibody 2, or an antigen-binding fragment thereof, comprising incubating a sample comprising the CAR T cells with an anti-idiotype antibody or antigen-binding fragment thereof targeting the CAR, thereby ablating and/or depleting CAR T cells in the sample. In some embodiments, the ablating and/or depleting is by antibody-dependent cell-mediated cytotoxicity (ADCC). In some embodiments, the anti-idiotype antibody is used in an amount sufficient to result in ablation and/or depletion of substantially all of the CAR T cells in the sample.

In some embodiments, there is provided a method of adjusting a CAR T cell therapy in an individual, wherein the CAR comprises a target antibody, such as Target Antibody 1 or Target Antibody 2, or an antigen-binding fragment thereof, comprising administering an antagonistic anti-idiotype antibody or antigen-binding fragment thereof targeting the CAR to the individual, thereby inactivating the CAR T cells. In some embodiments, the anti-idiotype antibody is administered in an amount sufficient to attenuate the activation of the CAR T cells in the individual. In some embodiments, the anti-idiotype antibody is administered in an amount sufficient to substantially inactivate the CAR T cells in the individual. In some embodiments, administration of the anti-idiotype antibody results in ablation and/or depletion of CAR T cells in the individual. In some embodiments, the anti-idiotype antibody is administered in an amount sufficient to result in clearance of the CAR T cells in the individual.

In some embodiments, there is provided a method of adjusting a CAR T cell therapy in an individual, wherein the CAR comprises a target antibody, such as Target Antibody 1 or Target Antibody 2, or an antigen-binding fragment thereof, comprising administering an anti-idiotype antibody immunoconjugate targeting the CAR to the individual, wherein the anti-idiotype antibody immunoconjugate comprises a cytotoxic agent. In some embodiments, the anti-idiotype antibody immunoconjugate is administered in an amount sufficient to attenuate the CAR T cell therapy in the individual. In some embodiments, the anti-idiotype antibody immunoconjugate is administered in an amount sufficient to substantially stop the CAR T cell therapy in the individual. In some embodiments, the anti-idiotype antibody immunoconjugate is administered in an amount sufficient to result in clearance of the CAR T cells in the individual. In some embodiments, the cytotoxic agent is selected from the group consisting of chemotherapeutic agents or drugs, growth inhibitory agents, toxins (e.g., protein toxins, enzymatically active toxins of bacterial, fungal, plant, or animal origin, or fragments thereof), and radioactive isotopes.

In some embodiments, there is provided a method of depleting cells, comprising administering, to a subject, a composition comprising an anti-idiotype antibody or antigen-binding fragment thereof as provided herein, or an immunoconjugate as provided herein, that binds to or recognizes a target antibody or antigen-binding fragment thereof (e.g., Target Antibody 1 or Target Antibody 2), wherein the subject has been administered a cell expressing a CAR comprising the target antibody or antigen-binding fragment thereof. In some embodiments, the depletion occurs via antibody-mediated cytotoxicity (ADCC).

In some embodiments, the target antibody is an anti-BCMA antibody. In some of any such embodiments, the anti-BCMA antibody is Target Antibody 1. In some of any such embodiments, the anti-BCMA antibody is Target Antibody 2, e.g., as described in section I.A.

In some of any such embodiments, the anti-idiotype antibody or antigen-binding fragment thereof is an anti-idiotype antibody or antigen-binding fragment thereof that binds to or recognizes Target Antibody 1. In some of any such embodiments, the anti-idiotype antibody or antigen-binding fragment thereof is an anti-idiotype antibody or antigen-binding fragment thereof that binds to or recognizes Target Antibody 2, such as any such anti-idiotype antibody or antigen-binding fragment thereof as described herein, e.g., in section I.A. In some of any such embodiments, the anti-idiotype antibody or antigen-binding fragment thereof is an anti-idiotype antibody or antigen-binding fragment thereof that binds to or recognizes Target Antibody 1 and Target Antibody 2, such as any such anti-idiotype antibody or antigen-binding fragment thereof as described herein, e.g., in section I.B.

D. Use in Binding Assay or Method

Provided herein are methods for assessing the presence or absence of a molecule in a sample that binds to a chimeric antigen receptor (CAR), such as the extracellular domain of a CAR or to a portion thereof containing the antigen-binding domain. In some embodiments, the methods can be used to assess the presence or absence of a humoral response or antibody response in a subject to an administered cell therapy comprising a chimeric antigen receptor (CAR). In some embodiments, the chimeric antigen receptor comprises a target antibody that is Target Antibody 1 or an antigen-binding fragment thereof. In some embodiments, the chimeric antigen receptor comprises a target antibody that is Target Antibody 2 or an antigen-binding fragment thereof. In some embodiments, an anti-idiotype antibody or antigen-binding fragment thereof that binds to or recognizes the extracellular domain of the CAR, such as any described herein, can be used as a positive control in the method.

In particular embodiments, the method includes contacting a sample with an anti-idiotype antibody or antigen-binding fragment thereof that binds toor recognizes the extracellular domain of the CAR at a concentration of between 10 ng/ml and 100 μg/ml, between 100 ng/ml and 1.0 μg/ml, between 250 ng/ml and 10 μg/ml, between 250 ng/ml and 1 μg/ml, between 1 μg/ml and 10 μg/ml, between 250 ng and 2.5 μg/ml, or between 1 μg/ml and 10 μg/ml of the anti-idiotype antibody. In some embodiments, the concentration of the anti-idiotype antibody between 250 ng/ml and 10 μg/ml. In certain embodiments, the concentration of the anti-idiotype antibody is about 0.1 μg/ml, 0.25 μg/ml, 0.5 μg/ml, 1.0 μg/ml, 1.25 μg/ml, 2 μg/ml, 2.5 μg/ml, or 5 μg/ml of the anti-idiotype antibody.

In some aspects, adoptive cell therapy may be associated with development of an immune response in the subject to the cells and/or construct administered. For example, in some cases, exposure to a chimeric receptor may be limited by host immune responses against the recombinant receptors expressed by the administered cells, which may prematurely eliminate the cells. It is observed that even in certain subjects having B cell malignancies, who often are immunocompromised, immune responses can be detected that are specific for regions of receptors expressed by cells administered in adoptive cell therapy. For example, subjects, e.g. human subjects, administered cells genetically engineered with a CAR can develop a specific immune response to an immunogenic region of the chimeric region, including regions that may contain non-human sequences (e.g. murine scFv) and or to a region containing the junction between two domains or portions of the chimeric receptor, e.g. the transmembrane and costimulatory domain of the CAR.

In some embodiments, there are provided methods that involve contacting or incubating a binding reagent with a sample from a subject having been administered a cell therapy comprising cell engineered with a chimeric antigen receptor in which the binding reagent is a protein that includes the extracellular domain of the CAR or a portion thereof containing the target antibody or the antigen-binding fragment thereof. In some embodiments, the methods further include detecting whether a complex is formed between the binding reagent and a molecule, e.g. binding molecule, such as an antibody, present in the sample, and/or detecting the presence or absence or level of such binding. In certain embodiments, the contacting or incubating is under conditions permissive for binding of the binding reagent to a molecule present in the sample from the subject. In certain aspects, the method can be further carried out on a positive control sample containing an anti-idiotypic antibody or antigen-binding fragment thereof that binds to or recognizes the CAR, such as any as described. In some embodiments, determining the presence, absence or level of binding of the molecule to the binding reagent can include comparison of the binding or detection to the binding or detection of the positive control sample to the binding reagent.

In some embodiments, the cell therapy is or comprises genetically engineered cells expressing an anti-BCMA CAR comprising a target antibody that is Target Antibody 1 or an antigen-binding fragment thereof, wherein the binding reagent comprises the extracellular domain of the CAR or a portion thereof comprising the Target Antibody 1 or the antigen-binding fragment thereof.

In some embodiments, the cell therapy is or comprises genetically engineered cells expressing an anti-BCMA CAR comprising a target antibody that is Target Antibody 2 or an antigen-binding fragment thereof, wherein the binding reagent comprise the extracellular domain of the CAR or a portion thereof comprising the Target Antibody 2 or the antigen-binding fragment thereof. In some embodiments, the positive control includes an anti-iditoypic antibody as described in subsection I.A.

In some embodiments, the methods include detecting whether a complex is formed between the binding reagent and a molecule, e.g. binding molecule, such as an antibody, present in the sample, and/or detecting the presence or absence or level of such binding. In certain embodiments, the contacting or incubating is under conditions permissive for binding of the binding reagent to a molecule present in the sample from the subject. In some aspects, the complex is detected by an immunoassay, optionally a sandwich or bridge assay. For examples, the immunoassay is an enzyme-linked immunosorbent assay (ELISA), chemiluminescent, electrochemiluminescent, surface plasmon resonance (SPR)-based biosensor (e.g., BIAcore), flow cytometry, or Western blot. In some embodiments, the immunoassay is or or includes meso scale discovery.

In some aspects, the immunoassay is a sandwich assay or a bridge assay. In a sandwich or bridge assay, the binding reagent is a first binding reagent and detecting the presence or absence of a molecule or a complex comprising a molecule includes contacting the complex formed between the first binding reagent and molecule with a second binding reagent in which the second binding reagent is an agent that is able to bind to the same or similar molecule as the first binding reagent. In some embodiments, the second binding reagent comprises the extracellular domain of the CAR or a portion thereof. In some aspects, the extracellular domain of the CAR or portion thereof of the first binding agent and the second binding agent is the same or substantially the same.

In some embodiments, the binding reagent, such as the first and/or second binding reagent, is detectably labeled or is capable of producing a detectable signal. The binding reagent, such as the first and/or second binding reagent, is linked, directly or indirectly, to a detectable label. In some embodiments, the detectable label is or includes a fluorescent label, a chemiluminescent label, an electroluminescent label, a colorimetric label, a bioluminescent label or a radiolabel. In some embodiments, the binding reagent, such as the first and/or second binding reagent is linked, directly or indirectly, to a SULFO-Tag. In some embodiments, at least one of the first and second binding reagent is detectably labeled or is capable of producing a detectable signal and the other of the first and second binding reagent is attached or immobilized to a solid support. In some aspects, the first binding reagent is attached or immobilized to a solid support or capable of being attached or immobilized to a solid support. Methods for directly or indirectly attaching an binding reagent to a solid support are well known in the art. Methods of attachment generally include non-specific adsorption of the binding reagent to the solid support or covalent attachment of the binding reagent, typically through a free amine group, to a chemically reactive group on the solid support, such as an activated carboxyl, hydroxyl, or aldehyde group. Methods of attachment also include indirect attachment of the binding reagent to the solid support such as by coating the solid support with a capture reagent, such as streptavidin, and adding affinity labeled binding reagents, such as biotin-labeled reagents, to the solid support so that the interaction between the affinity label (e.g., biotin) and capture reagent (e.g., streptavidin) link the binding reagent to the solid support. In some embodiments, the first binding reagent is linked, directly or indirectly, to a biotin. In some examples, the first soluble reagent is bound to a solid support coated with streptavidin. In some embodiments, the second binding reagent is linked, directly or indirectly, to a detectably label, optionally a SULFO-Tag.

In particular embodiments, the sample is contacted with a first binding reagent that is attached, bound, coated, and/or conjugated to a solid surface or support, e.g., a plate or a well. In certain embodiments, the first binding reagent has been attached, bound, coated, and/or conjugated to the solid surface or support by indirect attachment of the binding reagent to the solid support such as by coating the solid support with a capture reagent, such as streptavidin, and adding affinity labeled binding reagents, such as biotin-labeled reagents, to the solid support so that the interaction between the affinity label (e.g., biotin) and capture reagent (e.g., streptavidin) link the binding reagent to the solid support. In some embodiments, the sample is contacted with a second binding reagent that is linked, directly or indirectly, to a SULFO-Tag. In particular embodiments, the first and/or second binding reagent is used at a concentration of between 10 ng/ml and 100 μg/ml, between 100 ng/ml and 1.0 μg/ml, between 250 ng/ml and 10 μg/ml, between 250 ng/ml and 1 μg/ml, between 1 μg/ml and 10 μg/ml, between 250 ng and 2.5 μg/ml, or between 1 μg/ml and 10 μg/ml the anti-idiotype antibody. In some embodiments, the solid surface or support is incubated with between 250 ng/ml and 10 μg/ml. In certain embodiments, the solid surface or support is incubated with or with about 0.25 μg/ml, 0.5 μg/ml, 1.0 μg/ml, 1.25 μg/ml, 2 μg/ml, 2.5 μg/ml, 5 μg/ml or 10 μg/ml.

In some embodiments, the sample from a subject having been administered a cell therapy comprising cell engineered with a chimeric antigen receptor is or comprises any bodily fluid sample from the subject. In some aspects, the sample is or comprises whole blood, serum or plasma. In some embodiments, the sample is obtained from the subject within or about within 1 hour to 1 year after initiation of administration of the cell therapy or dose of cells, such as within or about within 6 hours, 12 hours, 24 hours, one week, two weeks, three weeks, one month, two months, three months, four months, five months, six months, seven months, eight months, nine months, ten months, eleven months or twelve months. In some aspects, the sample is obtained from the subject from or from about 1 month to 6 months of initiation of administration of the cell therapy, such as 2 months to 6 months or 2 months to 4 months, for example, about or approximately 2 months, 3 months, 4 months, 5 months or 6 months after initiation of administration of the cell therapy.

In some embodiments, the target antibody is an anti-BCMA antibody. In some of any such embodiments, the anti-BCMA antibody is Target Antibody 1 In some of any such embodiments, the anti-BCMA antibody is Target Antibody 2, e.g., as described in section I.A.

In some of any such embodiments, the anti-idiotype antibody or antigen-binding fragment thereof is an anti-idiotype antibody or antigen-binding fragment thereof that binds to or recognizes Target Antibody 1. In some of any such embodiments, the anti-idiotype antibody or antigen-binding fragment thereof is an anti-idiotype antibody or antigen-binding fragment thereof that binds to or recognizes Target Antibody 2, such as any such anti-idiotype antibody or antigen-binding fragment thereof as described herein, e.g., in section I.A. In some of any such embodiments, the anti-idiotype antibody or antigen-binding fragment thereof is an anti-idiotype antibody or antigen-binding fragment thereof that binds to or recognizes Target Antibody 1 and/or Target Antibody 2, such as any such anti-idiotype antibody or antigen-binding fragment thereof as described herein, e.g., in section I.B.

V. Articles of Manufacture or Kits

Also provided are articles of manufacture or kits containing the provided anti-idiotype antibodies and/or compositions. In some embodiments, provided are articles of manufacture comprising an anti-idiotype antibody or an antigen-binding fragment thereof. In some cases, the anti-idiotype antibody binds an anti-BCMA antibody or antigen-binding fragment thereof, or a chimeric antigen receptor comprising an anti-BCMA antibody or antigen-binding fragment thereof. In some examples, the anti-BCMA antibody is Target Antibody 1. In some examples, the anti-BCMA antibody is Target Antibody 2. In some aspects, a conjugate containing the anti-idiotype antibodies described herein are provided in the articles of manufacture or kits.

In some embodiments, the kit or article of manufacture includes the anti-idiotype antibody or antigen binding fragment thereof and a binding reagent containing the extracellular domain, or portion of an extracellular domain, of a chimeric antigen receptor (CAR) to which the anti-idiotype antibody binds, such as specifically binds, or recognizes. In some embodiments, the extracellular domain of the CAR is or includes the anti-BCMA antibody (e.g., Target Antibody 1 or Target Antibody 2), or an antigen-binding fragment thereof.

In some embodiments, the kit or article of manufacture includes the anti-idiotype antibody or antigen binding fragment thereof, and instructions for using the anti-idiotype antibody or antigen binding fragment thereof, to: (i) detect a target antibody or antigen-binding fragment thereof or a CAR comprising a target antibody or antigen-binding fragment thereof, and/or (ii) select or enrich, from a population of cells, engineered cells expressing a CAR comprising the target antibody or antigen-binding fragment thereof, and/or (iii) stimulate an input composition comprising cells expressing a CAR comprising the target antibody or antigen-binding fragment thereof.

In some embodiments, the kit or article of manufacture includes a binding reagent comprising an extracellular domain of a CAR comprising a target antibody or antigen-binding fragment thereof, said extracellular domain or portion thereof comprising the target antibody or antigen-binding fragment thereof, and an anti-idiotype antibody or antigen-binding fragment thereof, or immunoconjugate, as provided herein.

In some embodiments, the binding reagent is a first binding reagent and the kit or article of manufacture additionally includes a second binding reagent. In such examples, the second binding reagent is an agent that is able to bind to the same or similar molecule as the first binding reagent. In some embodiments, the second binding reagent comprises the extracellular domain of the CAR or a portion thereof. In some aspects, the extracellular domain of the CAR or portion thereof of the first binding agent and the second binding agent is the same or substantially the same In some embodiments, the binding reagent, or at least one of the first and second binding reagents, is attached to a label (e.g. detectable label) such as a label described herein. In some embodiments, at least one of the first and second binding reagent is attached to a solid support or capable of being attached to a solid support, such as a solid support described herein. In some aspects, one of the first and second binding reagent is detectably labeled or is capable of producing a detectable signal and the other of the first and seconding binding reagent is attached or immobilized to the solid support. In some embodiments, the binding reagents are provided as a kit or as part of a system as described elsewhere herein for use in connection with an immunoassay (e.g. sandwich or bridge assay). In some embodiments, the first binding reagent is bound to a solid support, optionally a streptavidin coated solid support. In some embodiments, the second soluble protein is linked directly or indirectly to a detectable label, such as SULFO-Tag.

In some embodiments, the kit further comprises an anti-idiotype antibody or antigen-binding fragment. In some aspects, the anti-idiotype antibody binds an anti-BCMA antibody or antigen-binding fragment thereof, or a chimeric antigen receptor comprising an anti-BCMA antibody or antigen-binding fragment thereof. In some examples, the anti-BCMA antibody is Target Antibody 1 or Target Antibody 2. In some embodiments, the anti-idiotype antibody or antigen-binding fragment thereof is provided as a positive control sample. In some examples, the positive control sample forms a complex with the first and second soluble proteins or reagents which contains regions of the extracellular domain of a chimeric antigen receptor (CAR) comprising the anti-BCMA antibody or an antigen-binding fragment thereof.

In some embodiments, the kit or article of manufacture includes a cartridge device, e.g., for use in any of the methods described in Section IV.A. In some embodiments, the microfluidic cartridge contains a sample composition chamber. In some embodiments, the microfluidic cartridge contains a blister compartment. In some embodiments, the microfluidic cartridge contains a treatment compartment adapted for fluid mixing, said treatment compartment in fluid communication with the sample composition chamber and the blister. In some embodiments, the microfluidic cartridge contains an evaluation chamber including a reading zone, wherein the evaluation chamber is in fluid communication with the treatment chamber. In some embodiments, the reading zone allows for analysis of the sample as it passes through the reading zone.

In some embodiments, the blister contains an anti-idiotype antibody or antigen binding fragment thereof. In some embodiments, the anti-idiotype antibody is conjugated to a detectable label, e.g., a fluorescent label. In some aspects, the anti-idiotype antibody binds an anti-BCMA antibody or antigen-binding fragment thereof, or a chimeric antigen receptor comprising an anti-BCMA antibody or antigen-binding fragment thereof. In some examples, the anti-BCMA antibody is the target anti-BCMA antibody as described in, e.g., Section I.A.

In some embodiments, the kit or article of manufacture includes a dried-down anti-idiotype antibody or antigen binding fragment thereof, e.g., for use in any of the methods described in Section IV.A. In some embodiments, the dried-down anti-idiotype antibody is conjugated to a detectable label, e.g., a fluorescent label. In some aspects, the dried-down anti-idiotype antibody binds an anti-BCMA antibody or antigen-binding fragment thereof, or a chimeric antigen receptor comprising an anti-BCMA antibody or antigen-binding fragment thereof. In some examples, the anti-BCMA antibody is the target anti-BCMA antibody as described in, e.g., Section I.A. In some embodiments, the dried-down anti-idiotype antibody or antigen binding fragment thereof is contained in a tube. In some embodiments, the tube further contains other dried-down reagents, e.g., other labelled antibodies, dyes, or cell lysing agents.

In some embodiments, the kit or article of manufacturer comprises reagents or components for carrying out any of the provided methods. In some embodiments, the article of manufacture or kit comprises one or more reagent or other materials desirable from a commercial, therapeutic, and user standpoint including secondary antibodies, affinity labels, capture reagents, buffers, diluents, signal detection agents, filters, needles, syringes, capillary tubes, and package inserts with instructions for use.

In some embodiments, the kits can be provided as articles of manufacture that include packing materials for the packaging of the antibodies or compositions thereof or the one or more additional reagents, e.g. binding reagents, or components. For example, the kits can contain containers, bottles, tubes, vial and any packaging material suitable for separating or organizing the components of the kit.

In some embodiments, the kit includes one or more containers. Suitable containers include, for example, bottles, vials (e.g., dual chamber vials), syringes (such as single or dual chamber syringes) and test tubes. The one or more containers may be formed from a variety of materials such as glass or plastic. The one or more containers hold a composition comprising an antibody or other reagents, e.g. binding reagents, for use in the methods. The article of manufacture or kit herein may comprise the antibodies or reagents in separate containers or in the same container. In some embodiments, the one or more containers holding the composition may be a single-use vial or a multi-use vial, which, in some cases, may allow for repeat use of the reconstituted composition.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

The articles of manufacture may include a container and a label or package insert on or associated with the container. Suitable containers include, for example, bottles, vials, syringes, IV solution bags, etc. The containers may be formed from a variety of materials such as glass or plastic. The container in some embodiments holds a composition containing an anti-idiotype antibody as provided herein which is by itself or is combined with another composition effective for treating, preventing and/or diagnosing a disease or condition. In some embodiments, the container has a sterile access port. Exemplary containers include an intravenous solution bags, vials, including those with stoppers pierceable by a needle for injection. The article of manufacture may include a first container with a composition contained therein, wherein the composition includes the anti-idiotype antibody. Alternatively, or additionally, the article of manufacture may further include another or the same container comprising an acceptable buffer. It may further include other materials such as other buffers, diluents, filters, needles, and/or syringes.

In some embodiments, the article of manufacture or kit comprises a solid support, including a solid support formed of glass (e.g., controlled pore glass), polysaccharides (e.g., agarose), polyacrylamides, polystyrene, polyvinyl alcohol, nitrocellulose, cellulose, nylon, silicones and other material well known in the art that is used in a solid support for direct or indirect attachment of a binding reagent as described. Solid supports included in the articles of manufacture or kits provided herein include, but are not limited to, a bead, column (e.g., chromatography column, etc.), an array (e.g., microarray, nanoarray, etc.), an assay plate, a cartridge, a stick, a filter, a strip or any other solid support described herein.

In some embodiments, the article of manufacture or kit may further comprise a second container comprising a suitable diluent. The article of manufacture or kit may further include other materials desirable from a commercial, therapeutic, and user standpoint, including other buffers, diluents, filters, needles, syringes, therapeutic agents and/or package inserts with instructions for use.

In some embodiments, the kit can, optionally, include instructions. Instructions typically include a tangible expression describing the antibodies and, optionally, other components included in the kit, e.g. binding reagent, and methods for using the antibodies and/or other components in or in conjunction with any of the uses or methods as described. In some embodiments, the instructions are provided as a label or a package insert, which is on or associated with the container. In some embodiments, the instructions may indicate directions for reconstitution and/or use of the composition.

In some embodiments, instructions are provided for using the anti-idiotype antibody to detect a Target Antibody 1 or antigen-binding fragment thereof or a chimeric antigen receptor comprising the Target Antibody 1 or antigen-binding fragment thereof, such as in accord with or conjunction with any of the methods or assays as described. In some examples, instructions are provided for using the anti-idiotype antibody to select or enrich, from a population of cells, engineered cells expressing a chimeric antigen receptor (CAR) comprising the Target Antibody 1 or an antigen-binding fragment thereof. In some examples, instructions are provided for using the anti-idiotype antibody to stimulate an input composition comprising cells expressing a chimeric antigen receptor comprising the Target Antibody 1 or antigen-binding fragment thereof.

In some embodiments, instructions are provided for using the anti-idiotype antibody to detect a Target Antibody 2 or antigen-binding fragment thereof or a chimeric antigen receptor comprising the Target Antibody 2 or antigen-binding fragment thereof, such as in accord with or conjunction with any of the methods or assays as described. In some aspects, instructions are provided for using the anti-idiotype antibody to to select or enrich, from a population of cells, engineered cells expressing a chimeric antigen receptor (CAR) comprising the Target Antibody 2 or an antigen-binding fragment thereof. In some embodiments, instructions are provided for using the anti-idiotype antibody to stimulate an input composition comprising cells expressing a chimeric antigen receptor comprising the Target Antibody 2 or antigen-binding fragment thereof.

In some embodiments, instructions are provided for use of the kit provided to detect a molecule that binds to a chimeric antigen receptor of the cell therapy, such as an antibody, e.g. an antibody produced by a humoral immune response to the chimeric antigen receptor (CAR). In some embodiments, the instructions are provided for contacting a binding reagent with a sample from a subject having been administered a cell therapy comprising cells engineered with a CAR comprising a target antibody that is the anti-BCMA antibody (e.g., Target Antibody 1 or Target Antibody 2) or an antigen-binding fragment thereof, wherein the binding reagent comprises the extracellular domain of the CAR or a portion of the extracellular domain comprising the target antibody or the antigen-binding fragment thereof. In some aspects, the instructions also specify detecting the presence or absence of a complex comprising the binding reagents and a molecule from the sample that binds to both the first and the second binding reagent, optionally wherein the molecule is or comprises an antibody. In some aspects, the BCMA antibody is Target Antibody 1. In some aspects, the BCMA antibody is Target Antibody 2. In some further embodiments, instructions for using the binding reagents and the positive control sample are provided.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, reference to a "corresponding form" of an antibody means that when comparing a property or activity of two antibodies, the property is compared using the same form of the antibody. For example, if it is stated that an antibody has greater activity compared to the activity of the corresponding form of a first antibody, that means that a particular form, such as a scFv of that antibody, has greater activity compared to the scFv form of the first antibody.

As used herein, recitation that nucleotides or amino acid positions "correspond to" nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, one skilled in the art can identify corresponding residues, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48: 1073).

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, MD, 1991.

The terms "full length antibody," "intact antibody," and "whole antibody" are used herein interchangeably to refer to an antibody having a structure substantially similar to a native antibody structure or having heavy chains that contain an Fc region as defined herein.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848: 79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-idiotype antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, "percent (%) amino acid sequence identity" and "percent identity" when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, the singular forms "a," "an," and "the" include plural referents unless the context clearly dictates otherwise. For example, "a" or "an" means "at least one" or "one or more." It is understood that aspects and variations described herein include "consisting" and/or "consisting essentially of" aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "polypeptide" and "protein" are used interchangeably to refer to a polymer of amino acid residues, and are not limited to a minimum length. Polypeptides, including the provided antibodies and antibody chains and other peptides, e.g., linkers, may include amino acid residues including natural and/or non-natural amino acid residues. The terms also include post-expression modifications of the polypeptide, for example, glycosylation, sialylation, acetylation, phosphorylation, and the like. In some aspects, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

As used herein, a composition refers to any mixture of two or more products, substances, or compounds, including cells. It may be a solution, a suspension, liquid, powder, a paste, aqueous, non-aqueous or any combination thereof.

As used herein, a statement that a cell or population of cells is "positive" for a particular marker refers to the detectable presence on or in the cell of a particular marker, typically a surface marker. When referring to a surface marker, the term refers to the presence of surface expression as detected by flow cytometry, for example, by staining with an antibody that binds to the marker (e.g., specifically binds to the marker) and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is "negative" for a particular marker refers to the absence of substantial detectable presence on or in the cell of a particular marker, typically a surface marker. When referring to a surface marker, the term refers to the absence of surface expression as detected by flow cytometry, for example, by staining with an antibody that binds to the marker (e.g., specifically binds to the marker) and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, a statement that an anti-idiotype antibody or antigen-binding fragment thereof "binds to or recognizes" a particular target(s), e.g., a target antibody or antigen-binding fragment thereof, or a particular feature of a particular target(s), e.g., an antigen-binding domain of a target antibody or antigen-binding fragment thereof, refers, in some embodiments, to an anti-idiotype antibody or antigen-binding fragment thereof that specifically binds to or specifically recognizes a particular target(s) or a particular feature of a particular target(s). For purposes herein, "specifically binds to" or "specifically recognizes" a particular target(s) refers to the ability of the anti-idiotype antibody or antigen-binding fragment thereof to specifically bind to or specifically recognize that particular target(s) but not other targets, e.g., binding to that particular target(s) is measurably different from a non-specific interaction.

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

VII. Exemplary Embodiments

Among the provided embodiments are:

1. An anti-idiotype antibody or antigen-binding fragment thereof that binds to an anti-BCMA target antibody or antigen-binding fragment thereof, wherein the anti-idiotype antibody or antigen-binding fragment comprises:

a VH region comprising a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and a VL region comprising a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

2. An anti-idiotype antibody or antigen-binding fragment thereof that binds to an anti-BCMA target antibody or antigen-binding fragment thereof, wherein the anti-idiotype antibody or antigen-binding fragment comprises:

a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 84 or 114; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 85 or 115.

3. An anti-idiotype antibody or antigen-binding fragment thereof that binds to an anti-BCMA target antibody or antigen-binding fragment thereof, wherein the anti-idiotype antibody or antigen-binding fragment comprises:

a VH region comprising an amino acid sequence having at least 90% sequence identity to the amino acid sequence set forth in SEQ ID NO: 84 or 114; and a VL region comprising an amino acid sequence having at least 90% sequence identity to the amino acid sequence set forth in SEQ ID NO: 85 or 115.

4. An anti-idiotype antibody or antigen-binding fragment thereof that binds to an anti-BCMA target antibody or antigen-binding fragment thereof, wherein the anti-idiotype antibody or antigen-binding fragment comprises:

a VH region comprising the amino acid sequence set forth in SEQ ID NO: 84 or 114; and a VL region comprising the amino acid sequence set forth in SEQ ID NO: 85 or 115.

5. The anti-idiotype antibody or antigen-binding fragment thereof of any one of embodiments 2-4, wherein:

the VH region comprises a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and the VL region comprises a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

6. The anti-idiotype antibody or antigen-binding fragment thereof of any one of embodiments 1-3 and 5, wherein:

the VH region comprises an amino acid sequence having at least 90% sequence identity to the amino acid sequence set forth in SEQ ID NO: 84, and the VL region comprises an amino acid sequence having at least 90% sequence identity to the amino acid sequence set forth in SEQ ID NO: 85; or the VH region comprises an amino acid sequence having at least 90% sequence identity to the amino acid sequence set forth in SEQ ID NO: 114, and the VL region comprises an amino acid sequence having at least 90% sequence identity to the amino acid sequence set forth in SEQ ID NO: 115.

7. The anti-idiotype antibody or antigen-binding fragment thereof of any one of embodiments 1-6, wherein:

the VH region comprises an amino acid sequence set forth in SEQ ID NO: 84, and the VL region comprises an amino acid sequence set forth in SEQ ID NO: 85; or the VH region comprises an amino acid sequence set forth in SEQ ID NO: 114, and the VL region comprises an amino acid sequence set forth in SEQ ID NO: 115.

8. The anti-idiotype antibody or antigen-binding fragment thereof of any one of embodiments 1-7, wherein:

the VH region comprises a CDR-H1 comprising the amino acid sequence set forth in SEQ ID NO: 74, a CDR-H2 comprising the amino acid sequence set forth in SEQ ID NO: 75, and a CDR-H3 comprising the amino acid sequence set forth in SEQ ID NO: 76; and the VL region comprises a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83.

9. The anti-idiotype antibody or antigen-binding fragment thereof of any one of embodiments 1-8, wherein the VH region comprises an amino acid sequence set forth in SEQ ID NO: 84, and the VL region comprises an amino acid sequence set forth in SEQ ID NO: 85.

10. The anti-idiotype antibody or antigen-binding fragment thereof of any one of embodiments 1-7, wherein:

the VH region comprises a CDR-H1 comprising the amino acid sequence set forth in SEQ ID NO: 104, a CDR-H2 comprising the amino acid sequence set forth in SEQ ID NO: 105, and a CDR-H3 comprising the amino acid sequence set forth in SEQ ID NO: 106; and the VL region comprises a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113.

11. The anti-idiotype antibody or antigen-binding fragment thereof of any one of embodiments 1-7 and 10, wherein the VH region comprises an amino acid sequence set forth in SEQ ID NO: 114, and the VL region comprises an amino acid sequence set forth in SEQ ID NO: 115.

12. The anti-idiotype antibody or antigen-binding fragment thereof of any one of embodiments 1-11, wherein the anti-BCMA target antibody or antigen-binding fragment thereof binds to human BCMA.

13. The anti-idiotype antibody or antigen-binding fragment thereof of any one of embodiments 1-12, wherein the anti-BCMA target antibody or antigen-binding fragment thereof comprises a VH region comprising the amino acid sequence set forth in SEQ ID NO: 25, and a VL region comprising the amino acid sequence set forth in SEQ ID NO: 26.

14. The anti-idiotype antibody or antigen-binding fragment thereof of embodiment 13, wherein the anti-BCMA target antibody or antigen-binding fragment thereof is a single chain fragment.

15. The anti-idiotype antibody or antigen-binding fragment thereof of embodiment 14, wherein the single chain fragment comprises a flexible linker positioned between the VH region and the VL region.

16. The anti-idiotype antibody or antigen-binding fragment thereof of embodiment 15, wherein the flexible linker comprises the amino acid sequence set forth in SEQ ID NO: 14.

17. The anti-idiotype antibody or antigen-binding fragment thereof of any one of embodiments 14-16, wherein the single chain fragment of the ani-BCMA target antibody or antigen-binding fragment thereof is a single chain variable fragment (scFv), optionally wherein the scFv comprises the amino acid sequence set forth in SEQ ID NO: 27.

18. The anti-idiotype antibody or antigen-binding fragment thereof of any one of embodiments 1-17, wherein the anti-idiotype antibody or antigen-binding fragment binds to an epitope within or including all or a portion of a CDR of the target antibody or antigen-binding fragment.

19. The anti-idiotype antibody or antigen-binding fragment thereof of any one of embodiments 1-18, wherein:
the anti-BCMA target antibody or antigen-binding fragment is within or included in an antigen-binding domain of an extracellular portion of a CAR; and/or
the anti-idiotype antibody or antigen-binding fragment binds the anti-BCMA target antibody or antigen-binding fragment comprised within or included in an antigen-binding domain of an extracellular portion of a CAR.

20. The anti-idiotype antibody or antigen-binding fragment thereof of embodiment 17 or embodiment 18, wherein:
the scFv is within or included in an extracellular portion of a CAR; and/or
the anti-idiotype antibody or antigen-binding fragment binds the scFv comprised within or included in an extracellular portion of a CAR.

21. The anti-idiotype antibody or antigen-binding fragment thereof of embodiment 19 or embodiment 20, wherein the CAR further comprises a transmembrane domain linked to the antigen-binding domain via a spacer.

22. The anti-idiotype antibody or antigen-binding fragment thereof of embodiment 21, wherein the spacer is an immunoglobulin spacer, optionally wherein the spacer comprises the amino acid sequence set forth in SEQ ID NO: 50.

23. The anti-idiotype antibody or antigen-binding fragment thereof of embodiment 21 or embodiment 22, wherein the transmembrane domain comprises a transmembrane portion of CD28, which optionally is human CD28.

24. The anti-idiotype antibody or antigen-binding fragment thereof of any one of embodiments 21-23, wherein the anti-idiotype antibody or antigen-binding fragment thereof does not bind to an epitope in the spacer domain of the CAR.

25. The anti-idiotype antibody or antigen-binding fragment thereof of any one of embodiments 1-24, wherein the anti-idiotype antibody or antigen-binding fragment thereof does not bind or does not specifically bind to CD28 or a portion thereof, which optionally is human CD28.

26. The anti-idiotype antibody or antigen-binding fragment thereof of any one of embodiments 1-25, wherein the anti-idiotype antibody or antigen-binding fragment thereof does not bind to an epitope in an Fc domain, which optionally is a human IgG1 Fc domain.

27. The anti-idiotype antibody or antigen-binding fragment thereof of any one of embodiments 1-26, wherein the anti-idiotype antibody or antigen-binding fragment thereof specifically binds to the anti-BCMA target antibody or antigen-binding fragment thereof.

28. The anti-idiotype antibody or antigen-binding fragment thereof of any one of embodiments 1-27, wherein the anti-idiotype antibody has a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

29. The anti-idiotype antibody or antigen-binding fragment thereof of any one of embodiments 1-28, wherein the anti-idiotype antibody or antigen-binding fragment thereof does not cross-react with another anti-BCMA antibody, which optionally is comprised in the extracellular antigen-binding domain of another CAR.

30. The anti-idiotype antibody or antigen-binding fragment thereof of embodiment 29, wherein the another anti-BCMA antibody:
(i) comprises a VH region comprising an amino acid sequence that has less than 90% sequence identity to the amino acid sequence set forth in SEQ ID NO: 25, and/or a VL region comprising an amino acid sequence that has less than 90% sequence identity to the amino acid sequence set forth in SEQ ID NO: 26; and/or
(ii) comprises an scFv that has less than 90% sequence identity to the amino acid sequence set forth in SEQ ID NO: 13; and/or
(iii) comprises a CDR-H1 that has 1, 2, 3, or 4 or more amino acid residues that are different from the CDR-H1 amino acid sequence as set forth in SEQ ID NO: 15, and/or a CDR-H2 that has 1, 2, 3, or 4 or more amino acid residues that are different from the CDR-H2 amino acid sequence as set forth in SEQ ID NO: 16, and/or a CDR-H3 that has 1, 2, 3, or 4 or more amino acid residues that are different from the CDR-H3 amino acid sequence as set forth in SEQ ID NO: 17, and/or a CDR-L1 that has 1, 2, 3, or 4 or more amino acid residues that are different from the CDR-L1 amino acid sequence as set forth in SEQ ID NO: 22, and/or a CDR-L2 that has 1, 2, 3, or 4 or more amino acid residues that are different from the CDR-L2 amino acid sequence as set forth in SEQ ID NO: 23, and/or a CDR-L3 that has 1, 2, 3, or 4 or more amino acid residues that are different from the CDR-L3 amino acid sequence as set forth in SEQ ID NO: 24; and/or (iv) binds to an epitope of human BCMA that is not the same epitope of human BCMA that the anti-BCMA target antibody or antigen-binding fragment thereof binds to.

31. The anti-idiotype antibody or antigen-binding fragment thereof of any one of embodiments 1-30, wherein the anti-idiotype antibody or antigen-binding fragment thereof is an agonist of a CAR comprising the anti-BCMA target antibody or antigen-binding fragment thereof.

32. The anti-idiotype antibody or antigen-binding fragment thereof of embodiment 31, wherein:

the anti-idiotype antibody or antigen-binding fragment thereof is an agonist of the CAR when in soluble form; and/or the anti-idiotype antibody or antigen-binding fragment thereof is an agonist of the CAR when immobilized to a support or a stationary phase, optionally wherein the support or stationary phase is a plate or a bead.

33. The anti-idiotype antibody or antigen-binding fragment thereof of any one of embodiments 1-32, wherein binding of the anti-idiotype antibody or antigen-binding fragment thereof to the anti-BCMA target antibody or antigen-binding fragment thereof is not blocked by human BCMA or human BCMA-Fc.

36. An anti-idiotype antibody or antigen-binding fragment thereof that binds to a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and a VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61.

37. An anti-idiotype antibody or antigen-binding fragment thereof that binds to a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 38 or 62; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 39 or 63.

38. An anti-idiotype antibody or antigen-binding fragment thereof that binds to a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising an amino acid sequence having at least 90% sequence identity to the amino acid sequence set forth in SEQ ID NO: 38 or 62; and a VL region comprising an amino acid sequence having at least 90% sequence identity to the amino acid sequence set forth in SEQ ID NO: 39 or 63.

39. An anti-idiotype antibody or antigen-binding fragment thereof that binds to a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising the amino acid sequence set forth in SEQ ID NO: 38 or 62; and a VL region comprising the amino acid sequence set forth in SEQ ID NO: 39 or 63.

40. The anti-idiotype antibody or antigen-binding fragment thereof of any one of embodiments 37-39, wherein:

the VH region comprises a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and the VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61.

41. The anti-idiotype antibody or antigen-binding fragment thereof of any one of embodiments 36, 37, and 40, wherein:

the VH region comprises an amino acid sequence having at least 90% sequence identity to the amino acid sequence set forth in SEQ ID NO: 38 or 62; and the VL region comprises an amino acid sequence having at least 90% sequence identity to the amino acid sequence set forth in SEQ ID NO: 39 or 63.

43. The anti-idiotype antibody or antigen-binding fragment thereof of any one of embodiments 36-38, 40, and 41, wherein:

the VH region comprises the amino acid sequence set forth in SEQ ID NO: 38 or 62; and the VL region comprises the amino acid sequence set forth in SEQ ID NO: 39 or 63.

44. The anti-idiotype antibody or antigen-binding fragment thereof of any one of embodiments 36-38, 40, and 41, wherein:

the VH region comprises an amino acid sequence having at least 90% sequence identity to the amino acid sequence set forth in SEQ ID NO: 38, and the VL region comprises an amino acid sequence having at least 90% sequence identity to the amino acid sequence set forth in SEQ ID NO: 39; or the VH region comprises an amino acid sequence having at least 90% sequence identity to the amino acid sequence set forth in SEQ ID NO: 62, and the VL region comprises an amino acid sequence having at least 90% sequence identity to the amino acid sequence set forth in SEQ ID NO: 63.

45. The anti-idiotype antibody or antigen-binding fragment thereof of any one of embodiments 36-44, wherein:

the VH region comprises the amino acid sequence set forth in SEQ ID NO: 38, and the VL region comprises the amino acid sequence set forth in SEQ ID NO: 39; or the VH region comprises the amino acid sequence set forth in SEQ ID NO: 62, and the VL region comprises the amino acid sequence set forth in SEQ ID NO: 63.

46. The anti-idiotype antibody or antigen-binding fragment thereof of any one of embodiments 36-45, wherein:

the VH region comprises a CDR-H1 comprising the amino acid sequence set forth in SEQ ID NO: 28, a CDR-H2 comprising the amino acid sequence set forth in SEQ ID NO: 29, and a CDR-H3 comprising the amino acid sequence set forth in SEQ ID NO: 30; and the VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37.

47. The anti-idiotype antibody or antigen-binding fragment thereof of any one of embodiments 36-46, wherein the VH region comprises the amino acid sequence set forth in SEQ ID NO: 38, and the VL region comprises the amino acid sequence set forth in SEQ ID NO: 39.

48. The anti-idiotype antibody or antigen-binding fragment thereof of any one of embodiments 36-45, wherein:

the VH region comprises a CDR-H1 comprising the amino acid sequence set forth in SEQ ID NO: 52, a CDR-H2 comprising the amino acid sequence set forth in SEQ ID NO: 53, and a CDR-H3 comprising the amino acid sequence set forth in SEQ ID NO: 54; and the VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61.

49. The anti-idiotype antibody or antigen-binding fragment thereof of any one of embodiments 36-45 and 48, wherein the VH region comprises the amino acid sequence set forth in SEQ ID NO: 62, and the VL region comprises the amino acid sequence set forth in SEQ ID NO: 63.

50. The anti-idiotype antibody or antigen-binding fragment thereof of any one of embodiments 36-49, wherein the first anti-BCMA target antibody or antigen-binding fragment thereof binds to human BCMA, and the second anti-BCMA target antibody or antigen-binding fragment thereof binds to human BCMA.

51. The anti-idiotype antibody or antigen-binding fragment thereof of any one of embodiments 36-50, wherein:

the first anti-BCMA target antibody or antigen-binding fragment thereof comprises a VH region comprising the amino acid sequence set forth in SEQ ID NO: 11, and a VL region comprising the amino acid sequence set forth in SEQ ID NO: 12; and the second anti-BCMA target antibody or antigen-binding fragment thereof comprises a VH region comprising the amino acid sequence set forth in SEQ ID NO: 25, and a VL region comprising the amino acid sequence set forth in SEQ ID NO: 26.

52. The anti-idiotype antibody or antigen-binding fragment thereof of embodiment 51, wherein the first anti-BCMA target antibody or antigen-binding fragment thereof is a first single chain fragment and the second anti-BCMA target antibody or antigen-binding fragment thereof is a second single chain fragment.

53. The anti-idiotype antibody or antigen-binding fragment thereof of embodiment 52, wherein the first single chain fragment comprises a flexible linker positioned between the VH region and the VL region, and the second single chain fragment comprises a flexible linker positioned between the VH region and the VL region.

54. The anti-idiotype antibody or antigen-binding fragment thereof of embodiment 53, wherein the flexible linker of the first single chain fragment and/or the second single chain fragment comprises the amino acid sequence set forth in SEQ ID NO: 14.

55. The anti-idiotype antibody or antigen-binding fragment thereof of any one of embodiments 52-54, wherein the first single chain fragment of the first anti-BCMA target antibody or antigen-binding fragment thereof is a first scFv, and the second single chain fragment of the second anti-BCMA target antibody or antigen-binding fragment thereof is a second scFv.

56. The anti-idiotype antibody or antigen-binding fragment thereof of embodiment 55, wherein the first scFv comprises the amino acid sequence set forth in SEQ ID NO: 13, and the second scFv comprises the amino acid sequence set forth in SEQ ID NO: 27.

57. The anti-idiotype antibody or antigen-binding fragment thereof of any one of embodiments 36-56, wherein the anti-idiotype antibody or antigen-binding fragment binds to:

an epitope within or including all or a portion of a CDR of the first anti-BCMA target antibody or antigen-binding fragment; and an epitope within or including all or a portion of a CDR of the second anti-BCMA target antibody or antigen-binding fragment.

58. The anti-idiotype antibody or antigen-binding fragment thereof of any one of embodiments 36-57, wherein:

the first anti-BCMA target antibody or antigen-binding fragment is within or included in an antigen-binding domain of an extracellular portion of a first CAR; and/or the anti-idiotype antibody or antigen-binding fragment binds the first anti-BCMA target antibody or antigen-binding fragment comprised within or included in an antigen-binding domain of an extracellular portion of a first CAR.

59. The anti-idiotype antibody or antigen-binding fragment thereof of any one of embodiments 36-58, wherein:

the second anti-BCMA target antibody or antigen-binding fragment is within or included in an antigen-binding domain of an extracellular portion of a second CAR; and/or the anti-idiotype antibody or antigen-binding fragment binds the second anti-BCMA target antibody or antigen-binding fragment comprised within or included in an antigen-binding domain of an extracellular portion of a second CAR.

60. The anti-idiotype antibody or antigen-binding fragment thereof of any one of embodiments 36-57, wherein:

the first scFv is within or included in an extracellular portion of a first CAR; and/or the anti-idiotype antibody or antigen-binding fragment binds the first scFv comprised within or included in an extracellular portion of a first CAR.

61. The anti-idiotype antibody or antigen-binding fragment thereof of any one of embodiments 36-57, wherein:
the second scFv is within or included in an extracellular portion of a second CAR; and/or
the anti-idiotype antibody or antigen-binding fragment binds the second scFv comprised within or included in an extracellular portion of a second CAR.

62. The anti-idiotype antibody or antigen-binding fragment thereof of any one of embodiments 58-61, wherein the first CAR further comprises a transmembrane domain linked to the antigen-binding domain via a spacer, and/or the second CAR further comprises a transmembrane domain linked to the antigen-binding domain via a spacer.

63. The anti-idiotype antibody or antigen-binding fragment thereof of embodiment 62, wherein the spacer of the first CAR and/or the second CAR is an immunoglobulin spacer, optionally wherein the spacer comprises the amino acid sequence set forth in SEQ ID NO: 50.

64. The anti-idiotype antibody or antigen-binding fragment thereof of embodiment 62 or embodiment 63, wherein the transmembrane domain of the first CAR and/or the second CAR comprises a transmembrane portion of CD28, which optionally is human CD28.

65. The anti-idiotype antibody or antigen-binding fragment thereof of any one of embodiments 62-64, wherein the anti-idiotype antibody or antigen-binding fragment thereof does not bind to an epitope in the spacer domain of the first CAR and/or the second CAR.

66. The anti-idiotype antibody or antigen-binding fragment thereof of any one of embodiments 36-65, wherein the anti-idiotype antibody or antigen-binding fragment thereof does not bind or does not specifically bind to CD28 or a portion thereof, which optionally is human CD28.

67. The anti-idiotype antibody or antigen-binding fragment thereof of any one of embodiments 36-66, wherein the anti-idiotype antibody or antigen-binding fragment thereof does not bind to an epitope in an Fc domain, which optionally is a human IgG1 Fc domain.

68. The anti-idiotype antibody or antigen-binding fragment thereof of any one of embodiments 36-67, wherein the anti-idiotype antibody or antigen-binding fragment thereof specifically binds to the first anti-BCMA target antibody or antigen-binding fragment thereof and the second anti-BCMA target antibody or antigen-binding fragment thereof.

69. The anti-idiotype antibody or antigen-binding fragment thereof of any one of embodiments 36-68, wherein the anti-idiotype antibody has a dissociation constant to the first anti-BCMA target antibody or antigen-binding fragment thereof and/or the second anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

70. The anti-idiotype antibody or antigen-binding fragment thereof of any one of embodiments 36-69, wherein the anti-idiotype antibody or antigen-binding fragment thereof is an agonist of a first CAR comprising the first anti-BCMA target antibody or antigen-binding fragment thereof, and/or is an agonist of a second CAR comprising the second anti-BCMA target antibody or antigen-binding fragment thereof.

71. The anti-idiotype antibody or antigen-binding fragment thereof of embodiment 70, wherein:
the anti-idiotype antibody or antigen-binding fragment thereof is an agonist of the first CAR and/or the second CAR when in soluble form; and/or
the anti-idiotype antibody or antigen-binding fragment thereof is an agonist of the first CAR and/or the second CAR when immobilized to a support or a stationary phase, optionally wherein the support or stationary phase is a plate or a bead.

72. The anti-idiotype antibody or antigen-binding fragment thereof of any one of embodiments 36-71, wherein binding of the anti-idiotype antibody or antigen-binding fragment thereof to the first anti-BCMA target antibody or antigen-binding fragment thereof and/or the second anti-BCMA target antibody or antigen-binding fragment thereof is not blocked by human BCMA or human BCMA-Fc.

73. The anti-idiotype antibody or antigen-binding fragment thereof of any one of embodiments 1-72, comprising at least a portion of an immunoglobulin constant region of a heavy chain and/or a light chain.

74. The anti-idiotype antibody or antigen-binding fragment thereof of embodiment 73, wherein the anti-idiotype antibody or antigen-binding fragment comprises a heavy chain constant region comprising an Fc region or a portion of the Fc comprising the CH2 and CH3 domains and/or a light chain constant region comprising a CL domain.

75. The anti-idiotype antibody or antigen-binding fragment thereof of embodiment 73 or embodiment 74, wherein the constant region is derived from IgG, optionally IgG1.

76. The anti-idiotype antibody or antigen-binding fragment thereof of embodiment 74 or embodiment 75, wherein the light chain constant region is from a kappa light chain.

77. The anti-idiotype antibody or antigen-binding fragment thereof of any one of embodiments 1-76, which is an intact antibody or full-length antibody.

78. The anti-idiotype antibody or antigen-binding fragment thereof of any one of embodiments 1-35 and 73-77, wherein the anti-idiotype antibody or antigen-binding fragment thereof comprises:
a heavy chain comprising an amino acid sequence having at least 90% sequence identity to the amino acid sequence set forth in SEQ ID NO: 86, and a light chain comprising an amino acid sequence having at least 90% sequence identity to the amino acid sequence set forth in SEQ ID NO: 87; or
a heavy chain comprising an amino acid sequence having at least 90% sequence identity to the amino acid sequence set forth in SEQ ID NO: 116, and a light chain comprising an amino acid sequence having at least 90% sequence identity to the amino acid sequence set forth in SEQ ID NO: 117.

79. The anti-idiotype antibody or antigen-binding fragment thereof of any one of embodiments 1-35 and 73-78, wherein the anti-idiotype antibody or antigen-binding fragment thereof comprises:

a heavy chain comprising the amino acid sequence set forth in SEQ ID NO: 86, and a light chain comprising the amino acid sequence set forth in SEQ ID NO: 87; or a heavy chain comprising the amino acid sequence set forth in SEQ ID NO: 116, and a light chain comprising the amino acid sequence set forth in SEQ ID NO: 117.

80. The anti-idiotype antibody or antigen-binding fragment thereof of any one of embodiments 1-9, 12-35, and 73-79, wherein the anti-idiotype antibody or antigen-binding fragment thereof comprises:

a heavy chain comprising the amino acid sequence set forth in SEQ ID NO: 86, and a light chain comprising the amino acid sequence set forth in SEQ ID NO: 87.

81. The anti-idiotype antibody or antigen-binding fragment thereof of any one of embodiments 1-7, 10-35, and 73-79, wherein the anti-idiotype antibody or antigen-binding fragment thereof comprises:

a heavy chain comprising the amino acid sequence set forth in SEQ ID NO: 116, and a light chain comprising the amino acid sequence set forth in SEQ ID NO: 117.

82. The anti-idiotype antibody or antigen-binding fragment thereof of any one of embodiments 36-77, wherein the anti-idiotype antibody or antigen-binding fragment thereof comprises:

a heavy chain comprising an amino acid sequence having at least 90% sequence identity to the amino acid sequence set forth in SEQ ID NO: 40 or 64; and a light chain comprising an amino acid sequence having at least 90% sequence identity to the amino acid sequence set forth in SEQ ID NO: 41 or 65.

83. The anti-idiotype antibody or antigen-binding fragment thereof of any one of embodiments 36-77 and 82, wherein the anti-idiotype antibody or antigen-binding fragment thereof comprises:

a heavy chain comprising an amino acid sequence having at least 90% sequence identity to the amino acid sequence set forth in SEQ ID NO: 40, and a light chain comprising an amino acid sequence having at least 90% sequence identity to the amino acid sequence set forth in SEQ ID NO: 41; or a heavy chain comprising an amino acid sequence having at least 90% sequence identity to the amino acid sequence set forth in SEQ ID NO: 64, and a light chain comprising an amino acid sequence having at least 90% sequence identity to the amino acid sequence set forth in SEQ ID NO: 65.

84. The anti-idiotype antibody or antigen-binding fragment thereof of any one of embodiments 36-77, 82, and 83, wherein the anti-idiotype antibody or antigen-binding fragment thereof comprises:

a heavy chain comprising the amino acid sequence set forth in SEQ ID NO: 40 or 64; and a light chain comprising the amino acid sequence set forth in SEQ ID NO: 41 or 65.

85. The anti-idiotype antibody or antigen-binding fragment thereof of any one of embodiments 36-77 and 82-84, wherein the anti-idiotype antibody or antigen-binding fragment thereof comprises:

a heavy chain comprising the amino acid sequence set forth in SEQ ID NO: 40, and a light chain comprising the amino acid sequence set forth in SEQ ID NO: 41; or a heavy chain comprising the amino acid sequence set forth in SEQ ID NO: 64, and a light chain comprising the amino acid sequence set forth in SEQ ID NO: 65.

86. The anti-idiotype antibody or antigen-binding fragment thereof of any one of embodiments 36-47, 50-77, and 82-85, wherein the anti-idiotype antibody or antigen-binding fragment thereof comprises:

a heavy chain comprising the amino acid sequence set forth in SEQ ID NO: 40, and a light chain comprising the amino acid sequence set forth in SEQ ID NO: 41.

87. The anti-idiotype antibody or antigen-binding fragment thereof of any one of embodiments 36-45, 48-77, and 82-85, wherein the anti-idiotype antibody or antigen-binding fragment thereof comprises:

a heavy chain comprising the amino acid sequence set forth in SEQ ID NO: 64, and a light chain comprising the amino acid sequence set forth in SEQ ID NO: 65.

88. The anti-idiotype antibody or antigen-binding fragment thereof of any one of embodiments 1-76, which is an antigen-binding fragment.

89. The anti-idiotype antibody or antigen-binding fragment thereof of embodiment 88, wherein the antigen-binding fragment is selected from among Fab fragments, F(ab')$_2$ fragments, Fab' fragments, Fv fragments, an scFv, or a single domain antibody.

90. The anti-idiotype antibody or antigen-binding fragment thereof of any one of embodiments 1-89, which is humanized.

91. The anti-idiotype antibody or antigen-binding fragment thereof of any one of embodiments 1-90, which is recombinant.

92. The anti-idiotype antibody or antigen-binding fragment thereof of any one of embodiments 1-91, which is monoclonal.

93. A conjugate, comprising the anti-idiotype antibody or antigen-binding fragment thereof of any one of embodiments 1-92 and a heterologous molecule or moiety.

94. The conjugate of embodiment 93, wherein the heterologous molecule or moiety is a label.

95. The conjugate of embodiment 94, wherein the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound or an oligonucleotide.

96. The conjugate of embodiment 94, wherein the heterologous molecule or moiety is a protein, peptide, nucleic acid or small molecule, which optionally is or comprises a toxin or a Strep-Tag.

97. A nucleic acid molecule(s) encoding the heavy chain and/or the light chain of the anti-idiotype antibody or antigen-binding fragment thereof of any one of embodiments 1-92.

98. The nucleic acid molecule(s) of embodiment 97, comprising:

a sequence of nucleotides encoding (i) the heavy chain variable region set forth in SEQ ID NO: 62, (ii) a heavy chain variable region that has at least 90% sequence identity to the amino acid sequence set forth in SEQ ID NO: 62; or (iii) a degenerate sequence of (i) or (ii); and a sequence of nucleotides encoding (iv) the light chain variable region set forth in SEQ ID NO: 63, (v) a light chain variable region that has at least 90% sequence identity to the amino acid sequence set forth in SEQ ID NO: 63; or (vi) a degenerate sequence of (iv) or (v).

99. The nucleic acid molecule(s) of embodiment 97, comprising:

a sequence of nucleotides encoding (i) the heavy chain variable region set forth in SEQ ID NO: 84, (ii) a heavy chain variable region that has at least 90% sequence identity to the amino acid sequence set forth in SEQ ID NO: 84; or (iii) a degenerate sequence of (i) or (ii); and a sequence of nucleotides encoding (iv) the light chain variable region set forth in SEQ ID NO: 85, (v) a light chain variable region that has at least 90% sequence identity to the amino acid sequence set forth in SEQ ID NO: 85; or (vi) a degenerate sequence of (iv) or (v).

100. The nucleic acid molecule(s) of embodiment 97, comprising:

a sequence of nucleotides encoding (i) the heavy chain variable region set forth in SEQ ID NO: 114, (ii) a heavy chain variable region that has at least 90% sequence identity to the amino acid sequence of nucleotides set forth in SEQ ID NO: 114; or (iii) a degenerate sequence of (i) or (ii); and a sequence of nucleotides encoding (iv) the light chain variable region set forth in SEQ ID NO: 115, (v) a light chain variable region that has at least 90% sequence identity to the amino acid sequence set forth in SEQ ID NO: 115; or (vi) a degenerate sequence of (iv) or (v).

101. The nucleic acid molecule(s) of embodiment 97, comprising:

a sequence of nucleotides encoding (i) the heavy chain variable region set forth in SEQ ID NO: 38, (ii) a heavy chain variable region that has at least 90% sequence identity to the sequence of nucleotides set forth in SEQ ID NO: 38; or (iii) a degenerate sequence of (i) or (ii); and a sequence of nucleotides encoding (iv) the light chain variable region set forth in SEQ ID NO: 39, (v) a light chain variable region that has at least 90% sequence identity to the amino acid sequence set forth in SEQ ID NO: 39; or (vi) a degenerate sequence of (iv) or (v).

102. The nucleic acid molecule(s) of embodiment 97, comprising:

a sequence of nucleotides encoding (i) the heavy chain set forth in SEQ ID NO: 64, (ii) a heavy chain that has at least 90% sequence identity to the amino acid sequence set forth in SEQ ID NO: 64; or (iii) a degenerate sequence of (i) or (ii); and a sequence of nucleotides encoding (iv) the light chain set forth in SEQ ID NO: 65, (v) a light chain that has at least 90% sequence identity to the amino acid sequence set forth in SEQ ID NO: 65; or (vi) a degenerate sequence of (iv) or (v).

103. The nucleic acid molecule(s) of embodiment 97, comprising:

a sequence of nucleotides encoding (i) the heavy chain set forth in SEQ ID NO: 86, (ii) a heavy chain that has at least 90% sequence identity to the amino acid sequence set forth in SEQ ID NO: 86; or (iii) a degenerate sequence of (i) or (ii); and a sequence of nucleotides encoding (iv) the light chain set forth in SEQ ID NO: 87, (v) a light chain that has at least 90% sequence identity to the amino acid sequence set forth in SEQ ID NO: 87; or (vi) a degenerate sequence of (iv) or (v).

104. The nucleic acid molecule(s) of embodiment 97, comprising:

a sequence of nucleotides encoding (i) the heavy chain set forth in SEQ ID NO: 116, (ii) a heavy chain that has at least 90% sequence identity to the amino acid sequence set forth in SEQ ID NO: 116; or (iii) a degenerate sequence of (i) or (ii); and a sequence of nucleotides encoding (iv) the light chain set forth in SEQ ID NO: 117, (v) a light chain that has at least 90% sequence identity to the amino acid sequence set forth in SEQ ID NO: 117; or (vi) a degenerate sequence of (iv) or (v).

105. The nucleic acid molecule(s) of embodiment 97, comprising:

a sequence of nucleotides encoding (i) the heavy chain set forth in SEQ ID NO: 40, (ii) a heavy chain that has at least 90% sequence identity to the sequence of nucleotides set forth in SEQ ID NO: 40; or (iii) a degenerate sequence of (i) or (ii); and a sequence of nucleotides encoding (iv) the light chain set forth in SEQ ID NO: 41, (v) a light chain that has at least 90% sequence identity to the sequence of nucleotides set forth in SEQ ID NO: 41; or (vi) a degenerate sequence of (iv) or (v).

106. The nucleic acid molecule(s) of any one of embodiments 97-105, wherein the nucleotide sequence encoding the heavy chain and/or light chain comprises a signal sequence.

107. The nucleic acid molecule(s) of any one of embodiments 97-106, wherein the nucleic acid molecule(s) comprise one or more nucleotide sequences selected from the group consisting of SEQ ID NOs: 42, 43, 48, 49, 66-69, 88-91, and 118-121.

108. A vector, comprising the nucleic acid molecule(s) of any one of embodiments 97-107.

109. A cell, comprising the anti-idiotype antibody or antigen-binding fragment thereof of any one of embodiments 1-92, the nucleic acid molecule of any one of embodiments 97-107, or the vector of embodiment 108.

110. A method of producing an anti-idiotype antibody or antigen-binding fragment thereof, comprising expressing the heavy and/or light chain encoded by the nucleic acid molecule(s) of any one of embodiments 97-107 or the vector of embodiment 108 in a suitable host cell and recovering or isolating the antibody.

111. A method of producing an anti-idiotype antibody or antigen-binding fragment thereof, comprising culturing the cell of embodiment 109 under conditions in which the heavy chain and/or light chain is expressed, and recovering or isolating the antibody.

112. An anti-idiotype antibody or antigen-binding fragment thereof produced by the method of embodiment 110 or embodiment 111.

113. A composition comprising the anti-idiotype antibody or antigen-binding fragment thereof of any one of embodiments 1-92, the conjugate of any one of embodiments 93-96, or the cell of embodiment 109.

114. The composition of embodiment 113, further comprising a pharmaceutically acceptable excipient.

115. A kit, comprising one or more of the anti-idiotype antibody or antigen-binding fragment thereof of any one of embodiments 1-92, the conjugate of any one of embodiments 93-96, the nucleic acid molecule(s) of any one of embodiments 97-107, and, optionally, instructions for use.

116. The kit of embodiment 115, further comprising a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

117. A method of detecting a target antibody or antigen-binding fragment thereof, comprising:

(a) contacting a composition comprising a target antibody or antigen-binding fragment thereof with the antiidiotype antibody or antigen-binding fragment thereof of any one of embodiments 1-92 or the conjugate of any one of embodiments 93-96 that specifically binds to the target antibody or antigen-binding fragment thereof; and (b) detecting the anti-idiotype antibody bound to the target antibody or antigen-binding fragment thereof.

118. The method of embodiment 117, wherein the target antibody or antigen-binding fragment thereof is bound to a cell or expressed on the surface of a cell and detecting in (b) comprises detecting cells bound with the anti-idiotype antibody or antigen-binding fragment thereof.

119. The method of embodiment 118, wherein the cell expresses on its surface a CAR comprising the target antibody or antigen-binding fragment thereof.

120. A method of detecting a CAR comprising a target antibody or antigen-binding fragment thereof, comprising:

(a) contacting a cell expressing a CAR comprising a target antibody or antigen-binding fragment thereof with the anti-idiotype antibody or antigen-binding fragment thereof of any one of embodiments 1-92, or the conjugate of any one of embodiments 93-96, that specifically binds to the target antibody or antigen-binding fragment thereof; and (b) detecting cells bound with the anti-idiotype antibody or antigen-binding fragment thereof.

121. The method of embodiment 120, wherein the anti-idiotype antibody or antigen-binding fragment thereof is directly or indirectly labeled for detection.

122. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of embodiments 1-92, or the conjugate of any one of embodiments 93-96, that specifically binds to the target antibody or antigen-binding fragment thereof; and (b) selecting cells bound with the anti-idiotype antibody or antigen-binding fragment thereof.

123. The method of embodiment 122, wherein the cells bound with the anti-idiotype antibody or antigen-binding fragment thereof are selected by affinity-based separation.

124. The method of embodiment 123, wherein the affinity-based separation is immunoaffinity-based separation.

125. The method of embodiment 123 or embodiment 124, wherein the affinity-based separation is by flow cytometry.

126. The method of embodiment 123 or embodiment 124, wherein the affinity-based separation is by magnetic activated cell sorting.

127. The method of embodiment 123 or embodiment 124, wherein the affinity-based separation comprises affinity chromatography.

128. The method of embodiment 126 or embodiment 127, wherein the anti-idiotype antibody or antigen-binding fragment thereof is reversibly bound or immobilized to a support or a stationary phase.

129. A method of stimulating cells, comprising incubating an input composition comprising cells expressing a CAR comprising a target antibody or antigen-binding fragment thereof with the anti-idiotype antibody or antigen-binding fragment thereof of any one of embodiments 1-92, or the conjugate of any one of embodiments 93-96, that specifically binds to the target antibody or antigen-binding fragment thereof, thereby generating an output composition comprising stimulated cells.

130. A method of producing a cell composition, comprising:

(a) introducing into cells a nucleic acid molecule(s) encoding a CAR, thereby generating an input composition; and (b) incubating the input composition with the anti-idiotype antibody or antigen-binding fragment thereof of any one of embodiments 1-92, or the conjugate of any one of embodiments 93-96, that specifically binds to an antigen receptor of the CAR, thereby producing the cell composition.

131. The method of embodiment 130, wherein the introducing in (a) comprises introducing the nucleic acid molecule(s) into the cells by viral transduction, transposition, electroporation, or chemical transfection.

132. The method of embodiment 130 or embodiment 131, wherein the introducing in (a) comprises introducing the nucleic acid molecule(s) in the cells by transduction with a viral vector comprising the nucleic acid molecule(s), optionally wherein the viral vector is a retroviral vector or a lentiviral vector.

133. The method of embodiment 130 or embodiment 131, wherein the introducing in (a) comprises introducing the nucleic acid molecule(s) in the cells by transposition with a transposon comprising the nucleic acid molecule(s).

134. The method of embodiment 130 or embodiment 131, wherein the introducing in (a) comprises introducing the nucleic acid molecule(s) in the cells by electroporation or transfection of a vector comprising the nucleic acid molecule(s).

135. The method of any one of embodiments 130-134, further comprising a step of activating the cells prior to step (a).

136. The method of embodiment 135, wherein the step of activating the cells comprises contacting the cells with an agonist of CD3 and optionally an agonist of CD28.

137. The method of embodiment 136, wherein the step of activating the cells comprises contacting the cells with a reagent comprising agonistic anti-CD3 and anti-CD28 antibodies.

138. The method of any one of embodiments 130-137, wherein the incubation is performed under conditions in which the anti-idiotype antibody or antigen-binding fragment thereof binds to the CAR, thereby inducing or modulating a signal in one or more cells in the input composition.

139. The method of any one of embodiments 130-138, wherein the cells comprise T cells.

140. The method of embodiment 139, wherein the T cells comprise CD4+ and/or CD8+ T cells.

141. The method of any one of embodiments 130-140, wherein the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof.

142. The method of any one of embodiments 130-140, wherein the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof.

143. The method of embodiment 141 or embodiment 142, wherein the reagent comprises a streptavidin mutein.

144. The method of any one of embodiments 130-143, wherein the incubation is for at least or about at least 5 minutes, 10 minutes, 30 minutes, 60 minutes, 2 hours, 6 hours, 12 hours, 24 hours, 36, 48 hours, 72 hours or 96 hours.

145. The method of any one of embodiments 130-144, wherein the input composition comprises less than or less than about 60%, less than or less than about 50%, less than or less than about 40%, less than or less than about 30%, less than or less than about 20% or less than or less than about 10% CAR-expressing cells as a percentage of the total cells in the composition.

146. The method of any one of embodiments 130-145, wherein:

the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more.

147. The method of any one of embodiments 130-146, wherein prior to the introducing and/or incubating the cells are not selected or enriched for CAR-expressing cells.

148. A method of purifying an anti-idiotype antibody or antigen-binding fragment thereof, comprising:

(a) contacting a composition comprising a target antibody or antigen-binding fragment thereof with the anti-idiotype antibody or antigen-binding fragment thereof of any one of embodiments 1-92, or the conjugate of any one of embodiments 93-96, that specifically binds to a target antibody or antigen-binding fragment thereof; and (b) isolating complexes comprising the anti-idiotype antibody or antigen-binding fragment thereof.

149. The method of embodiment 148, wherein the complexes comprising the anti-idiotype antibody or antigen-binding fragment thereof are isolated by affinity-based separation.

150. The method of embodiment 149, wherein the affinity-based separation is immunoaffinity-based separation.

151. The method of embodiment 150, wherein the affinity-based separation is magnetic-based separation.

152. The method of embodiment 150, wherein the affinity-based separation comprises affinity chromatography.

153. A method of depleting cells, comprising administering, to a subject, a composition comprising the anti-idiotype antibody or antigen-binding fragment thereof of any one of embodiments 1-92, or the conjugate of any one of embodiments 93-96, that specifically binds to a target antibody or antigen-binding fragment thereof, wherein the subject has been administered a cell expressing a CAR comprising the target antibody or antigen-binding fragment thereof.

154. The method of embodiment 153, wherein the depletion occurs via antibody-dependent cell-mediated cytotoxicity (ADCC).

155. The method of any one of embodiments 117-154, wherein the target antibody or antigen-binding fragment thereof is a single chain fragment.

156. The method of embodiment 155, wherein the single chain fragment comprises an scFv.

157. The method of any one of embodiments 117-156, wherein the target antibody or antigen-binding fragment thereof comprises a VH region comprising the amino acid sequence set forth in SEQ ID NO: 11, and a VL region comprising the amino acid sequence set forth in SEQ ID NO: 12.

158. The method of embodiment 157, wherein the target antibody or antigen-binding fragment thereof is an scFv and the VH region and the VL region are joined by a flexible linker.

159. The method of embodiment 158, wherein the flexible linker comprises the amino acid sequence set forth in SEQ ID NO: 14, and the scFv comprises the amino acid sequence set forth in SEQ ID NO: 13.

160. The method of any one of embodiments 117-156, wherein the target antibody or antigen-binding fragment thereof comprises a VH region comprising the amino acid sequence set forth in SEQ ID NO: 25, and a VL region comprising the amino acid sequence set forth in SEQ ID NO: 26.

161. The method of embodiment 160, wherein the target antibody or antigen-binding fragment thereof is an scFv and the VH region and the VL region are joined by a flexible linker.

162. The method of embodiment 161, wherein the flexible linker comprises the amino acid sequence set forth in SEQ ID NO: 14, and the scFv comprises the amino acid sequence set forth in SEQ ID NO: 27.

163. An article of manufacture comprising the anti-idiotype antibody or antigen-binding fragment thereof of any one of embodiments 1-92, or the conjugate of any one of embodiments 93-96, and instructions for using the anti-idiotype antibody or antigen-binding fragment thereof to:

detect a target antibody or antigen-binding fragment thereof or a CAR comprising a target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

164. An article of manufacture comprising:

a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of embodiments 1-92, or the conjugate of any one of embodiments 93-96.

165. The article of manufacture of embodiment 164, wherein the binding reagent is a first binding reagent and the article of manufacture further comprises a second binding reagent comprising the extracellular domain or portion thereof of the CAR.

166. The article of manufacture of embodiment 164 or embodiment 165, wherein the extracellular domain of the CAR or portion thereof of the first and second binding reagent is the same.

167. The article of manufacture of any of embodiments 164-166, further comprising instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising a target antibody that is the or antigen-binding fragment thereof.

168. The article of manufacture of any of embodiments 164-167, wherein the binding reagent, optionally the first and/or second binding reagent, is detectably labeled or capable of producing a detectable signal.

169. The article of manufacture of any of embodiments 165-168, wherein one of the first and second binding reagent is attached to a solid support of is capable of being attached to a solid support and the other of the first and second binding reagent is detectable label or is capable of producing a detectable signal.

170. The article of manufacture of embodiment 169, wherein the article of manufacture further comprises a solid support, optionally wherein the one of the first and second binding reagent is linked, directly or indirectly to biotin, and the solid support comprises a streptavidin-coated surface.

171. The article of manufacture of any one of embodiments 163-170, wherein the target antibody or antigen-binding fragment thereof is a single chain fragment.

172. The article of manufacture of embodiment 171, wherein the single chain fragment comprises an scFv.

173. The article of manufacture of any one of embodiments 163-172, wherein the target antibody or antigen-binding fragment thereof comprises a VH region comprising the amino acid sequence set forth in SEQ ID NO: 11, and a VL region comprising the amino acid sequence set forth in SEQ ID NO: 12.

174. The article of manufacture of embodiment 173, wherein the target antibody or antigen-binding fragment thereof is an scFv and the VH region and the VL region are joined by a flexible linker.

175. The article of manufacture of embodiment 174, wherein the flexible linker comprises the amino acid sequence set forth in SEQ ID NO: 14, and the scFv comprises the amino acid sequence set forth in SEQ ID NO: 13.

176. The article of manufacture of any one of embodiments 163-172, wherein the target antibody or antigen-binding fragment thereof comprises a VH region comprising the amino acid sequence set forth in SEQ ID NO: 25, and a VL region comprising the amino acid sequence set forth in SEQ ID NO: 26.

177. The article of manufacture of embodiment 176, wherein the target antibody or antigen-binding fragment thereof is an scFv and the VH region and the VL region are joined by a flexible linker.

178. The article of manufacture of embodiment 177, wherein the flexible linker comprises the amino acid sequence set forth in SEQ ID NO: 14, and the scFv comprises the amino acid sequence set forth in SEQ ID NO: 27.

Among the provided embodiments are:

1. An anti-idiotype antibody or antigen-binding fragment thereof that binds to or recognizes an anti-BCMA target antibody or antigen-binding fragment thereof, wherein the anti-idiotype antibody or antigen-binding fragment comprises:
a VH region comprising the amino acid sequence set forth in SEQ ID NO: 84 or 114; and
a VL region comprising the amino acid sequence set forth in SEQ ID NO: 85 or 115.

2. An anti-idiotype antibody or antigen-binding fragment thereof that binds to or recognizes an anti-BCMA target antibody or antigen-binding fragment thereof, wherein the anti-idiotype antibody or antigen-binding fragment comprises:
a VH region comprising an amino acid sequence having at least 90% sequence identity to the amino acid sequence set forth in SEQ ID NO: 84 or 114; and
a VL region comprising an amino acid sequence having at least 90% sequence identity to the amino acid sequence set forth in SEQ ID NO: 85 or 115.

3. An anti-idiotype antibody or antigen-binding fragment thereof that binds to or recognizes an anti-BCMA target antibody or antigen-binding fragment thereof, wherein the anti-idiotype antibody or antigen-binding fragment comprises:
a VH region comprising a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and
a VL region comprising a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

4. An anti-idiotype antibody or antigen-binding fragment thereof that binds to or recognizes an anti-BCMA target antibody or antigen-binding fragment thereof, wherein the anti-idiotype antibody or antigen-binding fragment comprises:
a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 84 or 114; and
a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 85 or 115.

5. The anti-idiotype antibody or antigen-binding fragment thereof of any one of embodiments 1, 2, and 4, wherein:
the VH region comprises a CDR-H1 comprising the amino acid sequence set forth in SEQ ID NO: 74 or 104, a CDR-H2 comprising the amino acid sequence set forth in SEQ ID NO: 75 or 105, and a CDR-H3 comprising the amino acid sequence set forth in SEQ ID NO: 76 or 106; and
the VL region comprises a CDR-L1 comprising the amino acid sequence set forth in SEQ ID NO: 81 or 111, a CDR-L2 comprising the amino acid sequence set forth in SEQ ID NO: 82 or 112, and a CDR-L3 comprising the amino acid sequence set forth in SEQ ID NO: 83 or 113.

6. The anti-idiotype antibody or antigen-binding fragment thereof of any one of embodiments 1, 2, 4, and 5, wherein:

the VH region comprises a CDR-H1 comprising the amino acid sequence set forth in SEQ ID NO: 74, a CDR-H2 comprising the amino acid sequence set forth in SEQ ID NO: 75, and a CDR-H3 comprising the amino acid sequence set forth in SEQ ID NO: 76; and the VL region comprises a CDR-L1 comprising the amino acid sequence set forth in SEQ ID NO: 81, a CDR-L2 comprising the amino acid sequence set forth in SEQ ID NO: 82, and a CDR-L3 comprising the amino acid sequence set forth in SEQ ID NO: 83.

7. The anti-idiotype antibody or antigen-binding fragment thereof of any one of embodiments 1-5, wherein:

the VH region comprises a CDR-H1 comprising the amino acid sequence set forth in SEQ ID NO: 104, a CDR-H2 comprising the amino acid sequence set forth in SEQ ID NO: 105, and a CDR-H3 comprising the amino acid sequence set forth in SEQ ID NO: 106; and the VL region comprises a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113.

8. The anti-idiotype antibody or antigen-binding fragment thereof of any one of embodiments 3-7, wherein:

the VH region comprises an amino acid sequence having at least 90% sequence identity to the amino acid sequence set forth in SEQ ID NO: 84, and the VL region comprises an amino acid sequence having at least 90% sequence identity to the amino acid sequence set forth in SEQ ID NO: 85; or the VH region comprises an amino acid sequence having at least 90% sequence identity to the amino acid sequence set forth in SEQ ID NO: 114, and the VL region comprises an amino acid sequence having at least 90% sequence identity to the amino acid sequence set forth in SEQ ID NO: 115.

9. The anti-idiotype antibody or antigen-binding fragment thereof of any one of embodiments 1-8, wherein:

the VH region comprises an amino acid sequence set forth in SEQ ID NO: 84, and the VL region comprises an amino acid sequence set forth in SEQ ID NO: 85; or the VH region comprises an amino acid sequence set forth in SEQ ID NO: 114, and the VL region comprises an amino acid sequence set forth in SEQ ID NO: 115.

10. The anti-idiotype antibody or antigen-binding fragment thereof of any one of embodiments 1-9, wherein the anti-idiotype antibody or antigen-binding fragment thereof comprises:

a heavy chain comprising an amino acid sequence having at least 90% sequence identity to the amino acid sequence set forth in SEQ ID NO: 86, and a light chain comprising an amino acid sequence having at least 90% sequence identity to the amino acid sequence set forth in SEQ ID NO: 87; or a heavy chain comprising an amino acid sequence having at least 90% sequence identity to the amino acid sequence set forth in SEQ ID NO: 116, and a light chain comprising an amino acid sequence having at least 90% sequence identity to the amino acid sequence set forth in SEQ ID NO: 117.

11. The anti-idiotype antibody or antigen-binding fragment thereof of any one of embodiments 1-10, wherein the anti-idiotype antibody or antigen-binding fragment thereof comprises:

a heavy chain comprising the amino acid sequence set forth in SEQ ID NO: 86, and a light chain comprising the amino acid sequence set forth in SEQ ID NO: 87; or a heavy chain comprising the amino acid sequence set forth in SEQ ID NO: 116, and a light chain comprising the amino acid sequence set forth in SEQ ID NO: 117.

12. The anti-idiotype antibody or antigen-binding fragment thereof of any one of embodiments 1-11, wherein the anti-BCMA target antibody or antigen-binding fragment thereof comprises a VH region comprising the amino acid sequence set forth in SEQ ID NO: 25, and a VL region comprising the amino acid sequence set forth in SEQ ID NO: 26.

13. The anti-idiotype antibody or antigen-binding fragment thereof of embodiment 12, wherein the anti-BCMA target antibody or antigen-binding fragment thereof is a single chain fragment.

14. The anti-idiotype antibody or antigen-binding fragment thereof of embodiment 13, wherein the single chain fragment comprises a flexible linker positioned between the VH region and the VL region.

15. The anti-idiotype antibody or antigen-binding fragment thereof of embodiment 14, wherein the flexible linker comprises the amino acid sequence set forth in SEQ ID NO: 14.

16. The anti-idiotype antibody or antigen-binding fragment thereof of any one of embodiments 13-15, wherein the single chain fragment of the ani-BCMA target antibody or antigen-binding fragment thereof is a single chain variable fragment (scFv), optionally wherein the scFv comprises the amino acid sequence set forth in SEQ ID NO: 27.

17. The anti-idiotype antibody or antigen-binding fragment thereof of any one of embodiments 1-16, wherein the anti-idiotype antibody or antigen-binding fragment binds to or recognizes an epitope within or including all or a portion of a CDR of the target antibody or antigen-binding fragment.

18. The anti-idiotype antibody or antigen-binding fragment thereof of any one of embodiments 1-17, wherein:

the anti-BCMA target antibody or antigen-binding fragment is within or included in an antigen-binding domain of an extracellular portion of a CAR; and/or the anti-idiotype antibody or antigen-binding fragment specifically binds the anti-BCMA target antibody or antigen-binding fragment comprised within or included in an antigen-binding domain of an extracellular portion of a CAR.

19. The anti-idiotype antibody or antigen-binding fragment thereof of any one of embodiments 16-17, wherein:

the scFv is within or included in an extracellular portion of a CAR; and/or the anti-idiotype antibody or antigen-binding fragment specifically binds the scFv comprised within or included in an extracellular portion of a CAR.

20. The anti-idiotype antibody or antigen-binding fragment thereof of embodiment 18 or embodiment 19, wherein the CAR further comprises a transmembrane domain linked to the antigen-binding domain via a spacer.

21. The anti-idiotype antibody or antigen-binding fragment thereof of embodiment 20, wherein the spacer is an immunoglobulin spacer, optionally wherein the spacer comprises the amino acid sequence set forth in SEQ ID NO: 50.

22. The anti-idiotype antibody or antigen-binding fragment thereof of embodiment 20 or embodiment 21, wherein the transmembrane domain comprises a transmembrane portion of CD28, which optionally is human CD28.

23. The anti-idiotype antibody or antigen-binding fragment thereof of any one of embodiments 20-22, wherein the anti-idiotype antibody or antigen-binding fragment thereof does not bind to an epitope in the spacer domain of the CAR.

24. The anti-idiotype antibody or antigen-binding fragment thereof of any one of embodiments 1-23, wherein the anti-idiotype antibody or antigen-binding fragment thereof does not bind or does not specifically bind to CD28 or a portion thereof, which optionally is human CD28.

25. The anti-idiotype antibody or antigen-binding fragment thereof of any one of embodiments 1-24, wherein the anti-idiotype antibody or antigen-binding fragment thereof does not bind to an epitope in an Fc domain, which optionally is a human IgG1 Fc domain.

26. The anti-idiotype antibody or antigen-binding fragment thereof of any one of embodiments 1-25, wherein the anti-BCMA target antibody or antigen-binding fragment thereof binds to or recognizes human BCMA.

27. The anti-idiotype antibody or antigen-binding fragment thereof of any one of embodiments 1-26, wherein the anti-idiotype antibody or antigen-binding fragment thereof does not cross-react with another anti-BCMA antibody, which optionally is comprised in the extracellular antigen-binding domain of another CAR.

28. The anti-idiotype antibody or antigen-binding fragment thereof of embodiment 27, wherein the another anti-BCMA antibody:

(i) comprises a VH region comprising an amino acid sequence that has less than 90% sequence identity to the amino acid sequence set forth in SEQ ID NO: 25, and/or a VL region comprising an amino acid sequence that has less than 90% sequence identity to the amino acid sequence set forth in SEQ ID NO: 26; and/or (ii) comprises an scFv that has less than 90% sequence identity to the amino acid sequence set forth in SEQ ID NO: 13; and/or (iii) comprises a CDR-H1 that has 1, 2, 3, or 4 or more amino acid residues that are different from the CDR-H1 amino acid sequence as set forth in SEQ ID NO: 15, and/or a CDR-H2 that has 1, 2, 3, or 4 or more amino acid residues that are different from the CDR-H2 amino acid sequence as set forth in SEQ ID NO: 16, and/or a CDR-H3 that has 1, 2, 3, or 4 or more amino acid residues that are different from the CDR-H3 amino acid sequence as set forth in SEQ ID NO: 17, and/or a CDR-L1 that has 1, 2, 3, or 4 or more amino acid residues that are different from the CDR-L1 amino acid sequence as set forth in SEQ ID NO: 22, and/or a CDR-L2 that has 1, 2, 3, or 4 or more amino acid residues that are different from the CDR-L2 amino acid sequence as set forth in SEQ ID NO: 23, and/or a CDR-L3 that has 1, 2, 3, or 4 or more amino acid residues that are different from the CDR-L3 amino acid sequence as set forth in SEQ ID NO: 24; and/or (iv) binds to or recognizes an epitope of human BCMA that is not the same epitope of human BCMA that the anti-BCMA target antibody or antigen-binding fragment thereof binds to or recognizes.

29. The anti-idiotype antibody or antigen-binding fragment thereof of any one of embodiments 1-28, wherein the anti-idiotype antibody or antigen-binding fragment thereof is an agonist of a CAR comprising the anti-BCMA target antibody or antigen-binding fragment thereof.

30. The anti-idiotype antibody or antigen-binding fragment thereof of embodiment 29, wherein:

the anti-idiotype antibody or antigen-binding fragment thereof is an agonist of the CAR when in soluble form; and/or the anti-idiotype antibody or antigen-binding fragment thereof is an agonist of the CAR when immobilized to a support or a stationary phase, optionally wherein the support or stationary phase is a plate or a bead.

31. The anti-idiotype antibody or antigen-binding fragment thereof of any one of embodiments 1-30, wherein the anti-idiotype antibody has a binding affinity (EC50) and/or a dissociation constant to the anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

32. The anti-idiotype antibody or antigen-binding fragment thereof of any one of embodiments 1-31, wherein binding of the anti-idiotype antibody or antigen-binding fragment thereof to the anti-BCMA target antibody or antigen-binding fragment thereof is not blocked by human BCMA or human BCMA-Fc.

33. An anti-idiotype antibody or antigen-binding fragment thereof that binds to or recognizes a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising the amino acid sequence set forth in SEQ ID NO: 38 or 62; and a VL region comprising the amino acid sequence set forth in SEQ ID NO: 39 or 63.

34. An anti-idiotype antibody or antigen-binding fragment thereof that binds to or recognizes a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising an amino acid sequence having at least 90% sequence identity to the amino acid sequence set forth in SEQ ID NO: 38 or 62; and a VL region comprising an amino acid sequence having at least 90% sequence identity to the amino acid sequence set forth in SEQ ID NO: 39 or 63.

35. An anti-idiotype antibody or antigen-binding fragment thereof that binds to or recognizes a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and a VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61.

36. An anti-idiotype antibody or antigen-binding fragment thereof that binds to or recognizes a first anti-BCMA target antibody or antigen-binding fragment thereof and a second anti-BCMA target antibody or antigen-binding fragment thereof, wherein the anti-idiotype antibody or antigen-binding fragment comprises:

a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 38 or 62; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 39 or 63.

37. The anti-idiotype antibody or antigen-binding fragment thereof of any one of embodiments 33, 34, and 36, wherein:

the VH region comprises a CDR-H1 comprising the amino acid sequence set forth in SEQ ID NO: 28 or 52, a CDR-H2 comprising the amino acid sequence set forth in SEQ ID NO: 29 or 53, and a CDR-H3 comprising the amino acid sequence set forth in SEQ ID NO: 30 or 54; and the VL region comprising a CDR-L1 comprising the amino acid sequence set forth in SEQ ID NO: 35 or 59, a CDR-L2 comprising the amino acid sequence set forth in SEQ ID NO: 36 or 60, and a CDR-L3 comprising the amino acid sequence set forth in SEQ ID NO: 37 or 61.

38. The anti-idiotype antibody or antigen-binding fragment thereof of any one of embodiments 33-37, wherein:

the VH region comprises a CDR-H1 comprising the amino acid sequence set forth in SEQ ID NO: 28, a CDR-H2 comprising the amino acid sequence set forth in SEQ ID NO: 29, and a CDR-H3 comprising the amino acid sequence set forth in SEQ ID NO: 30; and the VL region comprising a CDR-L1 comprising the amino acid sequence set forth in SEQ ID NO: 35, a CDR-L2 comprising the amino acid sequence set forth in SEQ ID NO: 36, and a CDR-L3 comprising the amino acid sequence set forth in SEQ ID NO: 37.

39. The anti-idiotype antibody or antigen-binding fragment thereof of any one of embodiments 33-37, wherein:

the VH region comprises a CDR-H1 comprising the amino acid sequence set forth in SEQ ID NO: 52, a CDR-H2 comprising the amino acid sequence set forth in SEQ ID NO: 53, and a CDR-H3 comprising the amino acid sequence set forth in SEQ ID NO: 54; and the VL region comprising a CDR-L1 comprising the amino acid sequence set forth in SEQ ID NO: 59, a CDR-L2 comprising the amino acid sequence set forth in SEQ ID NO: 60, and a CDR-L3 comprising the amino acid sequence set forth in SEQ ID NO: 61.

40. The anti-idiotype antibody or antigen-binding fragment thereof of any one of embodiments 35-39, wherein:

the VH region comprises an amino acid sequence having at least 90% sequence identity to the amino acid sequence set forth in SEQ ID NO: 38 or 62; and the VL region comprises an amino acid sequence having at least 90% sequence identity to the amino acid sequence set forth in SEQ ID NO: 39 or 63.

41. The anti-idiotype antibody or antigen-binding fragment thereof of any one of embodiments 35-40, wherein:

the VH region comprises an amino acid sequence having at least 90% sequence identity to the amino acid sequence set forth in SEQ ID NO: 38, and the VL region comprises an amino acid sequence having at least 90% sequence identity to the amino acid sequence set forth in SEQ ID NO: 39; or the VH region comprises an amino acid sequence having at least 90% sequence identity to the amino acid sequence set forth in SEQ ID NO: 62, and the VL region comprises an amino acid sequence having at least 90% sequence identity to the amino acid sequence set forth in SEQ ID NO: 63.

42. The anti-idiotype antibody or antigen-binding fragment thereof of any one of embodiments 34-41, wherein:

the VH region comprises the amino acid sequence set forth in SEQ ID NO: 38 or 62; and the VL region comprises the amino acid sequence set forth in SEQ ID NO: 39 or 63.

43. The anti-idiotype antibody or antigen-binding fragment thereof of any one of embodiments 34-42, wherein:

the VH region comprises the amino acid sequence set forth in SEQ ID NO: 38, and the VL region comprises the amino acid sequence set forth in SEQ ID NO: 39; or the VH region comprises the amino acid sequence set forth in SEQ ID NO: 62, and the VL region comprises the amino acid sequence set forth in SEQ ID NO: 63.

44. The anti-idiotype antibody or antigen-binding fragment thereof of any one of embodiments 33-43, wherein the anti-idiotype antibody or antigen-binding fragment thereof comprises:

a heavy chain comprising an amino acid sequence having at least 90% sequence identity to the amino acid sequence set forth in SEQ ID NO: 40 or 64; and a light chain comprising an amino acid sequence having at least 90% sequence identity to the amino acid sequence set forth in SEQ ID NO: 41 or 65.

45. The anti-idiotype antibody or antigen-binding fragment thereof of any one of embodiments 33-44, wherein the anti-idiotype antibody or antigen-binding fragment thereof comprises:

a heavy chain comprising an amino acid sequence having at least 90% sequence identity to the amino acid sequence set forth in SEQ ID NO: 40, and a light chain comprising an amino acid sequence having at least 90% sequence identity to the amino acid sequence set forth in SEQ ID NO: 41; or a heavy chain comprising an amino acid sequence having at least 90% sequence identity to the amino acid sequence set forth in SEQ ID NO: 64, and a light chain comprising an amino acid sequence having at least 90% sequence identity to the amino acid sequence set forth in SEQ ID NO: 65.

46. The anti-idiotype antibody or antigen-binding fragment thereof of any one of embodiments 33-45, wherein the anti-idiotype antibody or antigen-binding fragment thereof comprises:

a heavy chain comprising the amino acid sequence set forth in SEQ ID NO: 40 or 64; and a light chain comprising the amino acid sequence set forth in SEQ ID NO: 41 or 65.

47. The anti-idiotype antibody or antigen-binding fragment thereof of any one of embodiments 33-46, wherein the anti-idiotype antibody or antigen-binding fragment thereof comprises:

a heavy chain comprising the amino acid sequence set forth in SEQ ID NO: 40, and a light chain comprising the amino acid sequence set forth in SEQ ID NO: 41; or a heavy chain comprising the amino acid sequence set forth in SEQ ID NO: 64, and a light chain comprising the amino acid sequence set forth in SEQ ID NO: 65.

48. The anti-idiotype antibody or antigen-binding fragment thereof of any one of embodiments 33-47, wherein:

the first anti-BCMA target antibody or antigen-binding fragment thereof comprises a VH region comprising the amino acid sequence set forth in SEQ ID NO: 11, and a VL region comprising the amino acid sequence set forth in SEQ ID NO: 12; and the second anti-BCMA target antibody or antigen-binding fragment thereof comprises a VH region comprising the amino acid sequence set forth in SEQ ID NO: 25, and a VL region comprising the amino acid sequence set forth in SEQ ID NO: 26.

49. The anti-idiotype antibody or antigen-binding fragment thereof of embodiment 48, wherein the first anti-BCMA target antibody or antigen-binding fragment thereof is a first single chain fragment and the second anti-BCMA target antibody or antigen-binding fragment thereof is a second single chain fragment.

50. The anti-idiotype antibody or antigen-binding fragment thereof of embodiment 49, wherein the first single chain fragment comprises a flexible linker positioned between the VH region and the VL region, and the second single chain fragment comprises a flexible linker positioned between the VH region and the VL region.

51. The anti-idiotype antibody or antigen-binding fragment thereof of embodiment 50, wherein the flexible linker of the first single chain fragment and/or the second single chain fragment comprises the amino acid sequence set forth in SEQ ID NO: 14.

52. The anti-idiotype antibody or antigen-binding fragment thereof of any one of embodiments 49-51, wherein the first single chain fragment of the first anti-BCMA target antibody or antigen-binding fragment thereof is a first scFv, and the second single chain fragment of the second anti-BCMA target antibody or antigen-binding fragment thereof is a second scFv.

53. The anti-idiotype antibody or antigen-binding fragment thereof of embodiment 52, wherein the first scFv comprises the amino acid sequence set forth in SEQ ID NO: 13, and the second scFv comprises the amino acid sequence set forth in SEQ ID NO: 27.

54. The anti-idiotype antibody or antigen-binding fragment thereof of any one of embodiments 33-53, wherein the anti-idiotype antibody or antigen-binding fragment binds to or recognizes:

an epitope within or including all or a portion of a CDR of the first anti-BCMA target antibody or antigen-binding fragment; and an epitope within or including all or a portion of a CDR of the second anti-BCMA target antibody or antigen-binding fragment.

55. The anti-idiotype antibody or antigen-binding fragment thereof of any one of embodiments 33-54, wherein:

the first anti-BCMA target antibody or antigen-binding fragment is within or included in an antigen-binding domain of an extracellular portion of a first CAR; and/or the anti-idiotype antibody or antigen-binding fragment specifically binds the first anti-BCMA target antibody or antigen-binding fragment comprised within or included in an antigen-binding domain of an extracellular portion of a first CAR.

56. The anti-idiotype antibody or antigen-binding fragment thereof of any one of embodiments 33-55, wherein:

the second anti-BCMA target antibody or antigen-binding fragment is within or included in an antigen-binding domain of an extracellular portion of a second CAR; and/or the anti-idiotype antibody or antigen-binding fragment specifically binds the second anti-BCMA target antibody or antigen-binding fragment comprised within or included in an antigen-binding domain of an extracellular portion of a second CAR.

57. The anti-idiotype antibody or antigen-binding fragment thereof of any one of embodiments 33-54, wherein:

the first scFv is within or included in an extracellular portion of a first CAR; and/or the anti-idiotype antibody or antigen-binding fragment specifically binds the first scFv comprised within or included in an extracellular portion of a first CAR.

58. The anti-idiotype antibody or antigen-binding fragment thereof of any one of embodiments 33-54, wherein:

the second scFv is within or included in an extracellular portion of a second CAR; and/or the anti-idiotype antibody or antigen-binding fragment specifically binds the second scFv comprised within or included in an extracellular portion of a second CAR.

59. The anti-idiotype antibody or antigen-binding fragment thereof of any one of embodiments 55-58, wherein the first CAR further comprises a transmembrane domain linked to the antigen-binding domain via a spacer, and/or the second CAR further comprises a transmembrane domain linked to the antigen-binding domain via a spacer.

60. The anti-idiotype antibody or antigen-binding fragment thereof of embodiment 59, wherein the spacer of the first CAR and/or the second CAR is an immunoglobulin spacer, optionally wherein the spacer comprises the amino acid sequence set forth in SEQ ID NO: 50.

61. The anti-idiotype antibody or antigen-binding fragment thereof of embodiment 59 or embodiment 60, wherein the transmembrane domain of the first CAR and/or the second CAR comprises a transmembrane portion of CD28, which optionally is human CD28.

62. The anti-idiotype antibody or antigen-binding fragment thereof of any one of embodiments 59-61, wherein the anti-idiotype antibody or antigen-binding fragment thereof does not bind to an epitope in the spacer domain of the first CAR and/or the second CAR.

63. The anti-idiotype antibody or antigen-binding fragment thereof of any one of embodiments 33-62, wherein the anti-idiotype antibody or antigen-binding fragment thereof does not bind or does not specifically bind to CD28 or a portion thereof, which optionally is human CD28.

64. The anti-idiotype antibody or antigen-binding fragment thereof of any one of embodiments 33-63, wherein the anti-idiotype antibody or antigen-binding fragment thereof does not bind to an epitope in an Fe domain, which optionally is a human IgG1 Fe domain.

65. The anti-idiotype antibody or antigen-binding fragment thereof of any one of embodiments 33-64, wherein the first anti-BCMA target antibody or antigen-binding fragment thereof binds to or recognizes human BCMA, and the second anti-BCMA target antibody or antigen-binding fragment thereof binds to or recognizes human BCMA.

66. The anti-idiotype antibody or antigen-binding fragment thereof of any one of embodiments 33-65, wherein the anti-idiotype antibody or antigen-binding fragment thereof is an agonist of a first CAR comprising the first anti-BCMA target antibody or antigen-binding fragment thereof, and/or is an agonist of a second CAR comprising the second anti-BCMA target antibody or antigen-binding fragment thereof.

67. The anti-idiotype antibody or antigen-binding fragment thereof of embodiment 66, wherein:
the anti-idiotype antibody or antigen-binding fragment thereof is an agonist of the first CAR and/or the second CAR when in soluble form; and/or
the anti-idiotype antibody or antigen-binding fragment thereof is an agonist of the first CAR and/or the second CAR when immobilized to a support or a stationary phase, optionally wherein the support or stationary phase is a plate or a bead.

68. The anti-idiotype antibody or antigen-binding fragment thereof of any one of embodiments 33-67, wherein the anti-idiotype antibody has a binding affinity (EC50) and/or a dissociation constant to the first anti-BCMA target antibody or antigen-binding fragment thereof and/or the second anti-BCMA target antibody or antigen-binding fragment thereof that is at or about or less than at or about 100 nM, 50 nM, 40 nM, 30 nM, 25 nM, 20 nM, 19 nM, 18 nM, 17 nM, 16 nM, 15 nM, 14 nM, 13 nM, 12 nM, 11 nM, 10 nM, 9 nM, 8 nM, 7 nM, 6 nM, 5 nM, 4 nM, 3 nM, 2 nM, or 1 nM.

69. The anti-idiotype antibody or antigen-binding fragment thereof of any one of embodiments 33-68, wherein binding of the anti-idiotype antibody or antigen-binding fragment thereof to the first anti-BCMA target antibody or antigen-binding fragment thereof and/or the second anti-BCMA target antibody or antigen-binding fragment thereof is not blocked by human BCMA or human BCMA-Fc.

70. The anti-idiotype antibody or antigen-binding fragment thereof of any one of embodiments 1-69, which is humanized.

71. The anti-idiotype antibody or antigen-binding fragment thereof of any one of embodiments 1-70, which is recombinant.

72. The anti-idiotype antibody or antigen-binding fragment thereof of any one of embodiments 1-71, which is monoclonal.

73. The anti-idiotype antibody or antigen-binding fragment thereof of any one of embodiments 1-72, which is an antigen-binding fragment.

74. The anti-idiotype antibody or antigen-binding fragment thereof of embodiment 73, wherein the antigen-binding fragment is selected from among Fab fragments, F(ab')2 fragments, Fab' fragments, Fv fragments, an scFv, or a single domain antibody.

75. The anti-idiotype antibody or antigen-binding fragment thereof of any one of embodiments 1-74, comprising at least a portion of an immunoglobulin constant region.

76. The anti-idiotype antibody or antigen-binding fragment thereof of embodiment 75, wherein the at least a portion of an immunoglobulin constant region comprises an Fc region or a portion of the Fc comprising the CH2 and CH3 domains.

77. The anti-idiotype antibody or antigen-binding fragment thereof of embodiment 75 or embodiment 76, wherein the constant region is derived from human IgG.

78. The anti-idiotype antibody or antigen-binding fragment thereof of any one of embodiments 75-77, which is an intact antibody or full-length antibody.

79. A conjugate, comprising the anti-idiotype antibody or antigen-binding fragment thereof of any one of embodiments 1-78 and a heterologous molecule or moiety.

80. The conjugate of embodiment 79, wherein the heterologous molecule or moiety is a label.

81. The conjugate of embodiment 80, wherein the label is selected from a fluorescent dye, a fluorescent protein, a radioisotope, a chromophore, a metal ion, a gold particle, a silver particle, a magnetic particle, a polypeptide, an enzyme, a streptavidin, a biotin, a luminescent compound or an oligonucleotide.

82. The conjugate of embodiment 80, wherein the heterologous molecule or moiety is a protein, peptide, nucleic acid or small molecule, which optionally is or comprises a toxin or a Strep-Tag.

83. A nucleic acid molecule(s) encoding the heavy chain and/or the light chain of the anti-idiotype antibody or antigen-binding fragment thereof of any one of embodiments 1-78.

84. The nucleic acid molecule(s) of embodiment 83, comprising:
a sequence of nucleotides encoding (i) the heavy chain variable region set forth in SEQ ID NO: 62, (ii) a heavy chain variable region that has at least 90% sequence identity to the amino acid sequence set forth in SEQ ID NO: 62; or (iii) a degenerate sequence of (i) or (ii); and
a sequence of nucleotides encoding (iv) the light chain variable region set forth in SEQ ID NO: 63, (v) a light chain variable region that has at least 90% sequence identity to the amino acid sequence set forth in SEQ ID NO: 63; or (vi) a degenerate sequence of (iv) or (v).

85. The nucleic acid molecule(s) of embodiment 83, comprising:
a sequence of nucleotides encoding (i) the heavy chain variable region set forth in SEQ ID NO: 84, (ii) a heavy chain variable region that has at least 90% sequence identity to the amino acid sequence set forth in SEQ ID NO: 84; or (iii) a degenerate sequence of (i) or (ii); and
a sequence of nucleotides encoding (iv) the light chain variable region set forth in SEQ ID NO: 85, (v) a light chain variable region that has at least 90% sequence identity to the amino acid sequence set forth in SEQ ID NO: 85; or (vi) a degenerate sequence of (iv) or (v).

86. The nucleic acid molecule(s) of embodiment 83, comprising:
a sequence of nucleotides encoding (i) the heavy chain variable region set forth in SEQ ID NO: 114, (ii) a heavy chain variable region that has at least 90% sequence identity to the amino acid sequence of nucleotides set forth in SEQ ID NO: 114; or (iii) a degenerate sequence of (i) or (ii); and a sequence of nucleotides encoding (iv) the light chain variable region set forth in SEQ ID NO: 115, (v) a light chain variable region that has at least 90% sequence identity to the amino acid sequence set forth in SEQ ID NO: 115; or (vi) a degenerate sequence of (iv) or (v).

87. The nucleic acid molecule(s) of embodiment 83, comprising:

a sequence of nucleotides encoding (i) the heavy chain variable region set forth in SEQ ID NO: 38, (ii) a heavy chain variable region that has at least 90% sequence identity to the sequence of nucleotides set forth in SEQ ID NO: 38; or (iii) a degenerate sequence of (i) or (ii); and a sequence of nucleotides encoding (iv) the light chain variable region set forth in SEQ ID NO: 39, (v) a light chain variable region that has at least 90% sequence identity to the amino acid sequence set forth in SEQ ID NO: 39; or (vi) a degenerate sequence of (iv) or (v).

88. The nucleic acid molecule(s) of embodiment 83, comprising:

a sequence of nucleotides encoding (i) the heavy chain set forth in SEQ ID NO: 64, (ii) a heavy chain that has at least 90% sequence identity to the amino acid sequence set forth in SEQ ID NO: 64; or (iii) a degenerate sequence of (i) or (ii); and a sequence of nucleotides encoding (iv) the light chain set forth in SEQ ID NO: 65, (v) a light chain that has at least 90% sequence identity to the amino acid sequence set forth in SEQ ID NO: 65; or (vi) a degenerate sequence of (iv) or (v).

89. The nucleic acid molecule(s) of embodiment 83, comprising:

a sequence of nucleotides encoding (i) the heavy chain set forth in SEQ ID NO: 86, (ii) a heavy chain that has at least 90% sequence identity to the amino acid sequence set forth in SEQ ID NO: 86; or (iii) a degenerate sequence of (i) or (ii); and a sequence of nucleotides encoding (iv) the light chain set forth in SEQ ID NO: 87, (v) a light chain that has at least 90% sequence identity to the amino acid sequence set forth in SEQ ID NO: 87; or (vi) a degenerate sequence of (iv) or (v).

90. The nucleic acid molecule(s) of embodiment 83, comprising:

a sequence of nucleotides encoding (i) the heavy chain set forth in SEQ ID NO: 116, (ii) a heavy chain that has at least 90% sequence identity to the amino acid sequence set forth in SEQ ID NO: 116; or (iii) a degenerate sequence of (i) or (ii); and a sequence of nucleotides encoding (iv) the light chain set forth in SEQ ID NO: 117, (v) a light chain that has at least 90% sequence identity to the amino acid sequence set forth in SEQ ID NO: 117; or (vi) a degenerate sequence of (iv) or (v).

91. The nucleic acid molecule(s) of embodiment 83, comprising:

a sequence of nucleotides encoding (i) the heavy chain set forth in SEQ ID NO: 40, (ii) a heavy chain that has at least 90% sequence identity to the sequence of nucleotides set forth in SEQ ID NO: 40; or (iii) a degenerate sequence of (i) or (ii); and a sequence of nucleotides encoding (iv) the light chain set forth in SEQ ID NO: 41, (v) a light chain that has at least 90% sequence identity to the sequence of nucleotides set forth in SEQ ID NO: 41; or (vi) a degenerate sequence of (iv) or (v).

92. The nucleic acid molecule(s) of any one of embodiments 83-91, wherein the nucleotide sequence encoding the heavy chain and/or light chain comprises a signal sequence.

93. The nucleic acid molecule(s) of any one of embodiments 83-92, wherein the nucleic acid molecule(s) comprise one or more nucleotide sequences selected from the group consisting of SEQ ID NOs: 42, 43, 48, 49, 66-69, 88-91, and 118-121.

94. A vector, comprising the nucleic acid molecule(s) of any one of embodiments 83-93.

95. A cell, comprising the anti-idiotype antibody or antigen-binding fragment thereof of any one of embodiments 1-78, the nucleic acid molecule of any one of embodiments 83-93, or the vector of embodiment 94.

96. A method of producing an anti-idiotype antibody or antigen-binding fragment thereof, comprising expressing the heavy and/or light chain encoded by the nucleic acid molecule(s) of any one of embodiments 83-93 or the vector of embodiment 94 in a suitable host cell and recovering or isolating the antibody.

97. A method of producing an anti-idiotype antibody or antigen-binding fragment thereof, comprising culturing the cell of embodiment 95 under conditions in which the heavy chain and/or light chain is expressed, and recovering or isolating the antibody.

98. An anti-idiotype antibody or antigen-binding fragment thereof produced by the method of embodiment 96 or embodiment 97.

99. A composition comprising the anti-idiotype antibody or antigen-binding fragment thereof of any one of embodiments 1-78, the conjugate of any one of embodiments 79-82, or the cell of embodiment 95.

100. The composition of embodiment 99, further comprising a pharmaceutically acceptable excipient.

101. A kit, comprising one or more of the anti-idiotype antibody or antigen-binding fragment thereof of any one of embodiments 1-78, the conjugate of any one of embodiments 79-82, the nucleic acid molecule(s) of any one of embodiments 83-93, and, optionally, instructions for use.

102. The kit of embodiment 101, further comprising a reagent or support for immobilizing the anti-idiotype antibody or antigen-binding fragment thereof or the conjugate, wherein said reagent or support is a bead, a column, a microwell, a stick, a filter, a strip or a soluble oligomeric streptavidin mutein reagent.

103. A method of detecting a target antibody or antigen-binding fragment thereof, comprising:

(a) contacting a composition comprising a target antibody or antigen-binding fragment thereof with the anti-idiotype antibody or antigen-binding fragment thereof of any one of embodiments 1-78 or the conjugate of any one of embodiments 79-82 that specifically binds to the target antibody or antigen-binding fragment thereof; and (b) detecting the anti-idiotype antibody bound to the target antibody or antigen-binding fragment thereof.

104. The method of embodiment 103, wherein the target antibody or antigen-binding fragment thereof is bound to a cell or expressed on the surface of a cell and detecting in (b) comprises detecting cells bound with the anti-idiotype antibody or antigen-binding fragment thereof.

105. The method of embodiment 104, wherein the cell expresses on its surface a CAR comprising the target antibody or antigen-binding fragment thereof.

106. A method of detecting a CAR comprising a target antibody or antigen-binding fragment thereof, comprising:

(a) contacting a cell expressing a CAR comprising a target antibody or antigen-binding fragment thereof with the anti-idiotype antibody or antigen-binding fragment thereof of any one of embodiments 1-78, or the conjugate of any one of embodiments 79-82, that specifically binds to the target antibody or antigen-binding fragment thereof; and (b) detecting cells bound with the anti-idiotype antibody or antigen-binding fragment thereof.

107. The method of embodiment 106, wherein the anti-idiotype antibody or antigen-binding fragment thereof is directly or indirectly labeled for detection.

108. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of any one of embodiments 1-78, or the conjugate of any one of embodiments 79-82, that specifically binds to the target antibody or antigen-binding fragment thereof; and (b) selecting cells bound with the anti-idiotype antibody or antigen-binding fragment thereof.

109. The method of embodiment 108, wherein the cells bound with the anti-idiotype antibody or antigen-binding fragment thereof are selected by affinity-based separation.

110. The method of embodiment 109, wherein the affinity-based separation is immunoaffinity-based separation.

111. The method of embodiment 109 or embodiment 110, wherein the affinity-based separation is by flow cytometry.

112. The method of embodiment 109 or embodiment 110, wherein the affinity-based separation is by magnetic activated cell sorting.

113. The method of embodiment 109 or embodiment 110, wherein the affinity-based separation comprises affinity chromatography.

114. The method of embodiment 112 or embodiment 113, wherein the anti-idiotype antibody or antigen-binding fragment thereof is reversibly bound or immobilized to a support or a stationary phase.

115. A method of stimulating cells, comprising incubating an input composition comprising cells expressing a CAR comprising a target antibody or antigen-binding fragment thereof with the anti-idiotype antibody or antigen-binding fragment thereof of any one of embodiments 1-78, or the conjugate of any one of embodiments 79-82, that specifically binds to the target antibody or antigen-binding fragment thereof, thereby generating an output composition comprising stimulated cells.

116. A method of producing a cell composition, comprising:

(a) introducing into cells a nucleic acid molecule(s) encoding a CAR, thereby generating an input composition; and (b) incubating the input composition with the anti-idiotype antibody or antigen-binding fragment thereof of any one of embodiments 1-78, or the conjugate of any one of embodiments 79-82, that specifically binds to an antigen receptor of the CAR, thereby producing the cell composition.

117. The method of embodiment 116, wherein the introducing in (a) comprises introducing the nucleic acid molecule(s) into the cells by viral transduction, transposition, electroporation, or chemical transfection.

118. The method of embodiment 116 or embodiment 117, wherein the introducing in (a) comprises introducing the nucleic acid molecule(s) in the cells by transduction with a viral vector comprising the nucleic acid molecule(s), optionally wherein the viral vector is a retroviral vector or a lentiviral vector.

119. The method of embodiment 116 or embodiment 117, wherein the introducing in (a) comprises introducing the nucleic acid molecule(s) in the cells by transposition with a transposon comprising the nucleic acid molecule(s).

120. The method of embodiment 116 or embodiment 117, wherein the introducing in (a) comprises introducing the nucleic acid molecule(s) in the cells by electroporation or transfection of a vector comprising the nucleic acid molecule(s).

121. The method of any one of embodiments 116-120, further comprising a step of activating the cells prior to step (a).

122. The method of embodiment 121, wherein the step of activating the cells comprises contacting the cells with an agonist of CD3 and optionally an agonist of CD28.

123. The method of embodiment 122, wherein the step of activating the cells comprises contacting the cells with a reagent comprising agonistic anti-CD3 and anti-CD28 antibodies.

124. The method of any one of embodiments 116-123, wherein the incubation is performed under conditions in which the anti-idiotype antibody or antigen-binding fragment thereof binds to the CAR, thereby inducing or modulating a signal in one or more cells in the input composition.

125. The method of any one of embodiments 116-124, wherein the cells comprise T cells.

126. The method of embodiment 125, wherein the T cells comprise CD4+ and/or CD8+ T cells.

127. The method of any one of embodiments 116-126, wherein the anti-idiotype antibody or antigen-binding fragment thereof is immobilized to a solid support, which optionally comprises or is conjugated to a reagent comprising a plurality of binding sites capable of reversibly binding to the anti-idiotype antibody or antigen-binding fragment thereof.

128. The method of any one of embodiments 116-126, wherein the anti-idiotype antibody or antigen-binding fragment thereof is immobilized to a soluble reagent, which optionally is or comprises a plurality of binding sites capable of reversibly binding to the anti-idiotype antibody or antigen-binding fragment thereof.

129. The method of embodiment 127 or embodiment 128, wherein the reagent comprises a streptavidin mutein.

130. The method of any one of embodiments 116-129, wherein the incubation is for at least or about at least 5 minutes, 10 minutes, 30 minutes, 60 minutes, 2 hours, 6 hours, 12 hours, 24 hours, 36, 48 hours, 72 hours or 96 hours.

131. The method of any one of embodiments 116-130, wherein the input composition comprises less than or less than about 60%, less than or less than about 50%, less than or less than about 40%, less than or less than about 30%, less than or less than about 20% or less than or less than about 10% CAR-expressing cells as a percentage of the total cells in the composition.

132. The method of any one of embodiments 116-131, wherein:

the number of CAR-expressing cells in the output composition is increased by greater than 1.2-fold, 1.5-fold, 2.0-fold, 3.0-fold, 4.0-fold, 5.0-fold, 10-fold or more compared to the number of CAR-expressing cells in the input composition; and/or the percentage of CAR-expressing in the output composition compared to the total cells in the composition is increased by greater than 10%, 20%, 40%, 50%, 60%, 70%, 80% or more.

133. The method of any one of embodiments 116-132, wherein prior to the introducing and/or incubating the cells are not selected or enriched for CAR-expressing cells.

134. A method of purifying an anti-idiotype antibody or antigen-binding fragment thereof, comprising:

(a) contacting a composition comprising a target antibody or antigen-binding fragment thereof with the anti-idiotype antibody or antigen-binding fragment thereof of any one of embodiments 1-78, or the conjugate of any one of embodiments 79-82, that specifically binds to a target antibody or antigen-binding fragment thereof; and (b) isolating complexes comprising the anti-idiotype antibody or antigen-binding fragment thereof.

135. The method of embodiment 134, wherein the complexes comprising the anti-idiotype antibody or antigen-binding fragment thereof are isolated by affinity-based separation.

136. The method of embodiment 135, wherein the affinity-based separation is immunoaffinity-based separation.

137. The method of embodiment 136, wherein the affinity-based separation is magnetic-based separation.

138. The method of embodiment 136, wherein the affinity-based separation comprises affinity chromatography.

139. A method of depleting cells, comprising administering, to a subject, a composition comprising the anti-idiotype antibody or antigen-binding fragment thereof of any one of embodiments 1-78, or the conjugate of any one of embodiments 79-82, that specifically binds to a target antibody or antigen-binding fragment thereof, wherein the subject has been administered a cell expressing a CAR comprising the target antibody or antigen-binding fragment thereof.

140. The method of embodiment 139, wherein the depletion occurs via antibody-dependent cell-mediated cytotoxicity (ADCC).

141. The method of any one of embodiments 103-140, wherein the target antibody or antigen-binding fragment thereof is a single chain fragment.

142. The method of embodiment 141, wherein the single chain fragment comprises an scFv.

143. The method of any one of embodiments 103-142, wherein the target antibody or antigen-binding fragment thereof comprises a VH region comprising the amino acid sequence set forth in SEQ ID NO: 11, and a VL region comprising the amino acid sequence set forth in SEQ ID NO: 12.

144. The method of embodiment 143, wherein the target antibody or antigen-binding fragment thereof is an scFv and the VH region and the VL region are joined by a flexible linker.

145. The method of embodiment 144, wherein the flexible linker comprises the amino acid sequence set forth in SEQ ID NO: 14, and the scFv comprises the amino acid sequence set forth in SEQ ID NO: 13.

146. The method of any one of embodiments 103-142, wherein the target antibody or antigen-binding fragment thereof comprises a VH region comprising the amino acid sequence set forth in SEQ ID NO: 25, and a VL region comprising the amino acid sequence set forth in SEQ ID NO: 26.

147. The method of embodiment 146, wherein the target antibody or antigen-binding fragment thereof is an scFv and the VH region and the VL region are joined by a flexible linker.

148. The method of embodiment 147, wherein the flexible linker comprises the amino acid sequence set forth in SEQ ID NO: 14, and the scFv comprises the amino acid sequence set forth in SEQ ID NO: 27.

149. An article of manufacture comprising the anti-idiotype antibody or antigen-binding fragment thereof of any one of embodiments 1-78, or the conjugate of any one of embodiments 79-82, and instructions for using the anti-idiotype antibody or antigen-binding fragment thereof to:

detect a target antibody or antigen-binding fragment thereof or a CAR comprising a target antibody or antigen-binding fragment thereof; and/or select or enrich, from a population of cells, engineered cells expressing a CAR comprising the target antibody or antigen-binding fragment thereof; and/or stimulate an input composition comprising cells expressing a CAR comprising the target antibody or antigen-binding fragment thereof.

150. An article of manufacture comprising:

a binding reagent comprising an extracellular domain of a CAR comprising a target antibody or antigen-binding fragment thereof, said extracellular domain or portion thereof comprising the target antibody or antigen-binding fragment thereof; and an anti-idiotype antibody or antigen-binding fragment of any of embodiments 1-78, or the conjugate of any one of embodiments 79-82.

151. The article of manufacture of embodiment 150, wherein the binding reagent is a first binding reagent and the article of manufacture further comprises a second binding reagent comprising the extracellular domain or portion thereof of the CAR.

152. The article of manufacture of embodiment 150 or embodiment 151, wherein the extracellular domain of the CAR or portion thereof of the first and second binding reagent is the same.

153. The article of manufacture of any of embodiments 150-152, further comprising instructions for using the binding reagent, optionally the first and second binding reagent, for assaying a sample for the presence or absence of a molecule that binds to the binding reagent using an immunoassay, optionally wherein the immunoassay is a bridge or sandwich immunoassay, optionally wherein the sample is from a subject having been administered a cell therapy comprising cells engineered with a CAR comprising a target antibody that is the or antigen-binding fragment thereof.

154. The article of manufacture of any of embodiments 150-153, wherein the binding reagent, optionally the first and/or second binding reagent, is detectably labeled or capable of producing a detectable signal.

155. The article of manufacture of any of embodiments 151-154, wherein one of the first and second binding reagent is attached to a solid support of is capable of being attached to a solid support and the other of the first and second binding reagent is detectable label or is capable of producing a detectable signal.

156. The article of manufacture of embodiment 155, wherein the article of manufacture further comprises a solid support, optionally wherein the one of the first and second binding reagent is linked, directly or indirectly to biotin, and the solid support comprises a streptavidin-coated surface.

157. The article of manufacture of any one of embodiments 149-156, wherein the target antibody or antigen-binding fragment thereof is a single chain fragment.

158. The article of manufacture of embodiment 157, wherein the single chain fragment comprises an scFv.

159. The article of manufacture of any one of embodiments 149-158, wherein the target antibody or antigen-binding fragment thereof comprises a VH region comment thereof is an scFv and the VH region and the VL region are joined by a flexible linker.

164. The article of manufacture of embodiment 163, wherein the flexible linker comprises the amino acid sequence set forth in SEQ ID NO: 14, and the scFv comprises the amino acid sequence set forth in SEQ ID NO: 27.

VIII. Examples

The following examples are included for illustrative purposes only and are not intended to limit the scope of the invention.

Example 1: Generation and Assessment of
Anti-Idiotype Antibodies Against Anti-BCMA
Chimeric Antigen Receptors Anti-idiotypic antibodies that recognize the scFv portion of one or both of two exemplary anti-BCMA chimeric antigen receptors (CARs) were generated and assessed. Amino acid sequences (SEQ ID NOs) of exemplary anti-idiotypic antibodies that were generated are listed in Table E1. This includes antibody clones 10, 15, 16, and 19.

TABLE E1

| | | | | | Kabat | | Chothia | | AbM | |
|---|---|---|---|---|---|---|---|---|---|---|
| | | | | | CDR-H1 H2 H3 | CDR-L1 L2 L3 | CDR-H1 H2 H3 | CDR-L1 L2 L3 | CDR-H1 H2 H3 | CDR-L1 L2 L3 |
| Clone ID | VH | VL | Heavy Chain | Light Chain | | | | | | |
| 10 | 62 | 63 | 64 | 65 | 52 53 54 | 59 60 61 | 55 56 54 | 59 60 61 | 57 58 54 | 59 60 61 |
| 19 | 84 | 85 | 86 | 87 | 74 75 76 | 81 82 83 | 77 78 76 | 81 82 83 | 79 80 76 | 81 82 83 |
| 16 | 114 | 115 | 116 | 117 | 104 105 106 | 111 112 113 | 107 108 106 | 111 112 113 | 109 110 106 | 111 112 113 |
| 15 | 38 | 39 | 40 | 41 | 28 29 30 | 35 36 37 | 31 32 30 | 35 36 37 | 33 34 30 | 35 36 37 |

Exemplary amino acid sequences (SEQ ID NOs) of exemplary anti-idiotypic antibody clones prising the amino acid sequence set forth in SEQ ID NO: 11, and a VL region comprising the amino acid sequence set forth in SEQ ID NO: 12.

160. The article of manufacture of embodiment 159, wherein the target antibody or antigen-binding fragment thereof is an scFv and the VH region and the VL region are joined by a flexible linker.

161. The article of manufacture of embodiment 160, wherein the flexible linker comprises the amino acid sequence set forth in SEQ ID NO: 14, and the scFv comprises the amino acid sequence set forth in SEQ ID NO: 13.

162. The article of manufacture of any one of embodiments 149-158, wherein the target antibody or antigen-binding fragment thereof comprises a VH region comprising the amino acid sequence set forth in SEQ ID NO: 25, and a VL region comprising the amino acid sequence set forth in SEQ ID NO: 26.

163. The article of manufacture of embodiment 162, wherein the target antibody or antigen-binding frag- A. Anti-ID Antibodies Against Anti-BCMA CAR 1

Anti-idiotype antibodies (anti-IDs) recognizing the scFv portion of an exemplary anti-BCMA CAR 1 having an antigen-binding domain from anti-BCMA Target Antibody 1 were generated. The Anti-BCMA CAR 1 contained an anti-BCMA scFv with variable heavy and variable light chain regions derived from anti-BCMA Target Antibody 1 (having a variable region sequence of SEQ ID NO: 11 and 12, separated by a linker set forth in SEQ ID NO: 14; scFv sequence set forth in SEQ ID NO: 13), a human IgG-derived spacer, a human CD28-derived transmembrane domain, a human 4-1BB-derived intracellular signaling domain and a human CD3 zeta-derived signaling domain.

Mice were immunized with the anti-BCMA scFv fused to a mouse Fc. Immune cells were isolated from spleens of immunized mice, and antibody-producing spleen cells were fused with tumor cells (e.g. myeloma cells) to produce hybridoma fusion cells. Hybridoma cells were clonally expanded, and supernatant was screened by ELISA for its ability to bind to the recombinant soluble scFv-Fc and by flow cytometry for binding to anti-BCMA CAR 1-expressing cells. Supernatant from hybridoma clones were counterscreened by ELISA against a non-target scFv-Fc and by flow cytometry against cells expressing a non-target CAR. Each selected hybridoma clone was expanded and antibody purified for further characterization.

Exemplary selected anti-ID antibodies were assessed for the ability to specifically bind to T cells engineered with the anti-BCMA CAR 1. Approximately $2.5 \times 10^5$ of Jurkat T cells engineered to express anti-BCMA CAR 1 were placed in a multi-well plate and incubated with 5 μg/mL of each of the purified anti-ID antibody clones for 20 minutes at 4° C. The cells were washed and incubated with a secondary antibody (goat-anti-mouse IgG1, 2, 3 antibody) for detection of the anti-ID antibodies that were bound to anti-BCMA CAR 1 expressed on the surface of the cells. Cells were washed and assessed by flow cytometry.

Results of the initial screen of anti-ID antibody clones are shown in FIG. 1. As shown, clone 10 (see Table E1) exhibited near 100% binding to the anti-BCMA CAR 1-expressing cells in the sample, and exhibited higher mean fluorescence intensity (MFI) compared to other clones.

Antibodies that exhibited detectable binding were further assessed for binding to CAR-expressing T cells expressing anti-BCMA CAR 1 or a non-target anti-BCMA CAR (anti-BCMA CAR 2, see Example 1.B).

The anti-ID antibodies were assessed for the ability to specifically bind to T cells engineered with the anti-BCMA CAR 1 or anti-BCMA CAR 2. Binding with the anti-ID antibody clones was assessed as described above, except on either Jurkat T cells engineered to express anti-BCMA CAR 1 or anti-BCMA CAR 2 or non-engineered (parental) Jurkat cells as control. The anti-BCMA CAR 1- or CAR 2-expressing Jurkat cells were also subject to staining with recombinant BCMA-Fc (soluble human BCMA fused at its C-terminus to an Fc region of IgG) fusion polypeptide, which can bind to both anti-BCMA CAR 1 and anti-BCMA CAR 2, as a control.

Figure 2:
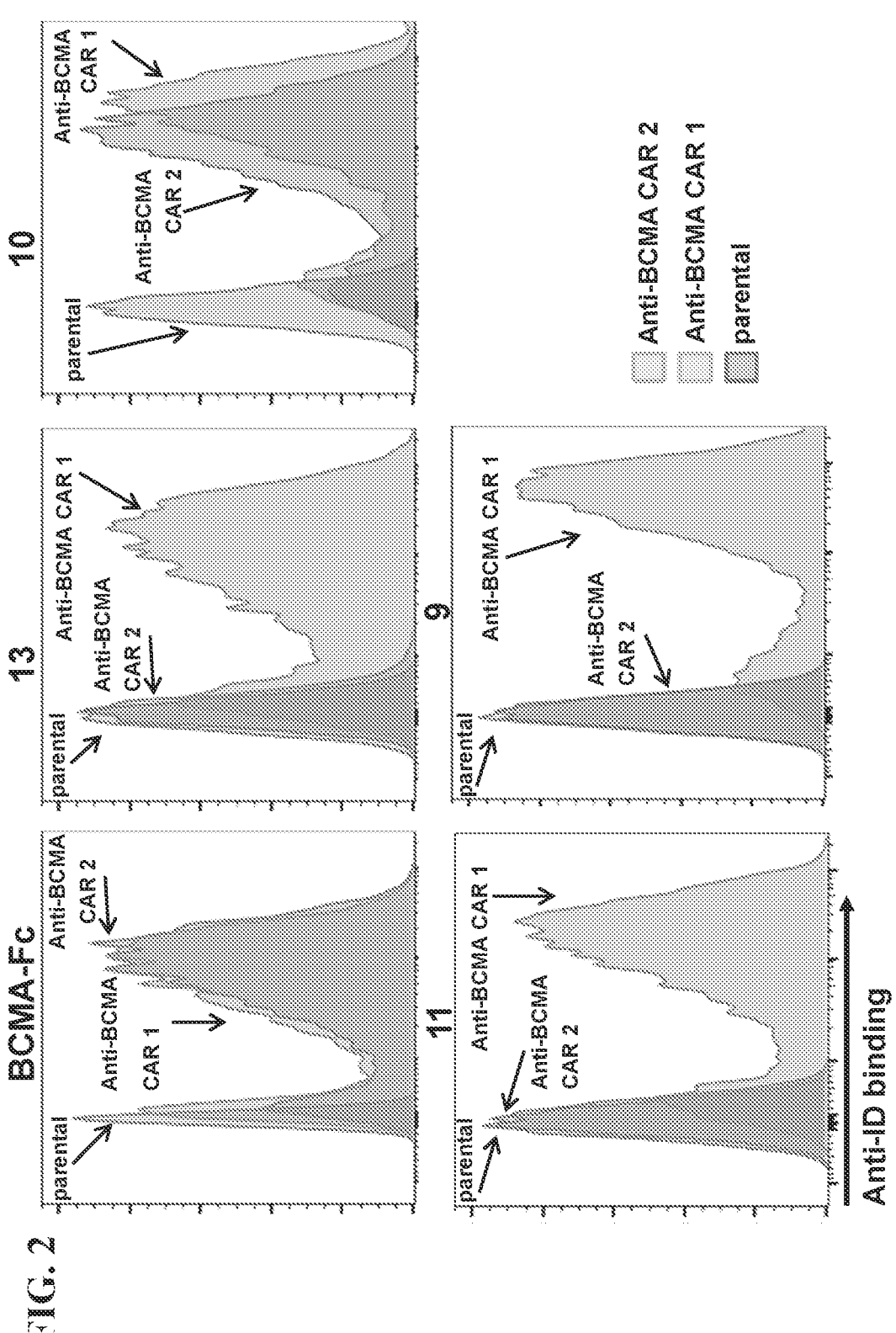
FIG. 2 depicts the results of an assay where anti-ID antibodies were assessed for the ability to specifically bind to T cells engineered with the anti-BCMA CAR 1 or the anti-BCMA CAR 2 by incubating the anti-ID antibodies with T cells engineered with the anti-BCMA CAR 1 or the anti-BCMA CAR 2 and then detecting the level of binding. The anti-BCMA CAR-expressing Jurkat cells were also subjected to staining with recombinant BCMA-Fc (soluble human BCMA fused at its C-terminus to an Fc region of IgG) fusion polypeptide, which can bind to both anti-BCMA CAR 1 and anti-BCMA CAR 2, as a control.

Results are shown in FIG. 2. As shown, clone 10 showed binding to both anti-BCMA CAR 1 and anti-BCMA CAR 2, with higher binding to anti-BCMA CAR 1.

B. Anti-ID Antibodies Against Anti-BCMA CAR 2

Anti-idiotype antibodies (anti-IDs) recognizing the scFv portion of a different exemplary anti-BCMA chimeric antigen receptor (CAR), anti-BCMA CAR 2 having an antigen-binding domain from anti-BCMA Target Antibody 2, were generated. Anti-BCMA CAR 2 contained an anti-BCMA scFv with variable heavy and variable light chain regions derived from anti-BCMA Target Antibody 2 (having a variable region sequence of SEQ ID NO: 25 and 26 separated by a linker set forth in SEQ ID NO: 14; scFv sequence set forth in SEQ ID NO: 27), a human IgG2 and IgG4-derived spacer, a human CD28-derived transmembrane domain, a human 4-1BB-derived intracellular signaling domain and a human CD3 zeta-derived signaling domain.

Mice were immunized with an extracellular domain (ECD) portion of the CAR, containing an anti-BCMA scFv with variable regions derived from anti-BCMA Target Antibody 2, similar to methods described above.

Serum isolated from immunized mice was tested by ELISA for its ability to bind to the recombinant soluble ECD portion by detection with a secondary antibody. Hybridoma fusion clones were generated and further characterized by ELISA for binding to the ECD, and positive clones were selected. Each selected hybridoma clone was expanded and antibody purified.

1. Assessment of Binding of Anti-Idiotypic Antibody to Anti-BCMA CAR by Flow Cytometry Anti-ID antibody clones were assessed for the ability to specifically bind to T cells engineered with the anti-BCMA CAR 2, to identify candidate clones that can be suitable for use in flow cytometry. $1 \times 10^5$ of Jurkat T cells engineered to express anti-BCMA CAR 1, anti-BCMA CAR 2, an unrelated control CAR specific for a different antigen (control CAR), or non-engineered (parental) Jurkat cells, were incubated with 2.5 μg/mL of anti-ID antibody clone conjugated to Alexa Fluor® 647 fluorophore for 20 minutes at 4° C. The cells were washed and subject to flow cytometry analysis. Cells were also subject to staining with recombinant BCMA-Fc, which can bind to both anti-BCMA CAR 1 and anti-BCMA CAR 2, as a control.

Figure 3A:
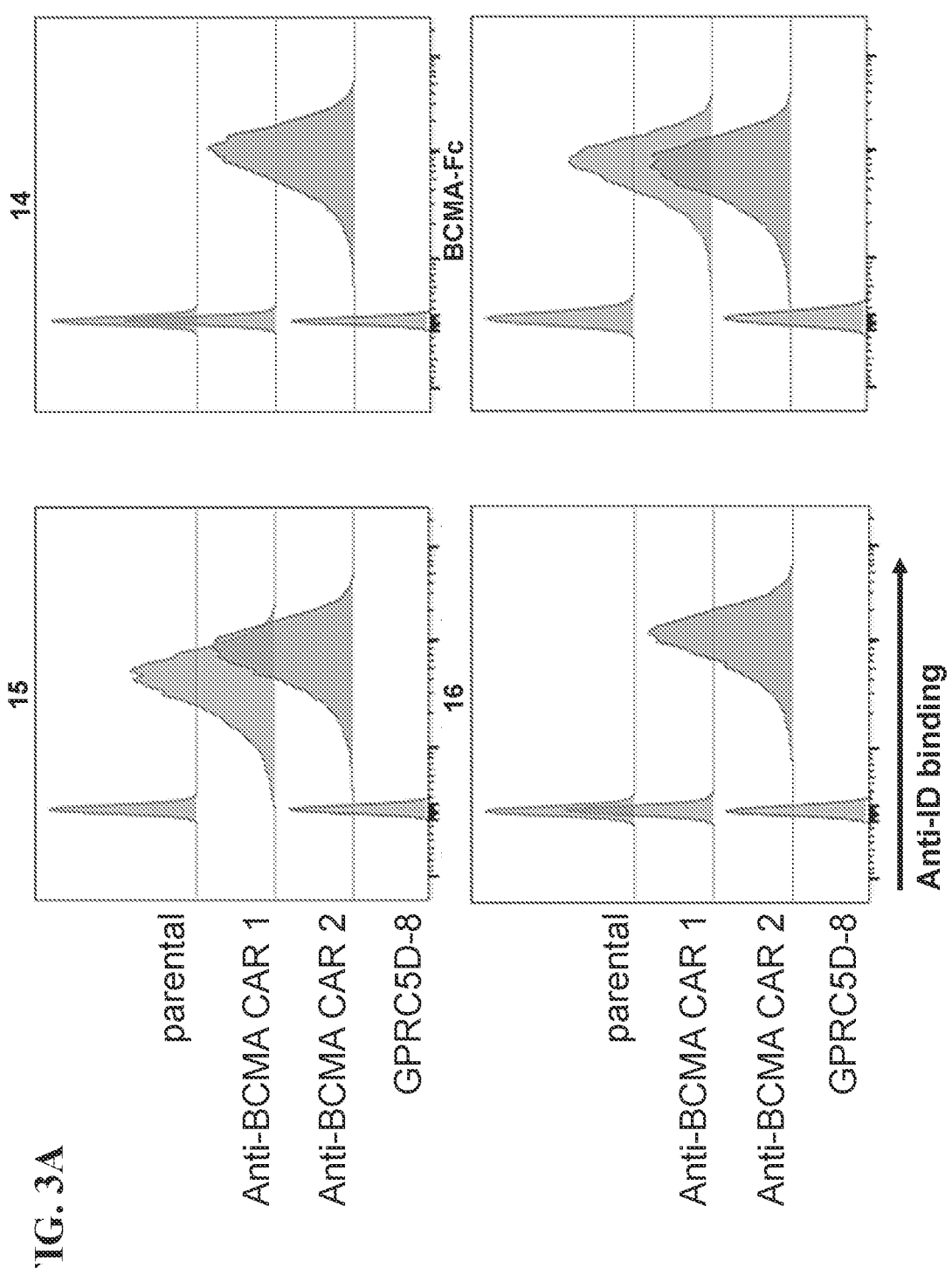
FIGS. 3A and 3B depict the results of an assay where anti-ID antibodies were assessed for the ability to specifically bind to T cells engineered with the anti-BCMA CAR 1 or the anti-BCMA CAR 2 by incubating the anti-ID antibodies with T cells engineered with the anti-BCMA CAR 1 or the anti-BCMA CAR 2 and then detecting the level of binding. Cells were also subjected to staining with recombinant BCMA-Fc, which can bind to both anti-BCMA CAR 1 and anti-BCMA CAR 2, as a control.
Figure 3B:
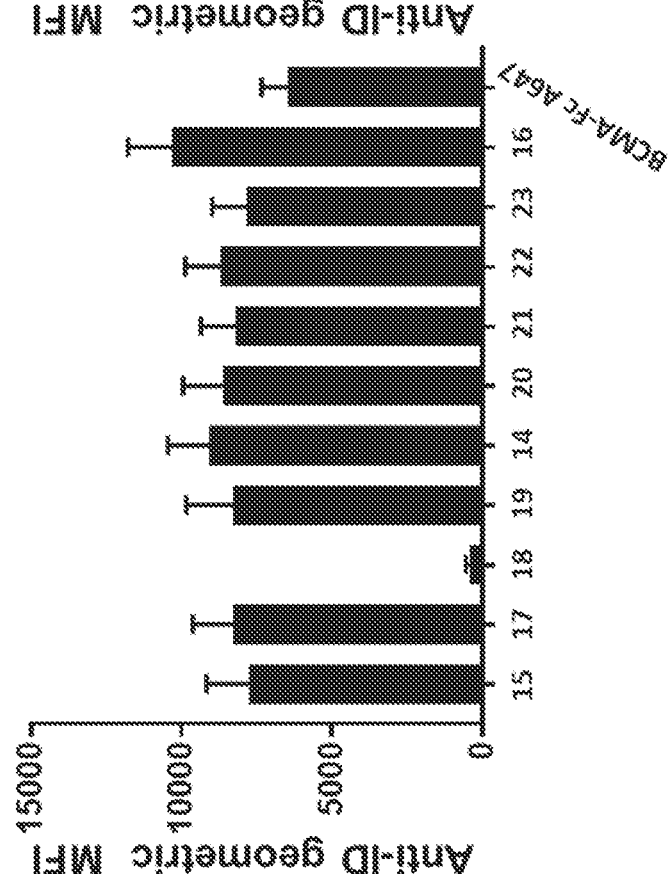

As shown in FIGS. 3A and 3B, clone 16 (Table E1) was observed to exhibit the highest mean fluorescence intensity (MFI) among various clones tested, for staining anti-BCMA CAR 2-expressing cells. Clone 15 (Table E1) was observed to bind to both anti-BCMA CAR 2- and anti-BCMA CAR 1-expressing cells (FIG. 3A). All anti-ID antibody clones tested, including 16 and 15, were observed to exhibit a higher MFI than that achieved when cells were stained with BCMA-Fc, with the exception of clone 18 (FIG. 3B).

2. Blocking of Binding by BCMA-Fc

Blocking of the binding of the anti-ID antibodies to the anti-BCMA CAR 2, by a recombinant BCMA-Fc fusion polypeptide, was assessed. Anti-BCMA CAR 2-expressing Jurkat cells were incubated with 2.5 μg/mL BCMA-Fc conjugated to Alexa Fluor® 488 fluorophore (BCMA-Fc pretreatment), for 20 minutes at 4° C. The cells were washed and were further incubated with 2.5 μg/mL of one of the anti-ID antibody clones conjugated to Alexa Fluor® 647 fluorophore for 20 minutes at 4° C. The geometric mean fluorescence intensity (MFI) by flow cytometry, was compared between cells stained with anti-ID antibody clones alone and cells pretreated with BCMA-Fc.

Figure 4A:
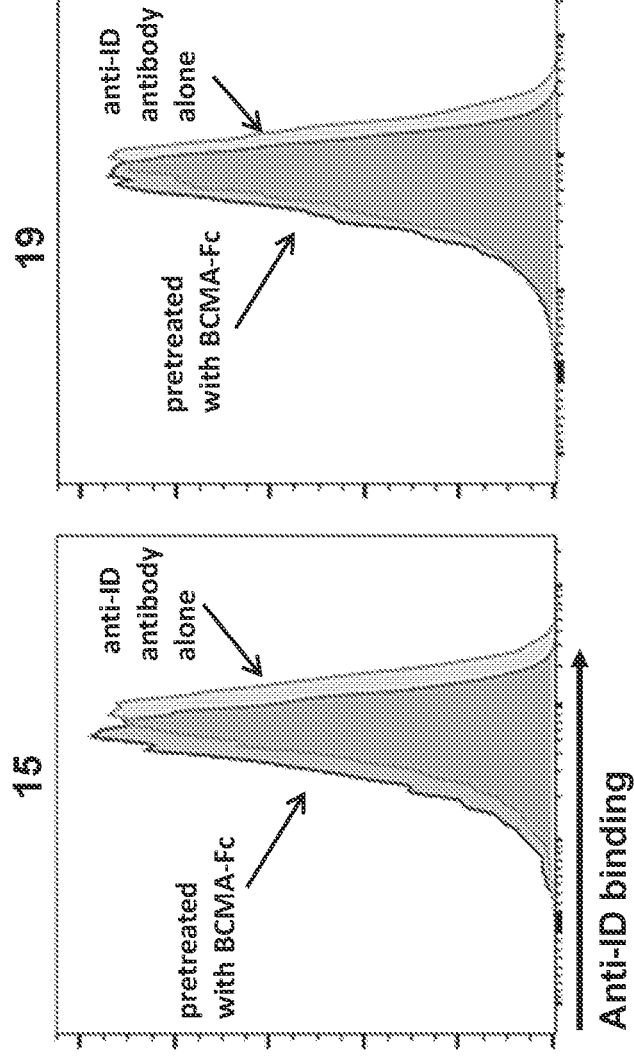
FIGS. 4A and 4B depict the results of an assay where it was assessed whether a recombinant BCMA-Fc fusion polypeptide was capable of blocking binding of certain anti-ID antibodies (clones 15, 19, and 23) to the anti-BCMA CAR 2.
Figure 4B:
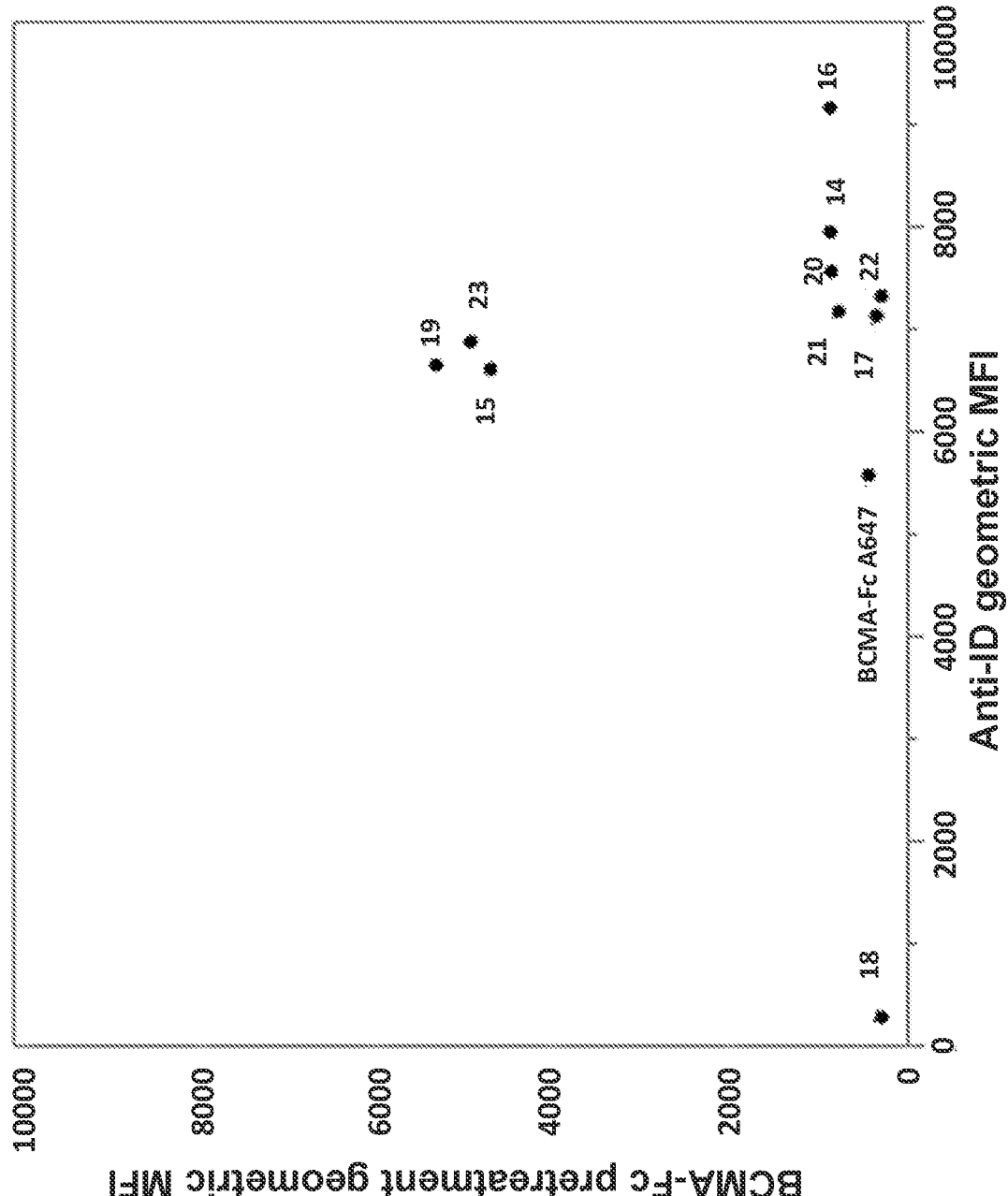

As shown in FIGS. 4A and 4B and Table E2 below, the binding of anti-ID clones 15 and 19 to the anti-BCMA CAR 2 was not substantially blocked by BCMA-Fc pretreatment. This is in contrast to several other anti-ID clones that demonstrated weak geometric MFI following pretreatment with BCMA-Fc (FIG. 4B).

TABLE E2

| | Blocking of Anti-ID Binding by BCMA-Fc | |
|---|---|---|
| Clone | Anti-ID only geometric MFI | BCMA-Fc pretreatment geometric MFI |
| 15 | 6621 | 4713 |
| 19 | 6660 | 5331 |

3. Assessment of T Cell Stimulation Agonistic Activity of Soluble or Plate-Bound Anti-Idiotype Antibodies Various anti-ID antibody clones described above were tested for their agonistic activity for T cell stimulation, using a reporter cell line.

A reporter cell line was generated containing a Nur77-tdTomato knock-in reporter, where the nucleic acid sequences encoding a tdTomato fluorescent protein was knocked-in at the endogenous Nur77 locus. Orphan nuclear hormone receptor Nur77 (also called Nr4a1) is an immediate-early response gene induced by activation of signal from the T cell receptor and/or via molecules containing immunoreceptor tyrosine-based activation motif (ITAM). A nucleic acid sequence encoding tdTomato was targeted for integration in-frame with the endogenous Nur77 gene at the final exon, prior to the stop codon, by introducing a genetic disruption using gene editing and targeting the nucleic acid sequence encoding tdTomato for integration at a site near the genetic disruption by homology-dependent repair (HDR).

The Nur77-tdTomato reporter cell line was engineered to express anti-BCMA CAR 2, and reporter expression was assessed after incubation with a soluble anti-ID antibody or a plate-bound anti-ID antibody. For assessing soluble anti-ID antibodies, a multi-well plate was blocked overnight with phosphate buffer saline (PBS) and 10% fetal bovine serum (FBS). 2.5 μg/mL of one of eight anti-ID antibody clones in RPMI media with 10% FBS was added to the plate. For assessing plate-bound anti-ID antibodies, a multi-well plate was coated with 2.5 μg/mL of one of the anti-ID antibody clones in PBS, overnight at 4° C. or 4 hours at 37° C., followed by washing with RPMI media with 10% FBS. 1×10$^5$ Nur77-tdTomato reporter cells were added to each well and incubated at 37° C. for 20 hours. The samples were stained with 4',6-diamidino-2-phenylindole (DAPI), and assessed by flow cytometry for DAPI staining and tdTomato fluorescence intensity.

Figure 5A:
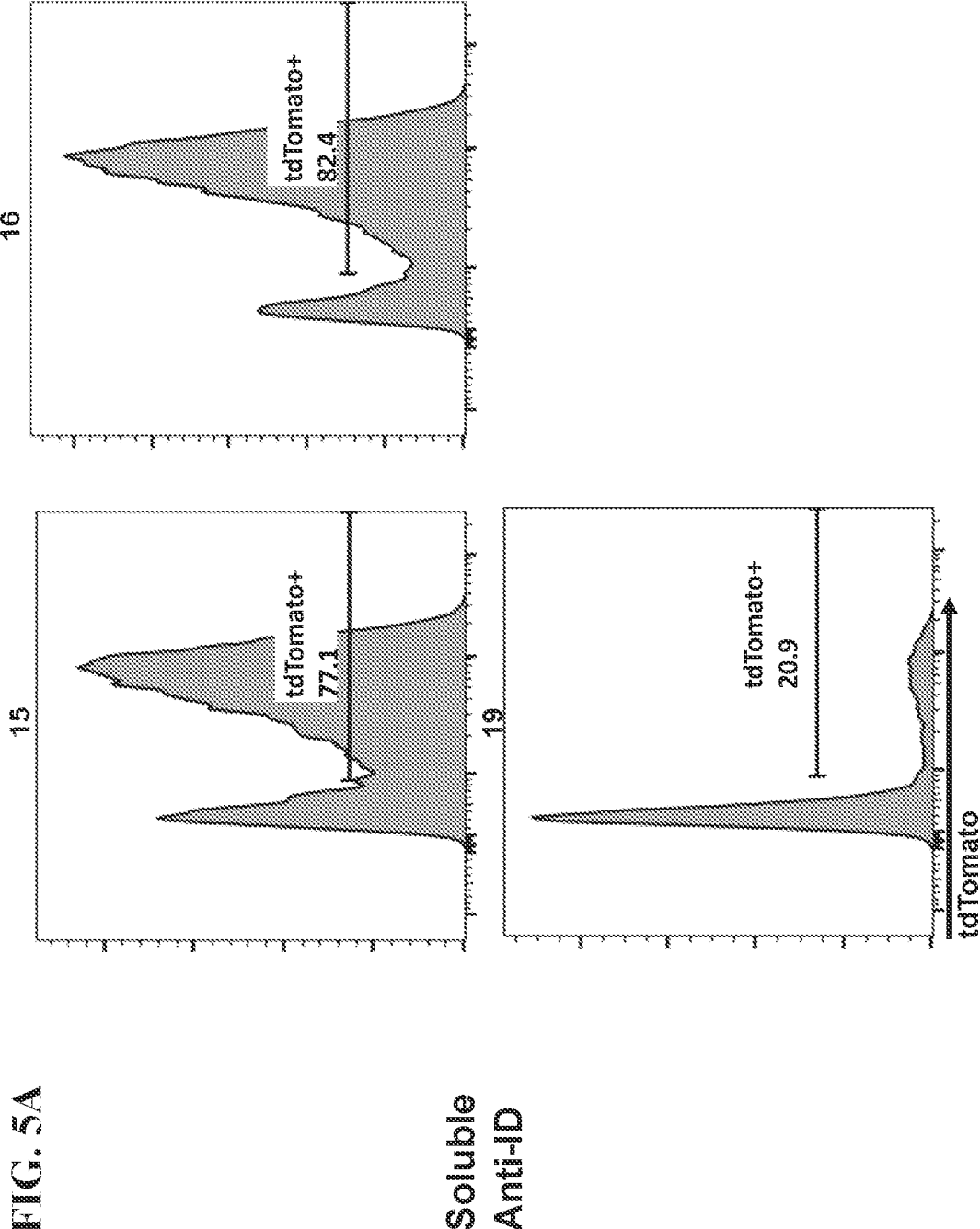
FIGS. 5A-5C depict the results of an assay that tested certain anti-ID antibodies for their agonistic activity for T cell stimulation, using a reporter cell line that was incubated with a soluble anti-ID antibody or a plate-bound anti-ID antibody.
Figure 5B:
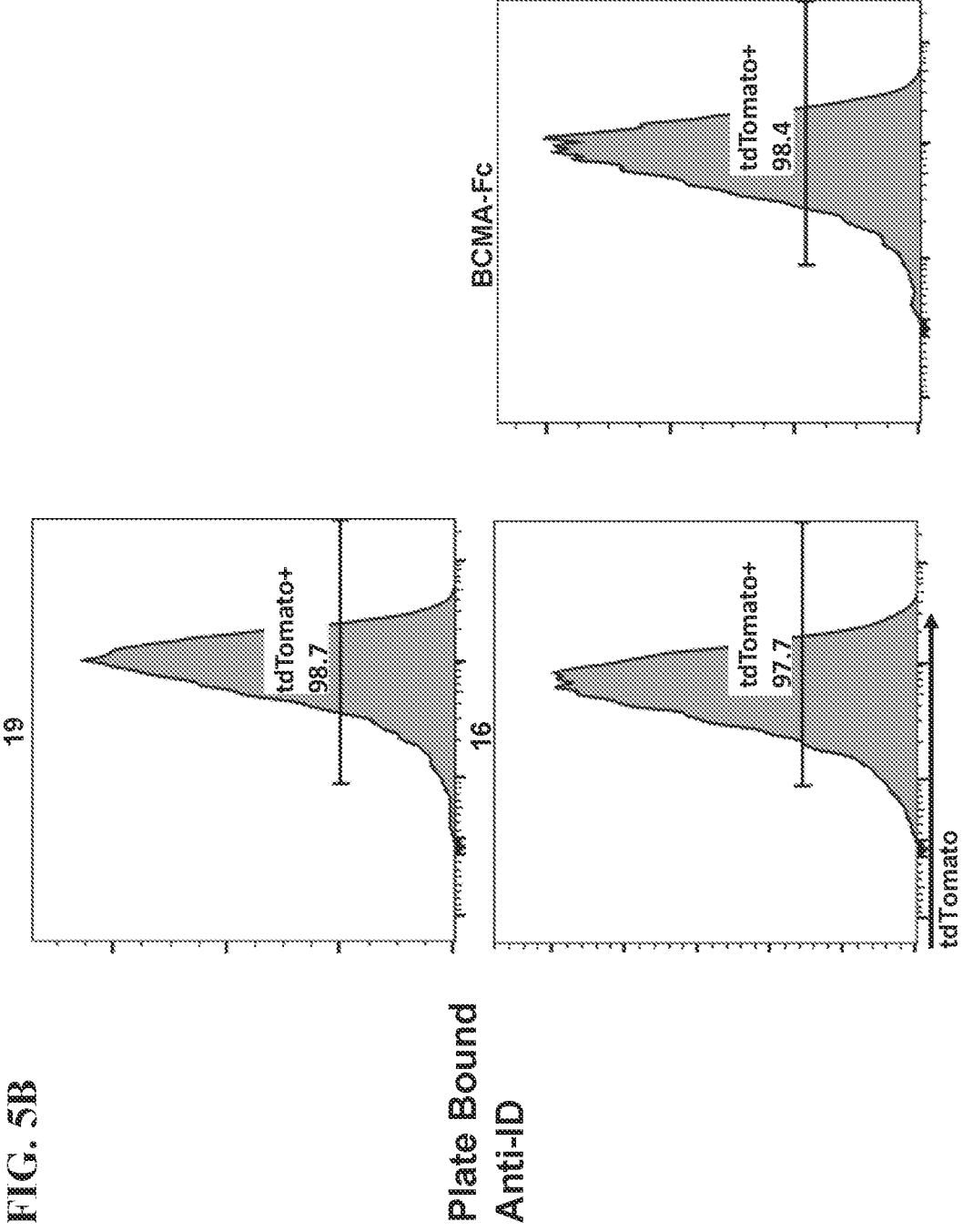
Figure 5C:
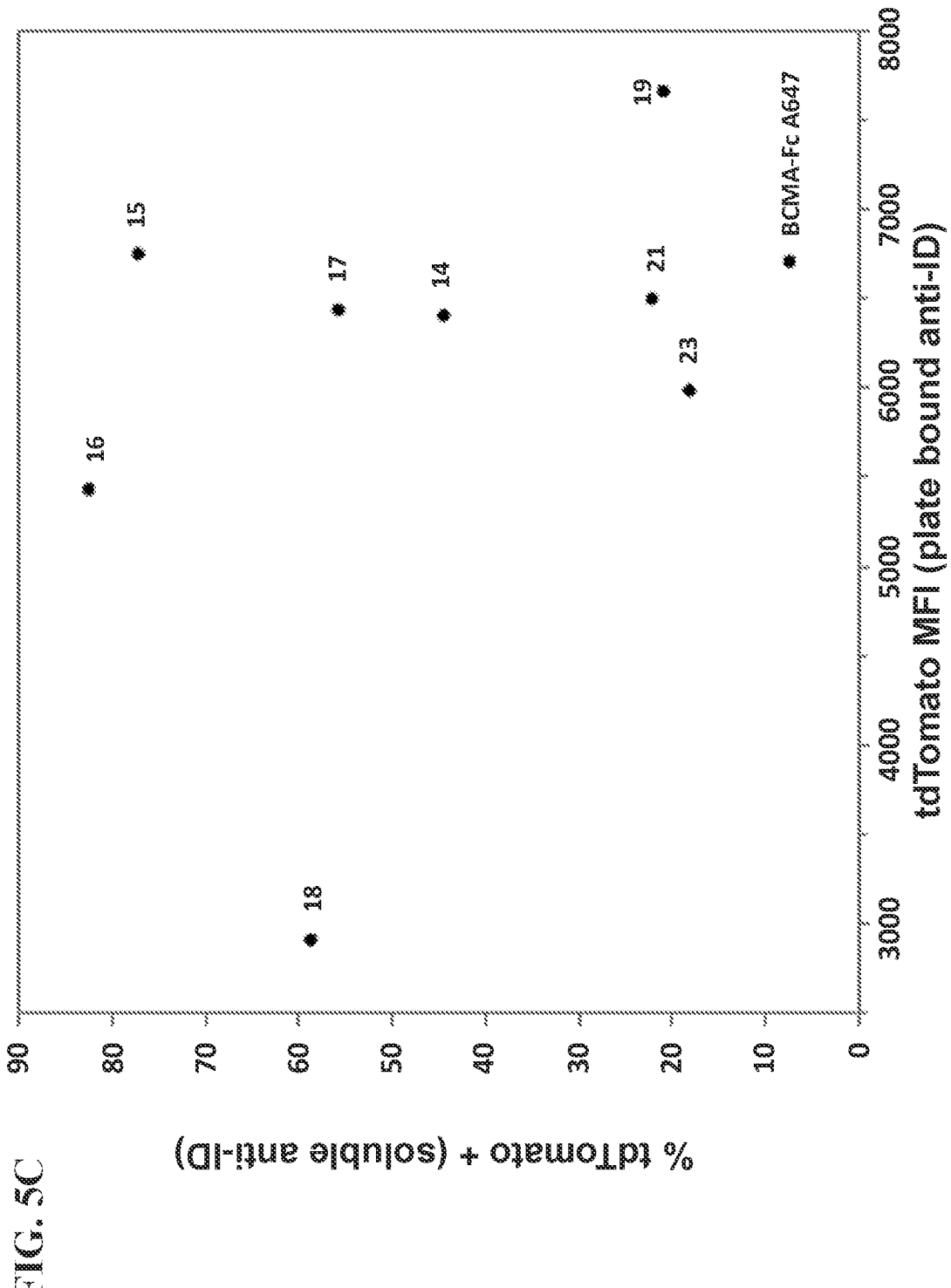

The results are shown in FIGS. 5A-5C. As shown in FIGS. 5A and 5C, incubation with soluble anti-ID clones 15 and 16 exhibited the highest percentage of tdTomato+ cells, indicating that these clones (15 and 16) exhibit agonistic activity in soluble form. As shown in FIGS. 5B and 5C, incubation with all anti-ID antibodies when plate-bound resulted in almost 100% of the cells expressing tdTomato, with the exception of clone 18 (FIG. 5C), indicating that clones 15 and 16 exhibit agonistic activity in plate-bound form.

Example 2: Anti-BCMA CAR-T Cell Stimulation by Candidate Anti-Idiotype Antibody The ability of a candidate anti-idiotype antibody (clone 16) to stimulate primary T cells expressing anti-BCMA CAR 2 was assessed. Separate compositions of primary CD4+ and CD8+ T cells were isolated by immunoaffinity-based enrichment from leukapheresis samples of eighty-nine healthy human donors, and the isolated cell compositions were cryofrozen. Using these compositions, anti-BCMA CAR-T cells were manufactured using an exemplary anti-BCMA CAR-T cell manufacturing process. In this process, isolated CD4+ and CD8+ T cells were thawed and mixed at approximately a 1:1 ratio of viable CD4+ T cells to viable CD8+ T cells, stimulated with anti-CD3/anti-CD28 antibodies, and transduced with lentiviral preparations encoding the exemplary anti-BCMA CAR described in Example 1, Section B (anti-BCMA CAR 2). The cells were then cultivated under conditions for expansion.

To assess the proliferative capacity of CAR-T cells generated by the above process, 96-well tissue culture plates were coated with 30 μg/mL of clone 16 in 200 μL of PBS overnight at 4° C. After coating, 15,000 total T cells were added to the coated wells and incubated for six days at 37° C. During incubation, cellular proliferation was monitored over time using an Incucyte imaging system.

Figure 6:
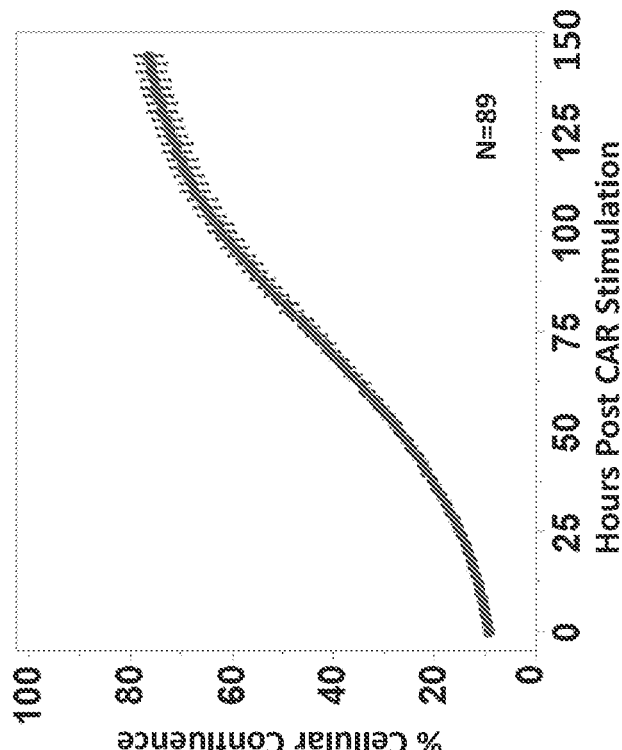
FIG. 6 shows the average growth curve (mean % cellular confluence) of CAR T cells expressing anti-BCMA CAR 2 during incubation with and stimulation by plate-bound anti-ID antibody clone 16. Error bars represent standard error of the mean.

FIG. 6 shows the average growth curve (i.e., mean percent cellular confluence in well) for manufactured CAR-T cells during incubation with plate-bound clone 16. Error bars shown represent the standard error of the mean. As shown in FIG. 6, CAR stimulation by plate-bound anti-idiotype antibody clone 16 led to proliferation of CAR-T cells. These results demonstrate that the manufacturing process resulted in engineered CAR-T cell compositions that showed vigorous CAR T cell-mediated proliferative capacity.

Together with the results of Example 1, these results support the finding that clone 16 exhibits agonistic activity in plate-bound form, including for CAR-T cells expressing the exemplary anti-BCMA CAR 2.

Example 3: Measuring CAR Expression Using Candidate Anti-Idiotype Antibody in Cartridge-Based Flow System The use of a candidate anti-idiotype antibody (clone 16) for measuring anti-BCMA CAR expression in a cartridge-based flow system (Accellix) was assessed. To test for specificity, clone 16 binding against primary T cells transduced to express anti-BCMA CAR 2 (described in Example 1, Section B), non-transduced primary T cells, and primary T cells transduced to express a non-target anti-CD19 CAR was assessed. The non-target anti-CD19 CAR contained an anti-CD19 scFv, an immunoglobulin spacer, a human CD28-derived transmembrane domain, a human 4-1BB-derived intracellular signaling domain, and a human CD3 zeta-derived signaling domain. To test for linearity of CAR detection frequency using clone 16 in the cartridge-based flow system, serially diluted samples of primary T cells expressing anti-BCMA CAR 2 were also prepared and analyzed.

To generate transduced CAR-T cells, separate compositions of primary CD4+ and CD8+ T cells were isolated by immunoaffinity-based enrichment from leukapheresis samples, and isolated CD4+ and CD8+ T cells were mixed at approximately a 1:1 ratio of viable CD4+ T cells to viable CD8+ T cells, stimulated with anti-CD3/anti-CD28 antibodies, and transduced with lentiviral preparations encoding the CAR. After transduction, cells were incubated at about 37.0° C. in an incubator, harvested 96 hours after the initiation of stimulation, and cryopreserved.

To prepare cell samples for testing, vials containing the cryopreserved anti-BCMA CAR-T cell compositions were thawed and washed in serum free culture media. Cell samples were then resuspended in serum free media at a concentration of about 20×10$^6$ cells/mL, after which the resuspended cell samples were incubated at 37.0° C.±2° C. with gas exchange for several hours prior to analysis. Cell samples containing non-transduced primary T cells or anti-CD19 CAR-T cells were similarly prepared.

For analysis using the cartridge-based flow system, approximately 40 μL of cell sample was dispensed into a dried-down reagent tube containing the fluorescently labeled anti-ID clone 16 or into a dried-down reagent tube that lacked the fluorescently labeled anti-ID clone 16 antibody as the fluorescence minus one (FMO) control. Both the sample and FMO control dried-down reagent tubes also contained the same additional fluorescently labeled antibodies for multi-color flow cytometry detection of other T cell markers (e.g., CD3, CD4, CD8, or CD45) and for staining for viable cells. The reagent tube was pulse vortexed for two minutes, and 15 μL of sample were transferred to a flow cartridge. The cartridge was then inserted into an Accellix benchtop instrument for signal acquisition and spectral analyses.

For all subsequent analyses, cells were gated to exclude fluorescent quality control beads and dead cells, and CD3, CD4, CD8, and/or CAR expression was measured as a percentage of viable CD45+ cells in full stain samples. FMO samples were used to set CAR+ gates, which were adjusted so that the frequency of CAR expression in the FMO samples was approximately 1.0% (% parent population).

A. Binding Specificity of Candidate Anti-Idiotype Antibody

To test the binding specificity of clone 16 for anti-BCMA CAR 2, FMO and full stain samples were prepared and analyzed as described above using cell samples containing primary T cells expressing anti-BCMA CAR 2, non-transduced primary T cells, or anti-CD19 CAR-T cells.

Table E4 shows the percentage of CD3+CAR+, CD4+CAR+, and CD8+CAR+ cells among viable CD45+ cells of the different cell samples. Primary T cells engineered to express anti-BCMA CAR 2 showed positive staining by fluorophore-conjugated clone 16, while non-transduced T cells and anti-CD19 CAR-T cells showed negative staining (less than or equal to 1% CAR frequency).

TABLE E4

| CAR Detection Frequency (% of Viable CD45+ Cells) Across Cell Samples and Subtypes | | | |
|---|---|---|---|
| Cell Sample | CD3+CAR+ | CD4+CAR+ | CD8+CAR+ |
| Anti-CD19 CAR | 0.11 | 0.06 | 0.03 |
| Non-Transduced | 0.01 | 0 | 0 |
| Anti-BCMA CAR 2 | 29.49 | 26.21 | 2.96 |

These results demonstrate the specificity of clone 16 for anti-BCMA CAR 2.

B. Linearity of CAR Detection Frequency Using Candidate Anti-Idiotype Antibody

To assess linearity, FMO and full stain samples were prepared and analyzed as described above using a cell sample containing primary T cells expressing anti-BCMA CAR 2. The frequency of CD3+ and CD3+CAR+ cells among viable CD45+ cells of the undiluted cell sample was first assessed. Based on this measurement, expected CD3+ and CD3+CAR+ frequencies were calculated for five sample dilution points (80%, 50%, 25%, 10%, and 5% cell sample), after which the cell sample was diluted and analyzed for observed CD3+ and CD3+CAR+ frequencies. For dilution, CD3-depleted, non-CAR expressing, washed apheresis product was used as the diluent matrix. Linearity of CD3+ and CD3+CAR+ detection was assessed based on the correlation of expected and observed frequencies.

Table E5 shows the expected and observed frequencies of CD3+ cells among viable CD45+ cells. Based on these values, the coefficient of correlation ($r^2$) value was 0.99, with the best-fit line having a slope of 0.99 and a y-intercept of 1.80.

TABLE E5

| Expected and Observed CD3+ Detection Frequencies (% of Viable CD45+ Cells) | | |
|---|---|---|
| Dilution Point (% Cell Sample) | Observed CD3+ | Expected CD3+ |
| 100 | 99.26 | 99.26 |
| 80 | 80.34 | 79.41 |
| 50 | 50.58 | 49.63 |
| 25 | 29.15 | 24.82 |
| 10 | 12.59 | 9.926 |
| 5 | 5.59 | 4.96 |

Table E6 shows the expected and observed frequencies of CD3+CAR+ cells among viable CD45+ cells. Based on these values, the $r^2$ value was 0.99, with the best-fit line having a slope of 0.94 and a y-intercept of 0.54.

TABLE E6

| Expected and Observed CD3+CAR+ Detection Frequencies (% of Viable CD45+ Cells) | | |
|---|---|---|
| Dilution Point (% Cell Sample) | Observed CD3+CAR+ | Expected CD3+CAR+ |
| 100 | 18.32 | 18.32 |
| 80 | 13.52 | 14.66 |
| 50 | 9.27 | 9.16 |
| 25 | 5.53 | 4.58 |
| 10 | 2.7 | 1.83 |
| 5 | 1.2 | 0.916 |

Taken together, these results show that use of the candidate anti-idiotype antibody (clone 16) allows for specific and accurate assessment of anti-BCMA CAR 2 expression in a cartridge-based flow system.

Example 4: Binding Kinetics and Affinity of Candidate Anti-ID Antibodies

The off rates ($k_{off}$) and equilibrium dissociation constants ($K_D$) of three candidate anti-idiotype antibodies (clones 15, 16, and 19) against the scFv portion of anti-BCMA CAR 2 were determined. Off rates and equilibrium dissociation constants were determined against a soluble monomeric scFv-Fc fusion protein as well as against a soluble dimeric scFv-Fc fusion protein. For comparison, the kinetics and affinity of soluble monomeric and dimeric BCMA-human Fc fusion proteins were also assessed against the monomeric and dimeric scFv-Fc fusion proteins, respectively. Off rates and equilibrium dissociation constants were determined using a BIAcore T200 instrument.

Table E7 shows off rates and equilibrium dissociation constants for the three candidate clones and the monomeric BCMA-Fc against the monomeric scFv-Fc. As shown, all three clones had off rates and lower equilibrium dissociation constants than did the monomeric BCMA-Fc.

TABLE E7

| Binding Kinetics and Affinity Against Monomeric scFv-Fc (scFv from anti-BCMA CAR 2) | | |
|---|---|---|
| Reagent | $k_{off}$ (1/s) | $K_D$ (M) |
| Clone 16 | 5.0E−03 | 1.2E−08 |
| Clone 15 | 3.6E−03 | 1.8E−08 |
| Clone 19 | 8.1E−03 | 5.5E−08 |
| Monomeric BCMA-Fc | 2.4E−02 | 2.9E−07 |

Table E8 shows off rates and equilibrium dissociation constants for the three candidate clones and the dimeric BCMA-Fc against the dimeric scFv-Fc. As shown, all three clones had lower equilibrium dissociation constants than did the dimeric BCMA-Fc. Clones 15 and 19 had off rates lower than did dimeric BCMA-Fc, while clone 16 had a comparable off rate.

TABLE E8

| Binding Kinetics and Affinity Against Dimeric scFv-Fc (scFv from anti-BCMA CAR 2) | | |
|---|---|---|
| Reagent | $k_{off}$ (1/s) | $K_D$ (M) |
| Clone 15 | 4.4E−05 | 2.2E−09 |
| Clone 16 | 1.4E−04 | 2.6E−09 |

TABLE E8-continued

| Binding Kinetics and Affinity Against Dimeric scFv-Fc (scFv from anti-BCMA CAR 2) | | |
|---|---|---|
| Reagent | $k_{off}$ (1/s) | $K_D$ (M) |
| Clone 19 | 6.2E−05 | 3.6E−09 |
| Dimeric BCMA-Fc | 1.4E−04 | 7.0E−09 |

Together, these results indicate that candidate anti-idiotype antibody clones 15, 16, and 19 have improved binding kinetics and affinity over soluble BCMA-Fc reagents, supporting that the anti-idiotype antibody clones are better able to target cells expressing anti-BCMA CAR 2.

Example 5: Detecting CAR-T Cells In Vivo Using Candidate Anti-ID Antibody

The ability of a candidate anti-idiotype antibody (clone 16) to detect CAR-T cells in vivo was assessed. Cells from the OPM-2 multiple myeloma (MM) cell line were engineered to express green fluorescent protein and red-shifted Italian firefly luciferase. After harvest, $2\times10^6$ engineered OPM-2 cells were injected intravenously into immune-deficient mice via tail vein. Fourteen days later, mice were administered intravenously via tail vein either approximately $5\times10^5$, $1\times10^6$, or $2\times10^6$ human CD4+ and CD8+ T cells engineered to express anti-BCMA CAR 2. On days 7, 14, 21, and 28 post CAR-T cell treatment, approximately 200 µL of blood was collected via retro-orbital sinus from the treated, anesthetized mice. The blood samples were then assessed for the presence of administered CAR-T cells by staining with an antibody cocktail that included fluorophore-conjugated anti-ID clone 16. Flow cytometry events were collected on a flow cytometer and analyzed.

Table E9 shows the mean count/µL of anti-BCMA CAR 2-expressing cells detected in blood using anti-ID clone 16 at days 7, 14, 21, or 28 post CAR-T cell treatment. Per treatment group, the values shown in Table E9 are the mean and standard deviation (SD) across four animals.

TABLE E9

| Quantification of CAR-T Cells in Peripheral Blood of Mice Treated With T Cells Expressing Anti-BCMA CAR 2 | | | | |
|---|---|---|---|---|
| CAR-T Cell Dose | Day 7 Mean (SD) of Count/µL | Day 14 Mean (SD) of Count/µL | Day 21 Mean (SD) of Count/µL | Day 28 Mean (SD) of Count/µL |
| $5\times10^5$ Cells | 0.617 (0.151) | 0.472 (0.322) | 0.115 (0.196) | 0.126 (0.052) |
| $1\times10^6$ Cells | 2.05 (0.85) | 0.442 (0.229) | 0.384 (0.643) | 0.154 (0.206) |
| $2\times10^6$ Cells | 4.42 (1.85) | 1.39 (0.75) | 0.326 (0.256) | 6.34 (10.68) |

These results indicate that candidate anti-idiotype antibody clone 16 can be used to detect and quantify T cells expressing anti-BCMA CAR 2 in vivo.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

| # | SEQUENCE | ANNOTATION |
|---|---|---|
| | Sequences | |
| 1 | SYWIG | CDR-H1; Kabat (Target Antibody 1) |
| 2 | IIYPGDSDTRYSPSFQG | CDR-H2; Kabat (Target Antibody 1) |
| 3 | YSGSFDN | CDR-H3; Kabat, Chothia; AbM (Target Antibody 1) |
| 4 | GYSFTSY | CDR-H1; Chothia (Target Antibody 1) |
| 5 | YPGDSD | CDR-H2; Chothia (Target Antibody 1) |
| 6 | GYSFTSYWIG | CDR-H1; AbM (Target Antibody 1) |
| 7 | IIYPGDSDTR | CDR-H2; AbM (Target Antibody 1) |
| 8 | SGTSSNIGSHSVN | CDR-L1; Kabat, Chothia, AbM (Target Antibody 1) |

-continued

| # | SEQUENCE | ANNOTATION |
|---|----------|------------|
| 9 | TNNQRPS | CDR-L2; Kabat, Chothia, AbM (Target Antibody 1) |
| 10 | AAWDGSLNGLV | CDR-L3; Kabat, Chothia, AbM (Target Antibody 1) |
| 11 | EVQLVQSGAEVKKPGESLKISCKGSGYSFTSYWIGWVRQ MPGKGLEWMGIIYPGDSDTRYSPSFQGHVTISADKSISTA YLQWSSLKASDTAMYYCARYSGSFDNWGQGTLVTVSS | VH (Target Antibody 1) |
| 12 | SYELTQPPSASGTPGQRVTMSCSGTSSNIGSHSVNWYQQL PGTAPKLLIYTNNQRPSGVPDRFSGSKSGTSASLAISGLQS EDEADYYCAAWDGSLNGLVFGGGTKLTVLG | VL (Target Antibody 1) |
| 13 | SYELTQPPSASGTPGQRVTMSCSGTSSNIGSHSVNWYQQL PGTAPKLLIYTNNQRPSGVPDRFSGSKSGTSASLAISGLQS EDEADYYCAAWDGSLNGLVFGGGTKLTVLGSRGGGGSG GGGSGGGGSLEMAEVQLVQSGAEVKKPGESLKISCKGSG YSFTSYWIGWVRQMPGKGLEWMGIIYPGDSDTRYSPSFQ GHVTISADKSISTAYLQWSSLKASDTAMYYCARYSGSFD NWGQGTLVTVSS | scFv (Target Antibody 1) |
| 14 | SRGGGGSGGGGSGGGGSLEMA | Linker |
| 15 | DYYVY | CDR-H1; Kabat (Target Antibody 2) |
| 16 | WINPNSGGTNYAQKFQG | CDR-H2; Kabat (Target Antibody 2) |
| 17 | SQRDGYMDY | CDR-H3; Kabat, Chothia; AbM (Target Antibody 2) |
| 18 | GYTFIDY | CDR-H1; Chothia (Target Antibody 2) |
| 19 | NPNSGG | CDR-H2; Chothia (Target Antibody 2) |
| 20 | GYTFIDYYVY | CDR-H1; AbM (Target Antibody 2) |
| 21 | WINPNSGGTN | CDR-H2; AbM (Target Antibody 2) |
| 22 | TGTSSDVG | CDR-L1; Kabat, Chothia, AbM (Target Antibody 2) |
| 23 | EDSKRPS | CDR-L2; Kabat, Chothia, AbM (Target Antibody 2) |
| 24 | SSNTRSSTLV | CDR-L3; Kabat, Chothia, AbM (Target Antibody 2) |

-continued

| # | SEQUENCE | ANNOTATION |
|---|----------|------------|

Sequences

| # | SEQUENCE | ANNOTATION |
|---|----------|------------|
| 25 | EVQLVQSGAEMKKPGASLKLSCKASGYTFIDYYVYWMR QAPGQGLESMGWINPNSGGTNYAQKFQGRVTMRDTSIS TAYMELSRLRSDDTAMYYCARSQRDGYMDYWGQGTLV TVSS | VH (Target Antibody 2) |
| 26 | QSALTQPASVSASPGQSIAISCTGTSSDVGWYQQHPGKAP KLMIYEDSKRPSGVSNRFSGSKSGNTASLTISGLQAEDEA DYYCSSNTRSSTLVFGGGTKLTVLG | VL (Target Antibody 2) |
| 27 | QSALTQPASVSASPGQSIAISCTGTSSDVGWYQQHPGKAP KLMIYEDSKRPSGVSNRFSGSKSGNTASLTISGLQAEDEA DYYCSSNTRSSTLVFGGGTKLTVLGSRGGGGSGGGGSGG GGSLEMAEVQLVQSGAEMKKPGASLKLSCKASGYTFIDY YVYWMRQAPGQGLESMGWINPNSGGTNYAQKFQGRVT MTRDTSISTAYMELSRLRSDDTAMYYCARSQRDGYMDY WGQGTLVTVSS | scFv<br><br>(Target Antibody 2) |
| 28 | SYWMN | CDR-H1; Kabat (clone 15) |
| 29 | QIYPGNGETNNNGKFKG | CDR-H2; Kabat (clone 15) |
| 30 | GGWYFDV | CDR-H3; Kabat, Chothia, AbM (clone 15) |
| 31 | GYAFSSY | CDR-H1; Chothia (clone 15) |
| 32 | YPGNGE | CDR-H2; Chothia (clone 15) |
| 33 | GYAFSSYWMN | CDR-H1; AbM (clone 15) |
| 34 | QIYPGNGETN | CDR-H2; AbM (clone 15) |
| 35 | RASENIYSYLA | CDR-L1; Kabat, Chothia, AbM (clone 15) |
| 36 | NAYTLAE | CDR-L2; Kabat, Chothia, AbM (clone 15) |
| 37 | QHHYGTPWT | CDR-L3; Kabat, Chothia, AbM (clone 15) |
| 38 | QVQLQQSGAELVKPGASVKISCKASGYAFSSYWMNWVK QRPGKGLEWIGQIYPGNGETNNNGKFKGKATLTADISSST AYMQLSSLTSEDSAVYFCARGGWYFDVWGTGTTVTVSS | VH (clone 15) |
| 39 | DIQMTQSPASLSASVGETVTITCRASENIYSYLAWYQQKQ GKSPHLLVYNAYTLAEGVPSRFSGSGSDTQFSLKINSLQPE DFGNYYCQHHYGTPWTFGGGTKVEIK | VL (clone 15) |
| 40 | QVQLQQSGAELVKPGASVKISCKASGYAFSSYWMNWVK QRPGKGLEWIGQIYPGNGETNNNGKFKGKATLTADISSST AYMQLSSLTSEDSAVYFCARGGWYFDVWGTGTTVTVSS AKTTPPSVYPLAPGSAAQTNSMVTLGCLVKGYFPEPVTV TWNSGSLSSGVHTFPAVLQSDLYTLSSSVTVPSSTWPSQT VTCNVAHPASSTKVDKKIVPRDCGCKPCICTVPEVSSVFIF PPKPKDVLTITLTPKVTCVVVDISKDDPEVQFSWFVDDVE VHTAQTKPREEQINSTFRSVSELPIMHQDWLNGKEFKCRV NSAAFPAPIEKTISKTKGRPKAPQVYTIPPPKEQMAKDKVS LTCMITNFFPEDITVEWQWNGQPAENYKNTQPIMDTDGS YFVYSKLNVQKSNWEAGNTFTCSVLHEGLHNHHTEKSLS HSPGK | Heavy chain (clone 15) |

-continued

| # | SEQUENCE | ANNOTATION |
|---|----------|------------|
| 41 | DIQMTQSPASLSASVGETVTITCRASENIYSYLAWYQQKQ GKSPHLLVYNAYTLAEGVPSRFSGSGSDTQFSLKINSLQPE DFGNYYCQHHYGTPWTFGGGTKVEIKRADAAPTVSIFPPS SEQLTSGGASVVCFLNNFYPKDINVKWKIDGSERQNGVL NSWTDQDSKDSTYSMSSTLTLTKDEYERHNSYTCEATHK TSTSPIVKSFNRNEC | Light chain (clone 15) |
| 42 | CAGGTTCAGCTGCAGCAGTCTGGGGCTGAGCTGGTGAA GCCTGGGGCCTCAGTGAAGATTTCCTGCAAAGCTTCTG GCTACGCATTCAGTAGCTACTGGATGAACTGGGTGAAG CAGAGGCCTGGAAAGGGTCTTGAATGGATTGGACAGA TTTATCCTGGAAATGGTGAAACTAACAACAACGGAAA GTTCAAGGGCAAGGCCACACTGACTGCAGACATATCCT CCAGCACAGCCTACATGCAGCTCAGCAGCCTGACATCT GAGGACTCTGCGGTCTATTTCTGTGCAAGAGGGGGCTG GTACTTCGATGTCTGGGGCACAGGGACCACGGTCACCG TCTCCTCAGCCAAAACGACACCCCCATCGTCTATCCA CTGGCCCCTGGATCTGCTGCCCAAACTAACTCCATGGT GACCCTGGGATGCCTGGTCAAGGGCTATTTCCCTGAGC CAGTGACAGTGACCTGGAACTCTGGATCCCTGTCCAGC GGTGTGCACACCTTCCCAGCTGTCCTGCAGTCTGACCT CTACACTCTGAGCAGCTCAGTGACTGTCCCCTCCAGCA CCTGGCCCAGCCAGACCGTCACCTGCAACGTTGCCCAC CCGGCCAGCAGCACCAAGGTGGACAAGAAAATTGTGC CCAGGGATTGTGGTTGTAAGCCTTGCATATGTACAGTC CCAGAAGTATCATCTGTCTTCATCTTCCCCCCAAAGCCC AAGGATGTGCTCACCATTACTCTGACTCCTAAGGTCAC GTGTGTTGTGGTAGACATCAGCAAGGATGATCCCGAGG TCCAGTTCAGCTGGTTTGTAGATGATGTGGAGGTGCAC ACAGCTCAGACGAAACCCCGGGAGGAGCAGATCAACA GCACTTTCCGTTCAGTCAGTGAACTTCCCATCATGCACC AGGACTGGCTCAATGGCAAGGAGTTCAAATGCAGGGT CAACAGTGCAGCTTTCCCTGCCCCCATCGAGAAAACCA TCTCCAAAACCAAAGGCAGACCGAAGGCTCCACAGGT GTACACCATTCCACCTCCCAAGGAGCAGATGGCCAAGG ATAAAGTCAGTCTGACCTGCATGATAACAAACTTCTTC CCTGAAGACATTACTGTGGAGTGGCAGTGGAATGGGC AGCCAGCGGAGAACTACAAGAACACTCAGCCCATCAT GGACACAGATGGCTCTTACTTCGTCTACAGCAAGCTCA ATGTGCAGAAGAGCAACTGGGAGGCAGGAAATACTTT CACCTGCTCTGTGTTACATGAGGGCCTGCACAACCACC ATACTGAGAAGAGCCTCTCCCACTCTCCTGGTAAATGA | Heavy chain; nucleotides (clone 15) |
| 43 | GACATCCAGATGACTCAGTCTCCAGCCTCCCTATCTGC ATCTGTGGGAGAAACTGTCACCATCACATGTCGAGCAA GTGAGAATATTTACAGTTATTTAGCATGGTATCAGCAG AAACAGGGAAAATCTCCTCACCTCCTGGTCTATAATGC ATACACCTTAGCAGAAGGTGTGCCATCAAGATTCAGTG GCAGTGGATCAGACACACAGTTTTCTCTGAAGATCAAC AGTCTGCAGCCTGAAGATTTTGGGAATTATTACTGTCA ACATCATTATGGTACTCCGTGGACGTTCGGTGGAGGCA CCAAGGTGGAAATCAAACGGGCTGATGCTGCACCAAC TGTATCCATCTTCCCACCATCCAGTGAGCAGTTAACAT CTGGAGGTGCCTCAGTCGTGTGCTTCTTGAACAACTTCT ACCCCAAAGACATCAATGTCAAGTGGAAGATTGATGG CAGTGAACGACAAAATGGCGTCCTGAACAGTTGGACT GATCAGGACAGCAAAGACAGCACCTACAGCATGAGCA GCACCCTCACGTTGACCAAGGACGAGTATGAACGACAT AACAGCTATACCTGTGAGGCCACTCACAAGACATCAAC TTCACCCATTGTCAAGAGCTTCAACAGGAATGAGTGTT AG | Light chain; nucleotides (clone 15) |
| 44 | MEWPLIFLFLLSGTAGVQS | Leader sequence; heavy chain (clone 15) |
| 45 | ATGGAATGGCCTTTGATCTTTCTCTTCCTCCTGTCAGGA ACTGCAGGTGTCCAATCC | Leader sequence; heavy chain, nucleotides (clone 15) |
| 46 | MSVPTQVLGLLLLWLTGARC | Leader sequence; light chain (clone 15) |

-continued

| Sequences | | |
|---|---|---|
| # | SEQUENCE | ANNOTATION |
| 47 | ATGAGTGTGCCCACTCAGGTCCTGGGGTTGCTGCTGCT GTGGCTTACAGGTGCCAGATGT | Leader sequence; light chain, nucleotides (clone 15) |
| 48 | CAGGTTCAGCTGCAGCAGTCTGGGGCTGAGCTGGTGAA GCCTGGGGCCTCAGTGAAGATTTCCTGCAAAGCTTCTG GCTACGCATTCAGTAGCTACTGGATGAACTGGGTGAAG CAGAGGCCTGGAAAGGGTCTTGAATGGATTGGACAGA TTTATCCTGGAAATGGTGAAACTAACAACAACGGAAA GTTCAAGGGCAAGGCCACACTGACTGCAGACATATCCT CCAGCACAGCCTACATGCAGCTCAGCAGCCTGACATCT GAGGACTCTGCGGTCTATTTCTGTGCAAGAGGGGGCTG GTACTTCGATGTCTGGGGCACAGGGACCACGGTCACCG TCTCCTCA | VH; nucleotides (clone 15) |
| 49 | GACATCCAGATGACTCAGTCTCCAGCCTCCCTATCTGC ATCTGTGGGAGAAACTGTCACCATCACATGTCGAGCAA GTGAGAATATTTACAGTTATTTAGCATGGTATCAGCAG AAACAGGGAAAATCTCCTCACCTCCTGGTCTATAATGC ATACACCTTAGCAGAAGGTGTGCCATCAAGATTCAGTG GCAGTGGATCAGACACACAGTTTTCTCTGAAGATCAAC AGTCTGCAGCCTGAAGATTTTGGGAATTATTACTGTCA ACATCATTATGGTACTCCGTGGACGTTCGGTGGAGGCA CCAAGGTGGAAATCAAA | VL; nucleotides (clone 15) |
| 50 | ESKYGPPCPPCPAPPVAGPSVFLFPPKPKDTLMISRTPEVT CVVVDVSQEDPEVQFNWYVDGVEVHNAKTKPREEQFQS TYRVVSVLTVLHQDWLNGKEYKCKVSNKGLPSSIEKTIS KAKGQPREPQVYTLPPSQEEMTKNQVSLTCLVKGFYPSDI AVEWESNGQPENNYKTTPPVLDSDGSFFLYSRLTVDKSR WQEGNVFSCSVMHEALHNHYTQKSLSLSLGK | Spacer |
| 51 | MLLLVTSLLLCELPHPAFLLIPRKVCNGIGIGEFKDSLSINA TNIKHFKNCTSISGDLHILPVAFRGDSFTHTPPLDPQELDIL KTVKEITGFLLIQAWPENRTDLHAFENLEIIRGRTKQHGQF SLAVVSLNITSLGLRSLKEISDGDVIISGNKNLCYANTINW KKLFGTSGQKTKIISNRGENSCKATGQVCHALCSPEGCW GPEPRDCVSCRNVSRGRECVDKCNLLEGEPREFVENSECI QCHPECLPQAMNITCTGRGPDNCIQCAHYIDGPHCVKTCP AGVMGENNTLVWKYADAGHVCHLCHPNCTYGCTGPGL EGCPTNGPKIPSIATGMVGALLLLLVVALGIGLFM | Truncated EGFR (tEGFR) |
| 52 | RYWMS | CDR-H1; Kabat (clone 10) |
| 53 | EINPDSSTINYTPSLKD | CDR-H2; Kabat (clone 10) |
| 54 | HGYYWYFDV | CDR-H3; Kabat, Chothia, AbM (clone 10) |
| 55 | GFDFSRY | CDR-H1; Chothia (clone 10) |
| 56 | NPDSST | CDR-H2; Chothia (clone 10) |
| 57 | GFDFSRYWMS | CDR-H1; AbM (clone 10) |
| 58 | EINPDSSTIN | CDR-H2; AbM (clone 10) |
| 59 | RASQDISNYLN | CDR-L1; Kabat, Chothia, AbM (clone 10) |
| 60 | YTSRLHS | CDR-L2; Kabat, Chothia, AbM (clone 10) |

-continued

| Sequences | | |
|---|---|---|
| # | SEQUENCE | ANNOTATION |
| 61 | QQGNTLPYT | CDR-L3; Kabat, Chothia, AbM (clone 10) |
| 62 | EVKLLESGGGLVQPGGSLKLSCAASGFDFSRYWMSWVR QAPGKGLEWIGEINPDSSTINYTPSLKDKFIISRDNAKNTL YLQMSKVRSEDTALYYCARHGYYWYFDVWGAGTTVTV SS | VH (clone 10) |
| 63 | DIQMTQTTSSLSASLGDRVTISCRASQDISNYLNWYQQKP DGTVKLLIYYTSRLHSGVPSRFSGSGSGTDYSLTISNLEQE DIATYFCQQGNTLPYTFGGGTKLEIK | VL (clone 10) |
| 64 | EVKLLESGGGLVQPGGSLKLSCAASGFDFSRYWMSWVR QAPGKGLEWIGEINPDSSTINYTPSLKDKFIISRDNAKNTL YLQMSKVRSEDTALYYCARHGYYWYFDVWGAGTTVTV SSAKTTPPSVYPLAPGSAAQTNSMVTLGCLVKGYFPEPVT VTWNSGSLSSGVHTFPAVLQSDLYTLSSSVTVPSSTWPSE TVTCNVAHPASSTKVDKKIVPRDCGCKPCICTVPEVSSVFI FPPKPKDVLTITLTPKVTCVVVDISKDDPEVQFSWFVDDV EVHTAQTQPREEQFNSTFRSVSELPIMHQDWLNGKEFKC RVNSAAFPAPIEKTISKTKGRPKAPQVYTIPPPKEQMAKD KVSLTCMITDFFPEDITVEWQWNGQPAENYKNTQPIMDT DGSYFVYSKLNVQKSNWEAGNTFTCSVLHEGLHNHHTE KSLSHSPGK | Heavy chain (clone 10) |
| 65 | DIQMTQTTSSLSASLGDRVTISCRASQDISNYLNWYQQKP DGTVKLLIYYTSRLHSGVPSRFSGSGSGTDYSLTISNLEQE DIATYFCQQGNTLPYTFGGGTKLEIKRADAAPTVSIFPPSS EQLTSGGASVVCFLNNFYPKDINVKWKIDGSERQNGVLN SWTDQDSKDSTYSMSSTLTLTKDEYERHNSYTCEATHKT STSPIVKSFNRNEC | Light chain (clone 10) |
| 66 | GAGGTGAAGCTTCTCGAGTCTGGAGGTGGCCTGGTGCA GCCTGGAGGATCCCTGAAACTCTCCTGTGCAGCCTCAG GATTCGATTTTAGTAGATACTGGATGAGTTGGGTCCGG CAGGCTCCAGGGAAAGGGCTAGAATGGATTGGAGAAA TTAATCCAGATAGCAGTACGATAAACTATACGCCATCT CTAAAGGATAAATTCATCATCTCCAGAGACAACGCCAA AAATACGCTGTACCTGCAAATGAGCAAAGTGAGATCTG AGGACACAGCCCTTTATTACTGTGCAAGACATGGTTAC TACTGGTACTTCGATGTCTGGGGCGCAGGGACCACGGT CACCGTCTCCTCAGCCAAAACGACACCCCCATCTGTCT ATCCACTGGCCCCTGGATCTGCTGCCCAAACTAACTCC ATGGTGACCCTGGGATGCCTGGTCAAGGGCTATTTCCC TGAGCCAGTGACAGTGACCTGGAACTCTGGATCCCTGT CCAGCGGTGTGCACACCTTCCCAGCTGTCCTGCAGTCT GACCTCTACACTCTGAGCAGCTCAGTGACTGTCCCCTC CAGCACCTGGCCCAGCGAGACCGTCACCTGCAACGTTG CCCACCCGGCCAGCAGCACCAAGGTGGACAAGAAAAT TGTGCCCAGGGATTGTGGTTGTAAGCCTTGCATATGTA CAGTCCCAGAAGTATCATCTGTCTTCATCTTCCCCCCAA AGCCCAAGGATGTGCTCACCATTACTCTGACTCCTAAG GTCACGTGTGTTGTGGTAGACATCAGCAAGGATGATCC CGAGGTCCAGTTCAGCTGGTTTGTAGATGATGTGGAGG TGCACACAGCTCAGACGCAACCCCGGGAGGAGCAGTT CAACAGCACTTTCCGCTCAGTCAGTGAACTTCCCATCA TGCACCAGGACTGGCTCAATGGCAAGGAGTTCAAATGC AGGGTCAACAGTGCAGCTTTCCCTGCCCCCATCGAGAA AACCATCTCCAAAACCAAAGGCAGACCGAAGGCTCCA CAGGTGTACACCATTCCACCTCCCAAGGAGCAGATGGC CAAGGATAAAGTCAGTCTGACCTGCATGATAACAGACT TCTTCCCTGAAGACATTACTGTGGAGTGGCAGTGGAAT GGGCAGCCAGCGGAGAACTACAAGAACACTCAGCCCA TCATGGACACAGATGGCTCTTACTTCGTCTACAGCAAG CTCAATGTGCAGAAGAGCAACTGGGAGGCAGGAAATA CTTTCACCTGCTCTGTGTTACATGAGGGCCTGCACAAC CACCATACTGAGAAGAGCCTCTCCCACTCTCCTGGTAA ATGA | Heavy chain; nucleotides (clone 10) |
| 67 | GAGGTGAAGCTTCTCGAGTCTGGAGGTGGCCTGGTGCA GCCTGGAGGATCCCTGAAACTCTCCTGTGCAGCCTCAG GATTCGATTTTAGTAGATACTGGATGAGTTGGGTCCGG CAGGCTCCAGGGAAAGGGCTAGAATGGATTGGAGAAA TTAATCCAGATAGCAGTACGATAAACTATACGCCATCT | VH; nucleotides (clone 10) |

-continued

| | Sequences | |
|---|---|---|
| # | SEQUENCE | ANNOTATION |
| | CTAAAGGATAAATTCATCATCTCCAGAGACAACGCCAA<br>AAATACGCTGTACCTGCAAATGAGCAAAGTGAGATCTG<br>AGGACACAGCCCTTTATTACTGTGCAAGACATGGTTAC<br>TACTGGTACTTCGATGTCTGGGGCGCAGGGACCACGGT<br>CACCGTCTCCTCA | |
| 68 | GATATCCAGATGACACAGACTACATCCTCCCTGTCTGC<br>CTCTCTGGGAGACAGAGTCACCATCAGTTGCAGGGCAA<br>GTCAGGACATTAGCAATTATTTAAACTGGTATCAGCAG<br>AAACCAGATGGAACTGTTAAACTCCTGATCTACTACAC<br>ATCAAGATTACACTCAGGAGTCCCATCAAGGTTCAGTG<br>GCAGTGGGTCTGGAACAGATTATTCTCTCACCATTAGC<br>AACCTGGAGCAAGAAGATATTGCCACTTACTTTTGCCA<br>ACAGGGTAATACGCTTCCGTACACGTTCGGAGGGGGG<br>ACCAAGCTGGAAATAAAA | VL; nucleotides<br>(clone 10) |
| 69 | GATATCCAGATGACACAGACTACATCCTCCCTGTCTGC<br>CTCTCTGGGAGACAGAGTCACCATCAGTTGCAGGGCAA<br>GTCAGGACATTAGCAATTATTTAAACTGGTATCAGCAG<br>AAACCAGATGGAACTGTTAAACTCCTGATCTACTACAC<br>ATCAAGATTACACTCAGGAGTCCCATCAAGGTTCAGTG<br>GCAGTGGGTCTGGAACAGATTATTCTCTCACCATTAGC<br>AACCTGGAGCAAGAAGATATTGCCACTTACTTTTGCCA<br>ACAGGGTAATACGCTTCCGTACACGTTCGGAGGGGGG<br>ACCAAGCTGGAAATAAAACGGGCTGATGCTGCACCAA<br>CTGTATCCATCTTCCCACCATCCAGTGAGCAGTTAACA<br>TCTGGAGGTGCCTCAGTCGTGTGCTTCTTGAACAACTTC<br>TACCCCAAAGACATCAATGTCAAGTGGAAGATTGATGG<br>CAGTGAACGACAAAATGGCGTCCTGAACAGTTGGACT<br>GATCAGGACAGCAAAGACAGCACCTACAGCATGAGCA<br>GCACCCTCACGTTGACCAAGGACGAGTATGAACGACAT<br>AACAGCTATACCTGTGAGGCCACTCACAAGACATCAAC<br>TTCACCCATTGTCAAGAGCTTCAACAGGAATGAGTGTT<br>AG | Light chain;<br>nucleotides<br>(clone 10) |
| 70 | MDFGLIFFIVALLKGVQC | Leader sequence;<br>heavy chain<br>(clone 10) |
| 71 | ATGGATTTTGGGCTGATTTTTTTTATTGTTGCTCTTTTAA<br>AAGGGGTCCAGTGT | Leader sequence;<br>heavy chain,<br>nucleotides<br>(clone 10) |
| 72 | MSSAQFLGLLLLCFQGTRC | Leader sequence;<br>light chain<br>(clone 10) |
| 73 | ATGTCCTCTGCTCAGTTCCTTGGTCTCCTGTTGCTCTGT<br>TTTCAAGGTACCAGATGT | Leader sequence;<br>light chain,<br>nucleotides<br>(clone 10) |
| 74 | AYWIE | CDR-H1; Kabat<br>(clone 19) |
| 75 | EILPGSGITKYSEKFKG | CDR-H2; Kabat<br>(clone 19) |
| 76 | DYYSDNY | CDR-H3; Kabat,<br>Chothia, AbM<br>(clone 19) |
| 77 | GYTFTAY | CDR-H1;<br>Chothia<br>(clone 19) |
| 78 | LPGSGI | CDR-H2;<br>Chothia<br>(clone 19) |
| 79 | GYTFTAYWIE | CDR-H1; AbM<br>(clone 19) |

-continued

| # | SEQUENCE | ANNOTATION |
|---|---|---|
| | Sequences | |
| 80 | EILPGSGITK | CDR-H2; AbM (clone 19) |
| 81 | KSSQSLLDSDGRTYLN | CDR-L1; Kabat, Chothia, AbM (clone 19) |
| 82 | LVSKLDS | CDR-L2; Kabat, Chothia, AbM (clone 19) |
| 83 | WQGTLFPYT | CDR-L3; Kabat, Chothia, AbM (clone 19) |
| 84 | QVQLQQSGAELMKPGASVKLSCKATGYTFTAYWIEWVK QRPGHGLEWIGEILPGSGITKYSEKFKGKATFTADTSSNTA YMQLSSLTTEDSAIYYCARDYYSDNYWGQGTSVTVSS | VH (clone 19) |
| 85 | DVVMTQIPLTLSVTIGQPASISCKSSQSLLDSDGRTYLNWL LQRPGQSPKRLIYLVSKLDSGVPDRFTGSGSGTDFTLKISR VEAEDLGVYYCWQGTLFPYTFGGGTKLEIK | VL (clone 19) |
| 86 | QVQLQQSGAELMKPGASVKLSCKATGYTFTAYWIEWVK QRPGHGLEWIGEILPGSGITKYSEKFKGKATFTADTSSNTA YMQLSSLTTEDSAIYYCARDYYSDNYWGQGTSVTVSSAK TTPPSVYPLAPGCGDTTGSSVTLGCLVKGYFPESVTVTWN SGSLSSSVHTFPALLQSGLYTMSSSVTVPSSTWPSQTVTCS VAHPASSTTVDKKLEPSGPISTINPCPPCKECHKCPAPNLE GGPSVFIFPPNIKDVLMISLTPKVTCVVVDVSEDDPDVRIS WFVNNVEVHTAQTQTHREDYNSTIRVVSALPIQHQDWM SGKEFKCKVNNKDLPSPIERTISKIKGLVRAPQVYILPPPAE QLSRKDVSLTCLVVGFNPGDISVEWTSNGHTEENYKDTA PVLDSDGSYFIYSKLDIKTSKWEKTDSFSCNVRHEGLKNY YLKKTISRSPGK | Heavy chain (clone 19) |
| 87 | DVVMTQIPLTLSVTIGQPASISCKSSQSLLDSDGRTYLNWL LQRPGQSPKRLIYLVSKLDSGVPDRFTGSGSGTDFTLKISR VEAEDLGVYYCWQGTLFPYTFGGGTKLEIKRADAAPTVS IFPPSSEQLTSGGASVVCFLNNFYPKDINVKWKIDGSERQN GVLNSWTDQDSKDSTYSMSSTLTLTKDEYERHNSYTCEA THKTSTSPIVKSFNRNEC | Light chain (clone 19) |
| 88 | CAGGTTCAGCTGCAGCAGTCTGGAGCTGAGCTGATGAA GCCTGGGGCCTCAGTGAAGCTTTCCTGCAAGGCTACTG GCTACACATTCACTGCCTACTGGATAGAGTGGGTAAAG CAGAGGCCTGGACATGGCCTTGAGTGGATTGGAGAGA TTTTACCTGGAAGTGGTATTACTAAATACAGTGAGAAG TTCAAGGGCAAGGCCACATTCACTGCAGATACATCCTC CAATACAGCCTACATGCAACTCAGCAGCCTGACAACTG AGGACTCTGCCATCTATTACTGTGCAAGAGACTACTAT AGTGACAACTACTGGGGTCAAGGAACCTCAGTCACCGT CTCCTCAGCCAAAACAACACCCCCATCAGTCTATCCAC TGGCCCCTGGGTGTGGAGATACAACTGGTTCCTCTGTG ACTCTGGGATGCCTGGTCAAGGGCTACTTCCCTGAGTC AGTGACTGTGACTTGGAACTCTGGATCCCTGTCCAGCA GTGTGCACACCTTCCCAGCTCTCCTGCAGTCTGGACTCT ACACTATGAGCAGCTCAGTGACTGTCCCCTCCAGCACC TGGCCAAGTCAGACCGTCACCTGCAGCGTTGCTCACCC AGCCAGCAGCACCACGGTGGACAAAAAACTTGAGCCC AGCGGGCCCATTTCAACAATCAACCCCTGTCCTCCATG CAAGGAGTGTCACAAATGCCCAGCTCCTAACCTCGAGG GTGGACCATCCGTCTTCATCTTCCCTCCAAATATCAAG GATGTACTCATGATCTCCCTGACACCCAAGGTCACGTG TGTGGTGGTGGATGTGAGCGAGGATGACCCAGACGTCC GGATCAGCTGGTTTGTGAACAACGTGGAAGTACACACA GCTCAGACACAAACCCATAGAGAGGATTACAACAGTA CTATCCGGGTGGTCAGTGCCCTCCCCATCCAGCACCAG GACTGGATGAGTGGCAAGGAGTTCAAATGCAAGGTCA ACAACAAAGACCTCCCATCACCCATCGAGAGAACCATC TCAAAAATTAAAGGGCTAGTCAGAGCTCCACAAGTATA CATCTTGCCGCCACCAGCAGAGCAGTTGTCCAGGAAAG ATGTCAGTCTCACTTGCCTGGTCGTGGGCTTCAACCCTG GAGACATCAGTGTGGAGTGGACCAGCAATGGGCATAC | Heavy chain; nucleotides (clone 19) |

US 12,686,728 B2

195                                                                                      196

-continued

| # | SEQUENCE | ANNOTATION |
|---|----------|------------|

AGAGGAGAACTACAAGGACACCGCACCAGTCCTGGAC
TCTGACGGTTCTTACTTCATATACAGCAAGCTCGATAT
AAAAACAAGCAAGTGGGAGAAAACAGATTCCTTCTCA
TGCAACGTGAGACACGAGGGTCTGAAAAATTACTACCT
GAAGAAGACCATCTCCCGGTCTCCGGGTAAATGA

89  GATGTTGTGATGACCCAGATTCCACTCACTTTGTCGGTT    Light chain;
    ACCATTGGACAACCAGCCTCCATCTCTTGCAAGTCAAG    nucleotides
    TCAGAGCCTCTTAGATAGTGATGGAAGGACATATTTGA    (clone 19)
    ATTGGTTGTTACAGAGGCCAGGCCAGTCTCCAAAGCGC
    CTAATCTATCTGGTGTCTAAACTGGACTCTGGAGTCCCT
    GACAGGTTCACTGGCAGTGGATCAGGGACAGATTTCAC
    ATTGAAAATCAGCAGAGTGGAGGCTGAGGATTTGGGA
    GTTTATTATTGCTGGCAAGGTACACTTTTTCCGTACACG
    TTCGGAGGGGGGACCAAGCTGGAGATAAAACGGGCTG
    ATGCTGCACCAACTGTATCCATCTTCCCACCATCCAGT
    GAGCAGTTAACATCTGGAGGTGCCTCAGTCGTGTGCTT
    CTTGAACAACTTCTACCCCAAAGACATCAATGTCAAGT
    GGAAGATTGATGGCAGTGAACGACAAAATGGCGTCCT
    GAACAGTTGGACTGATCAGGACAGCAAAGACAGCACC
    TACAGCATGAGCAGCACCCTCACGTTGACCAAGGACG
    AGTATGAACGACATAACAGCTATACCTGTGAGGCCACT
    CACAAGACATCAACTTCACCCATTGTCAAGAGCTTCAA
    CAGGAATGAGTGTTAG 90  CAGGTTCAGCTGCAGCAGTCTGGAGCTGAGCTGATGAA    VH; nucleotides
    GCCTGGGGCCTCAGTGAAGCTTTCCTGCAAGGCTACTG    (clone 19)
    GCTACACATTCACTGCCTACTGGATAGAGTGGGTAAAG
    CAGAGGCCTGGACATGGCCTTGAGTGGATTGGAGAGA
    TTTTACCTGGAAGTGGTATTACTAAATACAGTGAGAAG
    TTCAAGGGCAAGGCCACATTCACTGCAGATACATCCTC
    CAATACAGCCTACATGCAACTCAGCAGCCTGACAACTG
    AGGACTCTGCCATCTATTACTGTGCAAGAGACTACTAT
    AGTGACAACTACTGGGGTCAAGGAACCTCAGTCACCGT
    CTCCTCA 91  GATGTTGTGATGACCCAGATTCCACTCACTTTGTCGGTT    VL; nucleotides
    ACCATTGGACAACCAGCCTCCATCTCTTGCAAGTCAAG    (clone 19)
    TCAGAGCCTCTTAGATAGTGATGGAAGGACATATTTGA
    ATTGGTTGTTACAGAGGCCAGGCCAGTCTCCAAAGCGC
    CTAATCTATCTGGTGTCTAAACTGGACTCTGGAGTCCCT
    GACAGGTTCACTGGCAGTGGATCAGGGACAGATTTCAC
    ATTGAAAATCAGCAGAGTGGAGGCTGAGGATTTGGGA
    GTTTATTATTGCTGGCAAGGTACACTTTTTCCGTACACG
    TTCGGAGGGGGGACCAAGCTGGAGATAAAA 92  MEWTWVFLFLLSVTAGVHS                        Leader sequence;
                                               heavy chain
                                               (clone 19)

93  ATGGAATGGACCTGGGTCTTTCTCTTCCTCCTGTCAGTA    Leader sequence;
    ACTGCAGGTGTCCACTCC                         heavy chain,
                                               nucleotides
                                               (clone 19)

94  MSPAQFLFLLVLWIRETNG                        Leader sequence;
                                               light chain
                                               (clone 19)

95  ATGAGTCCTGCCCAGTTCCTGTTTCTGTTAGTGCTCTGG    Leader sequence;
    ATTCGGGAAACCAACGGT                         light chain,
                                               nucleotides
                                               (clone 19)

96  MFWVLVVVGGVLACYSLLVTVAFIIFWV               CD28
                                               transmembrane
                                               domain 97  RSKRSRLLHSDYMNMTPRRPGPTRKHYQPYAPPRDFAAY    CD28 (amino
    RS                                         acids 180-220 of
                                               P10747) Homo
                                               sapiens

| # | SEQUENCE | ANNOTATION |
|---|---|---|
| 98 | RSKRSRGGHSDYMNMTPRRPGPTRKHYQPYAPPRDFAA YRS | CD28 (LL to GG) *Homo sapiens* |
| 99 | KRGRKKLLYIFKQPFMRPVQTTQEEDGCSCRFPEEEEGGC EL | 4-1BB (amino acids 214-255 of Q07011.1) *Homo sapiens* |
| 100 | RVKFSRSADAPAYQQGQNQLYNELNLGRREEYDVLDKR RGRDPEMGGKPRRKNPQEGLYNELQKDKMAEAYSEIGM KGERRRGKGHDGLYQGLSTATKDTYDALHMQALPPR | CD3-zeta derived intracellular signaling domain |
| 101 | ESKYGPPCPPCP | Spacer (IgG4hinge) |
| 102 | ESKYGPPCPPCPGQPREPQVYTLPPSQEEMTKNQVSLTCL VKGFYPSDIAVEWESNGQPENNYKTTPPVLDSDGSFFLYS RLTVDKSRWQEGNVFSCSVMHEALHNHYTQKSLSLSLG K | Hinge-C$_H$3 spacer(aa) |
| 103 | ESKYGPPCPPCPAPEFLGGPSVFLFPPKPKDTLMISRTPEVT CVVVDVSQEDPEVQFNWYVDGVEVHNAKTKPREEQFNS TYRVVSVLTVLHQDWLNGKEYKCKVSNKGLPSSIEKTIS KAKGQPREPQVYTLPPSQEEMTKNQVSLTCLVKGFYPSDI AVEWESNGQPENNYKTTPPVLDSDGSFFLYSRLTVDKSR WQEGNVFSCSVMHEALHNHYTQKSLSLSLGK | Hinge-C$_H$2-C$_H$3 spacer(aa) |
| 104 | DFYIN | CDR-H1; Kabat (clone 16) |
| 105 | WIFPRSGSTYYNEKFKG | CDR-H2; Kabat (clone 16) |
| 106 | GDGYSGAMDY | CDR-H3; Kabat, Chothia, AbM (clone 16) |
| 107 | GYTGTDF | CDR-H1; Chothia (clone 16) |
| 108 | FPRSGS | CDR-H2; Chothia (clone 16) |
| 109 | GYTGTDFYIN | CDR-H1; AbM (clone 16) |
| 110 | WIFPRSGSTY | CDR-H2; AbM (clone 16) |
| 111 | SASQGIRNYLN | CDR-L1; Kabat, Chothia, AbM (clone 16) |
| 112 | YTSNLHS | CDR-L2; Kabat, Chothia, AbM (clone 16) |
| 113 | QQYNNLPRT | CDR-L3; Kabat, Chothia, AbM (clone 16) |
| 114 | QVQLQQSGPELVKPGASVKISCKASGYTFTDFYINWVKQ RPGQGLEWI GWIFPRSGSTYYNEKFKGKATLSVDKSSITAYMLLSSLTS EDSAVYFCARGDGYSGAMDYWGQGTSVTVSS | VH (clone 16) |
| 115 | DIQMTQTTSSLSASLGDRVTISCSASQGIRNYLNWYQQKP DGTVKLLI YYTSNLHSGVPSRFSGSGSGTDYSLTISNLEPEDIATYYCQ QYNNLPRTFGGGTKLEIK | VL (clone 16) |

-continued

| | Sequences | |
|---|---|---|
| # | SEQUENCE | ANNOTATION |
| 116 | QVQLQQSGPELVKPGASVKISCKASGYTFTDFYINWVKQ RPGQGLEWIGWIFPRSGSTYYNEKFKGKATLSVDKSSITA YMLLSSLTSEDSAVYFCARGDGYSGAMDYWGQGTSVTV SSAKTTPPSVYPLAPGSAAQTNSMVTLGCLVKGYFPEPVT VTWNSGSLSSGVHTFPAVLQSDLYTLSSSVTVPSSTWPSQ TVTCNVAHPASSTKVDKKIVPRDCGCKPCICTVPEVSSVFI FPPKPKDVLTITLTPKVTCVVVDISKDDPEVQFSWFVDDV EVHTAQTKPREEQINSTFRSVSELPIMHQDWLNGKEFKCR VNSAAFPAPIEKTISKTKGRPKAPQVYTIPPPKEQMAKDK VSLTCMITNFFPEDITVEWQWNGQPAENYKNTQPIMDTD GSYFVYSKLNVQKSNWEAGNTFTCSVLHEGLHNHHTEKS LSHSPGK | Heavy chain (clone 16) |
| 117 | DIQMTQTTSSLSASLGDRVTISCSASQGIRNYLNWYQQKP DGTVKLLI YYTSNLHSGVPSRFSGSGSGTDYSLTISNLEPEDIATYYCQ QYNNLPRTFGGGTKLEIKRADAAPTVSIFPPSSEQLTSGGA SVVCFLNNFYPKDINVKWKIDGSERQNGVLNSWTDQDSK DSTYSMSSTLTLTKDEYERHNSYTCEATHKTSTSPIVKSFN RNEC | Light chain (clone 16) |
| 118 | CAGGTCCAGCTACAGCAGTCTGGACCTGAGCTGGTGAA GCCTGGGGCTTCAGTGAAGATATCCTGCAAGGCTTCTG GCTACACCTTCACTGACTTCTATATAAACTGGGTGAAG CAGAGGCCTGGACAGGGACTTGAGTGGATTGGATGGA TTTTTCCTAGAAGTGGTAGTACTTACTACAATGAGAAG TTCAAGGGCAAGGCCACACTTAGTGTAGACAAATCTTC CATCACAGCCTACATGTTGCTCAGCAGCCTGACCTCTG AGGACTCTGCGGTCTATTTCTGTGCAAGGGGGGATGGT TACTCTGGAGCTATGGACTACTGGGGTCAAGGAACCTC AGTCACCGTCTCCTCAGCCAAAACGACACCCCCATCTG TCTATCCACTGGCCCCTGGATCTGCTGCCCAAACTAAC TCCATGGTGACCCTGGGATGCCTGGTCAAGGGCTATTT CCCTGAGCCAGTGACAGTGACCTGGAACTCTGGATCCC TGTCCAGCGGTGTGCACACCTTCCCAGCTGTCCTGCAG TCTGACCTCTACACTCTGAGCAGCTCAGTGACTGTCCC CTCCAGCACCTGGCCCAGCCAGACCGTCACCTGCAACG TTGCCCACCCGGCCAGCAGCACCAAGGTGGACAAGAA AATTGTGCCCAGGGATTGTGGTTGTAAGCCTTGCATAT GTACAGTCCCAGAAGTATCATCTGTCTTCATCTTCCCCC CAAAGCCCAAGGATGTGCTCACCATTACTCTGACTCCT AAGGTCACGTGTGTTGTGGTAGACATCAGCAAGGATGA TCCCGAGGTCCAGTTCAGCTGGTTTGTAGATGATGTGG AGGTGCACACAGCTCAGACGAAACCCCGGGAGGAGCA GATCAACAGCACTTTCCGTTCAGTCAGTGAACTTCCCA TCATGCACCAGGACTGGCTCAATGGCAAGGAGTTCAAA TGCAGGGTCAACAGTGCAGCTTTCCCTGCCCCCATCGA GAAAACCATCTCCAAAACCAAAGGCAGACCGAAGGCT CCACAGGTGTACACCATTCCACCTCCCAAGGAGCAGAT GGCCAAGGATAAAGTCAGTCTGACCTGCATGATAACA AACTTCTTCCCTGAAGACATTACTGTGGAGTGGCAGTG GAATGGGCAGCCAGCGGAGAACTACAAGAACACTCAG CCCATCATGGACACAGATGGCTCTTACTTCGTCTACAG CAAGCTCAATGTGCAGAAGAGCAACTGGGAGGCAGGA AATACTTTCACCTGCTCTGTGTTACATGAGGGCCTGCA CAACCACCATACTGAGAAGAGCCTCTCCCACTCTCCTG GTAAATGA | Heavy chain; nucleotide (clone 16) |
| 119 | GATATCCAGATGACACAGACTACATCCTCCCTGTCTGC CTCTCTGGGAGACAGAGTCACCATCAGTTGCAGTGCAA GTCAGGGCATTAGAAATTATTTAAACTGGTATCAGCAG AAACCAGATGGAACTGTTAAACTCCTGATCTATTACAC ATCAAATTTACACTCAGGAGTCCCATCAAGGTTCAGTG GCAGTGGGTCTGGGACAGATTATTCTCTCACCATCAGC AACCTGGAACCTGAAGATATTGCCACTTACTATTGTCA GCAGTATAATAACCTTCCTCGGACGTTCGGTGGAGGCA CCAAGCTGGAAATCAAACGGGCTGATGCTGCACCAACT GTATCCATCTTCCCACCATCCAGTGAGCAGTTAACATC TGGAGGTGCCTCAGTCGTGTGCTTCTTGAACAACTTCT ACCCCAAAGACATCAATGTCAAGTGGAAGATTGATGG CAGTGAACGACAAAATGGCGTCCTGAACAGTTGGACT GATCAGGACAGCAAAGACAGCACCTACAGCATGAGCA GCACCCTCACGTTGACCAAGGACGAGTATGAACGACAT AACAGCTATACCTGTGAGGCCACTCACAAGACATCAAC | Light chain; nucleotide (clone 16) |

-continued

| # | SEQUENCE | ANNOTATION |
|---|---|---|
| | TTCACCCATTGTCAAGAGCTTCAACAGGAATGAGTGTT<br>AG | |
| 120 | CAGGTCCAGCTACAGCAGTCTGGACCTGAGCTGGTGAA<br>GCCTGGGGCTTCAGTGAAGATATCCTGCAAGGCTTCTG<br>GCTACACCTTCACTGACTTCTATATAAACTGGGTGAAG<br>CAGAGGCCTGGACAGGGACTTGAGTGGATTGGATGGA<br>TTTTTCCTAGAAGTGGTAGTACTTACTACAATGAGAAG<br>TTCAAGGGCAAGGCCACACTTAGTGTAGACAAATCTTC<br>CATCACAGCCTACATGTTGCTCAGCAGCCTGACCTCTG<br>AGGACTCTGCGGTCTATTTCTGTGCAAGGGGGGATGGT<br>TACTCTGGAGCTATGGACTACTGGGGTCAAGGAACCTC<br>AGTCACCGTCTCCTCA | VH; nucleotide<br>(clone 16) |
| 121 | GATATCCAGATGACACAGACTACATCCTCCCTGTCTGC<br>CTCTCTGGGAGACAGAGTCACCATCAGTTGCAGTGCAA<br>GTCAGGGCATTAGAAATTATTTAAACTGGTATCAGCAG<br>AAACCAGATGGAACTGTTAAACTCCTGATCTATTACAC<br>ATCAAATTTACACTCAGGAGTCCCATCAAGGTTCAGTG<br>GCAGTGGGTCTGGGACAGATTATTCTCTCACCATCAGC<br>AACCTGGAACCTGAAGATATTGCCACTTACTATTGTCA<br>GCAGTATAATAACCTTCCTCGGACGTTCGGTGGAGGCA<br>CCAAGCTGGAAATCAAA | VL; nucleotide<br>(clone 16) |
| 122 | MGWSWIFLFLLSGTAGVHC | Leader sequence;<br>heavy chain<br>(clone 16) |
| 123 | ATGGGATGGAGCTGGATCTTTCTCTTCCTCCTGTCAGG<br>AACTGCAGGTGTCCATTGC | Leader sequence;<br>heavy chain,<br>nucleotides<br>(clone 16) |
| 124 | MSSAQFLGLLLLCFQGTRC | Leader sequence;<br>light chain<br>(clone 16) |
| 125 | ATGTCCTCTGCTCAGTTCCTTGGTCTCCTGTTGCTCTGT<br>TTTCAAGGTACCAGATGT | Leader sequence;<br>light chain,<br>nucleotides<br>(clone 16) |
| 126 | GSGEGRGSLLTCGDVEENPGP | T2A peptide (aa) |
| 127 | LEGGGEGRGSLLTCGDVEENPGPR | T2A peptide (aa) |
| 128 | ATNFSLLKQAGDVEENPGP | P2A peptide (aa) |
| 129 | GSGATNFSLLKQAGDVEENPGP | P2A peptide (aa) |
| 130 | QCTNYALLKLAGDVESNPGP | E2A peptide (aa) |
| 131 | GSGQCTNYALLKLAGDVESNPGP | E2A peptide (aa) |
| 132 | VKQTLNFDLLKLAGDVESNPGP | F2A peptide (aa) |
| 133 | GSGVKQTLNFDLLKLAGDVESNPGP | F2A peptide (aa) |
| 134 | EGRGSLLTCGDVEENPGP | T2A peptide |

---

The invention claimed is:

1. An anti-idiotype antibody or antigen-binding fragment thereof that binds to an anti-BCMA target antibody or antigen-binding fragment thereof, wherein the anti-idiotype antibody or antigen-binding fragment comprises:

(a) a VH region comprising a CDR-H1, a CDR-H2, and a CDR-H3, respectively, comprising the CDR-H1, CDR-H2, and CDR-H3 amino acid sequences contained within the amino acid sequence of SEQ ID NO: 114; and a VL region comprising a CDR-L1, a CDR-L2, and a CDR-L3, respectively, comprising the CDR-L1, CDR-L2, and CDR-L3 amino acid sequences contained within the amino acid sequence of SEQ ID NO: 115.

2. The anti-idiotype antibody or antigen-binding fragment thereof of claim 1, wherein:

the VH region comprises a CDR-H1 comprising the amino acid sequence set forth in SEQ ID NO: 104, a CDR-H2 comprising the amino acid sequence set forth in SEQ ID NO: 105, and a CDR-H3 comprising the amino acid sequence set forth in SEQ ID NO: 106; and the VL region comprises a CDR-L1 comprising the amino acid sequence set forth in SEQ ID NO: 111, a CDR-L2 comprising the amino acid sequence set forth in SEQ ID NO: 112, and a CDR-L3 comprising the amino acid sequence set forth in SEQ ID NO: 113.

3. The anti-idiotype antibody or antigen-binding fragment thereof of claim 2, wherein the anti-idiotype antibody or antigen-binding fragment thereof comprises:

a heavy chain comprising an amino acid sequence having at least 90% sequence identity to the amino acid sequence set forth in SEQ ID NO: 116, and a light chain comprising an amino acid sequence having at least 90% sequence identity to the amino acid sequence set forth in SEQ ID NO: 117.

4. The anti-idiotype antibody or antigen-binding fragment thereof of claim 2, wherein the anti-idiotype antibody or antigen-binding fragment thereof comprises a heavy chain comprising the amino acid sequence set forth in SEQ ID NO: 116, and a light chain comprising the amino acid sequence set forth in SEQ ID NO: 117.

5. The anti-idiotype antibody or antigen-binding fragment thereof of claim 1, wherein:

the VH region comprises an amino acid sequence having at least 90% sequence identity to the amino acid sequence set forth in SEQ ID NO: 114, and the VL region comprises an amino acid sequence having at least 90% sequence identity to the amino acid sequence set forth in SEQ ID NO: 115.

6. The anti-idiotype antibody or antigen-binding fragment thereof of claim 1, wherein:

the VH region comprises the amino acid sequence set forth in SEQ ID NO: 114, and the VL region comprises the amino acid sequence set forth in SEQ ID NO: 115.

7. The anti-idiotype antibody or antigen-binding fragment thereof of claim 1, wherein the anti-BCMA target antibody or antigen-binding fragment thereof comprises a VH region comprising the amino acid sequence set forth in SEQ ID NO: 25, and a VL region comprising the amino acid sequence set forth in SEQ ID NO: 26.

8. The anti-idiotype antibody or antigen-binding fragment thereof of claim 7, wherein the anti-BCMA target antibody or antigen-binding fragment thereof is a single chain variable fragment (scFv) comprising the amino acid sequence set forth in SEQ ID NO: 27.

9. The anti-idiotype antibody or antigen-binding fragment thereof of claim 1, wherein the anti-idiotype antibody or antigen-binding fragment binds the anti-BCMA target antibody or antigen-binding fragment comprised within or included in an antigen-binding domain of an extracellular portion of a CAR.

10. The anti-idiotype antibody or antigen-binding fragment thereof of claim 1, wherein:

the anti-idiotype antibody or antigen-binding fragment thereof is an agonist of a CAR comprising the anti-BCMA target antibody or antigen-binding fragment thereof.

11. The anti-idiotype antibody or antigen-binding fragment thereof of claim 1, wherein binding of the anti-idiotype antibody or antigen-binding fragment thereof to the anti-BCMA target antibody or antigen-binding fragment thereof is not blocked by human BCMA or human BCMA-Fc.

12. A conjugate, comprising the anti-idiotype antibody or antigen-binding fragment thereof of claim 1 and a heterologous molecule or moiety.

13. A composition comprising the anti-idiotype antibody or antigen-binding fragment thereof of claim 1 or a conjugate comprising the anti-idiotype antibody or antigen-binding fragment thereof of claim 1 and a heterologous molecule or moiety.

14. A nucleic acid molecule(s) encoding the heavy chain and/or the light chain of the anti-idiotype antibody or antigen-binding fragment thereof of claim 1.

15. A vector, comprising the nucleic acid molecule(s) of claim 14.

16. A cell, comprising the nucleic acid molecule of claim 14.

17. A method of producing an anti-idiotype antibody or antigen-binding fragment thereof, comprising expressing the heavy and/or light chain encoded by the nucleic acid molecule(s) of claim 14 in a suitable host cell and recovering or isolating the antibody.

18. A method of detecting a target antibody or antigen-binding fragment thereof, comprising:

(a) contacting a composition comprising a target antibody or antigen-binding fragment thereof with the anti-idiotype antibody or antigen-binding fragment thereof of claim 1 or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof; and (b) detecting the anti-idiotype antibody bound to the target antibody or antigen-binding fragment thereof.

19. The method of claim 18, wherein the target antibody or antigen-binding fragment thereof is bound to a cell or expressed on the surface of a cell and the detecting in (b) comprises detecting cells bound with the anti-idiotype antibody or antigen-binding fragment thereof, and wherein the cell expresses on its surface a CAR comprising the target antibody or antigen-binding fragment thereof.

20. A method of selecting cells from a cell population, comprising:

(a) contacting a cell population expressing a CAR comprising a target antibody or antigen-binding fragment thereof or a cell bound to a target antibody or antigen-binding fragment thereof with the anti-idiotype antibody or antigen-binding fragment thereof of claim 1, or a conjugate comprising the anti-idiotype antibody or antigen-binding fragment thereof of claim 1 and a heterologous molecule or moiety, wherein the anti-idiotype antibody or antigen-binding fragment thereof specifically binds to the target antibody or antigen-binding fragment thereof; and (b) selecting cells bound with the anti-idiotype antibody or antigen-binding fragment thereof.

* * * * *

SEQUENCE LISTING

<160> NUMBER OF SEQ ID NOS: 134

<210> SEQ ID NO 1
<211> LENGTH: 5
<212> TYPE: PRT
<213> ORGANISM: Artificial Sequence
<220> FEATURE:
<223> OTHER INFORMATION: CDR-H1; Kabat (Target Antibody 1)

```
<400> SEQUENCE: 1

Ser Tyr Trp Ile Gly
1               5

<210> SEQ ID NO 2
<211> LENGTH: 17
<212> TYPE: PRT
<213> ORGANISM: Artificial Sequence
<220> FEATURE:
<223> OTHER INFORMATION: CDR-H2; Kabat (Target Antibody 1)

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 7
<212> TYPE: PRT
<213> ORGANISM: Artificial Sequence
<220> FEATURE:
<223> OTHER INFORMATION: CDR-H3; Kabat, Chothia; AbM (Target Antibody 1)

<400> SEQUENCE: 3

Tyr Ser Gly Ser Phe Asp Asn
1               5

<210> SEQ ID NO 4
<211> LENGTH: 7
<212> TYPE: PRT
<213> ORGANISM: Artificial Sequence
<220> FEATURE:
<223> OTHER INFORMATION: CDR-H1; Chothia (Target Antibody 1)

<400> SEQUENCE: 4

Gly Tyr Ser Phe Thr Ser Tyr
1               5

<210> SEQ ID NO 5
<211> LENGTH: 6
<212> TYPE: PRT
<213> ORGANISM: Artificial Sequence
<220> FEATURE:
<223> OTHER INFORMATION: CDR-H2; Chothia (Target Antibody 1)

<400> SEQUENCE: 5

Tyr Pro Gly Asp Ser Asp
1               5

<210> SEQ ID NO 6
<211> LENGTH: 10
<212> TYPE: PRT
<213> ORGANISM: Artificial Sequence
<220> FEATURE:
<223> OTHER INFORMATION: CDR-H1; AbM (Target Antibody 1)

<400> SEQUENCE: 6

Gly Tyr Ser Phe Thr Ser Tyr Trp Ile Gly
1               5                   10

<210> SEQ ID NO 7
<211> LENGTH: 10
<212> TYPE: PRT
<213> ORGANISM: Artificial Sequence
<220> FEATURE:
<223> OTHER INFORMATION: CDR-H2; AbM (Target Antibody 1)
```

-continued

<400> SEQUENCE: 7

Ile Ile Tyr Pro Gly Asp Ser Asp Thr Arg
1               5                   10

<210> SEQ ID NO 8
<211> LENGTH: 13
<212> TYPE: PRT
<213> ORGANISM: Artificial Sequence
<220> FEATURE:
<223> OTHER INFORMATION: CDR-L1; Kabat, Chothia, AbM (Target Antibody 1)

<400> SEQUENCE: 8

Ser Gly Thr Ser Ser Asn Ile Gly Ser His Ser Val Asn
1               5                   10

<210> SEQ ID NO 9
<211> LENGTH: 7
<212> TYPE: PRT
<213> ORGANISM: Artificial Sequence
<220> FEATURE:
<223> OTHER INFORMATION: CDR-L2; Kabat, Chothia, AbM (Target Antibody 1)

<400> SEQUENCE: 9

Thr Asn Asn Gln Arg Pro Ser
1               5

<210> SEQ ID NO 10
<211> LENGTH: 11
<212> TYPE: PRT
<213> ORGANISM: Artificial Sequence
<220> FEATURE:
<223> OTHER INFORMATION: CDR-L3; Kabat, Chothia, AbM (Target Antibody 1)

<400> SEQUENCE: 10

Ala Ala Trp Asp Gly Ser Leu Asn Gly Leu Val
1               5                   10

<210> SEQ ID NO 11
<211> LENGTH: 116
<212> TYPE: PRT
<213> ORGANISM: Artificial Sequence
<220> FEATURE:
<223> OTHER INFORMATION: VH (Target Antibody 1)

<400> SEQUENCE: 11

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115

```
<210> SEQ ID NO 12
<211> LENGTH: 111
<212> TYPE: PRT
<213> ORGANISM: Artificial Sequence
<220> FEATURE:
<223> OTHER INFORMATION: VL (Target Antibody 1)

<400> SEQUENCE: 12

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110

<210> SEQ ID NO 13
<211> LENGTH: 248
<212> TYPE: PRT
<213> ORGANISM: Artificial Sequence
<220> FEATURE:
<223> OTHER INFORMATION: scFv (Target Antibody 1)

<400> SEQUENCE: 13

Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly Ser
            100                 105                 110

Arg Gly Gly Gly Gly Ser Gly Gly Gly Ser Gly Gly Gly Gly Ser
        115                 120                 125

Leu Glu Met Ala Glu Val Gln Leu Val Gln Ser Gly Ala Glu Val Lys
    130                 135                 140

Lys Pro Gly Glu Ser Leu Lys Ile Ser Cys Lys Gly Ser Gly Tyr Ser
145                 150                 155                 160

Phe Thr Ser Tyr Trp Ile Gly Trp Val Arg Gln Met Pro Gly Lys Gly
                165                 170                 175

Leu Glu Trp Met Gly Ile Ile Tyr Pro Gly Asp Ser Asp Thr Arg Tyr
                180                 185                 190

Ser Pro Ser Phe Gln Gly His Val Thr Ile Ser Ala Asp Lys Ser Ile
            195                 200                 205
```

-continued

```
Ser Thr Ala Tyr Leu Gln Trp Ser Ser Leu Lys Ala Ser Asp Thr Ala
    210             215             220

Met Tyr Tyr Cys Ala Arg Tyr Ser Gly Ser Phe Asp Asn Trp Gly Gln
225             230             235             240

Gly Thr Leu Val Thr Val Ser Ser
                245

<210> SEQ ID NO 14
<211> LENGTH: 21
<212> TYPE: PRT
<213> ORGANISM: Artificial Sequence
<220> FEATURE:
<223> OTHER INFORMATION: Linker

<400> SEQUENCE: 14

Ser Arg Gly Gly Gly Gly Ser Gly Gly Gly Gly Ser Gly Gly Gly Gly
1               5                   10                  15

Ser Leu Glu Met Ala
            20

<210> SEQ ID NO 15
<211> LENGTH: 5
<212> TYPE: PRT
<213> ORGANISM: Artificial Sequence
<220> FEATURE:
<223> OTHER INFORMATION: CDR-H1; Kabat (Target Antibody 2)

<400> SEQUENCE: 15

Asp Tyr Tyr Val Tyr
1               5

<210> SEQ ID NO 16
<211> LENGTH: 17
<212> TYPE: PRT
<213> ORGANISM: Artificial Sequence
<220> FEATURE:
<223> OTHER INFORMATION: CDR-H2; Kabat (Target Antibody 2)

<400> SEQUENCE: 16

Trp Ile Asn Pro Asn Ser Gly Gly Thr Asn Tyr Ala Gln Lys Phe Gln
1               5                   10                  15

Gly

<210> SEQ ID NO 17
<211> LENGTH: 9
<212> TYPE: PRT
<213> ORGANISM: Artificial Sequence
<220> FEATURE:
<223> OTHER INFORMATION: CDR-H3; Kabat, Chothia; AbM (Target Antibody 2)

<400> SEQUENCE: 17

Ser Gln Arg Asp Gly Tyr Met Asp Tyr
1               5

<210> SEQ ID NO 18
<211> LENGTH: 7
<212> TYPE: PRT
<213> ORGANISM: Artificial Sequence
<220> FEATURE:
<223> OTHER INFORMATION: CDR-H1; Chothia (Target Antibody 2)

<400> SEQUENCE: 18

Gly Tyr Thr Phe Ile Asp Tyr
1               5
```

-continued

```
<210> SEQ ID NO 19
<211> LENGTH: 6
<212> TYPE: PRT
<213> ORGANISM: Artificial Sequence
<220> FEATURE:
<223> OTHER INFORMATION: CDR-H2; Chothia (Target Antibody 2)

<400> SEQUENCE: 19

Asn Pro Asn Ser Gly Gly
1               5

<210> SEQ ID NO 20
<211> LENGTH: 10
<212> TYPE: PRT
<213> ORGANISM: Artificial Sequence
<220> FEATURE:
<223> OTHER INFORMATION: CDR-H1; AbM (Target Antibody 2)

<400> SEQUENCE: 20

Gly Tyr Thr Phe Ile Asp Tyr Tyr Val Tyr
1               5                   10

<210> SEQ ID NO 21
<211> LENGTH: 10
<212> TYPE: PRT
<213> ORGANISM: Artificial Sequence
<220> FEATURE:
<223> OTHER INFORMATION: CDR-H2; AbM (Target Antibody 2)

<400> SEQUENCE: 21

Trp Ile Asn Pro Asn Ser Gly Gly Thr Asn
1               5                   10

<210> SEQ ID NO 22
<211> LENGTH: 8
<212> TYPE: PRT
<213> ORGANISM: Artificial Sequence
<220> FEATURE:
<223> OTHER INFORMATION: CDR-L1; Kabat, Chothia, AbM (Target Antibody 2)

<400> SEQUENCE: 22

Thr Gly Thr Ser Ser Asp Val Gly
1               5

<210> SEQ ID NO 23
<211> LENGTH: 7
<212> TYPE: PRT
<213> ORGANISM: Artificial Sequence
<220> FEATURE:
<223> OTHER INFORMATION: CDR-L2; Kabat, Chothia, AbM (Target Antibody 2)

<400> SEQUENCE: 23

Glu Asp Ser Lys Arg Pro Ser
1               5

<210> SEQ ID NO 24
<211> LENGTH: 10
<212> TYPE: PRT
<213> ORGANISM: Artificial Sequence
<220> FEATURE:
<223> OTHER INFORMATION: CDR-L3; Kabat, Chothia, AbM (Target Antibody 2)

<400> SEQUENCE: 24

Ser Ser Asn Thr Arg Ser Ser Thr Leu Val
1               5                   10
```

-continued

```
<210> SEQ ID NO 25
<211> LENGTH: 118
<212> TYPE: PRT
<213> ORGANISM: Artificial Sequence
<220> FEATURE:
<223> OTHER INFORMATION: VH (Target Antibody 2)

<400> SEQUENCE: 25

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115

<210> SEQ ID NO 26
<211> LENGTH: 105
<212> TYPE: PRT
<213> ORGANISM: Artificial Sequence
<220> FEATURE:
<223> OTHER INFORMATION: VL (Target Antibody 2)

<400> SEQUENCE: 26

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105

<210> SEQ ID NO 27
<211> LENGTH: 244
<212> TYPE: PRT
<213> ORGANISM: Artificial Sequence
<220> FEATURE:
<223> OTHER INFORMATION: scFv (Target Antibody 2)

<400> SEQUENCE: 27

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
```

-continued

```
              20              25              30

Gln Gln His Pro Gly Lys Ala Pro Lys Leu Met Ile Tyr Glu Asp Ser
        35              40              45

Lys Arg Pro Ser Gly Val Ser Asn Arg Phe Ser Gly Ser Lys Ser Gly
        50              55              60

Asn Thr Ala Ser Leu Thr Ile Ser Gly Leu Gln Ala Glu Asp Glu Ala
65              70              75              80

Asp Tyr Tyr Cys Ser Ser Asn Thr Arg Ser Ser Thr Leu Val Phe Gly
                85              90              95

Gly Gly Thr Lys Leu Thr Val Leu Gly Ser Arg Gly Gly Gly Gly Ser
            100             105             110

Gly Gly Gly Gly Ser Gly Gly Gly Gly Ser Leu Glu Met Ala Glu Val
            115             120             125

Gln Leu Val Gln Ser Gly Ala Glu Met Lys Lys Pro Gly Ala Ser Leu
        130             135             140

Lys Leu Ser Cys Lys Ala Ser Gly Tyr Thr Phe Ile Asp Tyr Tyr Val
145             150             155             160

Tyr Trp Met Arg Gln Ala Pro Gly Gln Gly Leu Glu Ser Met Gly Trp
                165             170             175

Ile Asn Pro Asn Ser Gly Gly Thr Asn Tyr Ala Gln Lys Phe Gln Gly
            180             185             190

Arg Val Thr Met Thr Arg Asp Thr Ser Ile Ser Thr Ala Tyr Met Glu
            195             200             205

Leu Ser Arg Leu Arg Ser Asp Asp Thr Ala Met Tyr Tyr Cys Ala Arg
        210             215             220

Ser Gln Arg Asp Gly Tyr Met Asp Tyr Trp Gly Gln Gly Thr Leu Val
225             230             235             240

Thr Val Ser Ser
```

```
<210> SEQ ID NO 28
<211> LENGTH: 5
<212> TYPE: PRT
<213> ORGANISM: Artificial Sequence
<220> FEATURE:
<223> OTHER INFORMATION: CDR-H1; Kabat (clone 15)

<400> SEQUENCE: 28

Ser Tyr Trp Met Asn
1               5

<210> SEQ ID NO 29
<211> LENGTH: 17
<212> TYPE: PRT
<213> ORGANISM: Artificial Sequence
<220> FEATURE:
<223> OTHER INFORMATION: CDR-H2; Kabat (clone 15)

<400> SEQUENCE: 29

Gln Ile Tyr Pro Gly Asn Gly Glu Thr Asn Asn Asn Gly Lys Phe Lys
1               5               10              15

Gly

<210> SEQ ID NO 30
<211> LENGTH: 7
<212> TYPE: PRT
<213> ORGANISM: Artificial Sequence
<220> FEATURE:
<223> OTHER INFORMATION: CDR-H3; Kabat, Chothia, AbM (clone 15)
```

-continued

```
<400> SEQUENCE: 30

Gly Gly Trp Tyr Phe Asp Val
1               5

<210> SEQ ID NO 31
<211> LENGTH: 7
<212> TYPE: PRT
<213> ORGANISM: Artificial Sequence
<220> FEATURE:
<223> OTHER INFORMATION: CDR-H1; Chothia (clone 15)

<400> SEQUENCE: 31

Gly Tyr Ala Phe Ser Ser Tyr
1               5

<210> SEQ ID NO 32
<211> LENGTH: 6
<212> TYPE: PRT
<213> ORGANISM: Artificial Sequence
<220> FEATURE:
<223> OTHER INFORMATION: CDR-H2; Chothia (clone 15)

<400> SEQUENCE: 32

Tyr Pro Gly Asn Gly Glu
1               5

<210> SEQ ID NO 33
<211> LENGTH: 10
<212> TYPE: PRT
<213> ORGANISM: Artificial Sequence
<220> FEATURE:
<223> OTHER INFORMATION: CDR-H1; AbM (clone 15)

<400> SEQUENCE: 33

Gly Tyr Ala Phe Ser Ser Tyr Trp Met Asn
1               5                   10

<210> SEQ ID NO 34
<211> LENGTH: 10
<212> TYPE: PRT
<213> ORGANISM: Artificial Sequence
<220> FEATURE:
<223> OTHER INFORMATION: CDR-H2; AbM (clone 15)

<400> SEQUENCE: 34

Gln Ile Tyr Pro Gly Asn Gly Glu Thr Asn
1               5                   10

<210> SEQ ID NO 35
<211> LENGTH: 11
<212> TYPE: PRT
<213> ORGANISM: Artificial Sequence
<220> FEATURE:
<223> OTHER INFORMATION: CDR-L1; Kabat, Chothia, AbM (clone 15)

<400> SEQUENCE: 35

Arg Ala Ser Glu Asn Ile Tyr Ser Tyr Leu Ala
1               5                   10

<210> SEQ ID NO 36
<211> LENGTH: 7
<212> TYPE: PRT
<213> ORGANISM: Artificial Sequence
<220> FEATURE:
<223> OTHER INFORMATION: CDR-L2; Kabat, Chothia, AbM (clone 15)

<400> SEQUENCE: 36
```

-continued

```
Asn Ala Tyr Thr Leu Ala Glu
1               5

<210> SEQ ID NO 37
<211> LENGTH: 9
<212> TYPE: PRT
<213> ORGANISM: Artificial Sequence
<220> FEATURE:
<223> OTHER INFORMATION: CDR-L3; Kabat, Chothia, AbM (clone 15)

<400> SEQUENCE: 37

Gln His His Tyr Gly Thr Pro Trp Thr
1               5

<210> SEQ ID NO 38
<211> LENGTH: 116
<212> TYPE: PRT
<213> ORGANISM: Artificial Sequence
<220> FEATURE:
<223> OTHER INFORMATION: VH (clone 15)

<400> SEQUENCE: 38

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asn Gly Glu Thr Asn Asn Asn Gly Lys Phe
    50                  55                  60

Lys Gly Lys Ala Thr Leu Thr Ala Asp Ile Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Trp Tyr Phe Asp Val Trp Gly Thr Gly Thr Thr Val
            100                 105                 110

Thr Val Ser Ser
        115

<210> SEQ ID NO 39
<211> LENGTH: 107
<212> TYPE: PRT
<213> ORGANISM: Artificial Sequence
<220> FEATURE:
<223> OTHER INFORMATION: VL (clone 15)

<400> SEQUENCE: 39

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro His Leu Leu Val
        35                  40                  45

Tyr Asn Ala Tyr Thr Leu Ala Glu Gly Val Pro Ser Arg Phe Ser Gly
    50                  55                  60

Ser Gly Ser Asp Thr Gln Phe Ser Leu Lys Ile Asn Ser Leu Gln Pro
65                  70                  75                  80

Glu Asp Phe Gly Asn Tyr Tyr Cys Gln His His Tyr Gly Thr Pro Trp
                85                  90                  95
```

-continued

```
Thr Phe Gly Gly Gly Thr Lys Val Glu Ile Lys
            100                 105

<210> SEQ ID NO 40
<211> LENGTH: 440
<212> TYPE: PRT
<213> ORGANISM: Artificial Sequence
<220> FEATURE:
<223> OTHER INFORMATION: Heavy chain (clone 15)

<400> SEQUENCE: 40

Gln Val Gln Leu Gln Gln Ser Gly Ala Glu Leu Val Lys Pro Gly Ala
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Lys Gly Leu Glu Trp Ile
        35                  40                  45

Gly Gln Ile Tyr Pro Gly Asn Gly Glu Thr Asn Asn Asn Gly Lys Phe
    50                  55                  60

Lys Gly Lys Ala Thr Leu Thr Ala Asp Ile Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Gly Trp Tyr Phe Asp Val Trp Gly Thr Gly Thr Thr Val
            100                 105                 110

Thr Val Ser Ser Ala Lys Thr Thr Pro Pro Ser Val Tyr Pro Leu Ala
            115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
            165                 170                 175

Leu Tyr Thr Leu Ser Ser Ser Val Thr Val Pro Ser Ser Thr Trp Pro
            180                 185                 190

Ser Gln Thr Val Thr Cys Asn Val Ala His Pro Ala Ser Ser Thr Lys
            195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
            245                 250                 255

Val Asp Ile Ser Lys Asp Asp Pro Glu Val Gln Phe Ser Trp Phe Val
            260                 265                 270

Asp Asp Val Glu Val His Thr Ala Gln Thr Lys Pro Arg Glu Glu Gln
            275                 280                 285

Ile Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
            325                 330                 335

Lys Ala Pro Gln Val Tyr Thr Ile Pro Pro Pro Lys Glu Gln Met Ala
            340                 345                 350
```

```
Lys Asp Lys Val Ser Leu Thr Cys Met Ile Thr Asn Phe Phe Pro Glu
        355                 360                 365

Asp Ile Thr Val Glu Trp Gln Trp Asn Gly Gln Pro Ala Glu Asn Tyr
        370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
                405                 410                 415

Thr Cys Ser Val Leu His Glu Gly Leu His Asn His His Thr Glu Lys
                420                 425                 430

Ser Leu Ser His Ser Pro Gly Lys
        435                 440

<210> SEQ ID NO 41
<211> LENGTH: 214
<212> TYPE: PRT
<213> ORGANISM: Artificial Sequence
<220> FEATURE:
<223> OTHER INFORMATION: Light chain (clone 15)

<400> SEQUENCE: 41

Asp Ile Gln Met Thr Gln Ser Pro Ala Ser Leu Ser Ala Ser Val Gly
1                 5                 10                 15

Glu Thr Val Thr Ile Thr Cys Arg Ala Ser Glu Asn Ile Tyr Ser Tyr
                20                 25                 30

Leu Ala Trp Tyr Gln Gln Lys Gln Gly Lys Ser Pro His Leu Leu Val
            35                 40                 45

Tyr Asn Ala Tyr Thr Leu Ala Glu Gly Val Pro Ser Arg Phe Ser Gly
        50                 55                 60

Ser Gly Ser Asp Thr Gln Phe Ser Leu Lys Ile Asn Ser Leu Gln Pro
65                 70                 75                 80

Glu Asp Phe Gly Asn Tyr Tyr Cys Gln His His Tyr Gly Thr Pro Trp
                85                 90                 95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
                180                 185                 190

Thr Cys Glu Ala Thr His Lys Thr Ser Thr Ser Pro Ile Val Lys Ser
            195                 200                 205

Phe Asn Arg Asn Glu Cys
    210

<210> SEQ ID NO 42
<211> LENGTH: 1323
<212> TYPE: DNA
<213> ORGANISM: Artificial Sequence
<220> FEATURE:
<223> OTHER INFORMATION: Heavy chain (clone 15)

<400> SEQUENCE: 42
```

-continued

```
caggttcagc tgcagcagtc tgggggctgag ctggtgaagc ctggggcctc agtgaagatt      60
tcctgcaaag cttctggcta cgcattcagt agctactgga tgaactgggt gaagcagagg     120
cctggaaagg gtcttgaatg gattggacag atttatcctg gaaatggtga aactaacaac     180 aacgaaagt tcaagggcaa ggccacactg actgcagaca tatcctccag cacagcctac     240
atgcagctca gcagcctgac atctgaggac tctgcggtct atttctgtgc aagagggggc     300
tggtacttcg atgtctgggg cacagggacc acggtcaccg tctcctcagc caaaacgaca     360
cccccatctg tctatccact ggcccctgga tctgctgccc aaactaactc catggtgacc     420
ctgggatgcc tggtcaaggg ctatttccct gagccagtga cagtgacctg gaactctgga     480
tccctgtcca gcggtgtgca caccttccca gctgtcctgc agtctgacct ctacactctg     540
agcagctcag tgactgtccc ctccagcacc tggcccagcc agaccgtcac ctgcaacgtt     600
gcccacccgg ccagcagcac caaggtggac aagaaaattg tgcccaggga ttgtggttgt     660
aagccttgca tatgtacagt cccagaagta tcatctgtct tcatcttccc cccaaagccc     720
aaggatgtgc tcaccattac tctgactcct aaggtcacgt gtgttgtggt agacatcagc     780
aaggatgatc ccgaggtcca gttcagctgg tttgtagatg atgtggaggt gcacacagct     840
cagacgaaac cccgggagga gcagatcaac agcactttcc gttcagtcag tgaacttccc     900
atcatgcacc aggactggct caatggcaag gagttcaaat gcagggtcaa cagtgcagct     960
ttccctgccc ccatcgagaa aaccatctcc aaaaccaaag gcagaccgaa ggctccacag    1020
gtgtacacca ttccacctcc caaggagcag atggccaagg ataaagtcag tctgacctgc    1080
atgataacaa acttcttccc tgaagacatt actgtggagt ggcagtggaa tgggcagcca    1140
gcggagaact acaagaacac tcagcccatc atggacacag atggctctta cttcgtctac    1200
agcaagctca atgtgcagaa gagcaactgg gaggcaggaa atactttcac ctgctctgtg    1260
ttacatgagg gcctgcacaa ccaccatact gagaagagcc tctcccactc tcctggtaaa    1320
tga                                                                   1323
```

<210> SEQ ID NO 43
<211> LENGTH: 645
<212> TYPE: DNA
<213> ORGANISM: Artificial Sequence
<220> FEATURE:
<223> OTHER INFORMATION: Light chain (clone 15)

<400> SEQUENCE: 43

```
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcacctcct ggtctataat gcatacacct tagcagaagg tgtgccatca     180
agattcagtg gcagtggatc agacacacag ttttctctga agatcaacag tctgcagcct     240
gaagattttg ggaattatta ctgtcaacat cattatggta ctccgtggac gttcggtgga     300
ggcaccaagg tggaaatcaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga cgacataac agctatacct gtgaggccac tcacaagaca     600
tcaacttcac ccattgtcaa gagcttcaac aggaatgagt gttag                     645
```

```
<210> SEQ ID NO 44
<211> LENGTH: 19
<212> TYPE: PRT
<213> ORGANISM: Artificial Sequence
<220> FEATURE:
<223> OTHER INFORMATION: Leader sequence; heavy chain (clone 15)

<400> SEQUENCE: 44

Met Glu Trp Pro Leu Ile Phe Leu Phe Leu Leu Ser Gly Thr Ala Gly
1               5                   10                  15

Val Gln Ser

<210> SEQ ID NO 45
<211> LENGTH: 57
<212> TYPE: DNA
<213> ORGANISM: Artificial Sequence
<220> FEATURE:
<223> OTHER INFORMATION: Leader sequence; heavy chain (clone 15)

<400> SEQUENCE: 45
atggaatggc ctttgatctt tctcttcctc ctgtcaggaa ctgcaggtgt ccaatcc          57

<210> SEQ ID NO 46
<211> LENGTH: 20
<212> TYPE: PRT
<213> ORGANISM: Artificial Sequence
<220> FEATURE:
<223> OTHER INFORMATION: Leader sequence; light chain (clone 15)

<400> SEQUENCE: 46

Met Ser Val Pro Thr Gln Val Leu Gly Leu Leu Leu Leu Trp Leu Thr
1               5                   10                  15

Gly Ala Arg Cys
            20

<210> SEQ ID NO 47
<211> LENGTH: 60
<212> TYPE: DNA
<213> ORGANISM: Artificial Sequence
<220> FEATURE:
<223> OTHER INFORMATION: Leader sequence; light chain (clone 15)

<400> SEQUENCE: 47
atgagtgtgc ccactcaggt cctggggttg ctgctgctgt ggcttacagg tgccagatgt          60

<210> SEQ ID NO 48
<211> LENGTH: 348
<212> TYPE: DNA
<213> ORGANISM: Artificial Sequence
<220> FEATURE:
<223> OTHER INFORMATION: VH (clone 15)

<400> SEQUENCE: 48
caggttcagc tgcagcagtc tggggctgag ctggtgaagc ctggggcctc agtgaagatt          60
tcctgcaaag cttctggcta cgcattcagt agctactgga tgaactgggt gaagcagagg         120
cctggaaagg gtcttgaatg gattggacag atttatcctg gaaatggtga aactaacaac         180
aacggaaagt tcaagggcaa ggccacactg actgcagaca tatcctccag cacagcctac         240
atgcagctca gcagcctgac atctgaggac tctgcggtct atttctgtgc aagagggggc         300
tggtacttcg atgtctgggg cacagggacc acggtcaccg tctcctca                     348

<210> SEQ ID NO 49
```

-continued

```
<211> LENGTH: 321
<212> TYPE: DNA
<213> ORGANISM: Artificial Sequence
<220> FEATURE:
<223> OTHER INFORMATION: VL (clone 15)

<400> SEQUENCE: 49
gacatccaga tgactcagtc tccagcctcc ctatctgcat ctgtgggaga aactgtcacc      60
atcacatgtc gagcaagtga gaatatttac agttatttag catggtatca gcagaaacag     120
ggaaaatctc ctcacctcct ggtctataat gcatacacct tagcagaagg tgtgccatca     180
agattcagtg gcagtggatc agacacacag ttttctctga agatcaacag tctgcagcct     240
gaagattttg ggaattatta ctgtcaacat cattatggta ctccgtggac gttcggtgga     300
ggcaccaagg tggaaatcaa a                                               321

<210> SEQ ID NO 50
<211> LENGTH: 228
<212> TYPE: PRT
<213> ORGANISM: Artificial Sequence
<220> FEATURE:
<223> OTHER INFORMATION: Spacer

<400> SEQUENCE: 50

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225

<210> SEQ ID NO 51
<211> LENGTH: 357
<212> TYPE: PRT
```

<213> ORGANISM: Artificial Sequence
<220> FEATURE:
<223> OTHER INFORMATION: Truncated EGFR (tEGFR)

<400> SEQUENCE: 51

```
Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
            115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
            195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
            355
```

<210> SEQ ID NO 52
<211> LENGTH: 5
<212> TYPE: PRT

-continued

```
<213> ORGANISM: Artificial Sequence
<220> FEATURE:
<223> OTHER INFORMATION: CDR-H1; Kabat (clone 10)

<400> SEQUENCE: 52

Arg Tyr Trp Met Ser
1               5

<210> SEQ ID NO 53
<211> LENGTH: 17
<212> TYPE: PRT
<213> ORGANISM: Artificial Sequence
<220> FEATURE:
<223> OTHER INFORMATION: CDR-H2; Kabat (clone 10)

<400> SEQUENCE: 53

Glu Ile Asn Pro Asp Ser Ser Thr Ile Asn Tyr Thr Pro Ser Leu Lys
1               5                   10                  15

Asp

<210> SEQ ID NO 54
<211> LENGTH: 9
<212> TYPE: PRT
<213> ORGANISM: Artificial Sequence
<220> FEATURE:
<223> OTHER INFORMATION: CDR-H3; Kabat, Chothia, AbM (clone 10)

<400> SEQUENCE: 54

His Gly Tyr Tyr Trp Tyr Phe Asp Val
1               5

<210> SEQ ID NO 55
<211> LENGTH: 7
<212> TYPE: PRT
<213> ORGANISM: Artificial Sequence
<220> FEATURE:
<223> OTHER INFORMATION: CDR-H1; Chothia (clone 10)

<400> SEQUENCE: 55

Gly Phe Asp Phe Ser Arg Tyr
1               5

<210> SEQ ID NO 56
<211> LENGTH: 6
<212> TYPE: PRT
<213> ORGANISM: Artificial Sequence
<220> FEATURE:
<223> OTHER INFORMATION: CDR-H2; Chothia (clone 10)

<400> SEQUENCE: 56

Asn Pro Asp Ser Ser Thr
1               5

<210> SEQ ID NO 57
<211> LENGTH: 10
<212> TYPE: PRT
<213> ORGANISM: Artificial Sequence
<220> FEATURE:
<223> OTHER INFORMATION: CDR-H1; AbM (clone 10)

<400> SEQUENCE: 57

Gly Phe Asp Phe Ser Arg Tyr Trp Met Ser
1               5                   10

<210> SEQ ID NO 58
<211> LENGTH: 10
```

-continued

```
<212> TYPE: PRT
<213> ORGANISM: Artificial Sequence
<220> FEATURE:
<223> OTHER INFORMATION: CDR-H2; AbM (clone 10)

<400> SEQUENCE: 58

Glu Ile Asn Pro Asp Ser Ser Thr Ile Asn
1               5                   10

<210> SEQ ID NO 59
<211> LENGTH: 11
<212> TYPE: PRT
<213> ORGANISM: Artificial Sequence
<220> FEATURE:
<223> OTHER INFORMATION: CDR-L1; Kabat, Chothia, AbM (clone 10)

<400> SEQUENCE: 59

Arg Ala Ser Gln Asp Ile Ser Asn Tyr Leu Asn
1               5                   10

<210> SEQ ID NO 60
<211> LENGTH: 7
<212> TYPE: PRT
<213> ORGANISM: Artificial Sequence
<220> FEATURE:
<223> OTHER INFORMATION: CDR-L2; Kabat, Chothia, AbM (clone 10)

<400> SEQUENCE: 60

Tyr Thr Ser Arg Leu His Ser
1               5

<210> SEQ ID NO 61
<211> LENGTH: 9
<212> TYPE: PRT
<213> ORGANISM: Artificial Sequence
<220> FEATURE:
<223> OTHER INFORMATION: CDR-L3; Kabat, Chothia, AbM (clone 10)

<400> SEQUENCE: 61

Gln Gln Gly Asn Thr Leu Pro Tyr Thr
1               5

<210> SEQ ID NO 62
<211> LENGTH: 118
<212> TYPE: PRT
<213> ORGANISM: Artificial Sequence
<220> FEATURE:
<223> OTHER INFORMATION: VH (clone 10)

<400> SEQUENCE: 62

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg His Gly Tyr Tyr Trp Tyr Phe Asp Val Trp Gly Ala Gly Thr
            100                 105                 110
```

```
Thr Val Thr Val Ser Ser
        115

<210> SEQ ID NO 63
<211> LENGTH: 107
<212> TYPE: PRT
<213> ORGANISM: Artificial Sequence
<220> FEATURE:
<223> OTHER INFORMATION: VL (clone 10)

<400> SEQUENCE: 63

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Lys
            100                 105

<210> SEQ ID NO 64
<211> LENGTH: 442
<212> TYPE: PRT
<213> ORGANISM: Artificial Sequence
<220> FEATURE:
<223> OTHER INFORMATION: Heavy chain (clone 10)

<400> SEQUENCE: 64

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg His Gly Tyr Tyr Trp Tyr Phe Asp Val Trp Gly Ala Gly Thr
            100                 105                 110

Thr Val Thr Val Ser Ser Ala Lys Thr Thr Pro Pro Ser Val Tyr Pro
        115                 120                 125

Leu Ala Pro Gly Ser Ala Ala Gln Thr Asn Ser Met Val Thr Leu Gly
    130                 135                 140

Cys Leu Val Lys Gly Tyr Phe Pro Glu Pro Val Thr Val Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Pro Ser Ser Thr
```

-continued

```
                180             185             190
Trp Pro Ser Glu Thr Val Thr Cys Asn Val Ala His Pro Ala Ser Ser
            195             200             205
Thr Lys Val Asp Lys Lys Ile Val Pro Arg Asp Cys Gly Cys Lys Pro
        210             215             220
Cys Ile Cys Thr Val Pro Glu Val Ser Ser Val Phe Ile Phe Pro Pro
225             230             235             240
Lys Pro Lys Asp Val Leu Thr Ile Thr Leu Thr Pro Lys Val Thr Cys
            245             250             255
Val Val Val Asp Ile Ser Lys Asp Asp Pro Glu Val Gln Phe Ser Trp
            260             265             270
Phe Val Asp Asp Val Glu Val His Thr Ala Gln Thr Gln Pro Arg Glu
        275             280             285
Glu Gln Phe Asn Ser Thr Phe Arg Ser Val Ser Glu Leu Pro Ile Met
        290             295             300
His Gln Asp Trp Leu Asn Gly Lys Glu Phe Lys Cys Arg Val Asn Ser
305             310             315             320
Ala Ala Phe Pro Ala Pro Ile Glu Lys Thr Ile Ser Lys Thr Lys Gly
            325             330             335
Arg Pro Lys Ala Pro Gln Val Tyr Thr Ile Pro Pro Pro Lys Glu Gln
            340             345             350
Met Ala Lys Asp Lys Val Ser Leu Thr Cys Met Ile Thr Asp Phe Phe
            355             360             365
Pro Glu Asp Ile Thr Val Glu Trp Gln Trp Asn Gly Gln Pro Ala Glu
        370             375             380
Asn Tyr Lys Asn Thr Gln Pro Ile Met Asp Thr Asp Gly Ser Tyr Phe
385             390             395             400
Val Tyr Ser Lys Leu Asn Val Gln Lys Ser Asn Trp Glu Ala Gly Asn
            405             410             415
Thr Phe Thr Cys Ser Val Leu His Glu Gly Leu His Asn His His Thr
            420             425             430
Glu Lys Ser Leu Ser His Ser Pro Gly Lys
        435             440
```

```
<210> SEQ ID NO 65
<211> LENGTH: 214
<212> TYPE: PRT
<213> ORGANISM: Artificial Sequence
<220> FEATURE:
<223> OTHER INFORMATION: Light chain (clone 10)

<400> SEQUENCE: 65
```

```
Asp Ile Gln Met Thr Gln Thr Thr Ser Ser Leu Ser Ala Ser Leu Gly
1               5               10              15
Asp Arg Val Thr Ile Ser Cys Arg Ala Ser Gln Asp Ile Ser Asn Tyr
            20              25              30
Leu Asn Trp Tyr Gln Gln Lys Pro Asp Gly Thr Val Lys Leu Leu Ile
        35              40              45
Tyr Tyr Thr Ser Arg Leu His Ser Gly Val Pro Ser Arg Phe Ser Gly
    50              55              60
Ser Gly Ser Gly Thr Asp Tyr Ser Leu Thr Ile Ser Asn Leu Glu Gln
65              70              75              80
Glu Asp Ile Ala Thr Tyr Phe Cys Gln Gln Gly Asn Thr Leu Pro Tyr
                85              90              95
Thr Phe Gly Gly Gly Thr Lys Leu Glu Ile Lys Arg Ala Asp Ala Ala
```

-continued

```
            100              105              110
Pro Thr Val Ser Ile Phe Pro Pro Ser Ser Glu Gln Leu Thr Ser Gly
        115              120              125

Gly Ala Ser Val Val Cys Phe Leu Asn Asn Phe Tyr Pro Lys Asp Ile
    130              135              140

Asn Val Lys Trp Lys Ile Asp Gly Ser Glu Arg Gln Asn Gly Val Leu
145              150              155              160

Asn Ser Trp Thr Asp Gln Asp Ser Lys Asp Ser Thr Tyr Ser Met Ser
            165              170              175

Ser Thr Leu Thr Leu Thr Lys Asp Glu Tyr Glu Arg His Asn Ser Tyr
            180              185              190

Thr Cys Glu Ala Thr His Lys Thr Ser Thr Ser Pro Ile Val Lys Ser
        195              200              205

Phe Asn Arg Asn Glu Cys
    210
```

```
<210> SEQ ID NO 66
<211> LENGTH: 1329
<212> TYPE: DNA
<213> ORGANISM: Artificial Sequence
<220> FEATURE:
<223> OTHER INFORMATION: Heavy chain (clone 10)

<400> SEQUENCE: 66
gaggtgaagc ttctcgagtc tggaggtggc ctggtgcagc ctggaggatc cctgaaactc        60
tcctgtgcag cctcaggatt cgattttagt agatactgga tgagttgggt ccggcaggct       120
ccagggaaag ggctagaatg gattggagaa attaatccag atagcagtac gataaactat       180
acgccatctc taaaggataa attcatcatc tccagagaca cgccaaaaa tacgctgtac        240 ctgcaaatga gcaaagtgag atctgaggac acagcccttt attactgtgc aagacatggt       300
tactactggt acttcgatgt ctggggcgca gggaccacgg tcaccgtctc ctcagccaaa       360
acgacacccc catctgtcta tccactggcc cctggatctg ctgcccaaac taactccatg       420
gtgaccctgg gatgcctggt caagggctat ttccctgagc cagtgacagt gacctggaac       480
tctggatccc tgtccagcgg tgtgcacacc ttcccagctg tcctgcagtc tgacctctac       540
actctgagca gctcagtgac tgtcccctcc agcacctggc ccagcgagac cgtcacctgc       600
aacgttgccc accggccag cagcaccaag gtggacaaga aaattgtgcc cagggattgt        660
ggttgtaagc cttgcatatg tacagtccca gaagtatcat ctgtcttcat cttcccccca       720
aagcccaagg atgtgctcac cattactctg actcctaagg tcacgtgtgt tgtggtagac       780
atcagcaagg atgatcccga ggtccagttc agctggtttg tagatgatgt ggaggtgcac       840
acagctcaga cgcaacccg ggaggagcag ttcaacagca ctttccgctc agtcagtgaa       900
cttcccatca tgcaccagga ctggctcaat ggcaaggagt tcaaatgcag ggtcaacagt       960
gcagctttcc ctgcccccat cgagaaaacc atctccaaaa ccaaaggcag accgaaggct      1020
ccacaggtgt acaccattcc acctcccaag gagcagatgg ccaaggataa agtcagtctg      1080
acctgcatga taacagactt cttccctgaa gacattactg tggagtggca gtggaatggg      1140
cagccagcgg agaactacaa gaacactcag cccatcatgg acacagatgg ctcttacttc      1200
gtctacagca agctcaatgt gcagaagagc aactgggagg caggaaatac tttcacctgc      1260
tctgtgttac atgagggcct gcacaaccac catactgaga gagcctctc ccactctcct      1320 ggtaaatga                                                             1329
```

-continued

<210> SEQ ID NO 67
<211> LENGTH: 354
<212> TYPE: DNA
<213> ORGANISM: Artificial Sequence
<220> FEATURE:
<223> OTHER INFORMATION: VH (clone 10)

<400> SEQUENCE: 67

```
gaggtgaagc ttctcgagtc tggaggtggc ctggtgcagc ctggaggatc cctgaaactc      60
tcctgtgcag cctcaggatt cgattttagt agatactgga tgagttgggt ccggcaggct     120
ccagggaaag ggctagaatg gattggagaa attaatccag atagcagtac gataaactat     180
acgccatctc taaaggataa attcatcatc tccagagaca acgccaaaaa tacgctgtac     240
ctgcaaatga gcaaagtgag atctgaggac acagcccttt attactgtgc aagacatggt     300
tactactggt acttcgatgt ctggggcgca gggaccacgg tcaccgtctc ctca           354
```

<210> SEQ ID NO 68
<211> LENGTH: 321
<212> TYPE: DNA
<213> ORGANISM: Artificial Sequence
<220> FEATURE:
<223> OTHER INFORMATION: VL (clone 10)

<400> SEQUENCE: 68

```
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggaaataaa a                                              321
```

<210> SEQ ID NO 69
<211> LENGTH: 645
<212> TYPE: DNA
<213> ORGANISM: Artificial Sequence
<220> FEATURE:
<223> OTHER INFORMATION: Light chain (clone 10)

<400> SEQUENCE: 69

```
gatatccaga tgacacagac tacatcctcc ctgtctgcct ctctgggaga cagagtcacc      60
atcagttgca gggcaagtca ggacattagc aattatttaa actggtatca gcagaaacca     120
gatggaactg ttaaactcct gatctactac acatcaagat tacactcagg agtcccatca     180
aggttcagtg gcagtgggtc tggaacagat tattctctca ccattagcaa cctggagcaa     240
gaagatattg ccacttactt ttgccaacag ggtaatacgc ttccgtacac gttcggaggg     300
gggaccaagc tggaaataaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga acgacataac agctatacct gtgaggccac tcacaagaca     600
tcaacttcac ccattgtcaa gagcttcaac aggaatgagt gttag                     645
```

<210> SEQ ID NO 70
<211> LENGTH: 18

```
<212> TYPE: PRT
<213> ORGANISM: Artificial Sequence
<220> FEATURE:
<223> OTHER INFORMATION: Leader sequence; heavy chain (clone 10)

<400> SEQUENCE: 70

Met Asp Phe Gly Leu Ile Phe Phe Ile Val Ala Leu Leu Lys Gly Val
1               5                   10                  15

Gln Cys

<210> SEQ ID NO 71
<211> LENGTH: 54
<212> TYPE: DNA
<213> ORGANISM: Artificial Sequence
<220> FEATURE:
<223> OTHER INFORMATION: Leader sequence; heavy chain (clone 10)

<400> SEQUENCE: 71
atggattttg ggctgatttt ttttattgtt gctcttttaa aaggggtcca gtgt          54

<210> SEQ ID NO 72
<211> LENGTH: 19
<212> TYPE: PRT
<213> ORGANISM: Artificial Sequence
<220> FEATURE:
<223> OTHER INFORMATION: Leader sequence; light chain (clone 10)

<400> SEQUENCE: 72

Met Ser Ser Ala Gln Phe Leu Gly Leu Leu Leu Leu Cys Phe Gln Gly
1               5                   10                  15

Thr Arg Cys

<210> SEQ ID NO 73
<211> LENGTH: 57
<212> TYPE: DNA
<213> ORGANISM: Artificial Sequence
<220> FEATURE:
<223> OTHER INFORMATION: Leader sequence; light chain (clone 10)

<400> SEQUENCE: 73
atgtcctctg ctcagttcct tggtctcctg ttgctctgtt ttcaaggtac cagatgt          57

<210> SEQ ID NO 74
<211> LENGTH: 5
<212> TYPE: PRT
<213> ORGANISM: Artificial Sequence
<220> FEATURE:
<223> OTHER INFORMATION: CDR-H1; Kabat (clone 19)

<400> SEQUENCE: 74

Ala Tyr Trp Ile Glu
1               5

<210> SEQ ID NO 75
<211> LENGTH: 17
<212> TYPE: PRT
<213> ORGANISM: Artificial Sequence
<220> FEATURE:
<223> OTHER INFORMATION: CDR-H2; Kabat (clone 19)

<400> SEQUENCE: 75

Glu Ile Leu Pro Gly Ser Gly Ile Thr Lys Tyr Ser Glu Lys Phe Lys
1               5                   10                  15

Gly
```

-continued

<210> SEQ ID NO 76
<211> LENGTH: 7
<212> TYPE: PRT
<213> ORGANISM: Artificial Sequence
<220> FEATURE:
<223> OTHER INFORMATION: CDR-H3; Kabat, Chothia, AbM (clone 19)

<400> SEQUENCE: 76

Asp Tyr Tyr Ser Asp Asn Tyr
1               5

<210> SEQ ID NO 77
<211> LENGTH: 7
<212> TYPE: PRT
<213> ORGANISM: Artificial Sequence
<220> FEATURE:
<223> OTHER INFORMATION: CDR-H1; Chothia (clone 19)

<400> SEQUENCE: 77

Gly Tyr Thr Phe Thr Ala Tyr
1               5

<210> SEQ ID NO 78
<211> LENGTH: 6
<212> TYPE: PRT
<213> ORGANISM: Artificial Sequence
<220> FEATURE:
<223> OTHER INFORMATION: CDR-H2; Chothia (clone 19)

<400> SEQUENCE: 78

Leu Pro Gly Ser Gly Ile
1               5

<210> SEQ ID NO 79
<211> LENGTH: 10
<212> TYPE: PRT
<213> ORGANISM: Artificial Sequence
<220> FEATURE:
<223> OTHER INFORMATION: CDR-H1; AbM (clone 19)

<400> SEQUENCE: 79

Gly Tyr Thr Phe Thr Ala Tyr Trp Ile Glu
1               5                   10

<210> SEQ ID NO 80
<211> LENGTH: 10
<212> TYPE: PRT
<213> ORGANISM: Artificial Sequence
<220> FEATURE:
<223> OTHER INFORMATION: CDR-H2; AbM (clone 19)

<400> SEQUENCE: 80

Glu Ile Leu Pro Gly Ser Gly Ile Thr Lys
1               5                   10

<210> SEQ ID NO 81
<211> LENGTH: 16
<212> TYPE: PRT
<213> ORGANISM: Artificial Sequence
<220> FEATURE:
<223> OTHER INFORMATION: CDR-L1; Kabat, Chothia, AbM (clone 19)

<400> SEQUENCE: 81

Lys Ser Ser Gln Ser Leu Leu Asp Ser Asp Gly Arg Thr Tyr Leu Asn
1               5                   10                  15

-continued

```
<210> SEQ ID NO 82
<211> LENGTH: 7
<212> TYPE: PRT
<213> ORGANISM: Artificial Sequence
<220> FEATURE:
<223> OTHER INFORMATION: CDR-L2; Kabat, Chothia, AbM (clone 19)

<400> SEQUENCE: 82

Leu Val Ser Lys Leu Asp Ser
1               5

<210> SEQ ID NO 83
<211> LENGTH: 9
<212> TYPE: PRT
<213> ORGANISM: Artificial Sequence
<220> FEATURE:
<223> OTHER INFORMATION: CDR-L3; Kabat, Chothia, AbM (clone 19)

<400> SEQUENCE: 83

Trp Gln Gly Thr Leu Phe Pro Tyr Thr
1               5

<210> SEQ ID NO 84
<211> LENGTH: 116
<212> TYPE: PRT
<213> ORGANISM: Artificial Sequence
<220> FEATURE:
<223> OTHER INFORMATION: VH (clone 19)

<400> SEQUENCE: 84

Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Thr Phe Thr Ala Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Ile Thr Lys Tyr Ser Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Asp Tyr Tyr Ser Asp Asn Tyr Trp Gly Gln Gly Thr Ser Val
            100                 105                 110

Thr Val Ser Ser
        115

<210> SEQ ID NO 85
<211> LENGTH: 112
<212> TYPE: PRT
<213> ORGANISM: Artificial Sequence
<220> FEATURE:
<223> OTHER INFORMATION: VL (clone 19)

<400> SEQUENCE: 85

Asp Val Val Met Thr Gln Ile Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Arg Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
```

-continued

```
                50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr Leu Phe Pro Tyr Thr Phe Gly Gly Gly Thr Lys Leu Glu Ile Lys
            100                 105                 110

<210> SEQ ID NO 86
<211> LENGTH: 452
<212> TYPE: PRT
<213> ORGANISM: Artificial Sequence
<220> FEATURE:
<223> OTHER INFORMATION: Heavy chain (clone 19)

<400> SEQUENCE: 86

Gln Val Gln Leu Gln Gln Ser Gly Ala Glu Leu Met Lys Pro Gly Ala
1                   5                   10                  15

Ser Val Lys Leu Ser Cys Lys Ala Thr Gly Tyr Thr Phe Thr Ala Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Ile Thr Lys Tyr Ser Glu Lys Phe
        50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Asp Tyr Tyr Ser Asp Asn Tyr Trp Gly Gln Gly Thr Ser Val
            100                 105                 110

Thr Val Ser Ser Ala Lys Thr Thr Pro Pro Ser Val Tyr Pro Leu Ala
            115                 120                 125

Pro Gly Cys Gly Asp Thr Thr Gly Ser Ser Val Thr Leu Gly Cys Leu
        130                 135                 140

Val Lys Gly Tyr Phe Pro Glu Ser Val Thr Val Thr Trp Asn Ser Gly
145                 150                 155                 160

Ser Leu Ser Ser Ser Val His Thr Phe Pro Ala Leu Leu Gln Ser Gly
                165                 170                 175

Leu Tyr Thr Met Ser Ser Ser Val Thr Val Pro Ser Ser Thr Trp Pro
            180                 185                 190

Ser Gln Thr Val Thr Cys Ser Val Ala His Pro Ala Ser Ser Thr Thr
            195                 200                 205

Val Asp Lys Lys Leu Glu Pro Ser Gly Pro Ile Ser Thr Ile Asn Pro
        210                 215                 220

Cys Pro Pro Cys Lys Glu Cys His Lys Cys Pro Ala Pro Asn Leu Glu
225                 230                 235                 240

Gly Gly Pro Ser Val Phe Ile Phe Pro Pro Asn Ile Lys Asp Val Leu
                245                 250                 255

Met Ile Ser Leu Thr Pro Lys Val Thr Cys Val Val Val Asp Val Ser
                260                 265                 270

Glu Asp Asp Pro Asp Val Arg Ile Ser Trp Phe Val Asn Asn Val Glu
            275                 280                 285

Val His Thr Ala Gln Thr Gln Thr His Arg Glu Asp Tyr Asn Ser Thr
        290                 295                 300

Ile Arg Val Val Ser Ala Leu Pro Ile Gln His Gln Asp Trp Met Ser
```

-continued

```
305            310            315            320

Gly Lys Glu Phe Lys Cys Lys Val Asn Asn Lys Asp Leu Pro Ser Pro
              325            330            335

Ile Glu Arg Thr Ile Ser Lys Ile Lys Gly Leu Val Arg Ala Pro Gln
              340            345            350

Val Tyr Ile Leu Pro Pro Pro Ala Glu Gln Leu Ser Arg Lys Asp Val
              355            360            365

Ser Leu Thr Cys Leu Val Val Gly Phe Asn Pro Gly Asp Ile Ser Val
    370            375            380

Glu Trp Thr Ser Asn Gly His Thr Glu Glu Asn Tyr Lys Asp Thr Ala
385            390            395            400

Pro Val Leu Asp Ser Asp Gly Ser Tyr Phe Ile Tyr Ser Lys Leu Asp
              405            410            415

Ile Lys Thr Ser Lys Trp Glu Lys Thr Asp Ser Phe Ser Cys Asn Val
              420            425            430

Arg His Glu Gly Leu Lys Asn Tyr Tyr Leu Lys Lys Thr Ile Ser Arg
              435            440            445

Ser Pro Gly Lys
    450

<210> SEQ ID NO 87
<211> LENGTH: 219
<212> TYPE: PRT
<213> ORGANISM: Artificial Sequence
<220> FEATURE:
<223> OTHER INFORMATION: Light chain (clone 19)

<400> SEQUENCE: 87

Asp Val Val Met Thr Gln Ile Pro Leu Thr Leu Ser Val Thr Ile Gly
1              5              10             15

Gln Pro Ala Ser Ile Ser Cys Lys Ser Ser Gln Ser Leu Leu Asp Ser
              20             25             30

Asp Gly Arg Thr Tyr Leu Asn Trp Leu Leu Gln Arg Pro Gly Gln Ser
              35             40             45

Pro Lys Arg Leu Ile Tyr Leu Val Ser Lys Leu Asp Ser Gly Val Pro
    50             55             60

Asp Arg Phe Thr Gly Ser Gly Ser Gly Thr Asp Phe Thr Leu Lys Ile
65             70             75             80

Ser Arg Val Glu Ala Glu Asp Leu Gly Val Tyr Tyr Cys Trp Gln Gly
              85             90             95

Thr Leu Phe Pro Tyr Thr Phe Gly Gly Gly Thr Lys Leu Glu Ile Lys
              100            105            110

Arg Ala Asp Ala Ala Pro Thr Val Ser Ile Phe Pro Pro Ser Ser Glu
              115            120            125

Gln Leu Thr Ser Gly Gly Ala Ser Val Val Cys Phe Leu Asn Asn Phe
    130            135            140

Tyr Pro Lys Asp Ile Asn Val Lys Trp Lys Ile Asp Gly Ser Glu Arg
145            150            155            160

Gln Asn Gly Val Leu Asn Ser Trp Thr Asp Gln Asp Ser Lys Asp Ser
              165            170            175

Thr Tyr Ser Met Ser Ser Thr Leu Thr Leu Thr Lys Asp Glu Tyr Glu
              180            185            190

Arg His Asn Ser Tyr Thr Cys Glu Ala Thr His Lys Thr Ser Thr Ser
              195            200            205

Pro Ile Val Lys Ser Phe Asn Arg Asn Glu Cys
```

-continued

```
      210                 215
```

```
<210> SEQ ID NO 88
<211> LENGTH: 1359
<212> TYPE: DNA
<213> ORGANISM: Artificial Sequence
<220> FEATURE:
<223> OTHER INFORMATION: Heavy chain (clone 19)

<400> SEQUENCE: 88
caggttcagc tgcagcagtc tggagctgag ctgatgaagc ctgggggcctc agtgaagctt      60 tcctgcaagg ctactggcta cacattcact gcctactgga tagagtgggt aaagcagagg     120
cctggacatg gccttgagtg gattggagag attttacctg gaagtggtat tactaaatac     180
agtgagaagt tcaagggcaa ggccacattc actgcagata tcctccaa tacagcctac       240 atgcaactca gcagcctgac aactgaggac tctgccatct attactgtgc aagagactac     300
tatagtgaca actactgggg tcaaggaacc tcagtcaccg tctcctcagc caaaacaaca     360
cccccatcag tctatccact ggcccctggg tgtggagata caactggttc ctctgtgact     420
ctgggatgcc tggtcaaggg ctacttccct gagtcagtga ctgtgacttg gaactctgga     480
tccctgtcca gcagtgtgca caccttccca gctctcctgc agtctggact ctacactatg     540
agcagctcag tgactgtccc ctccagcacc tggccaagtc agaccgtcac ctgcagcgtt     600
gctcacccag ccagcagcac cacggtggac aaaaaacttg agcccagcgg gcccatttca     660
acaatcaacc cctgtcctcc atgcaaggag tgtcacaaat gcccagctcc taacctcgag     720
ggtggaccat ccgtcttcat cttccctcca aatatcaagg atgtactcat gatctccctg     780
acacccaagg tcacgtgtgt ggtggtggat gtgagcgagg atgacccaga cgtccggatc     840
agctggtttg tgaacaacgt ggaagtacac acagctcaga cacaaaccca tagagaggat     900
tacaacagta ctatccgggt ggtcagtgcc ctccccatcc agcaccagga ctggatgagt     960
ggcaaggagt tcaaatgcaa ggtcaacaac aaagacctcc catcacccat cgagagaacc    1020
atctcaaaaa ttaaagggct agtcagagct ccacaagtat acatcttgcc gccaccagca    1080
gagcagttgt ccaggaaaga tgtcagtctc acttgcctgg tcgtgggctt caaccctgga    1140
gacatcagtg tggagtggac cagcaatggg catacagagg agaactacaa ggacaccgca    1200
ccagtcctgg actctgacgg ttcttacttc atatacagca agctcgatat aaaaacaagc    1260
aagtgggaga aaacagattc cttctcatgc aacgtgagac acgagggtct gaaaaattac    1320
tacctgaaga gaccatctc ccggtctccg ggtaaatga                             1359

<210> SEQ ID NO 89
<211> LENGTH: 660
<212> TYPE: DNA
<213> ORGANISM: Artificial Sequence
<220> FEATURE:
<223> OTHER INFORMATION: Light chain (clone 19)

<400> SEQUENCE: 89
gatgttgtga tgacccagat tccactcact ttgtcggtta ccattggaca accagcctcc      60
atctcttgca gtcaagtca gagcctctta gatagtgatg gaggacata tttgaattgg       120 ttgttacaga ggccaggcca gtctccaaag cgcctaatct atctggtgtc taaactggac      180
tctggagtcc ctgacaggtt cactggcagt ggatcaggga cagatttcac attgaaaatc      240
agcagagtgg aggctgagga tttgggagtt tattattgct ggcaaggtac acttttccg       300 tacacgttcg gaggggggac caagctggag ataaaacggg ctgatgctgc accaactgta      360
```

```
tccatcttcc caccatccag tgagcagtta acatctggag gtgcctcagt cgtgtgcttc      420
ttgaacaact tctaccccaa agacatcaat gtcaagtgga agattgatgg cagtgaacga      480
caaaatggcg tcctgaacag ttggactgat caggacagca agacagcac ctacagcatg       540 agcagcaccc tcacgttgac caaggacgag tatgaacga ataacagcta tacctgtgag        600
gccactcaca agacatcaac ttcacccatt gtcaagagct tcaacaggaa tgagtgttag      660
```

```
<210> SEQ ID NO 90
<211> LENGTH: 348
<212> TYPE: DNA
<213> ORGANISM: Artificial Sequence
<220> FEATURE:
<223> OTHER INFORMATION: VH (clone 19)

<400> SEQUENCE: 90
caggttcagc tgcagcagtc tggagctgag ctgatgaagc ctggggcctc agtgaagctt       60
tcctgcaagg ctactggcta cacattcact gcctactgga tagagtgggt aaagcagagg      120
cctggacatg gccttgagtg gattggagag attttacctg gaagtggtat tactaaatac      180
agtgagaagt tcaagggcaa ggccacattc actgcagata catcctccaa tacagcctac      240
atgcaactca gcagcctgac aactgaggac tctgccatct attactgtgc aagagactac      300
tatagtgaca actactgggg tcaaggaacc tcagtcaccg tctcctca                   348
```

```
<210> SEQ ID NO 91
<211> LENGTH: 336
<212> TYPE: DNA
<213> ORGANISM: Artificial Sequence
<220> FEATURE:
<223> OTHER INFORMATION: VL (clone 19)

<400> SEQUENCE: 91
gatgttgtga tgacccagat tccactcact ttgtcggtta ccattggaca accagcctcc       60
atctcttgca agtcaagtca gagcctctta gatagtgatg gaaggacata tttgaattgg      120
ttgttacaga ggccaggcca gtctccaaag cgcctaatct atctggtgtc taaactggac      180
tctggagtcc ctgacaggtt cactggcagt ggatcaggga cagatttcac attgaaaatc      240
agcagagtgg aggctgagga tttgggagtt tattattgct ggcaaggtac acttttccg        300 tacacgttcg gaggggggac caagctggag ataaaa                                336
```

```
<210> SEQ ID NO 92
<211> LENGTH: 19
<212> TYPE: PRT
<213> ORGANISM: Artificial Sequence
<220> FEATURE:
<223> OTHER INFORMATION: Leader sequence; heavy chain (clone 19)

<400> SEQUENCE: 92

Met Glu Trp Thr Trp Val Phe Leu Phe Leu Leu Ser Val Thr Ala Gly
1               5                   10                  15

Val His Ser
```

```
<210> SEQ ID NO 93
<211> LENGTH: 57
<212> TYPE: DNA
<213> ORGANISM: Artificial Sequence
<220> FEATURE:
<223> OTHER INFORMATION: Leader sequence; heavy chain (clone 19)

<400> SEQUENCE: 93
```

```
atggaatgga cctgggtctt tctcttcctc ctgtcagtaa ctgcaggtgt ccactcc          57

<210> SEQ ID NO 94
<211> LENGTH: 19
<212> TYPE: PRT
<213> ORGANISM: Artificial Sequence
<220> FEATURE:
<223> OTHER INFORMATION: Leader sequence; light chain (clone 19)

<400> SEQUENCE: 94

Met Ser Pro Ala Gln Phe Leu Phe Leu Leu Val Leu Trp Ile Arg Glu
1               5                   10                  15

Thr Asn Gly

<210> SEQ ID NO 95
<211> LENGTH: 57
<212> TYPE: DNA
<213> ORGANISM: Artificial Sequence
<220> FEATURE:
<223> OTHER INFORMATION: Leader sequence; light chain (clone 19)

<400> SEQUENCE: 95
atgagtcctg cccagttcct gtttctgtta gtgctctgga ttcgggaaac caacggt          57

<210> SEQ ID NO 96
<211> LENGTH: 28
<212> TYPE: PRT
<213> ORGANISM: Homo sapiens
<220> FEATURE:
<223> OTHER INFORMATION: CD28 transmembrane domain

<400> SEQUENCE: 96

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 97
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 97

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 98
<211> LENGTH: 41
<212> TYPE: PRT
<213> ORGANISM: Homo sapiens
<220> FEATURE:
<223> OTHER INFORMATION: CD28 (LL to GG)

<400> SEQUENCE: 98

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
```

-continued

```
                20              25              30

Pro Arg Asp Phe Ala Ala Tyr Arg Ser
        35              40

<210> SEQ ID NO 99
<211> LENGTH: 42
<212> TYPE: PRT
<213> ORGANISM: Homo sapiens
<220> FEATURE:
<223> OTHER INFORMATION: 4-1BB (amino acids 214-255 of Q07011.1)

<400> SEQUENCE: 99

Lys Arg Gly Arg Lys Lys Leu Leu Tyr Ile Phe Lys Gln Pro Phe Met
1               5               10              15

Arg Pro Val Gln Thr Thr Gln Glu Glu Asp Gly Cys Ser Cys Arg Phe
                20              25              30

Pro Glu Glu Glu Glu Gly Gly Cys Glu Leu
        35              40

<210> SEQ ID NO 100
<211> LENGTH: 112
<212> TYPE: PRT
<213> ORGANISM: Homo sapiens
<220> FEATURE:
<223> OTHER INFORMATION: CD3-zeta derived intracellular signaling domain

<400> SEQUENCE: 100

Arg Val Lys Phe Ser Arg Ser Ala Asp Ala Pro Ala Tyr Gln Gln Gly
1               5               10              15

Gln Asn Gln Leu Tyr Asn Glu Leu Asn Leu Gly Arg Arg Glu Glu Tyr
                20              25              30

Asp Val Leu Asp Lys Arg Arg Gly Arg Asp Pro Glu Met Gly Gly Lys
        35              40              45

Pro Arg Arg Lys Asn Pro Gln Glu Gly Leu Tyr Asn Glu Leu Gln Lys
    50              55              60

Asp Lys Met Ala Glu Ala Tyr Ser Glu Ile Gly Met Lys Gly Glu Arg
65              70              75              80

Arg Arg Gly Lys Gly His Asp Gly Leu Tyr Gln Gly Leu Ser Thr Ala
                85              90              95

Thr Lys Asp Thr Tyr Asp Ala Leu His Met Gln Ala Leu Pro Pro Arg
            100             105             110

<210> SEQ ID NO 101
<211> LENGTH: 12
<212> TYPE: PRT
<213> ORGANISM: Homo sapiens
<220> FEATURE:
<223> OTHER INFORMATION: Spacer (IgG4hinge)

<400> SEQUENCE: 101

Glu Ser Lys Tyr Gly Pro Pro Cys Pro Pro Cys Pro
1               5               10

<210> SEQ ID NO 102
<211> LENGTH: 119
<212> TYPE: PRT
<213> ORGANISM: Homo sapiens
<220> FEATURE:
<223> OTHER INFORMATION: Hinge-CH3 spacer

<400> SEQUENCE: 102

Glu Ser Lys Tyr Gly Pro Pro Cys Pro Pro Cys Pro Gly Gln Pro Arg
```

-continued

```
1               5                    10                   15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
            35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
            85                  90                  95

Cys Ser Val Met His Glu Ala Leu His Asn His Tyr Thr Gln Lys Ser
            100                 105                 110

Leu Ser Leu Ser Leu Gly Lys
            115
```

```
<210> SEQ ID NO 103
<211> LENGTH: 229
<212> TYPE: PRT
<213> ORGANISM: Homo sapiens
<220> FEATURE:
<223> OTHER INFORMATION: Hinge-CH2-CH3 spacer

<400> SEQUENCE: 103

Glu Ser Lys Tyr Gly Pro Pro Cys Pro Pro Cys Pro Ala Pro Glu Phe
1               5                    10                   15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln
            130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys
225
```

-continued

```
<210> SEQ ID NO 104
<211> LENGTH: 5
<212> TYPE: PRT
<213> ORGANISM: Artificial Sequence
<220> FEATURE:
<223> OTHER INFORMATION: CDR-H1; Kabat (clone 16)

<400> SEQUENCE: 104

Asp Phe Tyr Ile Asn
1               5

<210> SEQ ID NO 105
<211> LENGTH: 17
<212> TYPE: PRT
<213> ORGANISM: Artificial Sequence
<220> FEATURE:
<223> OTHER INFORMATION: CDR-H2; Kabat (clone 16)

<400> SEQUENCE: 105

Trp Ile Phe Pro Arg Ser Gly Ser Thr Tyr Tyr Asn Glu Lys Phe Lys
1               5                   10                  15

Gly

<210> SEQ ID NO 106
<211> LENGTH: 10
<212> TYPE: PRT
<213> ORGANISM: Artificial Sequence
<220> FEATURE:
<223> OTHER INFORMATION: CDR-H3; Kabat, Chothia, AbM (clone 16)

<400> SEQUENCE: 106

Gly Asp Gly Tyr Ser Gly Ala Met Asp Tyr
1               5                   10

<210> SEQ ID NO 107
<211> LENGTH: 7
<212> TYPE: PRT
<213> ORGANISM: Artificial Sequence
<220> FEATURE:
<223> OTHER INFORMATION: CDR-H1; Chothia (clone 16)

<400> SEQUENCE: 107

Gly Tyr Thr Gly Thr Asp Phe
1               5

<210> SEQ ID NO 108
<211> LENGTH: 6
<212> TYPE: PRT
<213> ORGANISM: Artificial Sequence
<220> FEATURE:
<223> OTHER INFORMATION: CDR-H2; Chothia (clone 16)

<400> SEQUENCE: 108

Phe Pro Arg Ser Gly Ser
1               5

<210> SEQ ID NO 109
<211> LENGTH: 10
<212> TYPE: PRT
<213> ORGANISM: Artificial Sequence
<220> FEATURE:
<223> OTHER INFORMATION: CDR-H1; AbM (clone 16)

<400> SEQUENCE: 109

Gly Tyr Thr Gly Thr Asp Phe Tyr Ile Asn
1               5                   10
```

-continued

```
<210> SEQ ID NO 110
<211> LENGTH: 10
<212> TYPE: PRT
<213> ORGANISM: Artificial Sequence
<220> FEATURE:
<223> OTHER INFORMATION: CDR-H2; AbM (clone 16)

<400> SEQUENCE: 110

Trp Ile Phe Pro Arg Ser Gly Ser Thr Tyr
1               5                   10

<210> SEQ ID NO 111
<211> LENGTH: 11
<212> TYPE: PRT
<213> ORGANISM: Artificial Sequence
<220> FEATURE:
<223> OTHER INFORMATION: CDR-L1; Kabat, Chothia, AbM (clone 16)

<400> SEQUENCE: 111

Ser Ala Ser Gln Gly Ile Arg Asn Tyr Leu Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: CDR-L2; Kabat, Chothia, AbM (clone 16)

<400> SEQUENCE: 112

Tyr Thr Ser Asn Leu His Ser
1               5

<210> SEQ ID NO 113
<211> LENGTH: 9
<212> TYPE: PRT
<213> ORGANISM: Artificial Sequence
<220> FEATURE:
<223> OTHER INFORMATION: CDR-L3; Kabat, Chothia, AbM (clone 16)

<400> SEQUENCE: 113

Gln Gln Tyr Asn Asn Leu Pro Arg Thr
1               5

<210> SEQ ID NO 114
<211> LENGTH: 119
<212> TYPE: PRT
<213> ORGANISM: Artificial Sequence
<220> FEATURE:
<223> OTHER INFORMATION: VH (clone 16)

<400> SEQUENCE: 114

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Phe
            20                  25                  30

Tyr Ile Asn Trp Val Lys Gln Arg Pro Gly Gln Gly Leu Glu Trp Ile
        35                  40                  45

Gly Trp Ile Phe Pro Arg Ser Gly Ser Thr Tyr Tyr Asn Glu Lys Phe
    50                  55                  60

Lys Gly Lys Ala Thr Leu Ser Val Asp Lys Ser Ser Ile Thr Ala Tyr
65                  70                  75                  80

Met Leu Leu Ser Ser Leu Thr Ser Glu Asp Ser Ala Val Tyr Phe Cys
                85                  90                  95
```

-continued

```
Ala Arg Gly Asp Gly Tyr Ser Gly Ala Met Asp Tyr Trp Gly Gln Gly
            100                 105                 110

Thr Ser Val Thr Val Ser Ser
        115

<210> SEQ ID NO 115
<211> LENGTH: 107
<212> TYPE: PRT
<213> ORGANISM: Artificial Sequence
<220> FEATURE:
<223> OTHER INFORMATION: VL (clone 16)

<400> SEQUENCE: 115

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Gly Ile Arg Asn Tyr
            20                  25                  30

Leu Asn Trp Tyr Gln Gln Lys Pro Asp Gly Thr Val Lys Leu Leu Ile
        35                  40                  45

Tyr Tyr Thr Ser Asn Leu His Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Asn Asn Leu Pro Arg
                85                  90                  95

Thr Phe Gly Gly Gly Thr Lys Leu Glu Ile Lys
            100                 105

<210> SEQ ID NO 116
<211> LENGTH: 443
<212> TYPE: PRT
<213> ORGANISM: Artificial Sequence
<220> FEATURE:
<223> OTHER INFORMATION: Heavy chain (clone 16)

<400> SEQUENCE: 116

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Phe
            20                  25                  30

Tyr Ile Asn Trp Val Lys Gln Arg Pro Gly Gln Gly Leu Glu Trp Ile
        35                  40                  45

Gly Trp Ile Phe Pro Arg Ser Gly Ser Thr Tyr Tyr Asn Glu Lys Phe
    50                  55                  60

Lys Gly Lys Ala Thr Leu Ser Val Asp Lys Ser Ser Ile Thr Ala Tyr
65                  70                  75                  80

Met Leu Leu Ser Ser Leu Thr Ser Glu Asp Ser Ala Val Tyr Phe Cys
                85                  90                  95

Ala Arg Gly Asp Gly Tyr Ser Gly Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
```

-continued

```
                165              170              175
Gln Ser Asp Leu Tyr Thr Leu Ser Ser Ser Val Thr Val Pro Ser Ser
            180              185              190

Thr Trp Pro Ser Gln Thr Val Thr Cys Asn Val Ala His Pro Ala Ser
            195              200              205

Ser Thr Lys Val Asp Lys Lys Ile Val Pro Arg Asp Cys Gly Cys Lys
    210              215              220

Pro Cys Ile Cys Thr Val Pro Glu Val Ser Ser Val Phe Ile Phe Pro
225              230              235              240

Pro Lys Pro Lys Asp Val Leu Thr Ile Thr Leu Thr Pro Lys Val Thr
            245              250              255

Cys Val Val Val Asp Ile Ser Lys Asp Asp Pro Glu Val Gln Phe Ser
            260              265              270

Trp Phe Val Asp Asp Val Glu Val His Thr Ala Gln Thr Lys Pro Arg
            275              280              285

Glu Glu Gln Ile Asn Ser Thr Phe Arg Ser Val Ser Glu Leu Pro Ile
    290              295              300

Met His Gln Asp Trp Leu Asn Gly Lys Glu Phe Lys Cys Arg Val Asn
305              310              315              320

Ser Ala Ala Phe Pro Ala Pro Ile Glu Lys Thr Ile Ser Lys Thr Lys
            325              330              335

Gly Arg Pro Lys Ala Pro Gln Val Tyr Thr Ile Pro Pro Pro Lys Glu
            340              345              350

Gln Met Ala Lys Asp Lys Val Ser Leu Thr Cys Met Ile Thr Asn Phe
            355              360              365

Phe Pro Glu Asp Ile Thr Val Glu Trp Gln Trp Asn Gly Gln Pro Ala
    370              375              380

Glu Asn Tyr Lys Asn Thr Gln Pro Ile Met Asp Thr Asp Gly Ser Tyr
385              390              395              400

Phe Val Tyr Ser Lys Leu Asn Val Gln Lys Ser Asn Trp Glu Ala Gly
            405              410              415

Asn Thr Phe Thr Cys Ser Val Leu His Glu Gly Leu His Asn His His
            420              425              430

Thr Glu Lys Ser Leu Ser His Ser Pro Gly Lys
            435              440
```

<210> SEQ ID NO 117
<211> LENGTH: 214
<212> TYPE: PRT
<213> ORGANISM: Artificial Sequence
<220> FEATURE:
<223> OTHER INFORMATION: Light chain (clone 16)

<400> SEQUENCE: 117

```
Asp Ile Gln Met Thr Gln Thr Thr Ser Ser Leu Ser Ala Ser Leu Gly
1               5               10              15

Asp Arg Val Thr Ile Ser Cys Ser Ala Ser Gln Gly Ile Arg Asn Tyr
            20              25              30

Leu Asn Trp Tyr Gln Gln Lys Pro Asp Gly Thr Val Lys Leu Leu Ile
        35              40              45

Tyr Tyr Thr Ser Asn Leu His Ser Gly Val Pro Ser Arg Phe Ser Gly
    50              55              60

Ser Gly Ser Gly Thr Asp Tyr Ser Leu Thr Ile Ser Asn Leu Glu Pro
65              70              75              80

Glu Asp Ile Ala Thr Tyr Tyr Cys Gln Gln Tyr Asn Asn Leu Pro Arg
```

-continued

```
                     85                   90                   95
Thr Phe Gly Gly Gly Thr Lys Leu Glu Ile Lys Arg Ala Asp Ala Ala
            100                 105                 110
Pro Thr Val Ser Ile Phe Pro Pro Ser Ser Glu Gln Leu Thr Ser Gly
        115                 120                 125
Gly Ala Ser Val Val Cys Phe Leu Asn Asn Phe Tyr Pro Lys Asp Ile
    130                 135                 140
Asn Val Lys Trp Lys Ile Asp Gly Ser Glu Arg Gln Asn Gly Val Leu
145                 150                 155                 160
Asn Ser Trp Thr Asp Gln Asp Ser Lys Asp Ser Thr Tyr Ser Met Ser
            165                 170                 175
Ser Thr Leu Thr Leu Thr Lys Asp Glu Tyr Glu Arg His Asn Ser Tyr
        180                 185                 190
Thr Cys Glu Ala Thr His Lys Thr Ser Thr Ser Pro Ile Val Lys Ser
        195                 200                 205
Phe Asn Arg Asn Glu Cys
    210
```

<210> SEQ ID NO 118
<211> LENGTH: 1332
<212> TYPE: DNA
<213> ORGANISM: Artificial Sequence
<220> FEATURE:
<223> OTHER INFORMATION: Heavy chain (clone 16)

<400> SEQUENCE: 118

```
caggtccagc tacagcagtc tggacctgag ctggtgaagc ctgggggcttc agtgaagata    60 tcctgcaagg cttctggcta caccttcact gacttctata taaactgggt gaagcagagg   120
cctggacagg gacttgagtg gattggatgg atttttccta gaagtggtag tacttactac   180
aatgagaagt tcaagggcaa ggccacactt agtgtagaca atcttccat cacagcctac   240 atgttgctca gcagcctgac ctctgaggac tctgcggtct atttctgtgc aaggggggat   300
ggttactctg gagctatgga ctactggggt caaggaacct cagtcaccgt ctcctcagcc   360
aaaacgacac cccatctgt ctatccactg gcccctggat ctgctgccca aactaactcc   420
atggtgaccc tgggatgcct ggtcaagggc tatttccctg agccagtgac agtgacctgg   480
aactctggat ccctgtccag cggtgtgcac accttcccag ctgtcctgca gtctgacctc   540
tacactctga gcagctcagt gactgtcccc tccagcacct ggcccagcca gaccgtcacc   600
tgcaacgttg cccacccggc cagcagcacc aaggtggaca gaaaattgt gcccagggat   660 tgtggttgta agccttgcat atgtacagtc ccagaagtat catctgtctt catcttcccc   720
ccaaagccca aggatgtgct caccattact ctgactccta aggtcacgtg tgttgtggta   780
gacatcagca aggatgatcc cgaggtccag ttcagctggt ttgtagatga tgtggaggtg   840
cacacagctc agacgaaacc ccgggaggag cagatcaaca gcactttccg ttcagtcagt   900
gaacttccca tcatgcacca ggactggctc aatggcaagg agttcaaatg cagggtcaac   960
agtgcagctt ccctgcccc catcgagaaa accatctcca aaaccaaagg cagaccgaag  1020
gctccacagg tgtacaccat tccacctccc aaggagcaga tggccaagga taaagtcagt  1080
ctgacctgca tgataacaaa cttcttccct gaagacatta ctgtggagtg gcagtggaat  1140
gggcagccag cggagaacta caagaacact cagcccatca tggacacaga tggctcttac  1200
ttcgtctaca gcaagctcaa tgtgcagaag agcaactggg aggcaggaaa tactttcacc  1260
tgctctgtgt acatgagggg cctgcacaac caccatactg agaagagcct ctcccactct  1320
```

-continued

```
cctggtaaat ga                                                     1332

<210> SEQ ID NO 119
<211> LENGTH: 645
<212> TYPE: DNA
<213> ORGANISM: Artificial Sequence
<220> FEATURE:
<223> OTHER INFORMATION: Light chain (clone 16)

<400> SEQUENCE: 119
gatatccaga tgacacagac tacatcctcc ctgtctgcct ctctgggaga cagagtcacc      60
atcagttgca gtgcaagtca gggcattaga aattatttaa actggtatca gcagaaacca     120
gatggaactg ttaaactcct gatctattac acatcaaatt tacactcagg agtcccatca     180
aggttcagtg gcagtgggtc tgggacagat tattctctca ccatcagcaa cctggaacct     240
gaagatattg ccacttacta ttgtcagcag tataataacc ttcctcggac gttcggtgga     300
ggcaccaagc tggaaatcaa acgggctgat gctgcaccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag caccctcacg     540
ttgaccaagg acgagtatga cgacataac agctatacct gtgaggccac tcacaagaca     600
tcaacttcac ccattgtcaa gagcttcaac aggaatgagt gttag                     645

<210> SEQ ID NO 120
<211> LENGTH: 357
<212> TYPE: DNA
<213> ORGANISM: Artificial Sequence
<220> FEATURE:
<223> OTHER INFORMATION: VH (clone 16)

<400> SEQUENCE: 120
caggtccagc tacagcagtc tggacctgag ctggtgaagc ctggggcttc agtgaagata      60
tcctgcaagg cttctggcta caccttcact gacttctata aaactgggt gaagcagagg      120 cctggacagg gacttgagtg gattggatgg attttcta gaagtggtag tacttactac      180
aatgagaagt tcaagggcaa ggccacactt agtgtagaca aatcttccat cacagcctac      240
atgttgctca gcagcctgac ctctgaggac tctgcggtct atttctgtgc aagggggggat      300 ggttactctg gagctatgga ctactggggt caaggaacct cagtcaccgt ctcctca        357

<210> SEQ ID NO 121
<211> LENGTH: 321
<212> TYPE: DNA
<213> ORGANISM: Artificial Sequence
<220> FEATURE:
<223> OTHER INFORMATION: VL (clone 16)

<400> SEQUENCE: 121
gatatccaga tgacacagac tacatcctcc ctgtctgcct ctctgggaga cagagtcacc      60
atcagttgca gtgcaagtca gggcattaga aattatttaa actggtatca gcagaaacca     120
gatggaactg ttaaactcct gatctattac acatcaaatt tacactcagg agtcccatca     180
aggttcagtg gcagtgggtc tgggacagat tattctctca ccatcagcaa cctggaacct     240
gaagatattg ccacttacta ttgtcagcag tataataacc ttcctcggac gttcggtgga     300
ggcaccaagc tggaaatcaa a                                               321
```

-continued

```
<210> SEQ ID NO 122
<211> LENGTH: 19
<212> TYPE: PRT
<213> ORGANISM: Artificial Sequence
<220> FEATURE:
<223> OTHER INFORMATION: Leader sequence; heavy chain (clone 16)

<400> SEQUENCE: 122

Met Gly Trp Ser Trp Ile Phe Leu Phe Leu Leu Ser Gly Thr Ala Gly
1               5                   10                  15

Val His Cys

<210> SEQ ID NO 123
<211> LENGTH: 57
<212> TYPE: DNA
<213> ORGANISM: Artificial Sequence
<220> FEATURE:
<223> OTHER INFORMATION: Leader sequence; heavy chain (clone 16)

<400> SEQUENCE: 123
atgggatgga gctggatctt tctcttcctc ctgtcaggaa ctgcaggtgt ccattgc          57

<210> SEQ ID NO 124
<211> LENGTH: 19
<212> TYPE: PRT
<213> ORGANISM: Artificial Sequence
<220> FEATURE:
<223> OTHER INFORMATION: Leader sequence; light chain (clone 16)

<400> SEQUENCE: 124

Met Ser Ser Ala Gln Phe Leu Gly Leu Leu Leu Leu Cys Phe Gln Gly
1               5                   10                  15

Thr Arg Cys

<210> SEQ ID NO 125
<211> LENGTH: 57
<212> TYPE: DNA
<213> ORGANISM: Artificial Sequence
<220> FEATURE:
<223> OTHER INFORMATION: Leader sequence; light chain (clone 16)

<400> SEQUENCE: 125
atgtcctctg ctcagttcct tggtctcctg ttgctctgtt ttcaaggtac cagatgt          57

<210> SEQ ID NO 126
<211> LENGTH: 21
<212> TYPE: PRT
<213> ORGANISM: Artificial Sequence
<220> FEATURE:
<223> OTHER INFORMATION: T2A peptide

<400> SEQUENCE: 126

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 127
<211> LENGTH: 24
<212> TYPE: PRT
<213> ORGANISM: Artificial Sequence
<220> FEATURE:
<223> OTHER INFORMATION: T2A peptide

<400> SEQUENCE: 127
```

```
Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 128
<211> LENGTH: 19
<212> TYPE: PRT
<213> ORGANISM: Artificial Sequence
<220> FEATURE:
<223> OTHER INFORMATION: P2A peptide

<400> SEQUENCE: 128

Ala Thr Asn Phe Ser Leu Leu Lys Gln Ala Gly Asp Val Glu Glu Asn
1               5                   10                  15

Pro Gly Pro

<210> SEQ ID NO 129
<211> LENGTH: 22
<212> TYPE: PRT
<213> ORGANISM: Artificial Sequence
<220> FEATURE:
<223> OTHER INFORMATION: P2A peptide

<400> SEQUENCE: 129

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 130
<211> LENGTH: 20
<212> TYPE: PRT
<213> ORGANISM: Artificial Sequence
<220> FEATURE:
<223> OTHER INFORMATION: E2A peptide

<400> SEQUENCE: 130

Gln Cys Thr Asn Tyr Ala Leu Leu Lys Leu Ala Gly Asp Val Glu Ser
1               5                   10                  15

Asn Pro Gly Pro
            20

<210> SEQ ID NO 131
<211> LENGTH: 23
<212> TYPE: PRT
<213> ORGANISM: Artificial Sequence
<220> FEATURE:
<223> OTHER INFORMATION: E2A peptide

<400> SEQUENCE: 131

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 132
<211> LENGTH: 22
<212> TYPE: PRT
<213> ORGANISM: Artificial Sequence
<220> FEATURE:
<223> OTHER INFORMATION: F2A peptide

<400> SEQUENCE: 132
```

Val Lys Gln Thr Leu Asn Phe Asp Leu Leu Lys Leu Ala Gly Asp Val
1               5                   10                  15

Glu Ser Asn Pro Gly Pro
          20

<210> SEQ ID NO 133
<211> LENGTH: 25
<212> TYPE: PRT
<213> ORGANISM: Artificial Sequence
<220> FEATURE:
<223> OTHER INFORMATION: F2A peptide

<400> SEQUENCE: 133

Gly Ser Gly Val Lys Gln Thr Leu Asn Phe Asp Leu Leu Lys Leu Ala
1               5                   10                  15

Gly Asp Val Glu Ser Asn Pro Gly Pro
          20                  25

<210> SEQ ID NO 134
<211> LENGTH: 18
<212> TYPE: PRT
<213> ORGANISM: Artificial Sequence
<220> FEATURE:
<223> OTHER INFORMATION: T2A peptide

<400> SEQUENCE: 134

Glu Gly Arg Gly Ser Leu Leu Thr Cys Gly Asp Val Glu Glu Asn Pro
1               5                   10                  15

Gly Pro